US012679839B2

(12) United States Patent
Mevellec et al.

(10) Patent No.: US 12,679,839 B2
(45) Date of Patent: Jul. 14, 2026

(54) CYCLIN-DEPENDENT KINASE 7 (CDK7) NON-COVALENT INHIBITORS

(71) Applicant: JANSSEN PHARMACEUTICA NV, Beerse (BE)

(72) Inventors: Laurence Anne Mevellec, Issy-les Moulineaux (FR); Sophie Coupa ép. Descamps, Issy-les Moulineaux (FR); Christiphe Denis Pascal Adelinet, Issy-les Moulineaux (FR); Yannick Aimé Eddy Ligny, Issy-les Moulineaux (FR); Christophe Meyer, Issy-les Moulineaux (FR); Ian Stansfield, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 561 days.

(21) Appl. No.: 18/245,801

(22) PCT Filed: Sep. 24, 2021

(86) PCT No.: PCT/EP2021/076409
§ 371 (c)(1),
(2) Date: Mar. 17, 2023

(87) PCT Pub. No.: WO2022/064009
PCT Pub. Date: Mar. 31, 2022

(65) Prior Publication Data

US 2024/0101554 A1 Mar. 28, 2024

(30) Foreign Application Priority Data

Sep. 25, 2020 (EP) .................................... 20198367

(51) Int. Cl.

| | |
|---|---|
| ***C07D 471/04*** | (2006.01) |
| ***A61K 31/4375*** | (2006.01) |
| ***A61K 31/519*** | (2006.01) |
| ***A61K 35/00*** | (2006.01) |
| ***A61P 35/00*** | (2006.01) |
| ***C07D 519/00*** | (2006.01) |

(52) U.S. Cl.
CPC ........... *C07D 471/04* (2013.01); *A61P 35/00* (2018.01); *C07D 519/00* (2013.01)

(58) Field of Classification Search
CPC ..... C07D 471/04; C07D 519/00; A61P 35/00; A61K 31/519
USPC ...................................................... 514/264.1
See application file for complete search history.

(56) References Cited

U.S. PATENT DOCUMENTS

| | | | | |
|---|---|---|---|---|
| 2013/0338140 | A1 | 12/2013 | Blake et al. | |
| 2018/0044344 | A1 | 2/2018 | Behenna et al. | |
| 2019/0276440 | A1* | 9/2019 | Zhao | C07D 495/04 |
| 2023/0062491 | A1 | 3/2023 | Marineau et al. | |

FOREIGN PATENT DOCUMENTS

| | | | | |
|---|---|---|---|---|
| CN | 103635472 | A | 3/2014 | |
| CN | 110156754 | A | 8/2019 | |
| RU | 2726115 | C1 | 7/2020 | |
| RU | 2019103870 | A | 8/2020 | |
| TW | 202421138 | A * | 6/2024 | C07D 471/04 |
| WO | 2012/118850 | A1 | 9/2012 | |
| WO | 2016/105528 | A2 | 6/2016 | |
| WO | 2018/218051 | A1 | 11/2018 | |
| WO | 2019/001572 | A1 | 1/2019 | |
| WO | 2019/200120 | A1 | 10/2019 | |
| WO | WO-2025087267 | A1 * | 5/2025 | C07D 471/04 |

OTHER PUBLICATIONS

Golub et al.Science, vol. 286, Oct. 15, 1999, pp. 531-537.*
Antunes et al., Bioengineering (Basel), Apr 7, 2022;9(4):166, pp. 1-15.*
Dictionary.com, "Prophylaxis", Jul. 18, 2025.*
"Fundamentals of Preventive Medicine", Educational and methodological manual for students of advanced training at state professional educational institutions. Novosibirsk, 2016, pp. 13-21.
Ahapkina et al., "The fundamentals of the modulator concept and classification of modulatory drugs", RMJ, No. 19, 2012, pp. 933-951.
Alekseev, "Optical Isomerism and Pharmacological Activity of Drug Products", Soros Educational Journal, No. 11, 1998, pp. 49-55.

(Continued)

*Primary Examiner* — Brian-Yong S Kwon
(74) *Attorney, Agent, or Firm* — BakerHostetler

(57) ABSTRACT

The invention relates to pharmaceutical compounds of formula (I) and pharmaceutical compositions comprising said compounds, to processes for the preparation of said compounds and to the use of said compounds as inhibitors of cyclin-dependent kinase 7 (CDK7) and to their use in the treatment of diseases, e.g. cancer.

(I)

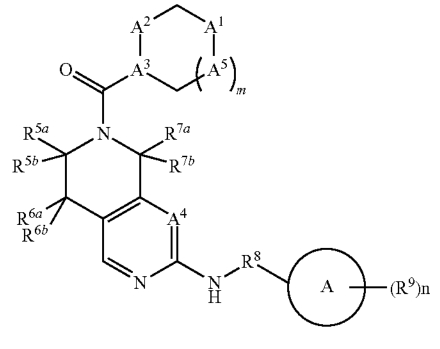

15 Claims, 4 Drawing Sheets

(56) References Cited

OTHER PUBLICATIONS

Bastin et al., "Salt Selection and Optimisation Procedures for Pharmaceutical New Chemical Entities", Organic Process Research & Development, 2000, vol. 4, No. 5, pp. 427-435.
Belikov, Pharmacevticeskaâ himiâ [Pharmaceutical Chemistry], Textbook, 4th ed. Moscow: MEDpressinform, 2007, pp. 11, 27-29.
Durnov et al., Pediatric Oncology, Second Edition, 2002, p. 139.
Dyson et al., "Chemistry of Synthetic Drugs", 1964, pp. 12-19.
Knunanc, Chemical Encyclopedia Dictionary, 1983, pp. 130-131.
Kummerer, "Pharmaceuticals in the environment," Annual Review of Environment and Resources, 2010, vol. 35, pp. 57-75.
Mironov, Guidelines for conducting preclinical studies of drugs, Part one, Moscow: Chapter 39, 2012.
Sava et al., "CDK7 inhibitors as anticancer drugs", Cancer and Metastasis Reviews (2020) 39:805-823.

* cited by examiner

CYCLIN-DEPENDENT KINASE 7 (CDK7) NON-COVALENT INHIBITORS

CROSS-REFERENCE

This application is the National Stage Application of International Patent Application No. PCT/EP2021/076409, filed Sep. 24, 2021, which claims benefit of EP Application Serial No. 20198367.3, filed on Sep. 25, 2020, which is herein incorporated by reference in its entirety.

FIELD OF THE INVENTION

The invention relates to pharmaceutical compounds and pharmaceutical compositions comprising said compounds, to processes for the preparation of said compounds and to the use of said compounds as inhibitors of cyclin-dependent kinase 7 (CDK7) and to their use in the treatment of diseases, e.g., cancer.

BACKGROUND OF THE INVENTION

The members of the cyclin-dependent kinase (CDK) family play critical regulatory roles in proliferation. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression. In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation. Together, the two functions of CDK7, i.e., CAK and CTD phosphorylation, support critical facets of cellular proliferation, cell cycling, and transcription.

Disruption of RNAP II CTD phosphorylation has been shown to preferentially affect proteins with short half-lives, including those of the anti-apoptotic BCL-2 family. Cancer cells have demonstrated ability to circumvent pro-cell death signaling through upregulation of BCL-2 family members. Therefore, inhibition of human CDK7 kinase activity is likely to result in anti-proliferative activity.

The discovery of selective inhibitors of CDK7 has been hampered by the high sequence and structural similarities of the kinase domain of CDK family members. Therefore, there is a need for the discovery and development of selective CDK7 inhibitors. Such CKD7 inhibitors hold promise as therapeutic agents for the treatment of chronic lymphocytic leukemia and other cancers.

WO 2012/118850 A1 discloses 5,8-dihydro-6H-pyrido[3,4-d]pyrimidines substituted with amine and carbonyl groups for the use in the treatment of neoplastic diseases by inhibiting serine/threonine kinase; in particular the compounds are disclosed as selective ERK inhibitors.

WO 2016/105528 A2 discloses 4,6-dihydropyrrolo[3,4-c]pyrazoles substituted with a carbonyl group for the use in the treatment of proliferative diseases; in particular the compounds are disclosed as inhibitors of the kinase CDK7.

SUMMARY OF THE INVENTION

The present invention relates to a compound of formula (I), including any tautomeric and stereochemically isomeric form, isotopically labeled derivative, or a pharmaceutically acceptable salt or solvate thereof:

(I)

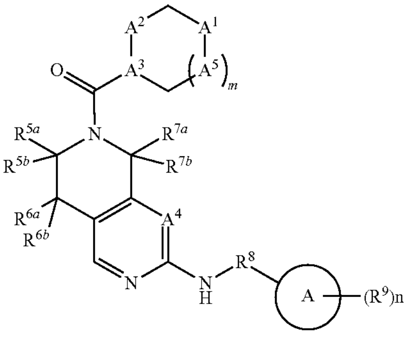

wherein, $A^1$ is $CR^{1a}R^{1b}$ or $NR^2$;

$A^2$ is $CR^{3a}R^{3b}$ or $NR^4$;

$A^3$ and $A^4$ each independently represent CH or N;

$A^5$ is —$CH_2$— or —$CH(CH_3)$—;

m is 0 or 1;

each $R^{1a}$ and $R^{1b}$, independently, is hydrogen, $C_{1-6}$alkyl, or —$N(C_{1-4}alkyl)_2$;

$R^2$ is hydrogen; halo$C_{1-6}$alkyl; $C_{1-6}$alkoxy; $C_{1-6}$alkyloxycarbonyl; $C_{2-6}$alkenyl; $C_{2-6}$alkynyl; —C(═O)—$NH_2$; —C(═O)—NH($C_{1-4}$alkyl); —C(═O)—N($C_{1-4}$alkyl)$_2$; $C_{3-6}$cycloalkyl; phenyl; a 4 to 7 membered monocyclic heterocyclyl containing at least one heteroatom selected from N, O or S; or $C_{1-6}$alkyl optionally substituted with deuterium, hydroxyl, $C_{1-6}$alkoxy, cyano, $C_{3-6}$cycloalkyl, phenyl, or with a 4 to 7 membered monocyclic heterocyclyl containing at least one heteroatom selected from N, O or S;

each $R^{3a}$ and $R^{3b}$, independently, is hydrogen; $C_{1-6}$alkyl; halo$C_{1-6}$alkyl; $C_{1-6}$alkoxy; $C_{1-6}$alkyloxycarbonyl; $C_{2-6}$alkenyl; $C_{2-6}$alkynyl; cyano$C_{1-6}$alkyl; hydroxy$C_{1-6}$ alkyl; —C(═O)—$NH_2$; —C(═O)—NH($C_{1-4}$alkyl); —C(═O)—N($C_{1-4}$alkyl)$_2$; —N($C_{1-4}$alkyl)$_2$; $C_{3-6}$cycloalkyl; aryl; a 4 to 7 membered monocyclic heterocyclyl containing at least one heteroatom selected from N, O or S; a 5 to 6 membered monocyclic heteroaryl containing at least one heteroatom selected from N, O or S; wherein said aryl, heterocyclyl, and heteroaryl, each independently, is optionally substituted with one or more halo, hydroxy, mercapto, carboxyl, halo$C_{1-6}$alkyl, mono- or di($C_{1-6}$alkyl)amino, mono- or di($C_{1-6}$alkyl)aminocarbonyl, $C_{1-6}$alkylcarbonyl, $C_{1-6}$alkylcarbonylamino, $C_{1-6}$alkoxy, $C_{1-6}$alkoxycarbonyl, $C_{1-6}$alkylthio, cyano, nitro, halo$C_{1-6}$alkoxy, aminocarbonyl, $C_{3-6}$cycloalkyl, or $C_{1-6}$alkyl optionally substituted with deuterium, amino, hydroxy, mono- or di($C_{1-6}$ alkyl)amino, $C_{1-6}$alkylcarbonylamino, [(mono- or di$C_{1-6}$alkyl)amino-$C_{1-6}$alkyl]carbonylamino, or with $C_{1-6}$alkylsulfonylamino;

$R^4$ is $C_{1-6}$alkyl; or phenyl optionally substituted with one, two, three, four, or five substituents each independently selected from halo, hydroxy, mercapto, carboxyl, halo$C_{1-6}$alkyl, mono- or di($C_{1-6}$alkyl)amino, mono- or di($C_{1-6}$alkyl)aminocarbonyl, $C_{1-6}$alkylcarbonyl, $C_{1-6}$alkylcarbonylamino, $C_{1-6}$alkoxy, $C_{1-6}$alkoxycarbonyl, $C_{1-6}$alkylthio, cyano, nitro, halo$C_{1-6}$alkoxy, aminocarbonyl, $C_{3-6}$cycloalkyl, or $C_{1-6}$alkyl optionally substituted with deuterium, amino, hydroxy, mono- or di($C_{1-6}$alkyl)amino, $C_{1-6}$alkylcarbonylamino, [(mono- or di$C_{1-6}$alkyl)amino-$C_{1-6}$alkyl]carbonylamino, or with $C_{1-6}$alkylsulfonylamino;

each $R^{5a}$, $R^{5b}$, $R^{6a}$, $R^{6b}$, $R^{7a}$, and $R^{7b}$, independently, is hydrogen; $C_{1-6}$alkyl; halo$C_{1-6}$alkyl; or $R^{5a}$ and $R^{5b}$ may form a $C_{3-6}$cycloalkyl together with the carbon atom to which they are bound; or $R^{6a}$ and $R^{6b}$ may form a $C_{3-6}$cycloalkyl together with the carbon atom to which they are bound; or $R^{5b}$ and $R^{6a}$ may form a cyclopropyl together with the carbon atoms to which they are bound; and provided that not each and all of $R^{5a}$, $R^{5b}$, $R^{6a}$, $R^{6b}$, $R^{7a}$, and $R^{7b}$, are hydrogen;

$R^8$ is a direct bond, $C_{1-4}$alkanediyl optionally substituted with hydroxy, halo, deuterium, or $C_{1-4}$alkoxy; —$CH_2$—C(═O)—; a spiro-$C_{3-6}$cycloalkyl; or a 4 to 7 membered spiro-monocyclic heterocyclyl containing at least one heteroatom selected from N, O or S;

A is a $C_{3-6}$cycloalkyl; aryl; a 5 to 12 membered heteroaryl containing at least one heteroatom selected from N, O or S; or a 4 to 12 membered heterocyclyl containing at least one heteroatom selected from N, O or S;

$R^9$ is $C_{1-6}$alkyl optionally substituted with $C_{3-6}$cycloalkyl, cyano, halo, halo$C_{1-6}$alkyl, $C_{1-6}$alkoxy optionally substituted with $C_{3-6}$cycloalkyl, halo$C_{1-6}$alkoxy, hydroxyl, hydroxy$C_{1-6}$alkyl, oxo, —$SO_2$—$C_{1-4}$alkyl, —$SO_2$—$C_{3-6}$cycloalkyl, —$SO_2$—$NH_2$, —$SO_2$—NH($C_{1-4}$alkyl), —$SO_2$—N($C_{1-4}$alkyl)$_2$, —NH—C(═O)—$C_{2-6}$alkenyl, —C(═O)—$C_{1-6}$alkyl, —C(═O)—$C_{1-6}$alkyl-$C_{3-6}$cycloalkyl, —C(═O)—$C_{3-6}$cycloalkyl, —C(═O)—$C_{2-6}$alkenyl, $C_{3-6}$cycloalkyl, spiro-$C_{3-6}$cycloalkyl, phenyl, a 4 to 7 membered monocyclic heterocyclyl containing at least one heteroatom selected from N, O or S; or a 4 to 7 membered spiro monocyclic heterocyclyl containing at least one heteroatom selected from N, O or S; and n is 0, 1, 2, 3, 4, or 5.

The compound may be a compound of formula (II), including any tautomeric and stereochemically isomeric form, isotopically labeled derivative, or a pharmaceutically acceptable salt or solvate thereof:

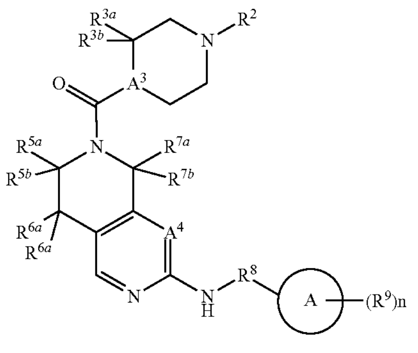

(II)

wherein, $A^3$ is CH or N;

$A^4$ is CH or N;

$R^2$ is hydrogen; halo$C_{1-6}$alkyl; $C_{1-6}$alkoxy; $C_{1-6}$alkyloxycarbonyl; $C_{2-6}$alkenyl; $C_{2-6}$alkynyl; —C(═O)—$NH_2$; —C(═O)—NH($C_{1-4}$alkyl); —C(═O)—N($C_{1-4}$alkyl)$_2$; $C_{3-6}$cycloalkyl; phenyl; a 4 to 7 membered monocyclic heterocyclyl containing at least one heteroatom selected from N, O or S; or $C_{1-6}$alkyl optionally substituted with deuterium, hydroxyl, $C_{1-6}$alkoxy, cyano, $C_{3-6}$cycloalkyl, phenyl, or with a 4 to 7 membered monocyclic heterocyclyl containing at least one heteroatom selected from N, O or S;

each $R^{3a}$ and $R^{3b}$, independently, is hydrogen; $C_{1-6}$alkyl; halo$C_{1-6}$alkyl; $C_{1-6}$alkoxy; $C_{1-6}$alkyloxycarbonyl; $C_{2-6}$alkenyl; $C_{2-6}$alkynyl; cyano$C_{1-6}$alkyl; hydroxy$C_{1-6}$alkyl; —C(═O)—$NH_2$; —C(═O)—NH($C_{1-4}$alkyl); —C(═O)—N($C_{1-4}$alkyl)$_2$; —N($C_{1-4}$alkyl)$_2$; $C_{3-6}$cycloalkyl; aryl; a 4 to 7 membered monocyclic heterocyclyl containing at least one heteroatom selected from N, O or S; a 5 to 6 membered monocyclic heteroaryl containing at least one heteroatom selected from N, O or S; wherein said aryl, heterocyclyl, and heteroaryl, each independently, is optionally substituted with one or more halo, hydroxy, mercapto, carboxyl, halo$C_{1-6}$alkyl, mono- or di($C_{1-6}$alkyl)amino, mono- or di($C_{1-6}$alkyl)aminocarbonyl, $C_{1-6}$alkylcarbonyl, $C_{1-6}$alkylcarbonylamino, $C_{1-6}$alkoxy, $C_{1-6}$alkoxycarbonyl, $C_{1-6}$alkylthio, cyano, nitro, halo$C_{1-6}$alkoxy, aminocarbonyl, $C_{3-6}$cycloalkyl, or $C_{1-6}$alkyl optionally substituted with deuterium, amino, hydroxy, mono- or di($C_{1-6}$alkyl)amino, $C_{1-6}$alkylcarbonylamino, [(mono- or di$C_{1-6}$alkyl)amino-$C_{1-6}$alkyl]carbonylamino, or with $C_{1-6}$alkylsulfonylamino;

each $R^{5a}$, $R^{5b}$, $R^{6a}$, $R^{6b}$, $R^{7a}$, and $R^{7b}$, independently, is hydrogen; $C_{1-6}$alkyl; halo$C_{1-6}$alkyl; or $R^{5a}$ and $R^{5b}$ may form a $C_{3-6}$cycloalkyl together with the carbon atom to which they are bound; or $R^{6a}$ and $R^{6b}$ may form a $C_{3-6}$cycloalkyl together with the carbon atom to which they are bound; or $R^{5b}$ and $R^{6a}$ may form a cyclopropyl together with the carbon atoms to which they are bound; and provided that not each and all of $R^{5a}$, $R^{5b}$, $R^{6a}$, $R^{6b}$, $R^{7a}$, and $R^{7b}$, are hydrogen;

$R^8$ is a direct bond, $C_{1-4}$alkanediyl optionally substituted with hydroxy, halo, deuterium, or $C_{1-4}$alkoxy; —$CH_2$—C(═O)—; a spiro-$C_{3-6}$cycloalkyl; or a 4 to 7 membered spiro-monocyclic heterocyclyl containing at least one heteroatom selected from N, O or S;

A is a $C_{3-6}$cycloalkyl; aryl; a 5 to 12 membered heteroaryl containing at least one heteroatom selected from N, O or S; or a 4 to 12 membered heterocyclyl containing at least one heteroatom selected from N, O or S;

$R^9$ is $C_{1-6}$alkyl optionally substituted with $C_{3-6}$cycloalkyl; cyano, halo; halo$C_{1-6}$alkyl; $C_{1-6}$alkoxy optionally substituted with $C_{3-6}$cycloalkyl; halo$C_{1-6}$alkoxy; hydroxyl; hydroxy$C_{1-6}$alkyl; oxo; —$SO_2$—$C_{1-4}$alkyl; —$SO_2$—$C_{3-6}$cycloalkyl; —$SO_2$—$NH_2$, —$SO_2$—NH($C_{1-4}$alkyl); —$SO_2$—N($C_{1-4}$alkyl)$_2$; —NH—C(═O)—$C_{2-6}$alkenyl; —C(═O)—$C_{1-6}$alkyl; —C(═O)—$C_{1-6}$alkyl-$C_{3-6}$cycloalkyl; —C(═O)—$C_{3-6}$cycloalkyl; —C(═O)—$C_{2-6}$alkenyl; $C_{3-6}$cycloalkyl; spiro-$C_{3-6}$cycloalkyl; phenyl; a 4 to 7 membered monocyclic heterocyclyl containing at least one heteroatom selected from N, O or S; or a 4 to 7 membered spiro monocyclic heterocyclyl containing at least one heteroatom selected from N, O or S; and n is 0, 1, 2, 3, 4, or 5.

In the compounds of formula (I) or (II), including any tautomeric and stereochemically isomeric form, isotopically labeled derivative, or a pharmaceutically acceptable salt or solvate thereof, preferably $A^3$ is CH;

$A^4$ is CH or N;

$R^2$ is hydrogen; or $C_{1-6}$alkyl optionally substituted with deuterium, hydroxyl, $C_{1-6}$alkoxy, or with a 4 to 7 membered monocyclic heterocyclyl containing at least one heteroatom selected from N, O or S;

each $R^{3a}$ and $R^{3b}$, independently, is hydrogen; $C_{1-6}$alkyl; halo$C_{1-6}$alkyl; —N($C_{1-4}$alkyl)$_2$; $C_{3-6}$cycloalkyl; phenyl; a 5 to 6 membered monocyclic heteroaryl containing at least one heteroatom selected from N, O or S; wherein said aryl and heteroaryl, each independently, is optionally substituted with one or more halo, hydroxy, mercapto, carboxyl, halo$C_{1-6}$alkyl, mono- or di($C_{1-6}$ alkyl)amino, mono- or di($C_{1-6}$alkyl)aminocarbonyl, $C_{1-6}$alkylcarbonyl, $C_{1-6}$alkylcarbonylamino, $C_{1-6}$alkoxy, $C_{1-6}$alkoxycarbonyl, $C_{1-6}$alkylthio, cyano, nitro, halo$C_{1-6}$alkoxy, aminocarbonyl, $C_{3-6}$cycloalkyl, or $C_{1-6}$alkyl optionally substituted with deuterium, amino, hydroxy, mono- or di($C_{1-6}$alkyl)amino, $C_{1-6}$alkylcarbonylamino, [(mono- or di$C_{1-6}$alkyl)amino-$C_{1-6}$alkyl]carbonylamino, or with $C_{1-6}$alkylsulfonylamino;

each $R^{5a}$, $R^{5b}$, $R^{6a}$, $R^{6b}$, $R^{7a}$, and $R^{7b}$, independently, is hydrogen or $C_{1-6}$alkyl; or $R^{5a}$ and $R^{5b}$ may form a $C_{3-6}$cycloalkyl together with the carbon atom to which they are bound; or $R^{5b}$ and $R^{6a}$ may form a cyclopropyl together with the carbon atoms to which they are bound;

$R^8$ is a direct bond, $C_{1-4}$alkanediyl optionally substituted with hydroxy, deuterium, or $C_{1-4}$alkoxy; —$CH_2$—C(═O)—; a spiro-$C_{3-6}$cycloalkyl; or a 4 to 7 membered spiro-monocyclic heterocyclyl containing at least one heteroatom selected from N, O or S;

A is a $C_{3-6}$cycloalkyl; aryl; a 5 to 12 membered heteroaryl containing at least one heteroatom selected from N, O or S;

$R^9$ is $C_{1-6}$alkyl optionally substituted with $C_{3-6}$cycloalkyl; halo; halo$C_{1-6}$alkyl; $C_{1-6}$alkoxy optionally substituted with $C_{3-6}$cycloalkyl; halo$C_{1-6}$alkoxy; hydroxyl; hydroxy$C_{1-6}$alkyl; oxo; —$SO_2$—$C_{3-6}$cycloalkyl; —C(═O)—$C_{1-6}$alkyl-$C_{3-6}$cycloalkyl; —C(═O)—$C_{3-6}$ cycloalkyl; $C_{3-6}$cycloalkyl; spiro-$C_{3-6}$cycloalkyl; a 4 to 7 membered monocyclic heterocyclyl containing at least one heteroatom selected from N, O or S; and n is 0, 1, 2, 3, or 4.

The present invention also relates to a compound of formula (IIIa) or (IIIb), including any tautomeric form and stereochemically isomeric form, isotopically labeled derivative, or a pharmaceutically acceptable salt or solvate thereof:

(IIIa)

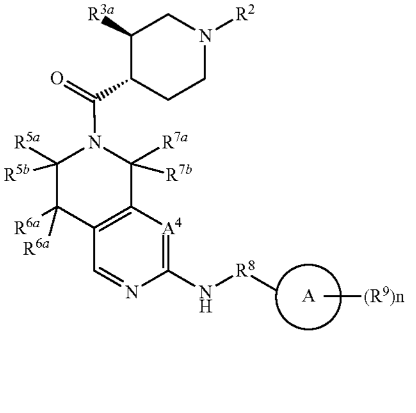

-continued (IIIb)

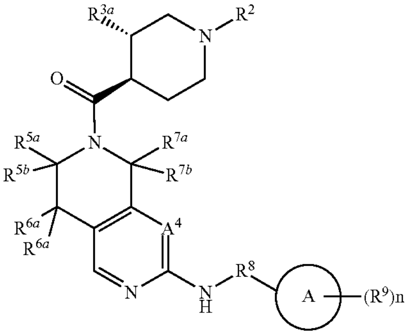

wherein, $A^4$ is CH or N;

$R^2$ is hydrogen; halo$C_{1-6}$alkyl; $C_{1-6}$alkoxy; $C_{1-6}$alkyloxycarbonyl; $C_{2-6}$alkenyl; $C_{2-6}$alkynyl; —C(═O)—$NH_2$; —C(═O)—NH($C_{1-4}$alkyl); —C(═O)—N($C_{1-4}$ alkyl)$_2$; $C_{3-6}$cycloalkyl; phenyl; a 4 to 7 membered monocyclic heterocyclyl containing at least one heteroatom selected from N, O or S; or $C_{1-6}$alkyl optionally substituted with deuterium, hydroxyl, $C_{1-6}$alkoxy, cyano, $C_{3-6}$cycloalkyl, phenyl, or with a 4 to 7 membered monocyclic heterocyclyl containing at least one heteroatom selected from N, O or S;

$R^{3a}$ is $C_{1-6}$alkyl; halo$C_{1-6}$alkyl; $C_{1-6}$alkoxy; $C_{1-6}$alkyloxycarbonyl; $C_{2-6}$alkenyl; $C_{2-6}$alkynyl; cyano$C_{1-6}$alkyl; hydroxy$C_{1-6}$alkyl; —C(═O)—$NH_2$; —C(═O)—NH ($C_{1-4}$alkyl); —C(═O)—N($C_{1-4}$alkyl)$_2$; —N($C_{1-4}$ alkyl)$_2$; $C_{3-6}$cycloalkyl; aryl; a 4 to 7 membered monocyclic heterocyclyl containing at least one heteroatom selected from N, O or S; a 5 to 6 membered monocyclic heteroaryl containing at least one heteroatom selected from N, O or S; wherein said aryl, heterocyclyl, and heteroaryl, each independently, is optionally substituted with one or more halo, hydroxy, mercapto, carboxyl, halo$C_{1-6}$alkyl, mono- or di($C_{1-6}$alkyl)amino, mono- or di($C_{1-6}$alkyl)aminocarbonyl, $C_{1-6}$alkylcarbonyl, $C_{1-6}$alkylcarbonylamino, $C_{1-6}$alkoxy, $C_{1-6}$alkoxycarbonyl, $C_{1-6}$alkylthio, cyano, nitro, halo$C_{1-6}$alkoxy, aminocarbonyl, $C_{3-6}$cycloalkyl, or $C_{1-6}$alkyl optionally substituted with deuterium, amino, hydroxy, mono- or di($C_{1-6}$alkyl)amino, $C_{1-6}$alkylcarbonylamino, [(mono- or di$C_{1-6}$alkyl)amino-$C_{1-6}$alkyl]carbonylamino, or with $C_{1-6}$alkylsulfonylamino;

each $R^{5a}$, $R^{5b}$, $R^{6a}$, $R^{6b}$, $R^{7a}$, and $R^{7b}$, independently, is hydrogen; $C_{1-6}$alkyl; halo$C_{1-6}$alkyl; or $R^{5a}$ and $R^{5b}$ may form a $C_{3-6}$cycloalkyl together with the carbon atom to which they are bound; or $R^{6a}$ and $R^{6b}$ may form a $C_{3-6}$cycloalkyl together with the carbon atom to which they are bound; or $R^{5b}$ and $R^{6a}$ may form a cyclopropyl together with the carbon atoms to which they are bound;

$R^8$ is a direct bond, $C_{1-4}$alkanediyl optionally substituted with hydroxy, halo, deuterium, or $C_{1-4}$alkoxy; —$CH_2$—C(═O)—; a spiro-$C_{3-6}$cycloalkyl; or a 4 to 7 membered spiro-monocyclic heterocyclyl containing at least one heteroatom selected from N, O or S;

A is a $C_{3-6}$cycloalkyl; aryl; a 5 to 12 membered heteroaryl containing at least one heteroatom selected from N, O or S; or a 4 to 12 membered heterocyclyl containing at least one heteroatom selected from N, O or S;

$R^9$ is $C_{1-6}$alkyl optionally substituted with $C_{3-6}$cycloalkyl; cyano, halo; halo$C_{1-6}$alkyl; $C_{1-6}$alkoxy optionally substituted with $C_{3-6}$cycloalkyl; halo$C_{1-6}$alkoxy; hydroxyl; hydroxy$C_{1-6}$alkyl; oxo; —$SO_2$—$C_{1-4}$alkyl; —$SO_2$—$C_{3-6}$cycloalkyl; —$SO_2$—$NH_2$, —$SO_2$—NH($C_{1-4}$alkyl); —$SO_2$—N($C_{1-4}$alkyl)$_2$; —NH—C(═O)—$C_{2-6}$ alkenyl; —C(═O)—$C_{1-6}$alkyl; —C(═O)—$C_{1-6}$alkyl-$C_{3-6}$cycloalkyl; —C(═O)—$C_{3-6}$cycloalkyl; —C(═O)—$C_{2-6}$alkenyl; $C_{3-6}$cycloalkyl; spiro-$C_{3-6}$cycloalkyl; phenyl; a 4 to 7 membered monocyclic heterocyclyl containing at least one heteroatom selected from N, O or S; or a 4 to 7 membered spiro monocyclic heterocyclyl containing at least one heteroatom selected from N, O or S; and n is 0, 1, 2, 3, 4, or 5.

The present invention also relates to compounds of formula (IVa) or (IVb), including any tautomeric form and stereochemically isomeric form, isotopically labeled derivative, or a pharmaceutically acceptable salt or solvate thereof:

(IVa)

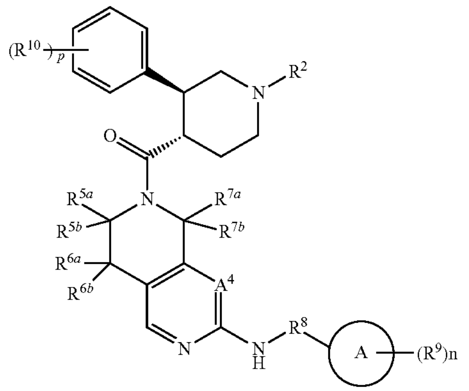

(IVb)

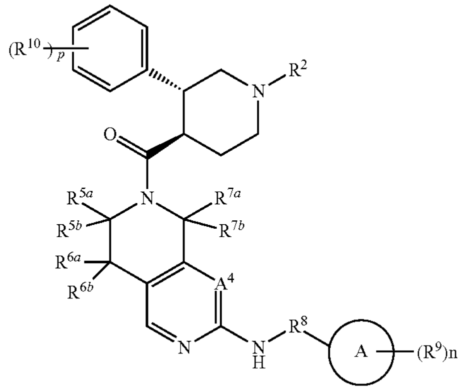

wherein, each of $A^4$, $R^2$, $R^{5a}$, $R^{5b}$, $R^{6a}$, $R^{6b}$, $R^{7a}$, $R^{7b}$, $R^8$, A, $R^9$, and n, independently, is as defined herein above;

$R^{10}$ is hydrogen, halo, hydroxy, mercapto, carboxyl, halo$C_{1-6}$alkyl, mono- or di($C_{1-6}$alkyl)amino, mono- or di($C_{1-6}$alkyl)aminocarbonyl, $C_{1-6}$alkylcarbonyl, $C_{1-6}$alkylcarbonylamino, $C_{1-6}$alkoxy, $C_{1-6}$alkoxycarbonyl, $C_{1-6}$alkylthio, cyano, nitro, halo$C_{1-6}$alkoxy, aminocarbonyl, $C_{3-6}$cycloalkyl, or $C_{1-6}$alkyl optionally substituted with deuterium, amino, hydroxy, mono- or di($C_{1-6}$alkyl)amino, $C_{1-6}$alkylcarbonylamino, [(mono- or di$C_{1-6}$alkyl)amino-$C_{1-6}$alkyl]carbonylamino, or with $C_{1-6}$alkylsulfonylamino; and p is 0, 1, 2, 3, 4, or 5.

The present invention also relates to compounds of formula (Va) or (Vb), including any tautomeric and stereochemically isomeric form, isotopically labeled derivative, or a pharmaceutically acceptable salt or solvate thereof:

(Va)

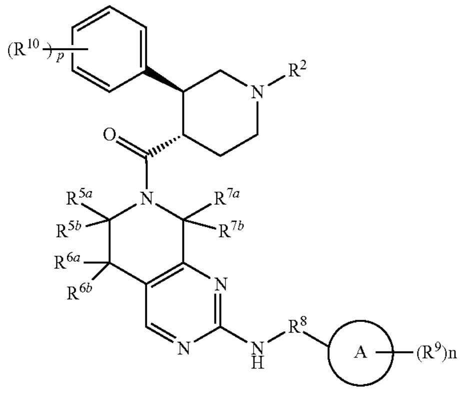

(Vb)

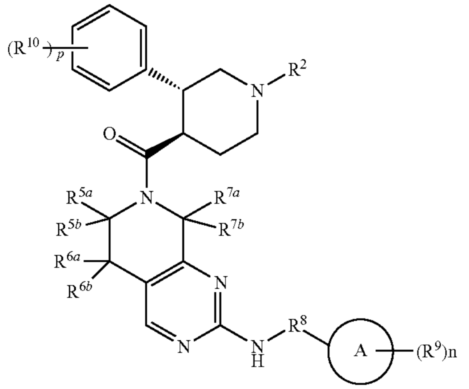

wherein, $R^2$ is hydrogen; halo$C_{1-6}$alkyl; $C_{1-6}$alkoxy; $C_{1-6}$alkyloxycarbonyl; $C_{2-6}$alkenyl; $C_{2-6}$alkynyl; —C(═O)—$NH_2$; —C(═O)—NH($C_{1-4}$alkyl); —C(═O)—N($C_{1-4}$ alkyl)$_2$; $C_{3-6}$cycloalkyl; phenyl; a 4 to 7 membered monocyclic heterocyclyl containing at least one heteroatom selected from N, O or S; or $C_{1-6}$alkyl optionally substituted with deuterium, hydroxyl, $C_{1-6}$alkoxy, cyano, $C_{3-6}$cycloalkyl, phenyl, or with a 4 to 7 membered monocyclic heterocyclyl containing at least one heteroatom selected from N, O or S;

each $R^{5a}$, $R^{5b}$, $R^{6a}$, $R^{6b}$, $R^{7a}$, and $R^{7b}$, independently, is hydrogen; $C_{1-6}$alkyl; halo$C_{1-6}$alkyl; or $R^{5a}$ and $R^{5b}$ may form a $C_{3-6}$cycloalkyl together with the carbon atom to which they are bound; or $R^{6a}$ and $R^{6b}$ may form a $C_{3-6}$cycloalkyl together with the carbon atom to which they are bound; or $R^{5b}$ and $R^{6a}$ may form a cyclopropyl together with the carbon atoms to which they are bound;

$R^8$ is a direct bond, $C_{1-4}$alkanediyl optionally substituted with hydroxy, halo, deuterium, or $C_{1-4}$alkoxy; —$CH_2$—C(═O)—; a spiro-$C_{3-6}$cycloalkyl; or a 4 to 7 membered spiro-monocyclic heterocyclyl containing at least one heteroatom selected from N, O or S;

A is a $C_{3-6}$cycloalkyl; aryl; a 5 to 12 membered heteroaryl containing at least one heteroatom selected from N, O or S; or a 3 to 12 membered heterocyclyl containing at least one heteroatom selected from N, O or S;

$R^9$ is $C_{1-6}$alkyl optionally substituted with $C_{3-6}$cycloalkyl; cyano, halo; halo$C_{1-6}$alkyl; $C_{1-6}$alkoxy optionally substituted with $C_{3-6}$cycloalkyl; halo$C_{1-6}$alkoxy; hydroxyl; hydroxy$C_{1-6}$alkyl; oxo; —$SO_2$—$C_{1-4}$alkyl; —$SO_2$—$C_{3-6}$cycloalkyl; —$SO_2$—$NH_2$, —$SO_2$—NH($C_{1-4}$alkyl); —$SO_2$—N($C_{1-4}$alkyl)$_2$; —NH—C(═O)—$C_{2-6}$ alkenyl; —C(═O)—$C_{1-6}$alkyl; —C(═O)—$C_{1-6}$alkyl-$C_{3-6}$cycloalkyl; —C(═O) $C_{3-6}$cycloalkyl; —C(═O)—$C_{2-6}$alkenyl; $C_{3-6}$cycloalkyl; spiro-$C_{3-6}$cycloalkyl; phenyl; a 4 to 7 membered monocyclic heterocyclyl containing at least one heteroatom selected from N, O or S; or a 4 to 7 membered spiro monocyclic heterocyclyl containing at least one heteroatom selected from N, O or S;

n is 0, 1, 2, 3, 4, or 5;

$R^{10}$ is hydrogen, halo, hydroxy, mercapto, carboxyl, halo$C_{1-6}$alkyl, mono- or di($C_{1-6}$alkyl)amino, mono- or di($C_{1-6}$alkyl)aminocarbonyl, $C_{1-6}$alkylcarbonyl, $C_{1-6}$alkylcarbonylamino, $C_{1-6}$alkoxy, $C_{1-6}$alkoxycarbonyl, $C_{1-6}$alkylthio, cyano, nitro, halo$C_{1-6}$alkoxy, aminocarbonyl, $C_{3-6}$cycloalkyl, or $C_{1-6}$alkyl optionally substituted with deuterium, amino, hydroxy, mono- or di($C_{1-6}$alkyl)amino, $C_{1-6}$alkylcarbonylamino, [(mono- or di$C_{1-6}$alkyl)amino-$C_{1-6}$alkyl]carbonylamino, or with $C_{1-6}$alkylsulfonylamino; and p is 0, 1, 2, 3, 4, or 5.

In the compounds of formula (Va) or (Vb), including any tautomeric and stereochemically isomeric form, isotopically labeled derivative, or a pharmaceutically acceptable salt or solvate thereof, preferably $R^2$ is hydrogen; or $C_{1-6}$alkyl optionally substituted with deuterium, hydroxyl, $C_{1-6}$alkoxy, or with a 4 to 7 membered monocyclic heterocyclyl containing at least one heteroatom selected from N, O or S;

each $R^{5a}$, $R^{5b}$, $R^{6a}$, $R^{6b}$, $R^{7a}$, and $R^{7b}$, independently, is hydrogen; $C_{1-6}$alkyl; halo$C_{1-6}$alkyl; or $R^{5a}$ and $R^{5b}$ may form a $C_{3-6}$cycloalkyl together with the carbon atom to which they are bound; or $R^{6a}$ and $R^{6b}$ may form a $C_{3-6}$cycloalkyl together with the carbon atom to which they are bound; or $R^{5b}$ and $R^{6a}$ may form a cyclopropyl together with the carbon atoms to which they are bound;

$R^8$ is a direct bond, $C_{1-4}$alkanediyl optionally substituted with hydroxy, deuterium, or $C_{1-4}$alkoxy; —$CH_2$—C(═O)—; a spiro-$C_{3-6}$cycloalkyl; or a 4 to 7 membered spiro-monocyclic heterocyclyl containing at least one heteroatom selected from N, O or S;

A is a $C_{3-6}$cycloalkyl; aryl; a 5 to 12 membered heteroaryl containing at least one heteroatom selected from N, O or S;

$R^9$ is $C_{1-6}$alkyl optionally substituted with $C_{3-6}$cycloalkyl; halo; halo$C_{1-6}$alkyl; $C_{1-6}$alkoxy optionally substituted with $C_{3-6}$cycloalkyl; halo$C_{1-6}$alkoxy; hydroxyl; hydroxy$C_{1-6}$alkyl; oxo; —$SO_2$—$C_{3-6}$cycloalkyl; —C(═O)—$C_{1-6}$alkyl-$C_{3-6}$cycloalkyl; —C(═O)—$C_{3-6}$ cycloalkyl; $C_{3-6}$cycloalkyl; spiro-$C_{3-6}$cycloalkyl; a 4 to 7 membered monocyclic heterocyclyl containing at least one heteroatom selected from N, O or S;

n is 0, 1, 2, 3, or 4;

$R^{10}$ is hydrogen, halo, hydroxy, mercapto, carboxyl, halo$C_{1-6}$alkyl, mono- or di($C_{1-6}$alkyl)amino, mono- or di($C_{1-6}$alkyl)aminocarbonyl, $C_{1-6}$alkylcarbonyl, $C_{1-6}$alkylcarbonylamino, $C_{1-6}$alkoxy, $C_{1-6}$alkoxycarbonyl, $C_{1-6}$alkylthio, cyano, nitro, halo$C_{1-6}$alkoxy, aminocarbonyl, $C_{3-6}$cycloalkyl, or $C_{1-6}$alkyl optionally substituted with deuterium, amino, hydroxy, mono- or di($C_{1-6}$alkyl)amino, $C_{1-6}$alkylcarbonylamino, [(mono- or di$C_{1-6}$alkyl)amino-$C_{1-6}$alkyl]carbonylamino, or with $C_{1-6}$alkylsulfonylamino; and p is 0, 1, 2, or 3.

In the compound of the present invention, including any tautomeric and stereochemically isomeric form, isotopically labeled derivative, or a pharmaceutically acceptable salt or solvate thereof, preferably $A^1$ is N and $R^2$ is $C_{1-6}$alkyl optionally substituted with deuterium.

In the compounds of the present invention, including any tautomeric and stereochemically isomeric form, isotopically labeled derivative, or a pharmaceutically acceptable salt or solvate thereof, preferably $R^{5a}$ is $C_{1-6}$alkyl; or $R^{5a}$ and $R^{5b}$ may form a cyclopropyl together with the carbon atom to which they are bound; or $R^{6a}$ and $R^{6b}$ may form a cyclopropyl together with the carbon atom to which they are bound; or $R^{5b}$ and $R^{6a}$ may form a cyclopropyl together with the carbon atoms to which they are bound.

In the compounds of the present invention, including any tautomeric and stereochemically isomeric form, isotopically labeled derivative, or a pharmaceutically acceptable salt or solvate thereof, preferably $R^8$ is $C_{1-4}$alkanediyl optionally substituted with hydroxy or deuterium;

A is a 5 to 12 membered heteroaryl containing at least one heteroatom selected from N, O or S;

$R^9$ is $C_{1-6}$alkyl; and n is 1.

The present invention relates compounds, including any tautomeric and stereochemically isomeric form, isotopically labeled derivative, or a pharmaceutically acceptable salt or solvate thereof, selected from:

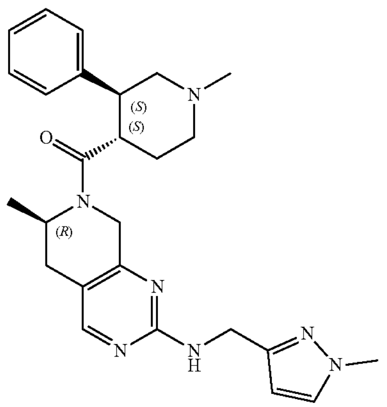

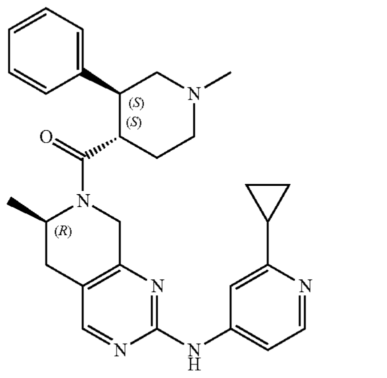

-continued
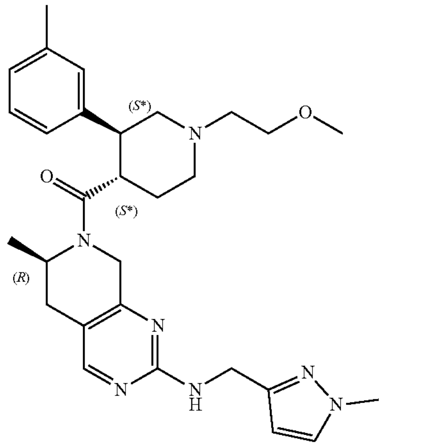
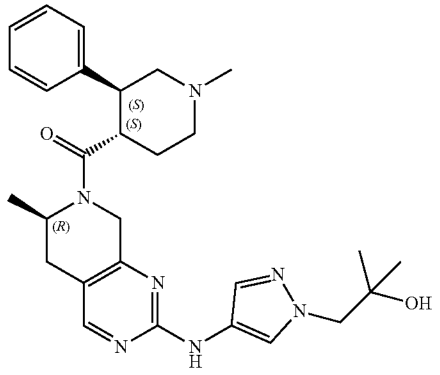
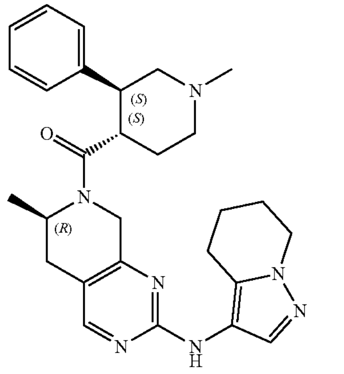
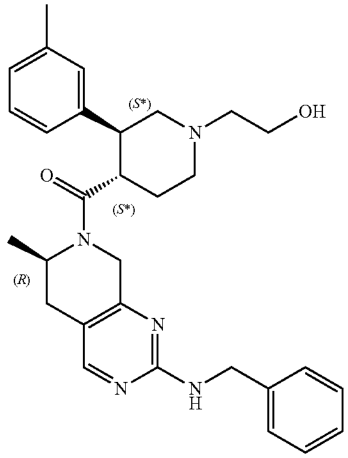
-continued
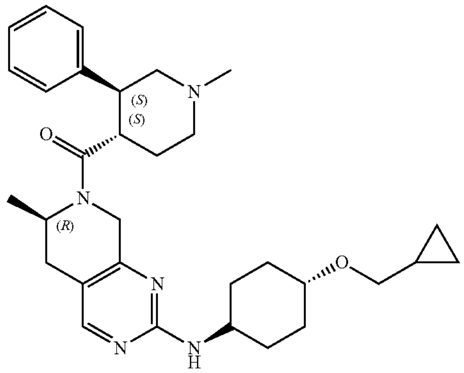
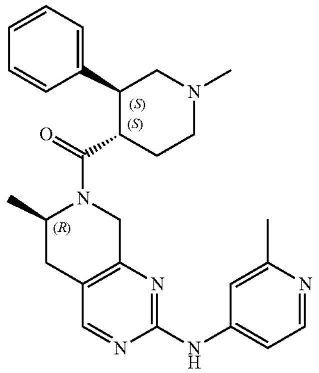
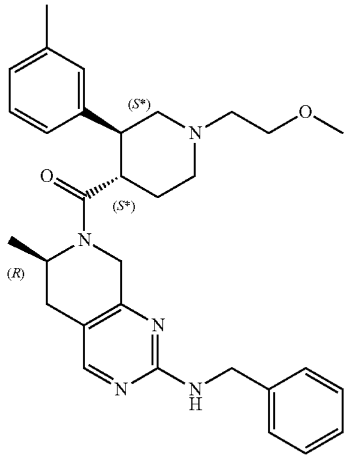
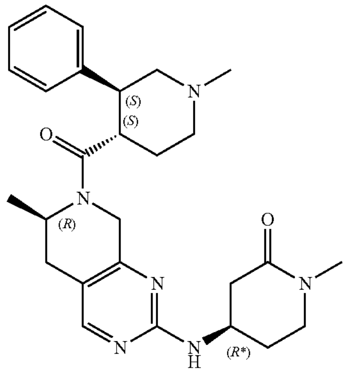

-continued
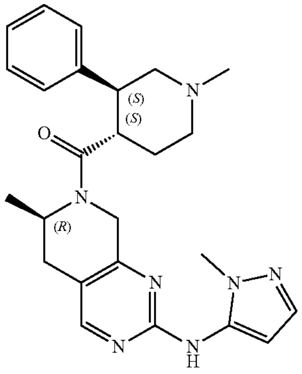
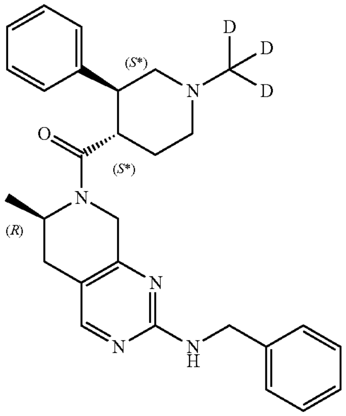
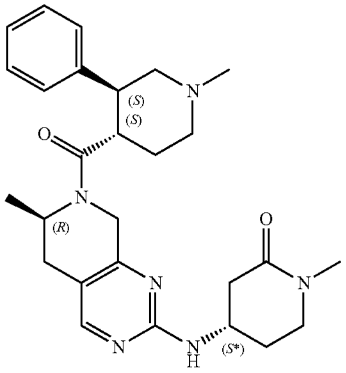
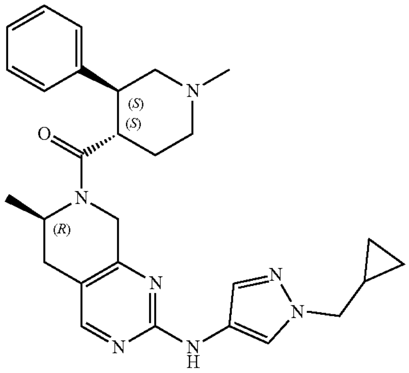
-continued
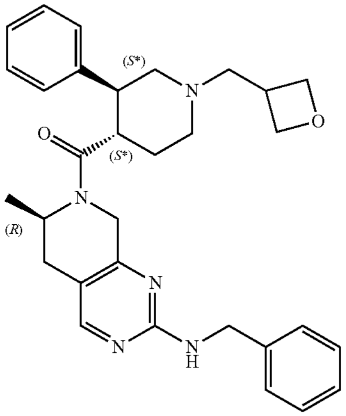
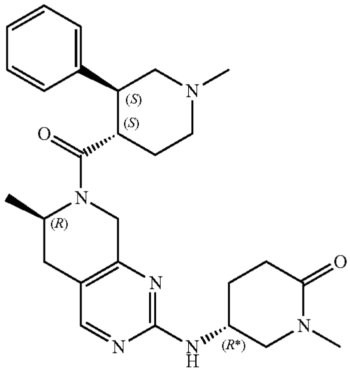
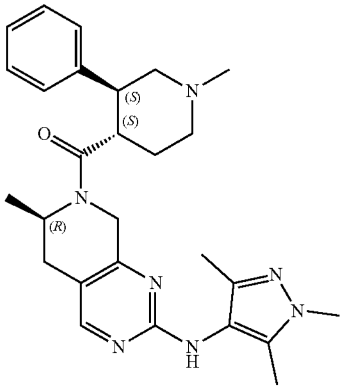
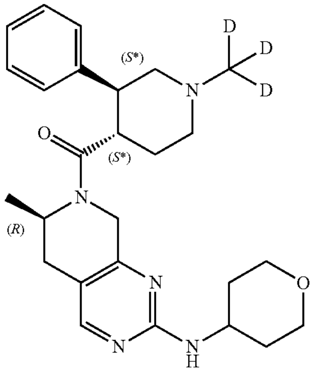

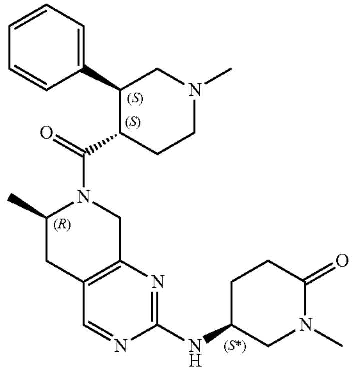
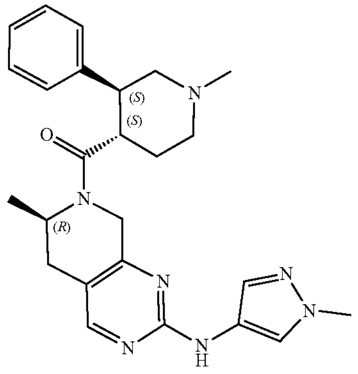
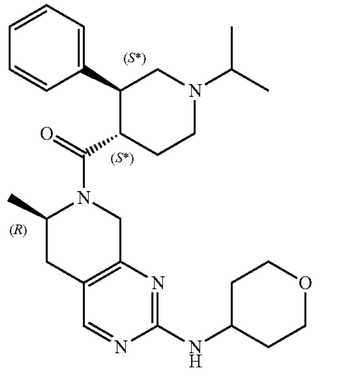
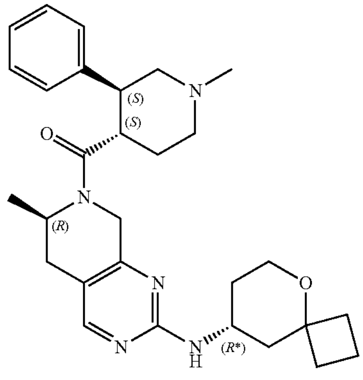
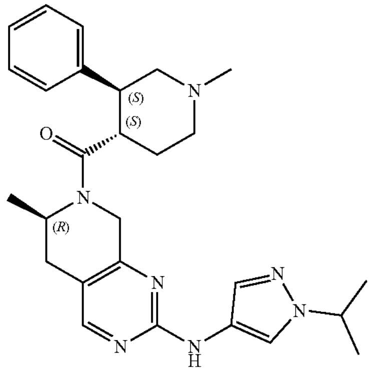
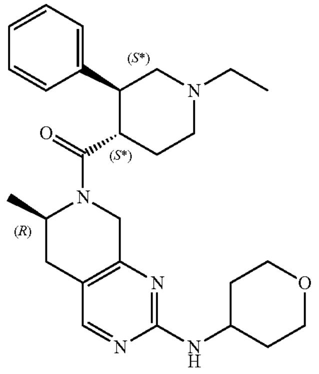
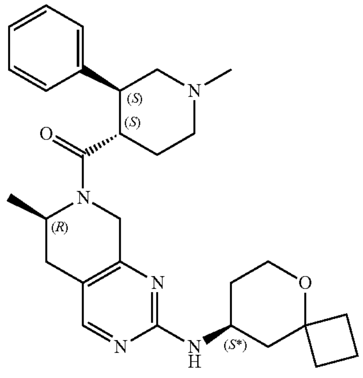
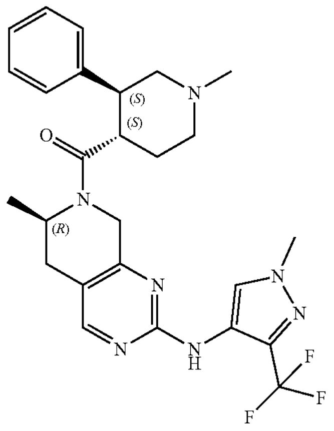

-continued
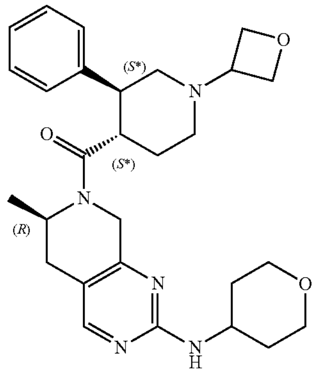
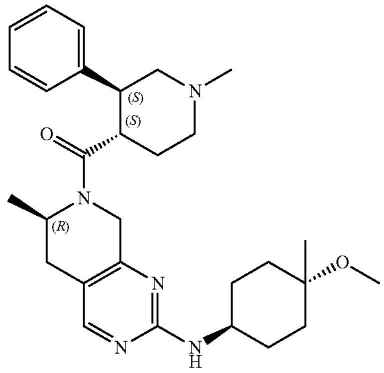
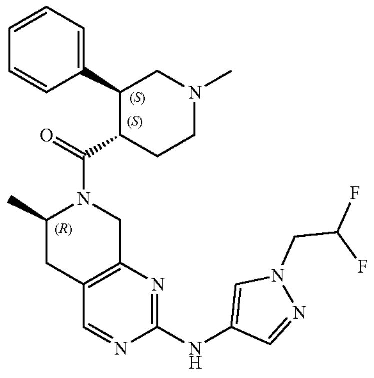
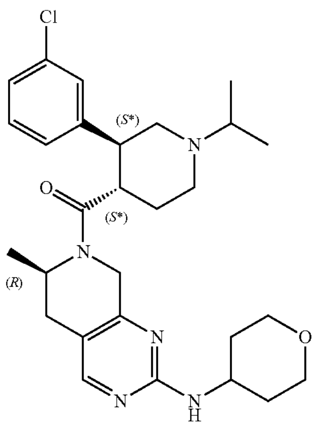
-continued
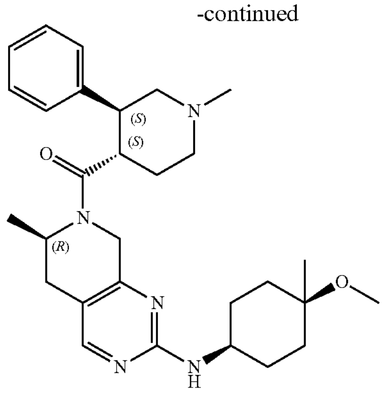
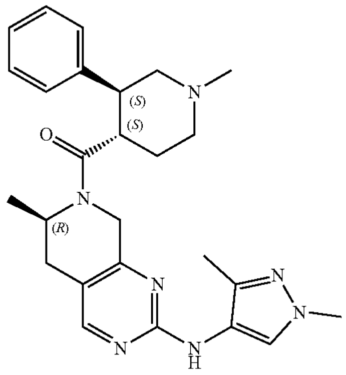
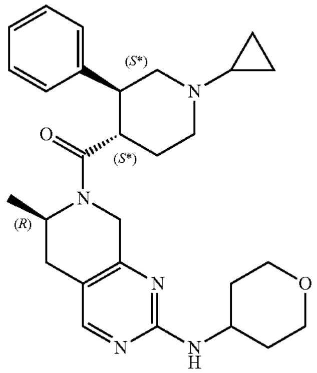
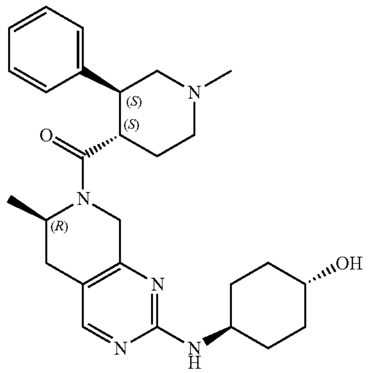

-continued
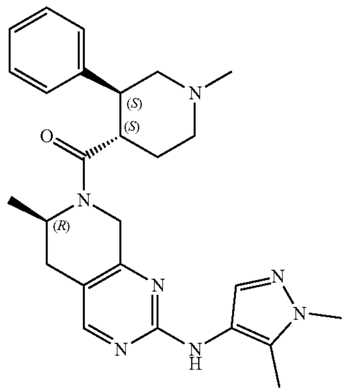
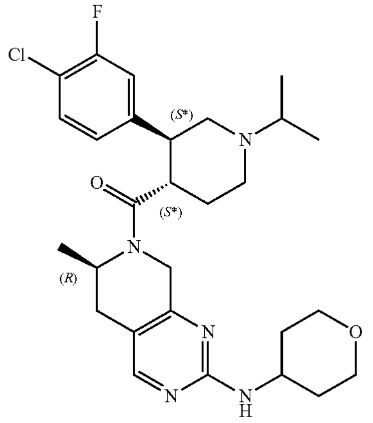
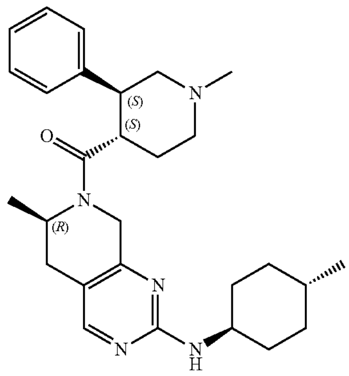
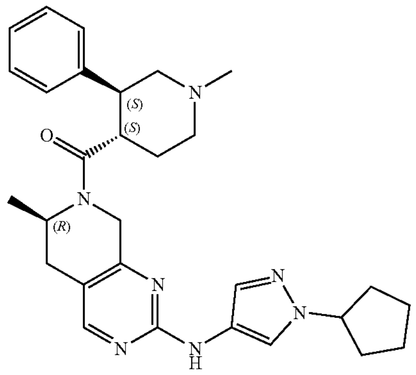
-continued
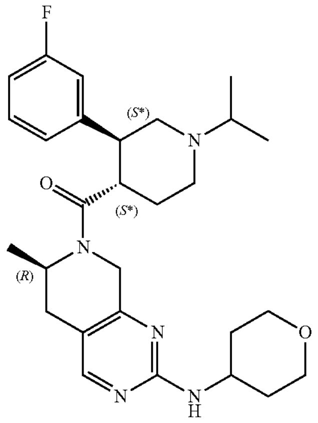
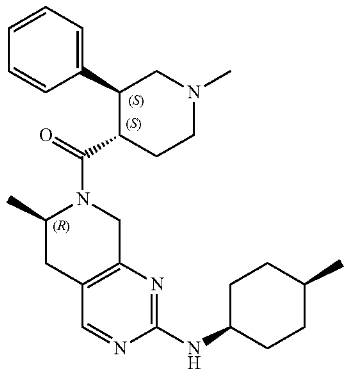
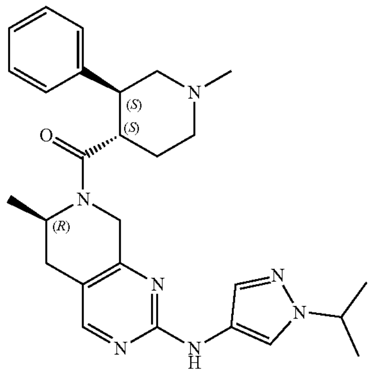
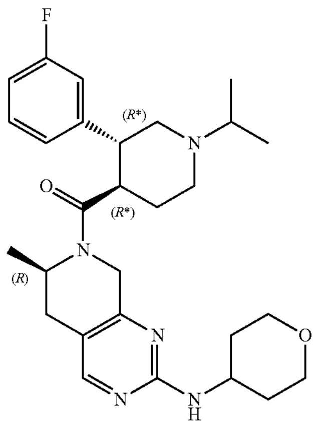

-continued
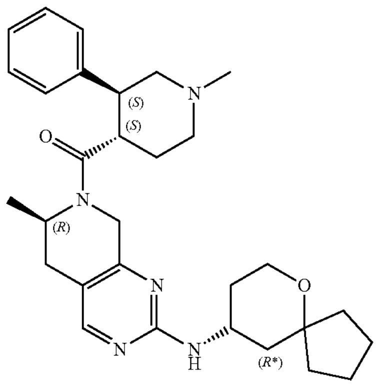
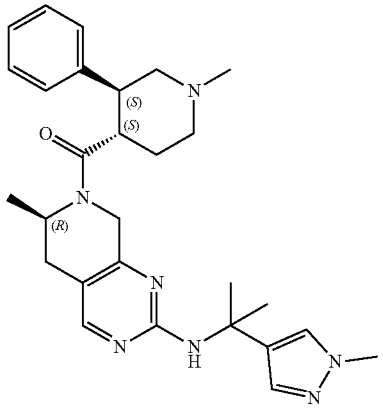
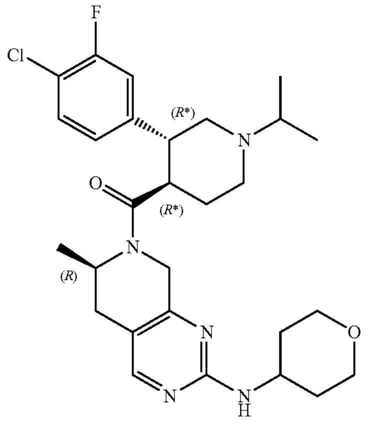
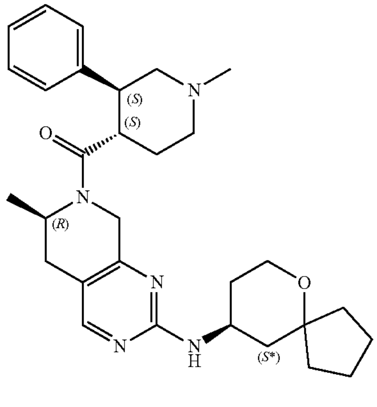
-continued
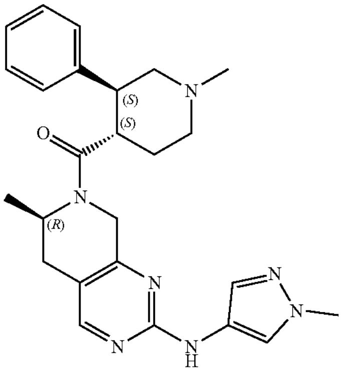
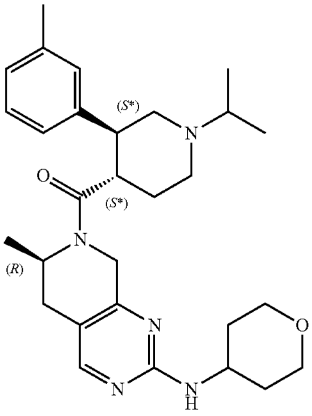
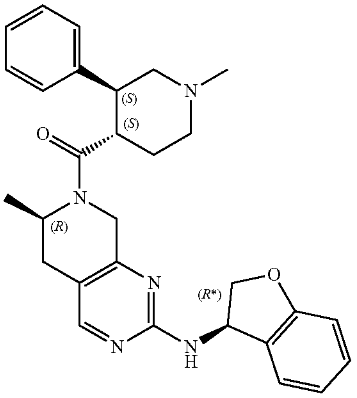
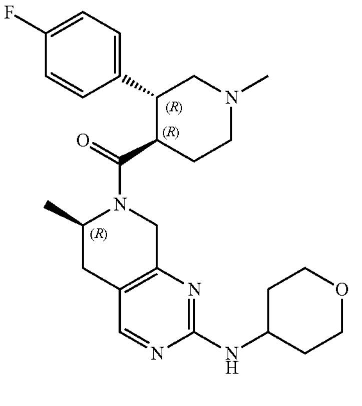

-continued
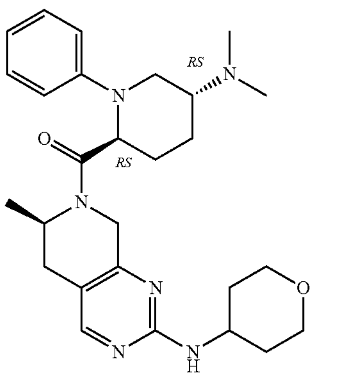
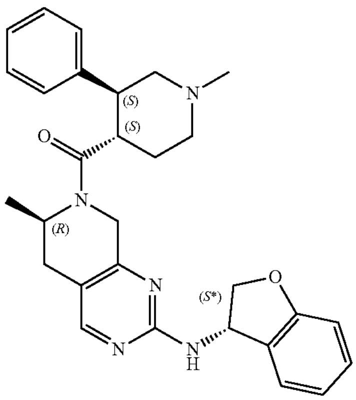
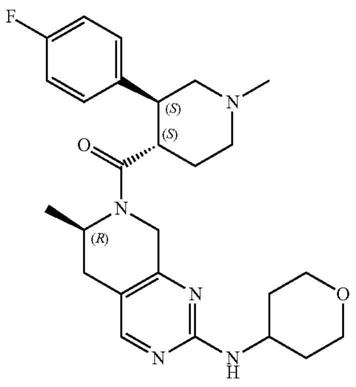
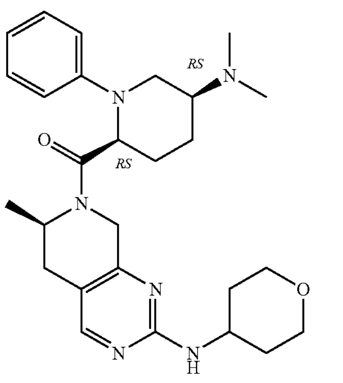
-continued
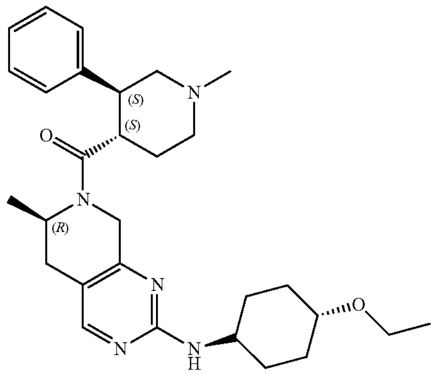
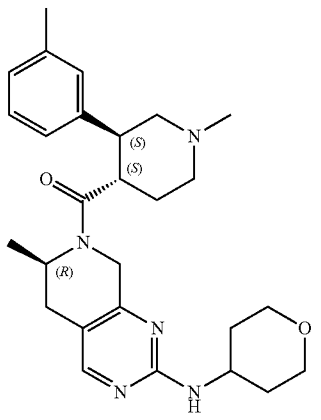
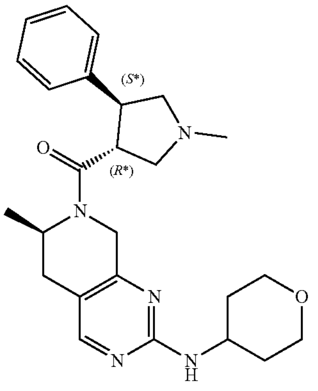
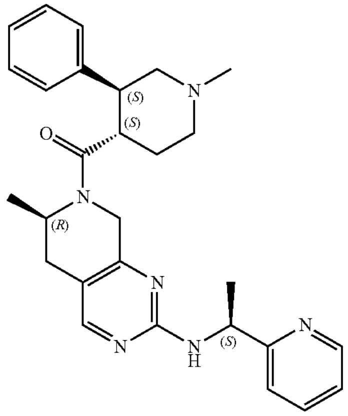

-continued
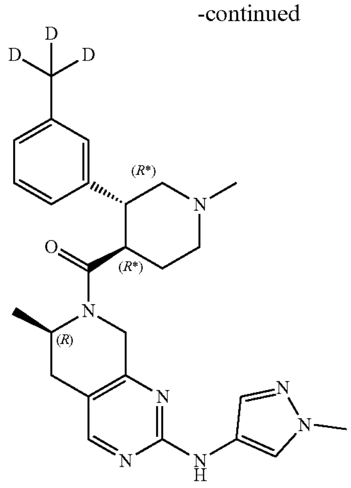
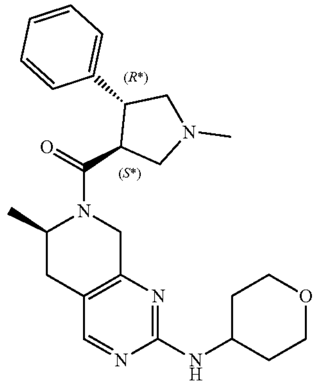
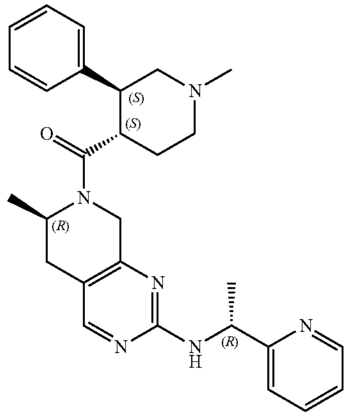
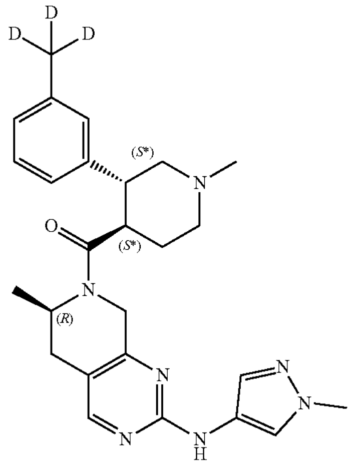
-continued
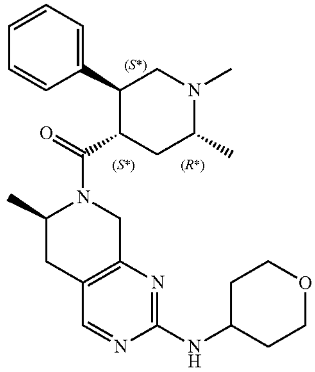
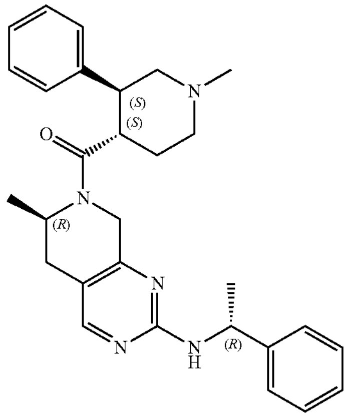
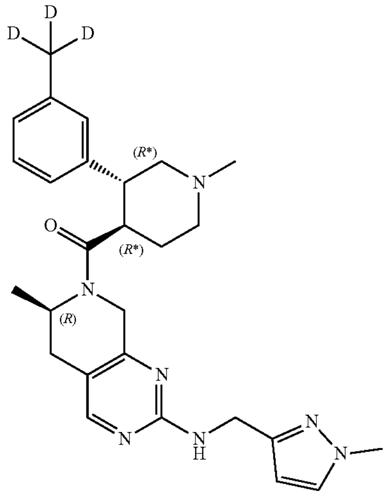
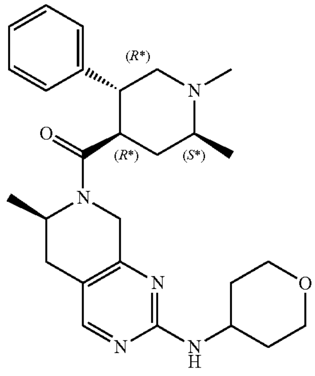

-continued
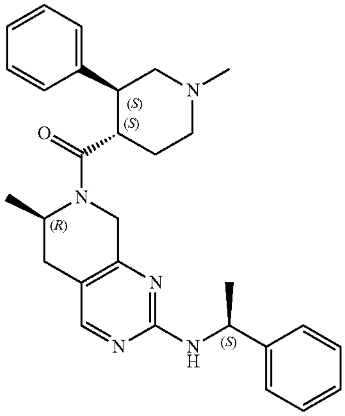
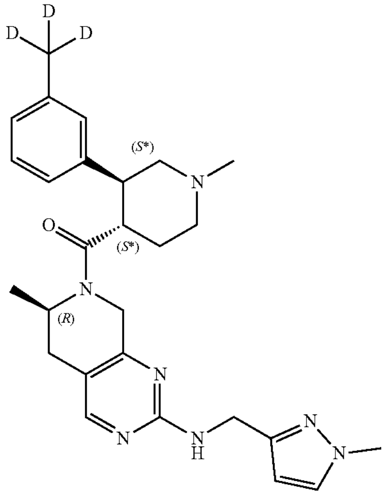
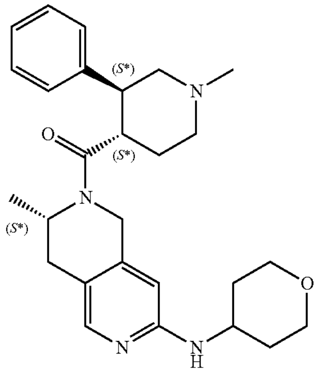
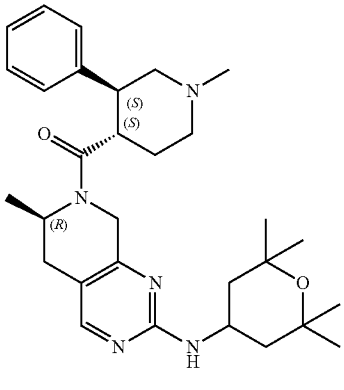
-continued
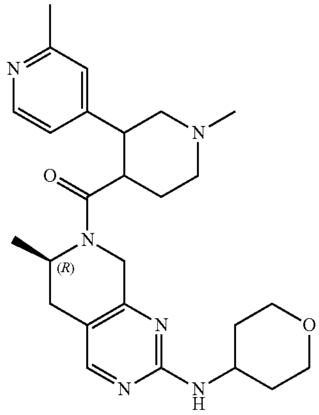
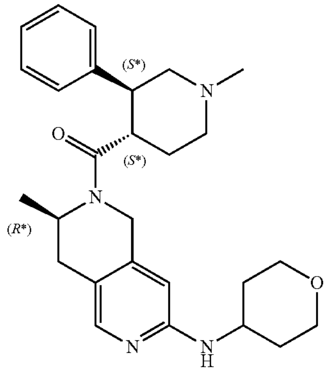
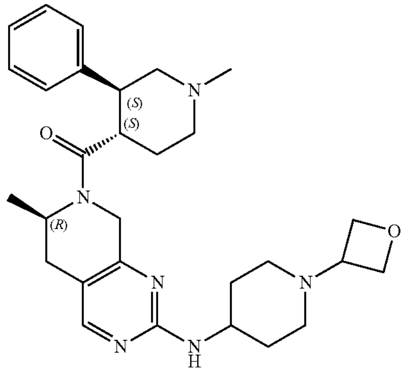
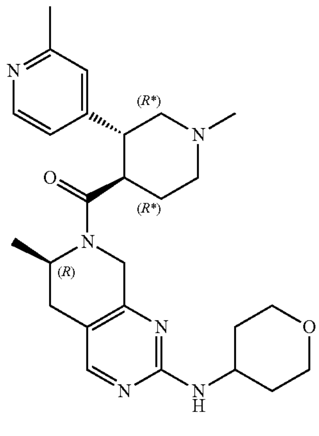

-continued
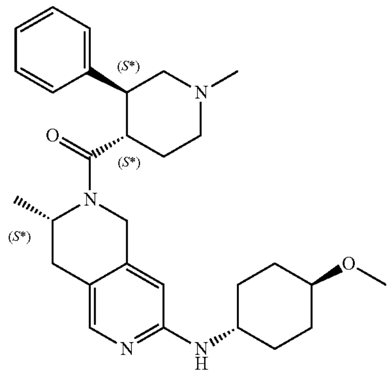
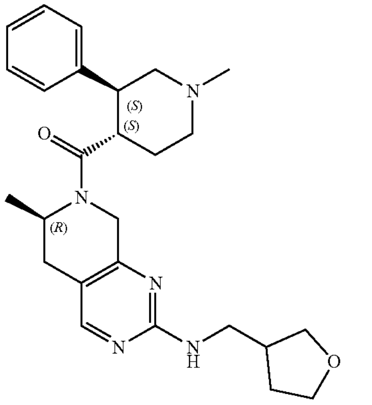
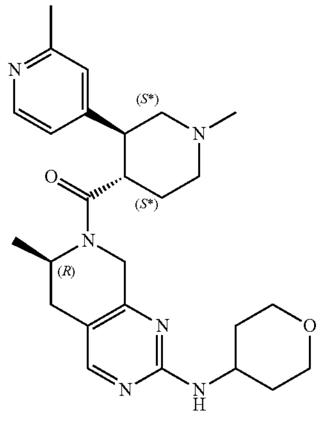
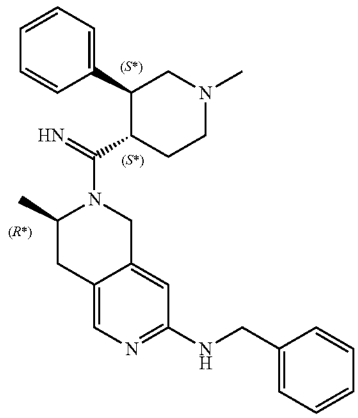
-continued
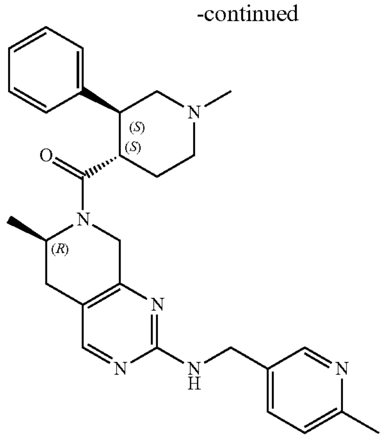
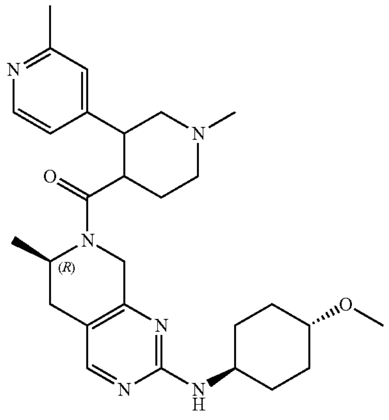
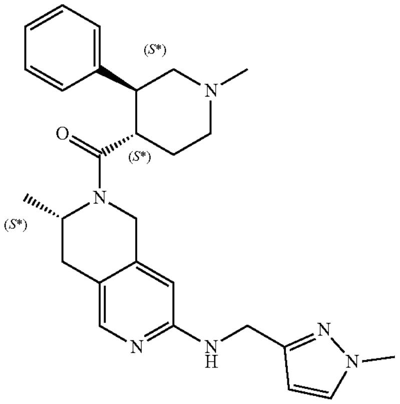
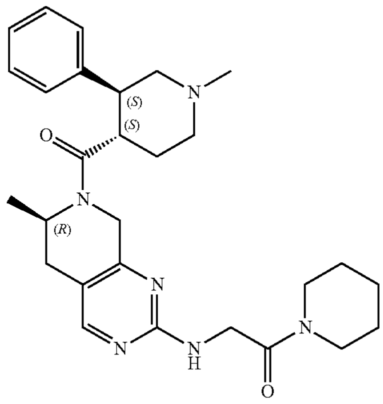

-continued
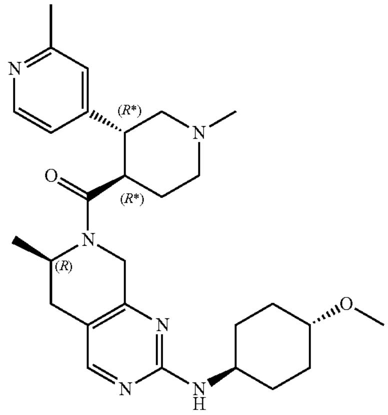
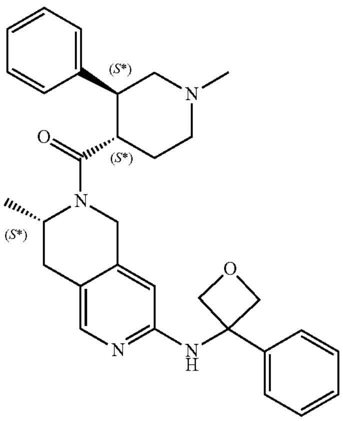
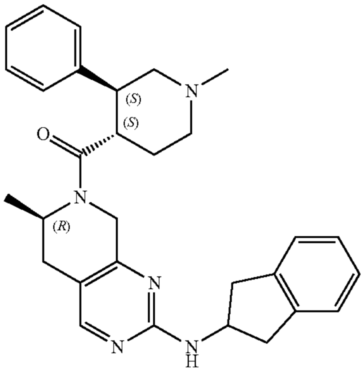
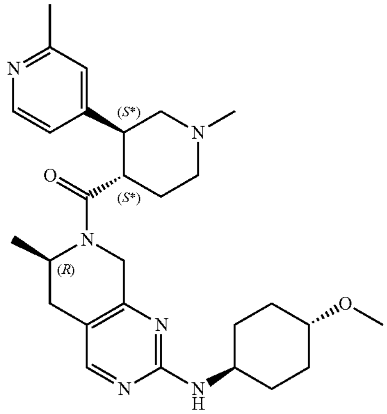
-continued
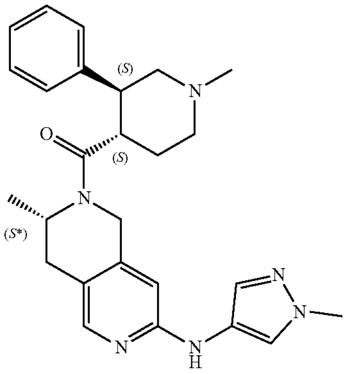
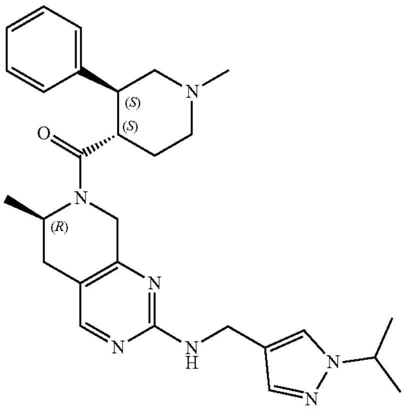
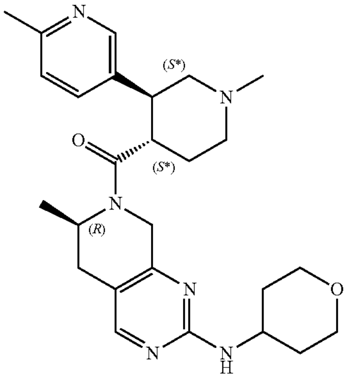
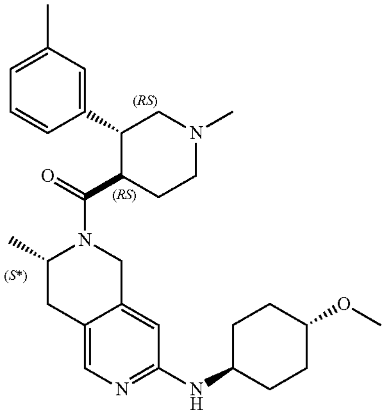

-continued
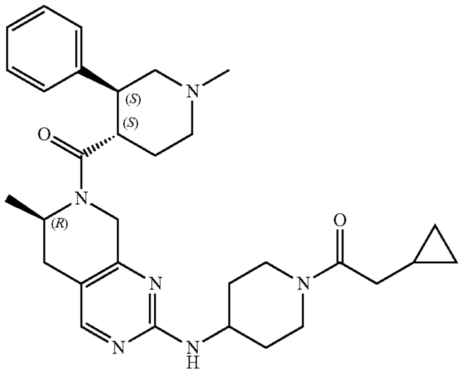
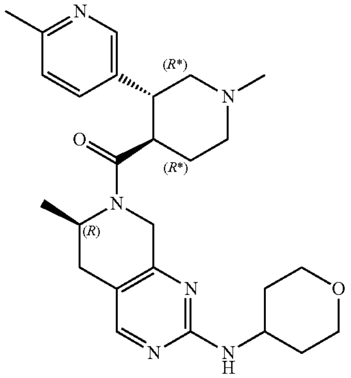
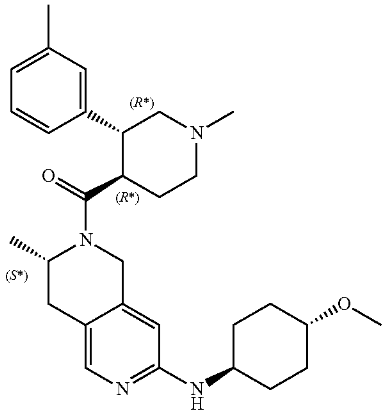
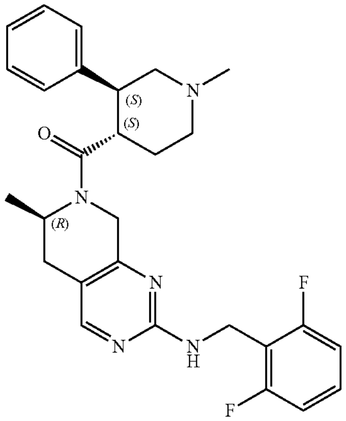
-continued
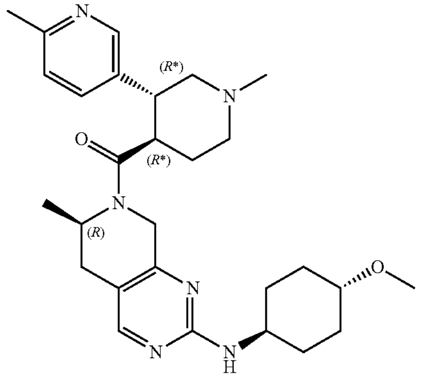
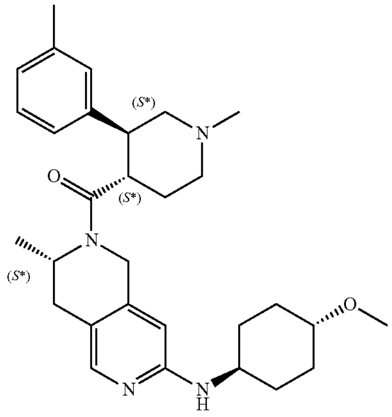
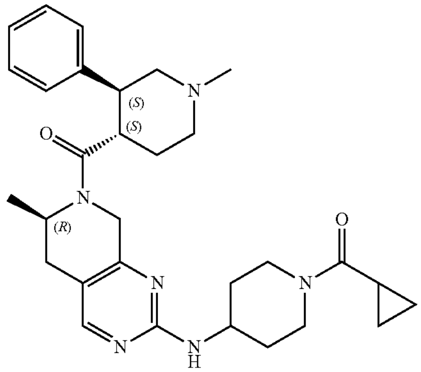
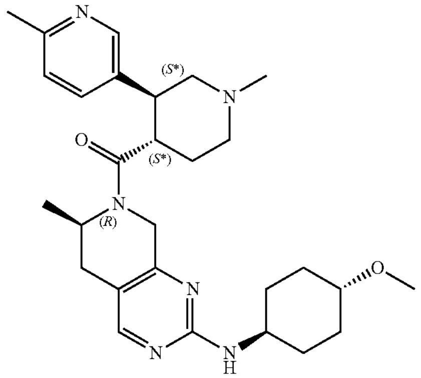

-continued
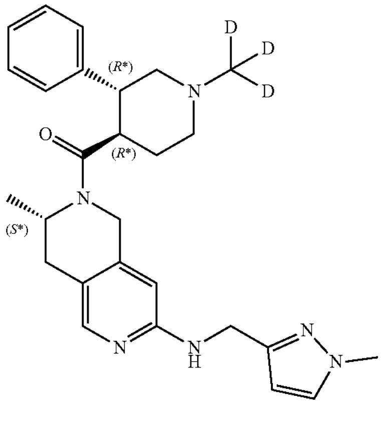
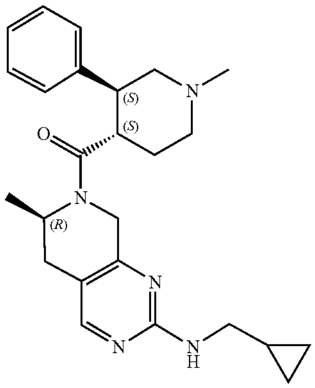
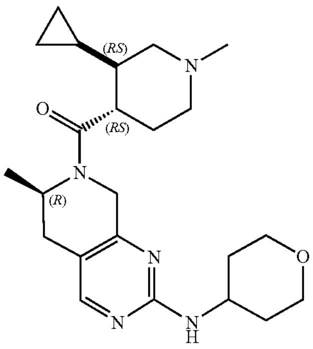
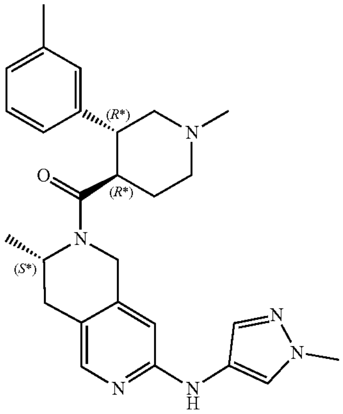
-continued
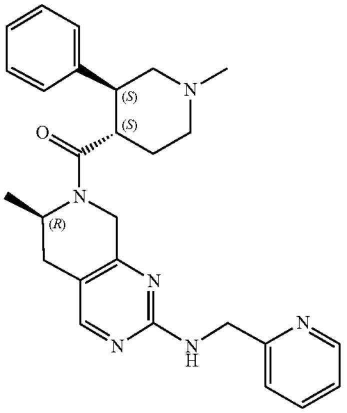
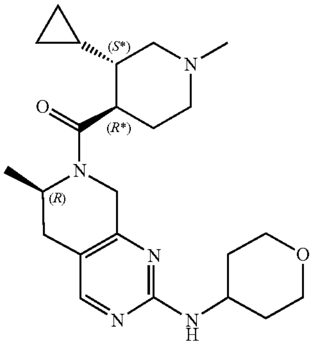
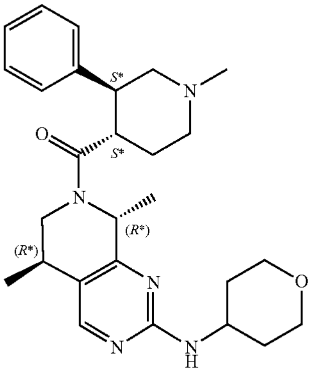
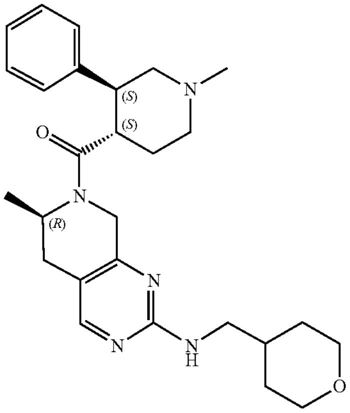

-continued
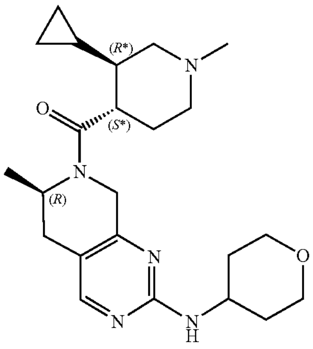
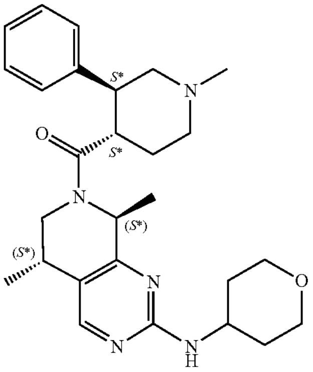
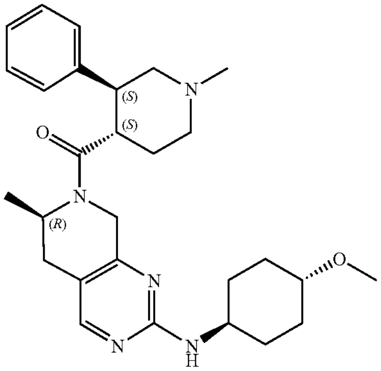
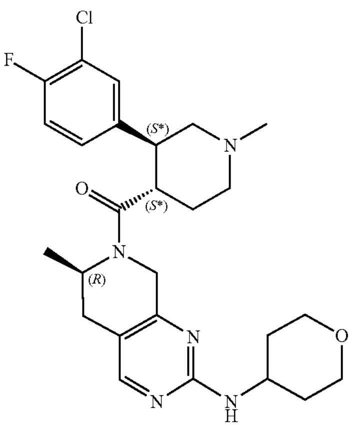
-continued
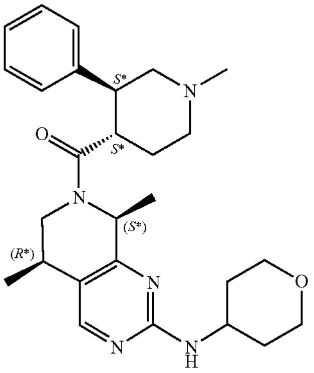
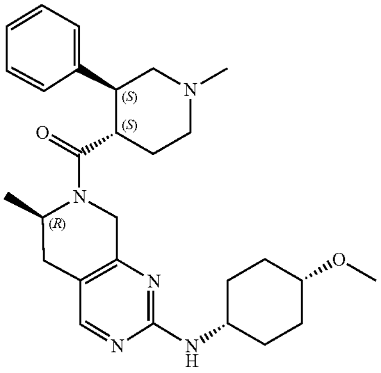
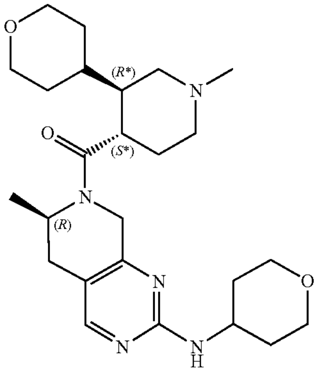
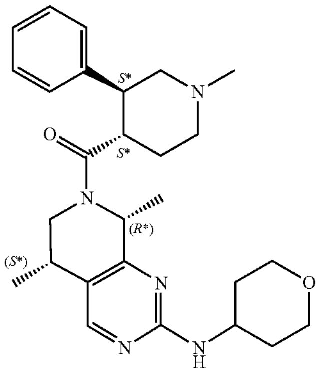

-continued
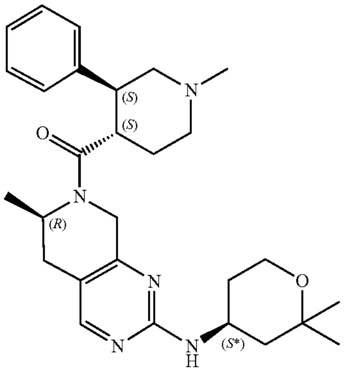
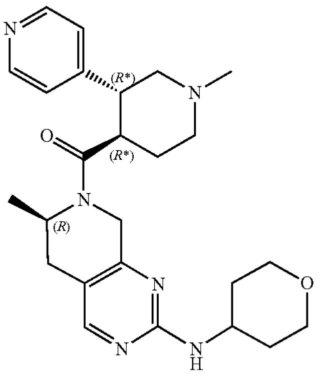
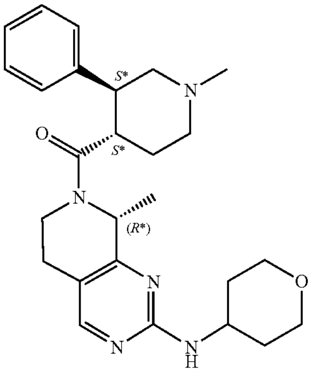
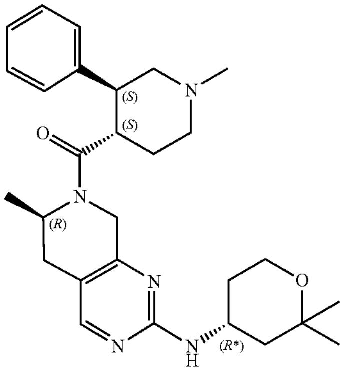
-continued
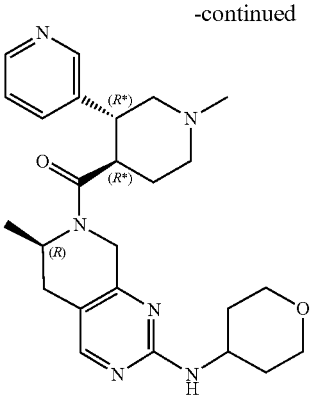
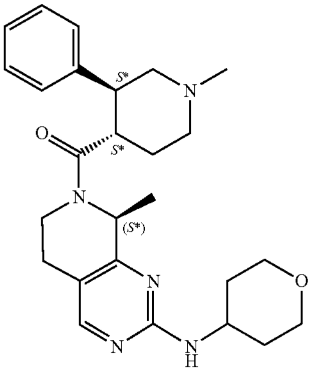
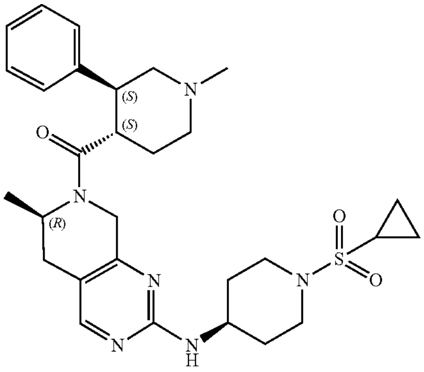
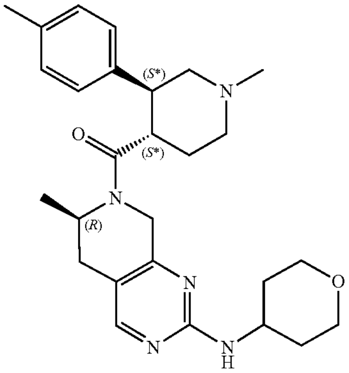

-continued
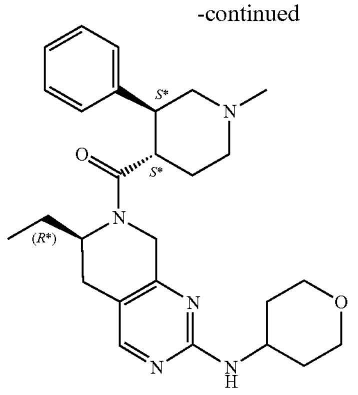
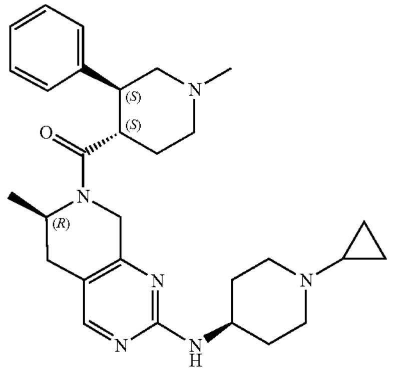
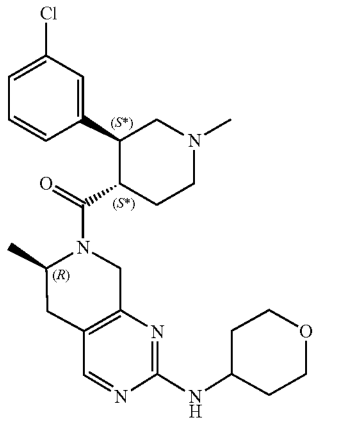
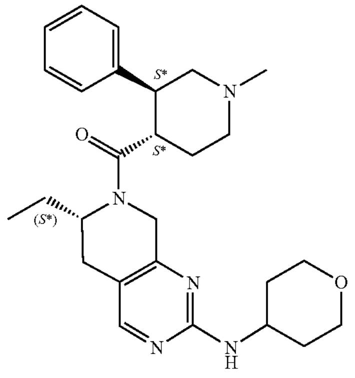
-continued
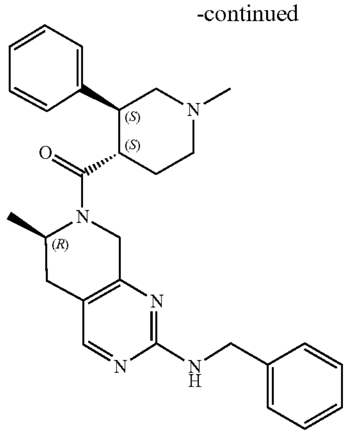
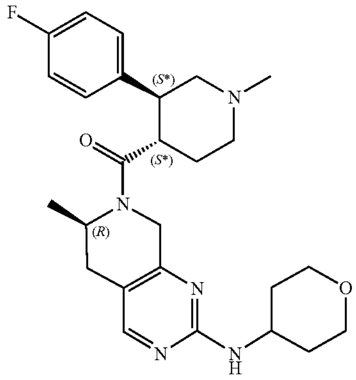
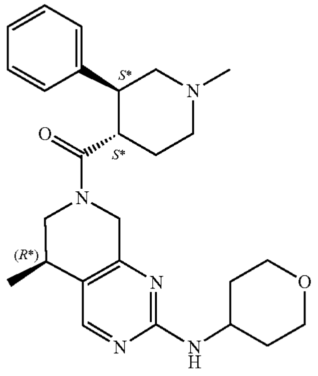
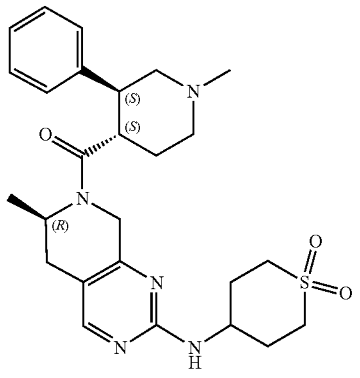

-continued
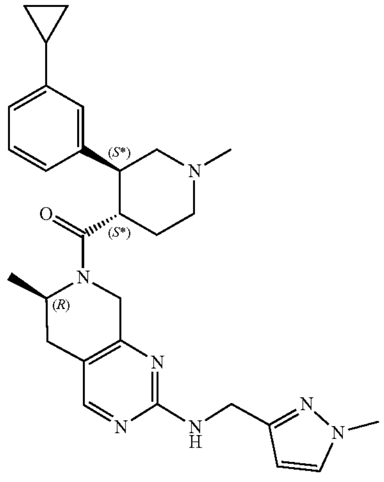
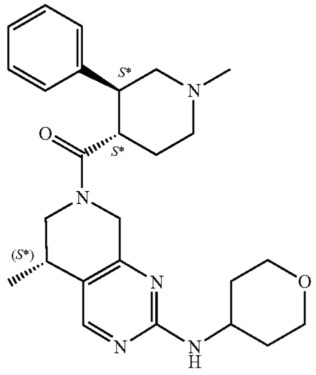
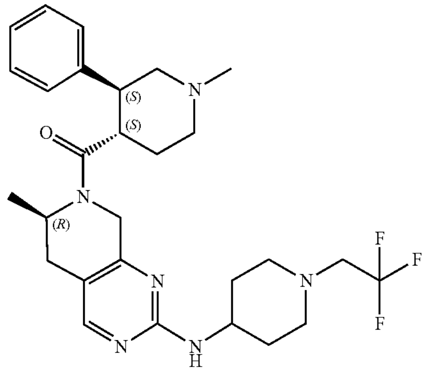
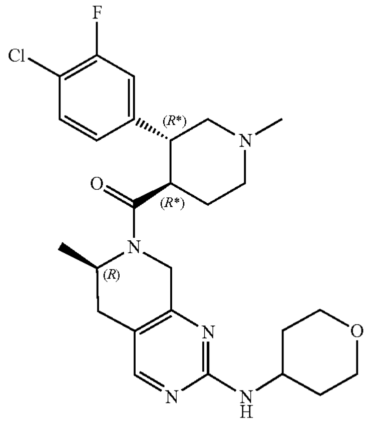
-continued
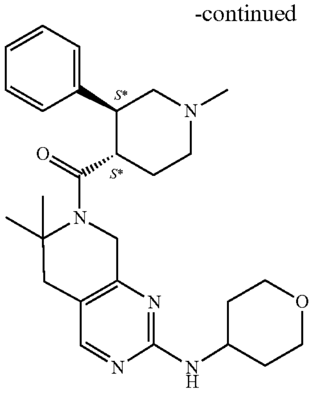
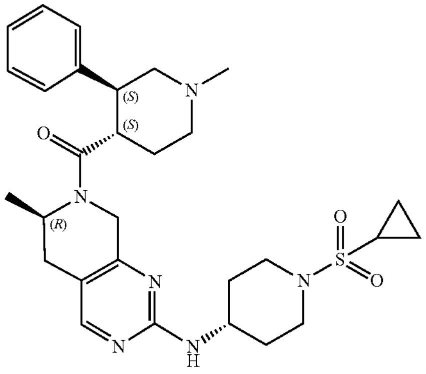
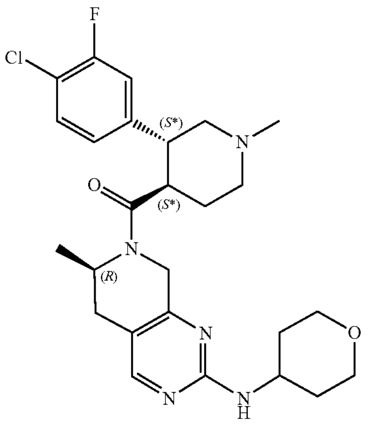
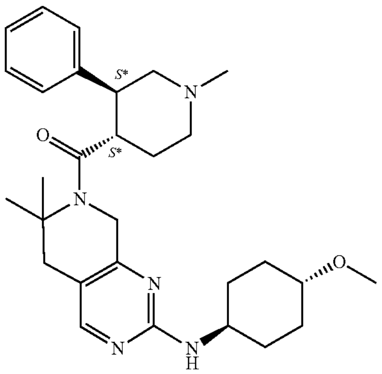

-continued
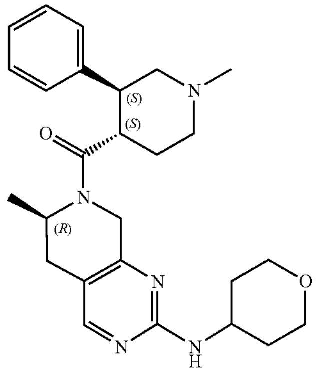
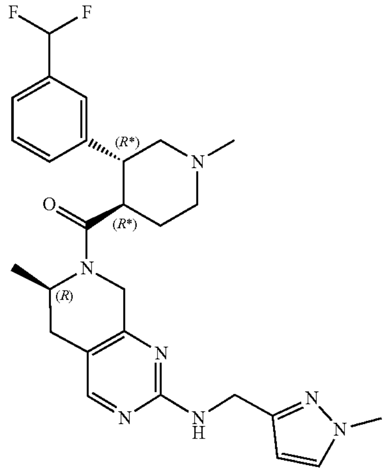
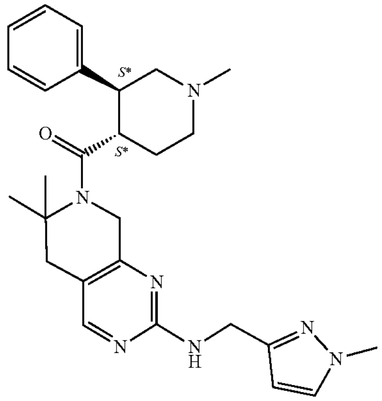
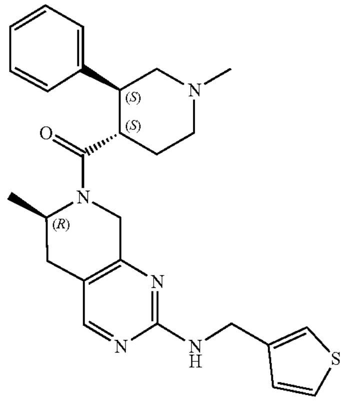
-continued
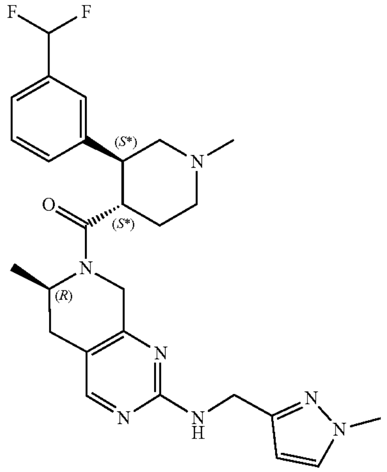
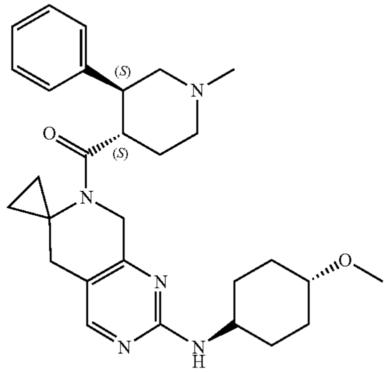
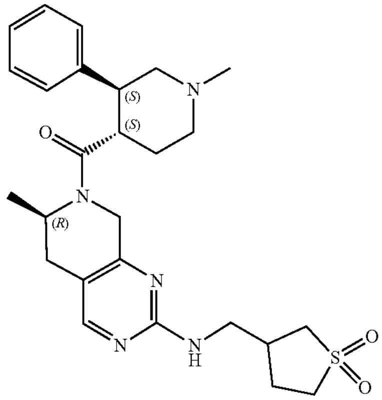
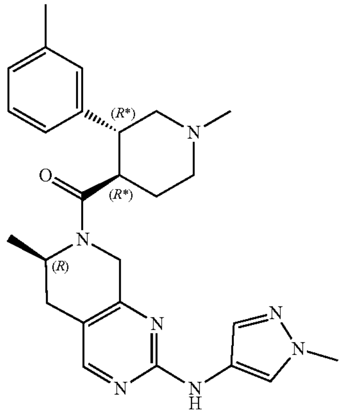

-continued
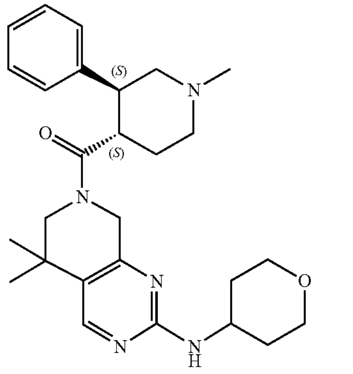
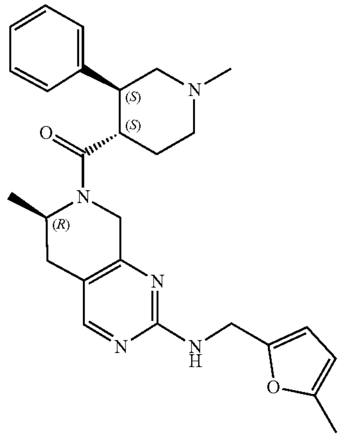
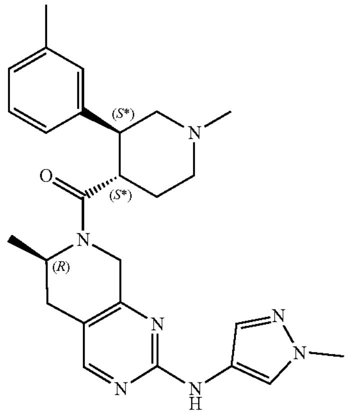
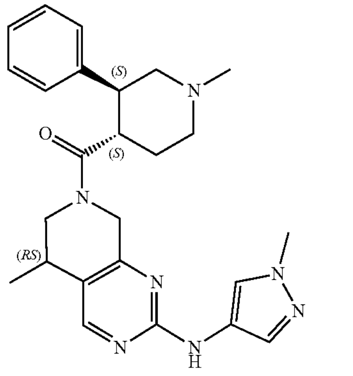
-continued
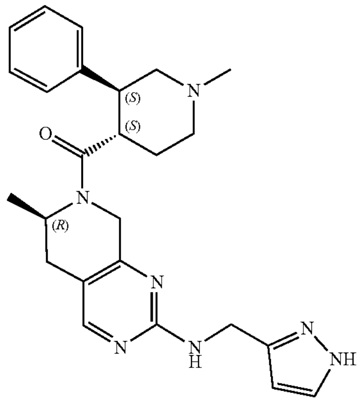
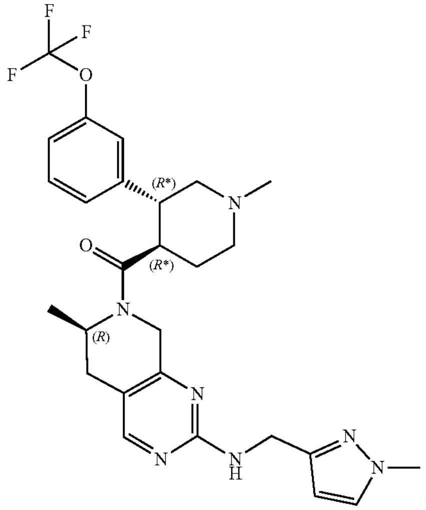
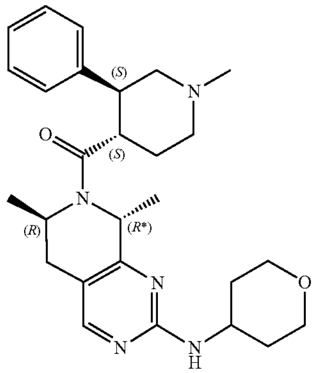
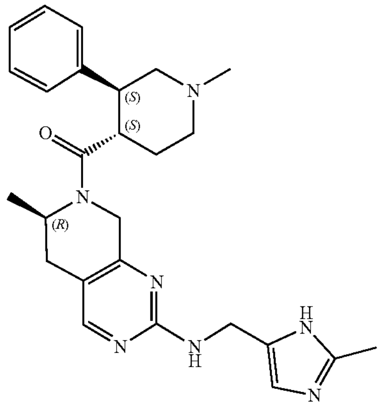

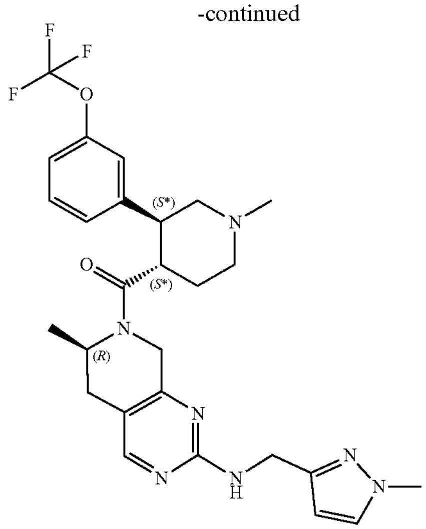
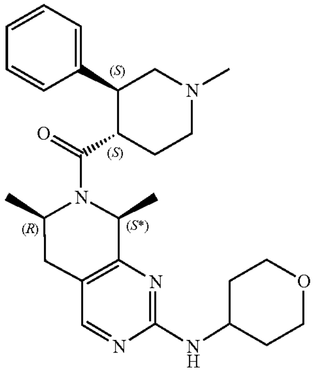
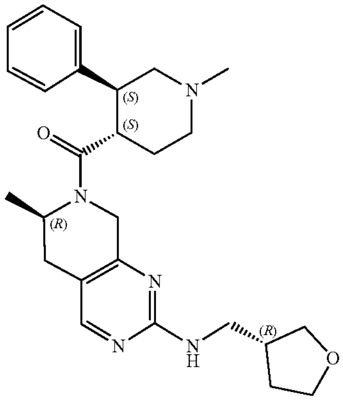
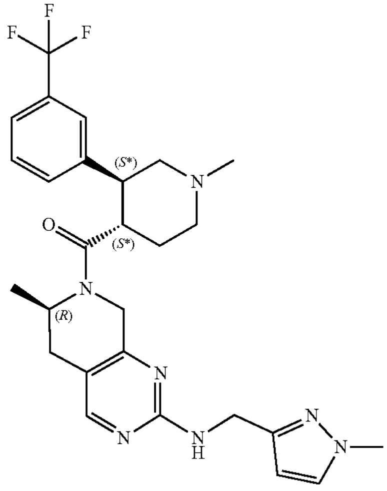
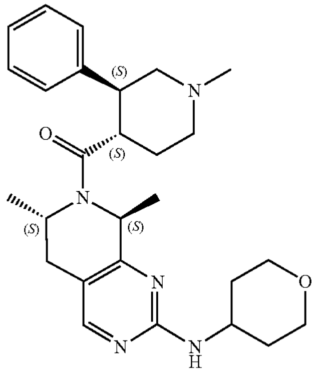
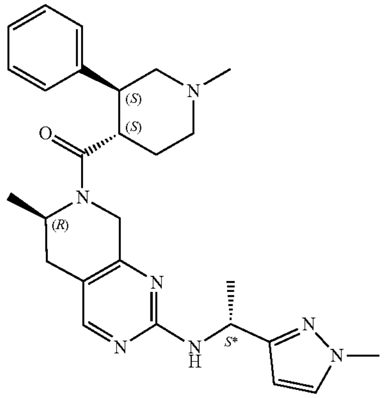
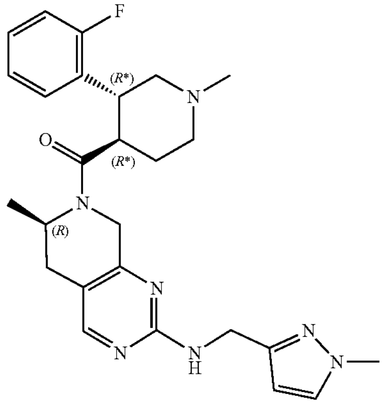

-continued
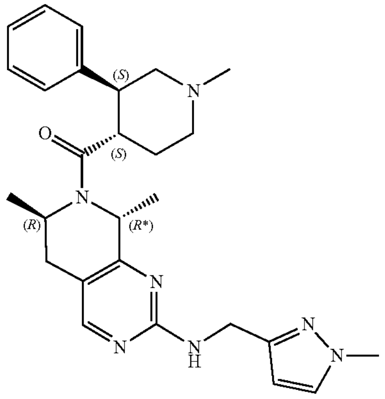
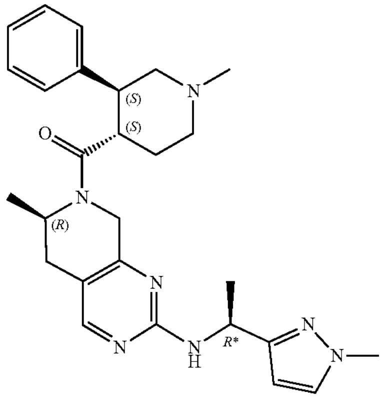
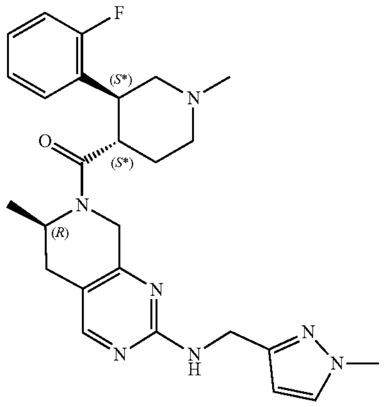
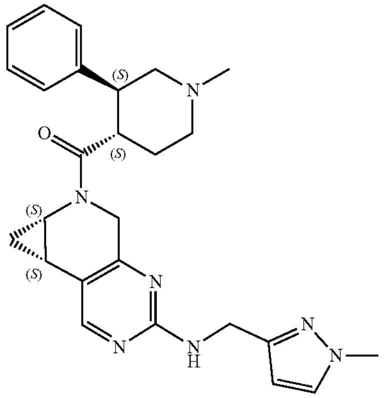
-continued
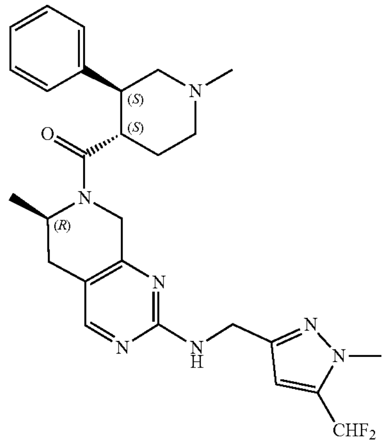
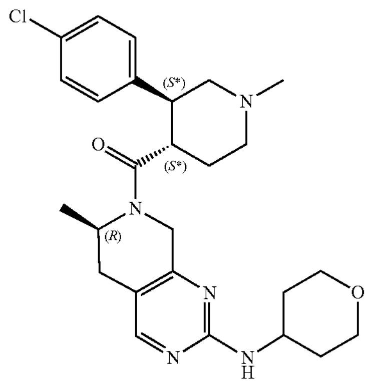
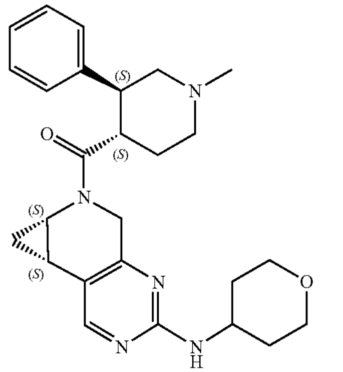
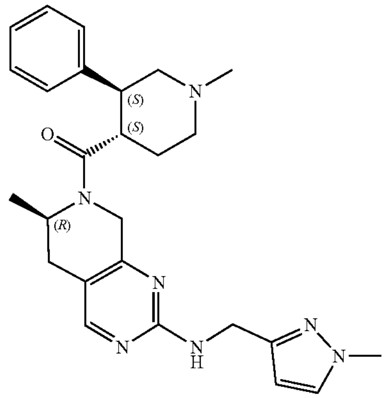

-continued
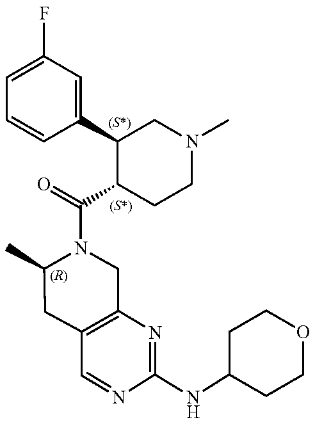
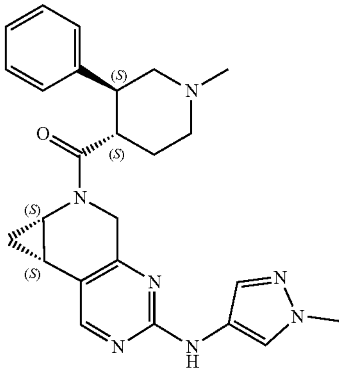
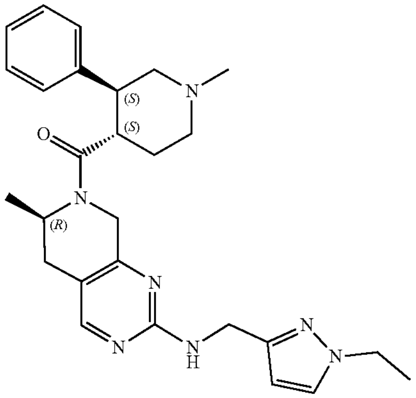
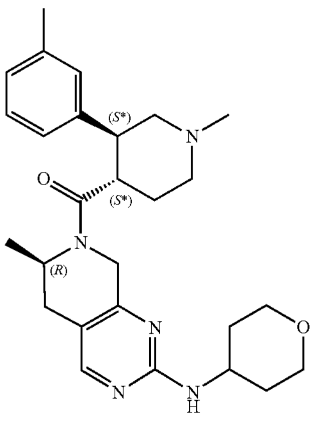
-continued
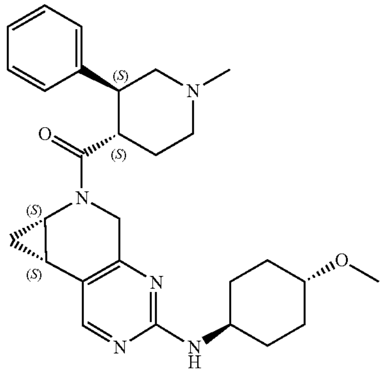
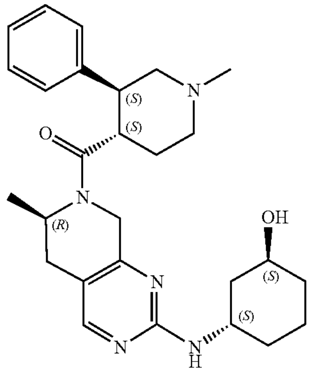
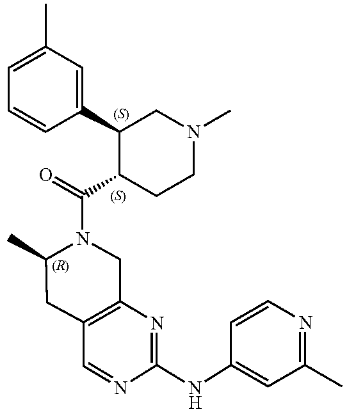
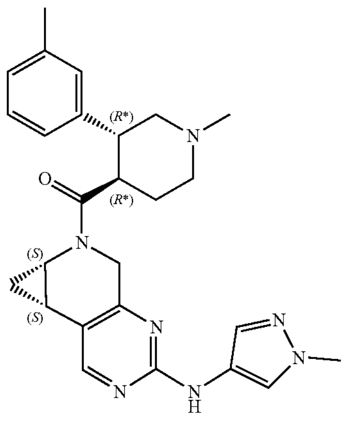

-continued
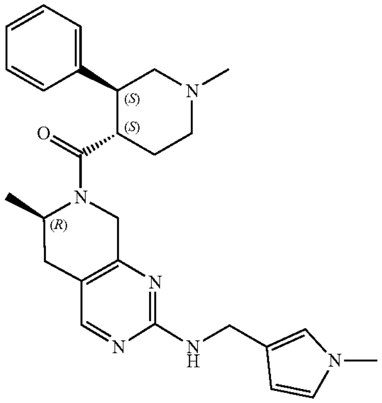
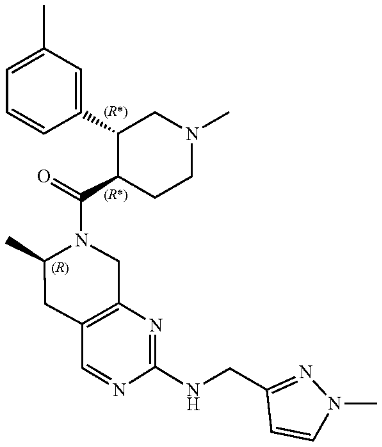
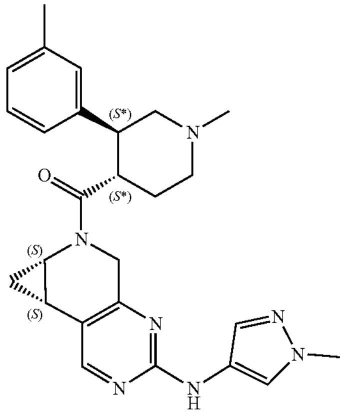
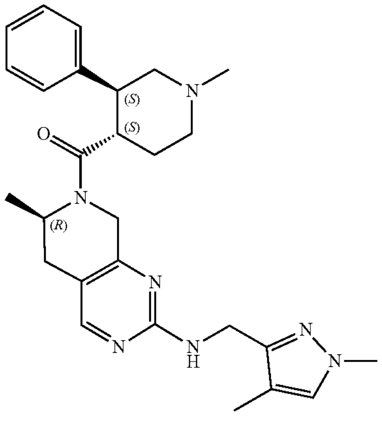
-continued
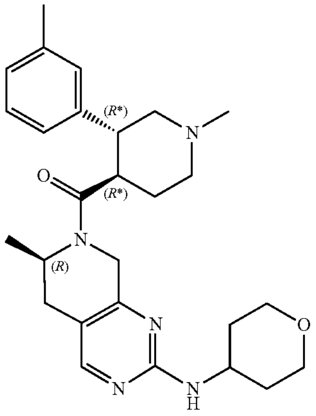
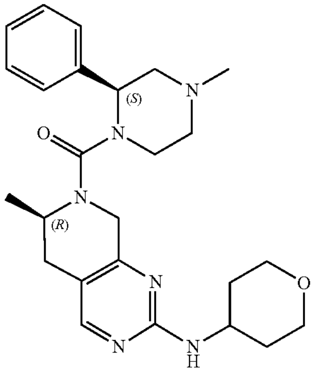
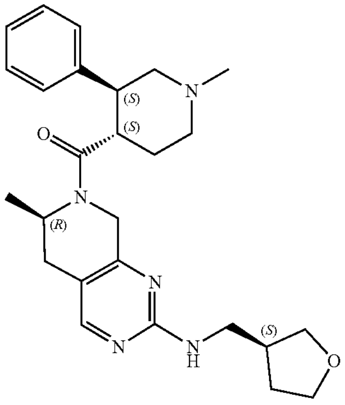
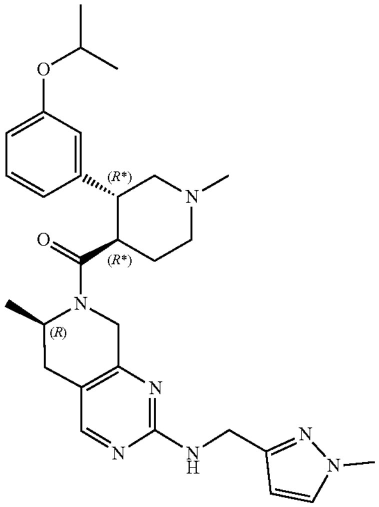

-continued
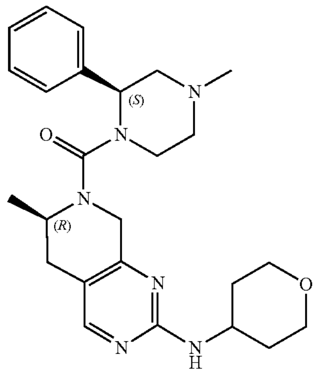
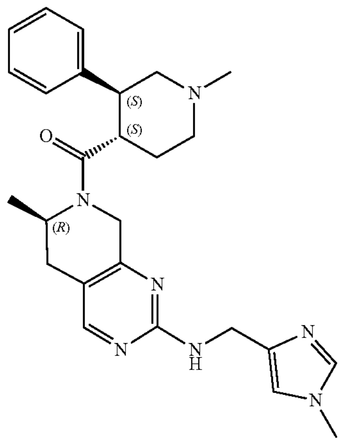
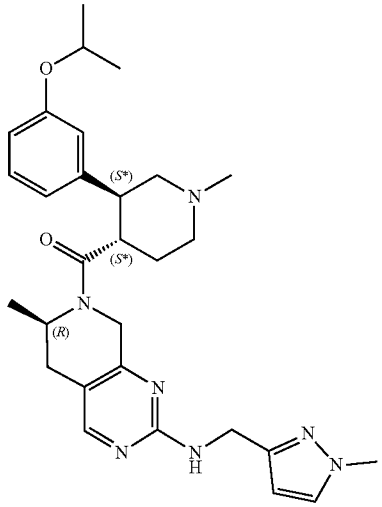
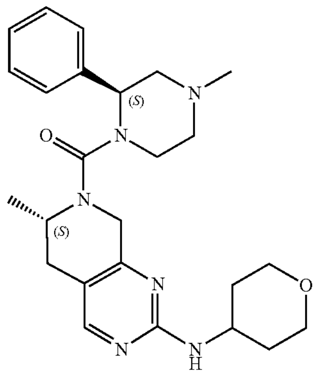
-continued
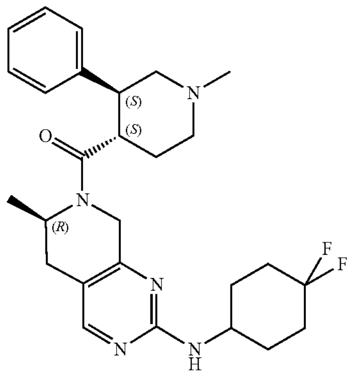
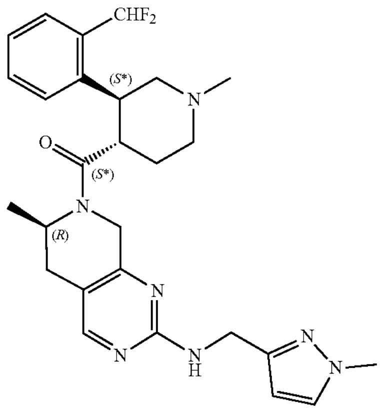
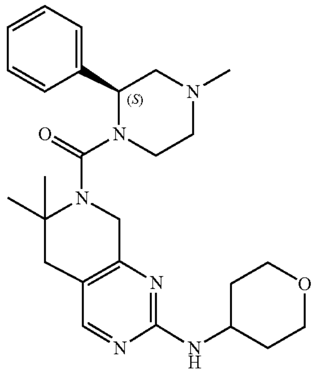
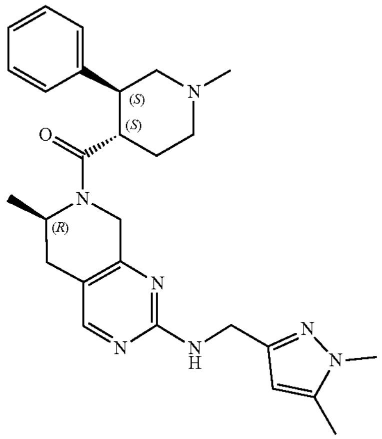

-continued
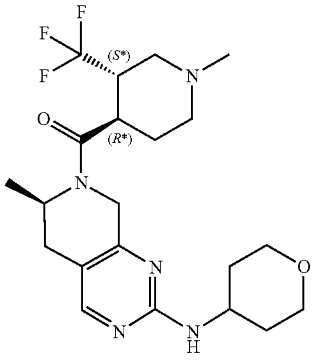
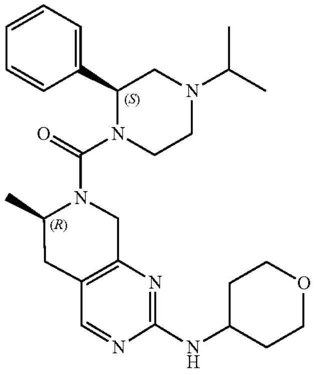
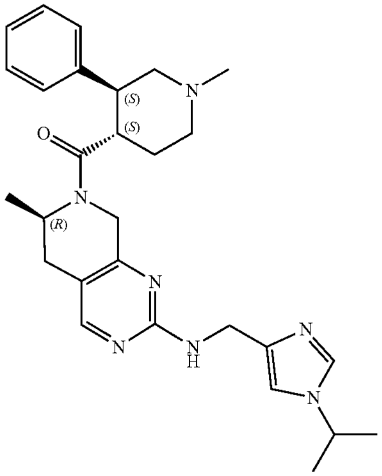
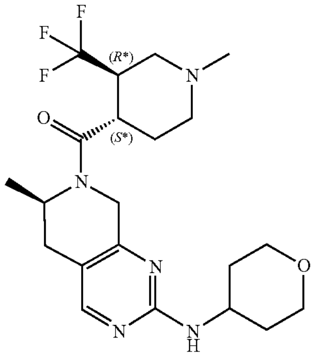
-continued
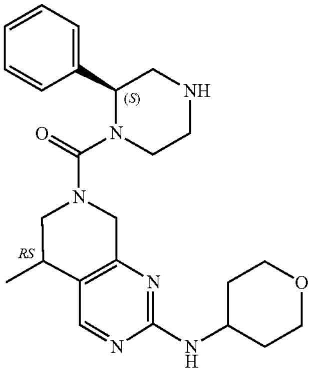
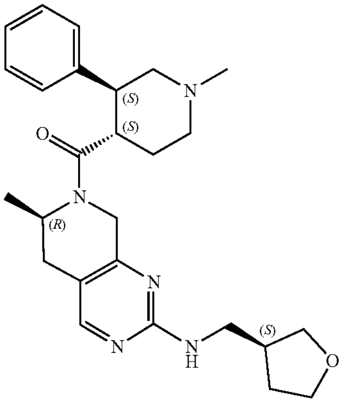
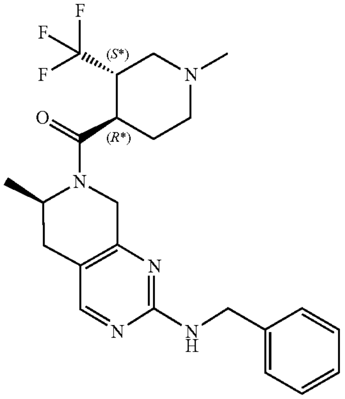
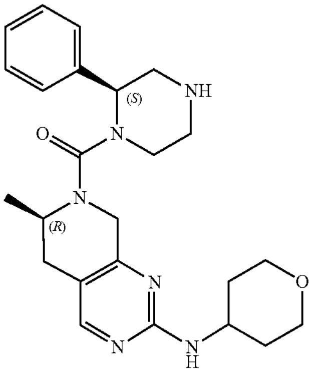

-continued
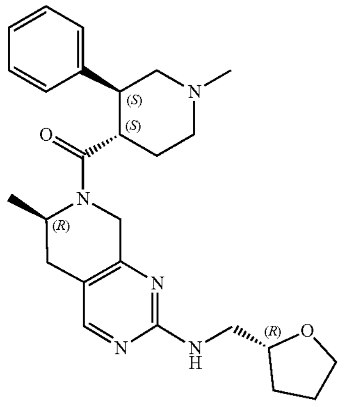
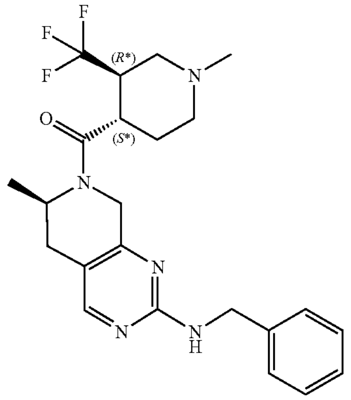
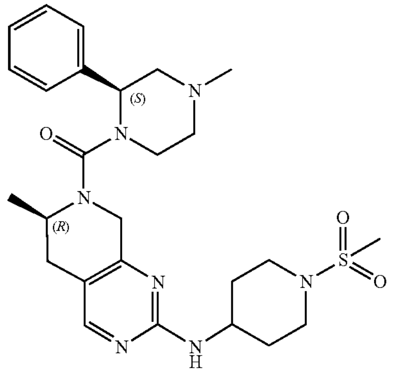
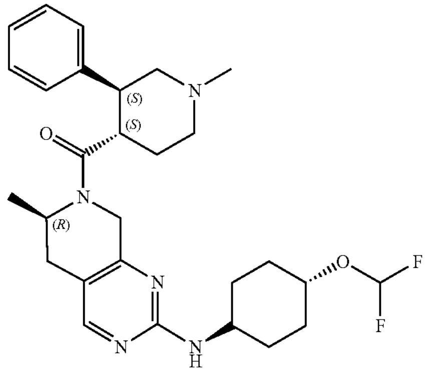
-continued
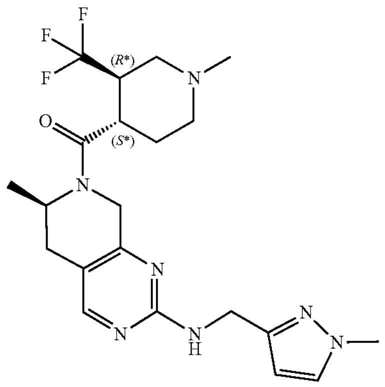
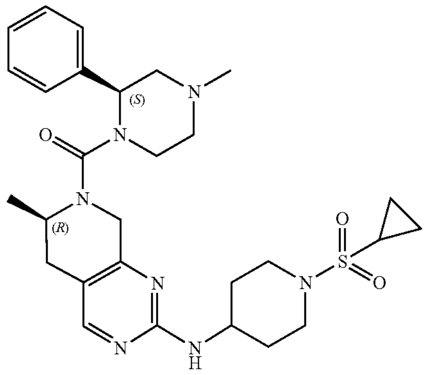
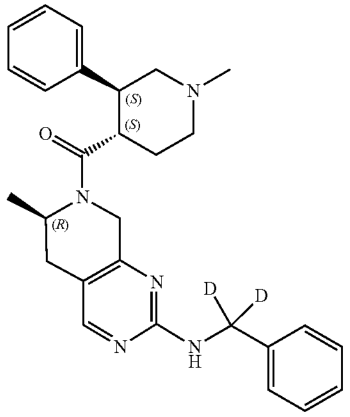
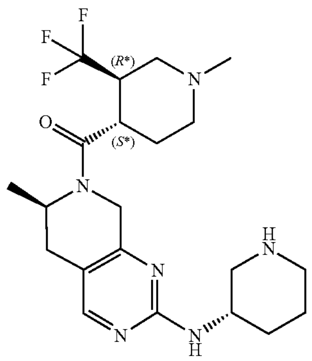

-continued
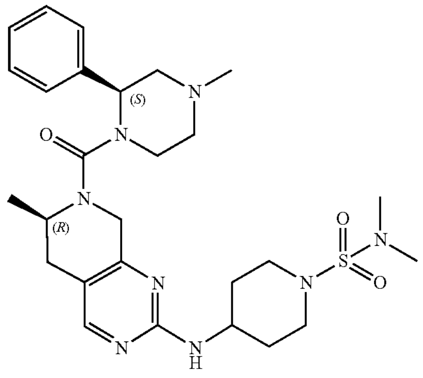
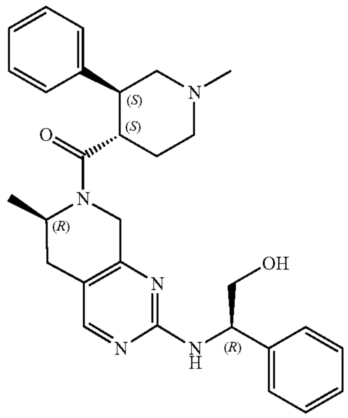
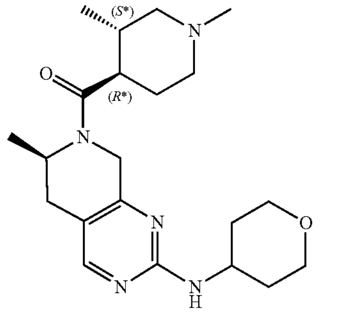
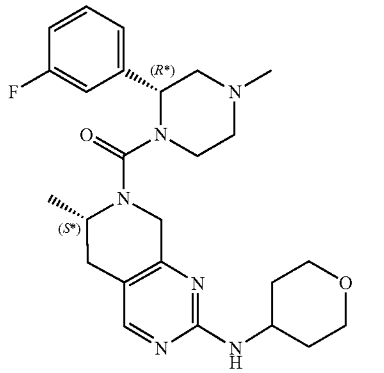
-continued
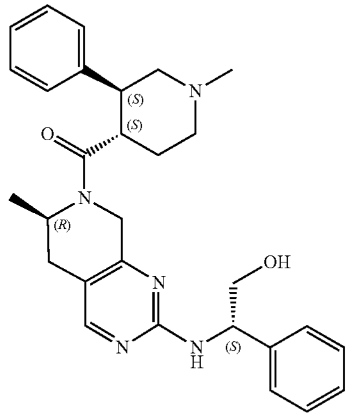
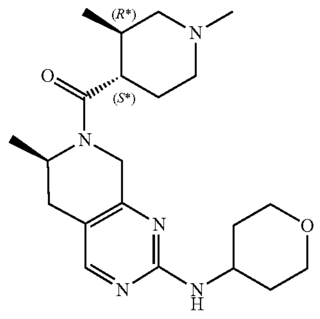
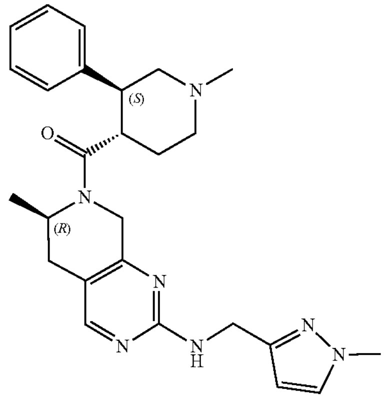
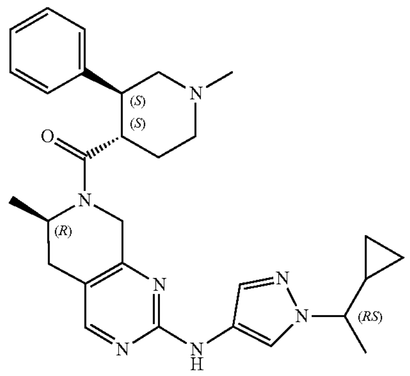

-continued

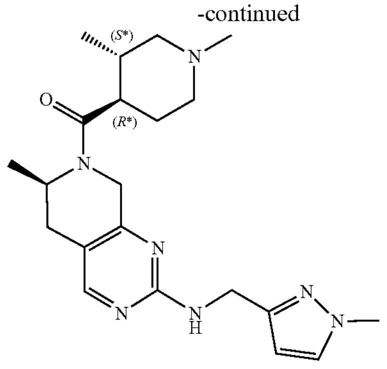

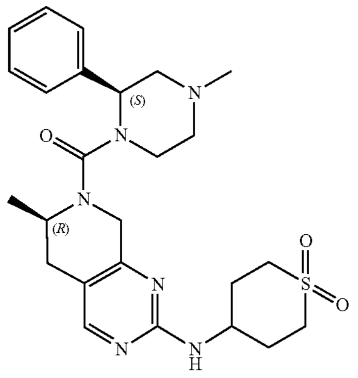

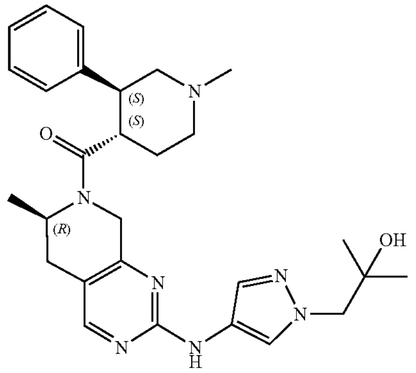

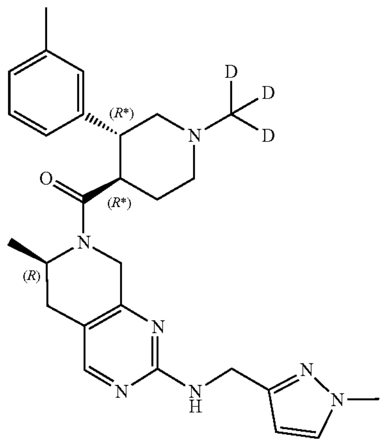

-continued

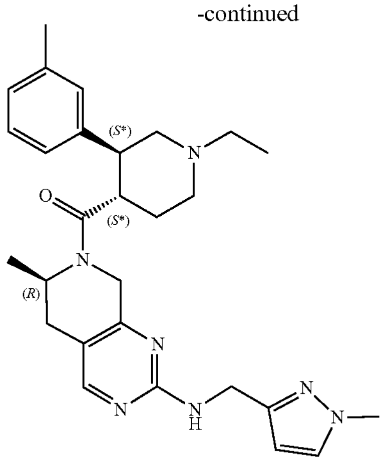

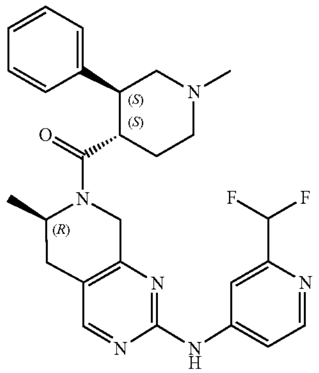

and

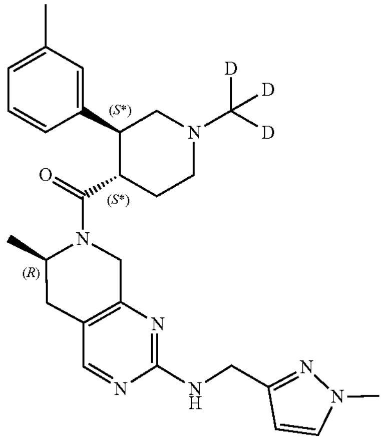

The present invention further relates to a pharmaceutical composition comprising a compound disclosed herein and a pharmaceutically acceptable carrier.

The present invention further relates to a compound as disclosed herein for use in therapy.

The present invention further relates to a compound disclosed herein for use in the prophylaxis and/or treatment of a disease state or condition mediated by a cyclin-dependent kinase 7 (CDK7).

The disease state or condition mediated by a cyclin-dependent kinase 7 (CDK7) may be a proliferative disease.

The proliferative disease may be cancer, leukemia, chronic lymphocytic leukemia (CLL), acute lymphoblastic leukemia (ALL), T-cell acute lymphoblastic leukemia (T-ALL), chronic myelogenous leukemia (CML), acute myeloid leukemia (AML), lymphoma, Hodgkin's lymphoma, non-Hodgkin's lymphoma, melanoma, multiple myeloma, bone cancer, osteosarcoma, Ewing's sarcoma, triple-negative breast cancer (TNBC), brain cancer, neuroblastoma, lung cancer, small cell lung cancer (SCLC), large cell lung cancer, benign neoplasm, angiogenesis, inflammatory diseases, rheumatoid arthritis, autoinflammatory diseases, autoimmune diseases, or infectious diseases.

The present invention further relates to the use of a compound as defined herein for the manufacture of a medicament for the prophylaxis or treatment of cancer; in particular for the treatment of cancer.

The present invention further relates to a method for the prophylaxis or treatment of a disease state or condition mediated by a CDK7, which method comprises administering to a subject in need thereof a compound as defined herein.

The subject may be a mammal.

The present invention further relates to an in vitro method of modulating CDK7 activity comprising contacting the CDK7 protein, or portion thereof, with a compound, or a pharmaceutically acceptable salt, or solvate thereof, as disclosed herein.

INCORPORATION BY REFERENCE

Figure 1:
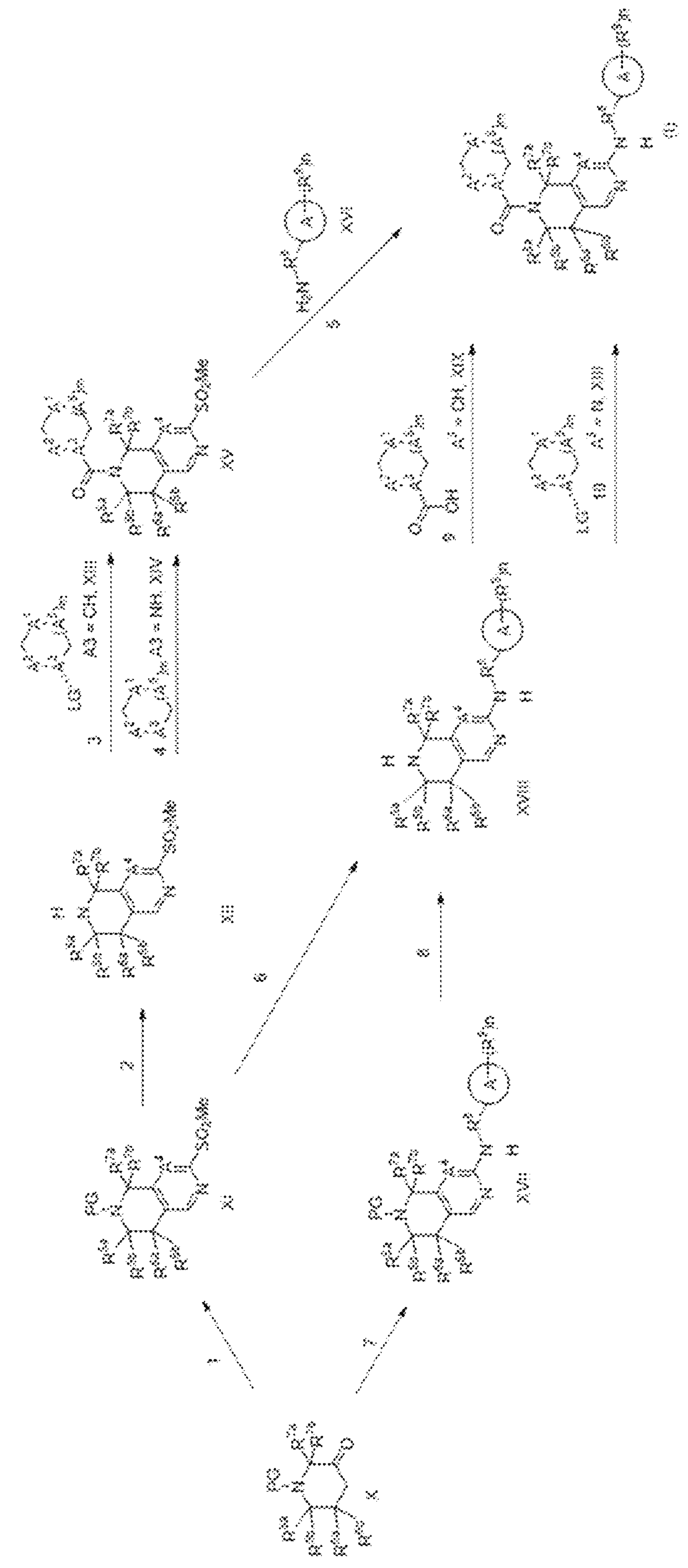
FIG. 1. Scheme 1.

All publications, patents, patent applications, and published nucleotide and amino acid sequences (e.g., sequences available in GenBank or other databases) mentioned in this specification are herein incorporated by reference to the same extent as if each individual publication, patent, patent application, or published nucleotide and amino acid sequence, was specifically and individually indicated to be incorporated by reference.

DETAILED DESCRIPTION OF THE INVENTION

Definitions

Unless defined otherwise, all technical and scientific terms used herein have the same meaning as is commonly understood to which the claimed subject matter belongs. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed.

In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included."

Some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions and acceptable error margins, for such given value.

As used herein, the expression "one or more" refers to at least one, for example one, two, three, four, five or more, whenever possible and depending on the context.

Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

Hereinbefore and hereinafter, the term "compound of formula (I)" is meant to include the addition salts, the solvates and the stereoisomers thereof.

As used herein, "$C_{x-y}$" (where x and y are integers) refers to the number of carbon atoms that make up the moiety to which it designates (excluding optional substituents). Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term "halo" or, alternatively, "halogen" means fluoro, chloro, bromo and iodo.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_{1-6}$alkyl" or similar designations.

By way of example, the term "$C_{1-4}$alkyl", or "$C_{1-6}$alkyl" as used herein as a group or part of a group refers to a linear or branched saturated hydrocarbon group containing from 1 to 4 or 1 to 6 carbon atoms, respectively. Examples of such groups include methyl, ethyl, n-propyl, isopropyl, n-butyl, isobutyl, sec-butyl, tert-butyl, n-pentyl, isopentyl, neopentyl, hexyl, and the like.

The term "alkenyl" refers to a type of alkyl group in which at least two atoms of the alkyl group form a double bond that is not part of an aromatic group. Non-limiting examples of an alkenyl group include $-CH{=}CH_2$, $-C(CH_3){=}CH_2$, $-CH{=}CHCH_3$, $-CH{=}C(CH_3)_2$ and $-C(CH_3){=}CHCH_3$. The alkenyl moiety may be branched or a straight chain. Alkenyl groups may have 2 to 6 carbons. Alkenyl groups can be substituted or unsubstituted. Depending on the structure, an alkenyl group can be a monoradical or a diradical (i.e., an alkenylene group). Examples of "alkenyl" include also "$C_{2-4}$alkenyl" or "$C_{2-6}$alkenyl".

The term "alkynyl" refers to a type of alkyl group in which at least two atoms of the alkyl group form a triple bond. Non-limiting examples of an alkynyl group include $-C{\equiv}CH$, $-C{\equiv}CCH_3$, $-C{\equiv}CCH_2CH_3$ and $-C{\equiv}CCH_2CH_2CH_3$. The alkynyl moiety may be branched or a straight chain. An alkynyl group can have 2 to 6 carbons. Alkynyl groups can be substituted or unsubstituted. Depending on the structure, an alkynyl group can be a monoradical or a diradical (i.e., an alkynylene group). Examples of "alkynyl" include also "$C_{2-4}$alkynyl" or "$C_{2-6}$alkynyl".

An "alkoxy" refers to a "—O-alkyl" group, where alkyl is as defined herein.

The term "$C_{1-4}$alkoxy" or "$C_{1-6}$alkoxy" as used herein as a group or part of a group refers to an —O—$C_{1-4}$alkyl group or an —O—$C_{1-6}$alkyl group wherein $C_{1-4}$alkyl and $C_{1-6}$alkyl are as defined herein. Examples of such groups include methoxy, ethoxy, propoxy, butoxy, and the like.

The term "hydroxy$C_{1-4}$alkyl" or "hydroxy$C_{1-6}$alkyl" as used herein as a group or part of a group refers to a $C_{1-4}$alkyl or $C_{1-6}$alkyl group as defined herein wherein one or more than one hydrogen atoms are replaced with a hydroxyl group. The terms "hydroxy$C_{1-4}$alkyl" or "hydroxy$C_{1-6}$alkyl" therefore include monohydroxy$C_{1-4}$alkyl, monohydroxy$C_{1-6}$alkyl and also polyhydroxy$C_{1-4}$alkyl and polyhydroxy$C_{1-6}$alkyl. There may be one, two, three or more hydrogen atoms replaced with a hydroxyl group, so the hydroxy$C_{1-4}$alkyl or hydroxy$C_{1-6}$alkyl may have one; two, three or more hydroxyl groups. Examples of such groups include hydroxymethyl, hydroxyethyl, hydroxypropyl and the like.

The term "haloalkyl" refers to an alkyl group as defined herein wherein one or more than one hydrogen atom is replaced with one or more halogens. The term "haloalkyl" includes "halo$C_{1-4}$alkyl", "halo$C_{1-6}$alkyl", monohalo$C_{1-4}$alkyl, monohalo$C_{1-6}$alkyl, polyhalo$C_{1-4}$alkyl, and polyhalo$C_{1-6}$alkyl. There may be one, two, three or more hydrogen atoms replaced with a halogen, so the halo$C_{1-4}$alkyl or halo$C_{1-6}$alkyl may have one, two, three or more halogens. The halogens may the same or they may be different. Non-limiting examples of haloalkyls include $-CH_2Cl$, $-CF_3$, $-CHF_2$, $-CH_2CF_3$, $-CF_2CF_3$, $-CF(CH_3)_2$, fluoroethyl, fluoromethyl, trifluoroethyl, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, $-CH_2-O-CH_3$, $-CH_2-CH_2-O-CH_3$, $-CH_2-NH-CH_3$, $-CH_2-CH_2-NH-CH_3$, $-CH_2-N(CH_3)-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH_2-NH-OCH_3$, $-CH_2-O-Si(CH_3)_3$, $CH_2-CH{=}N-OCH_3$, and $-CH{=}CH-N(CH_3)-CH_3$. In addition, up to two heteroatoms may be consecutive, such as, by way of example, $-CH_2-NH-OCH_3$ and $-CH_2-O-Si(CH_3)_3$. Excluding the number of heteroatoms, a "heteroalkyl" may have from 1 to 6 carbon atoms.

The term "halo$C_{1-4}$alkoxy" or "halo$C_{1-6}$alkoxy" as used herein as a group or part of a group refers to a —O—$C_{1-4}$alkyl group or a —O—$C_{1-6}$ alkyl group as defined herein wherein one or more than one hydrogen atom is replaced with a halogen. The terms "halo$C_{1-6}$alkoxy" or "halo$C_{1-6}$ alkoxy" therefore include monohalo$C_{1-6}$alkoxy, monohalo$C_{1-6}$alkoxy and also polyhalo$C_{1-6}$alkoxy and polyhalo$C_{1-6}$ alkoxy. There may be one, two, three or more hydrogen atoms replaced with a halogen, so the halo$C_{1-4}$alkoxy or halo$C_{1-6}$alkoxy may have one, two, three or more halogens. Examples of such groups include fluoroethyloxy, difluoromethoxy, or trifluoromethoxy and the like.

The terms "fluoroalkyl" and "fluoroalkoxy" include alkyl and alkoxy groups, respectively, that are substituted with one or more fluorine atoms. Non-limiting examples of fluoroalkyls include $-CF_3$, $-CHF_2$, $-CH_2F$, $-CH_2CF_3$, $-CF_2CF_3$, $-CF_2CF_2CF_3$, $-CF(CH_3)_3$, and the like. Non-limiting examples of fluoroalkoxy groups, include $-OCF_3$, $-OCHF_2$, $-OCH_2F$, $-OCH_2CF_3$, $-OCF_2CF_3$, $-OCF_2CF_2CF_3$, $-OCF(CH_3)_2$, and the like.

The term "cyano$C_{1-4}$alkyl" or "cyano$C_{1-6}$alkyl" as used herein refers to a $C_{1-4}$alkyl or $C_{1-6}$alkyl group as defined herein which is substituted with one or two cyano groups, in particular with one cyano group.

"Amino" refers to a $-NH_2$ group.

The term "alkylamine" or "alkylamino" refers to the $-N(alkyl)_xH_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a $-N(alkyl)_2$ group, where alkyl is as defined herein.

The terms "carboxy" or "carboxyl" refer to $-CO_2H$. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

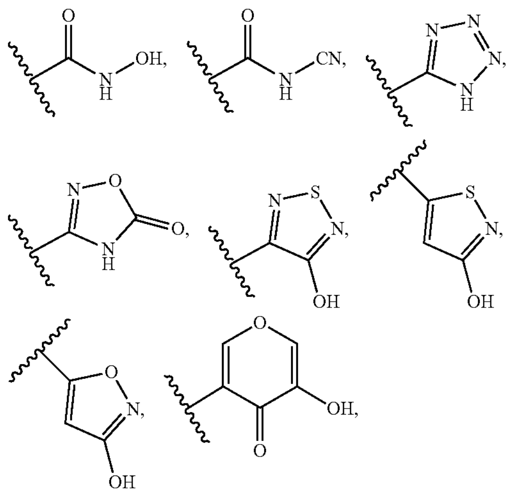

and the like.

The term "carbocyclyl" as used herein, unless the context indicates otherwise, includes aromatic, non-aromatic, unsaturated, partially saturated, and fully saturated carbon ring systems. In general, unless the context indicates otherwise, such ring systems may be monocyclic or bicyclic or bridged and may contain, for example, 3 to 12 ring members, or 4 to 10 ring members, or more usually 5 to 10 ring members. Reference to 3 to 6 ring members include 3, 4, 5, or 6 atoms in the ring, reference to 4 to 7 ring members include 4, 5, 6 or 7 atoms in the ring, and reference to 4 to 6 ring members include 4, 5, or 6 atoms in the ring. Examples of monocyclic carbocyclyl ring systems are ring systems containing 3, 4, 5, 6, 7 and 8 ring members, more usually 3 to 7, and preferably 4, 5, 6 or 7 ring members, more preferably 5 or 6 ring members. Examples of bicyclic carbocyclyl ring systems are those containing 8, 9, 10, 11 and 12 ring members, and more usually 9 or 10 ring members. Where reference is made herein to a carbocyclyl ring system, the carbocyclyl ring can, unless the context indicates otherwise, be optionally substituted (i.e. unsubstituted or substituted) by one or more substituents as discussed herein. Particular examples of 3 to 12 membered carbocycles include cyclopropyl, cyclobutyl, cyclopentyl, cyclohexyl, cycloheptyl, cyclooctyl, phenyl naphthyl, indenyl, tetrahydronaphthyl, azulenyl, norbornane (1,4-endo-methylene-cyclohexane), adamantane ring systems.

The term "aromatic" refers to a planar ring having a delocalized-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

The term "non-aromatic group" embraces, unless the context indicates otherwise, unsaturated ring systems without aromatic character, partially saturated and fully saturated heterocyclyl ring systems.

The terms "unsaturated" and "partially saturated" refer to rings wherein the ring structure(s) contains atoms sharing more than one valence bond i.e. the ring contains at least one multiple bond e.g. a C═C, C≡C or N═C bond.

The term "fully saturated" refers to rings where there are no multiple bonds between ring atoms. Saturated heterocyclyl groups include piperidine, morpholine, thiomorpholine, piperazine. Partially saturated heterocyclyl groups include pyrazolines, for example 2-pyrazoline and 3-pyrazoline.

The carbocyclyl ring systems can be aryl ring systems.

The term "aryl" as used herein refers to carbocyclyl aromatic groups and embraces polycyclic (e.g. bicyclic) ring systems wherein one or more rings are non-aromatic, provided that at least one ring is aromatic. In such polycyclic systems, the ring system may be attached to the remainder of the compound by an aromatic ring or by a non-aromatic ring. The term "aryl" includes phenyl, naphthyl or naphthalenyl, indenyl, and tetrahydronaphthyl groups. Depending on the structure, an aryl group can be a monoradical or a diradical (i.e., an arylene group).

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. An example of a "cycloalkyl" is "$C_{3-6}$cycloalkyl". Cycloalkyls may be fused with an aromatic ring (in which case the cycloalkyl is bonded through a non-aromatic ring carbon atom). Cycloalkyl groups include groups having from 3 to 10 ring atoms. Illustrative examples of cycloalkyl groups include, but are not limited to, the following moieties:

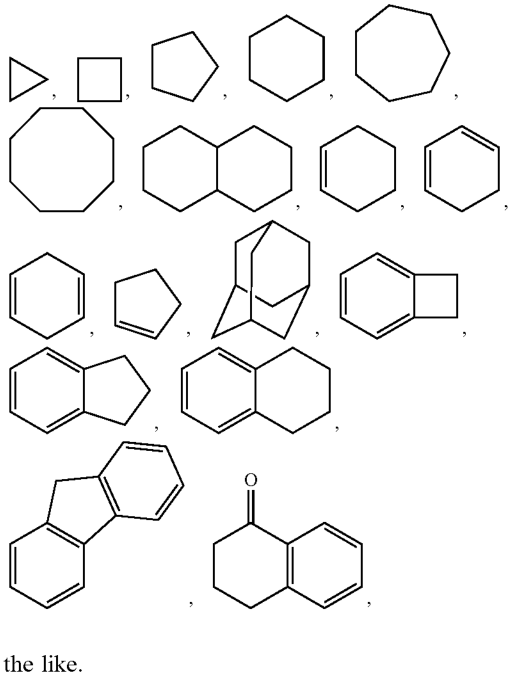

and the like.

The term "heterocyclyl", "heterocycloalkyl", or "heteroalicyclic" group refers to a carbocyclyl, as defined herein, containing at least one heteroatom typically selected from nitrogen, oxygen or sulphur, in particular containing up to 5, up to 4, up to 3, up to 2, or a single heteroatom. Where reference is made herein to a heterocyclyl ring system, the heterocyclyl ring can, unless the context indicates otherwise, be optionally substituted (i.e. unsubstituted or substituted) by one or more substituents as discussed herein. The radicals may be fused with an aryl or heteroaryl. Illustrative examples of heterocycloalkyl groups, also referred to as non-aromatic heterocycles, include:

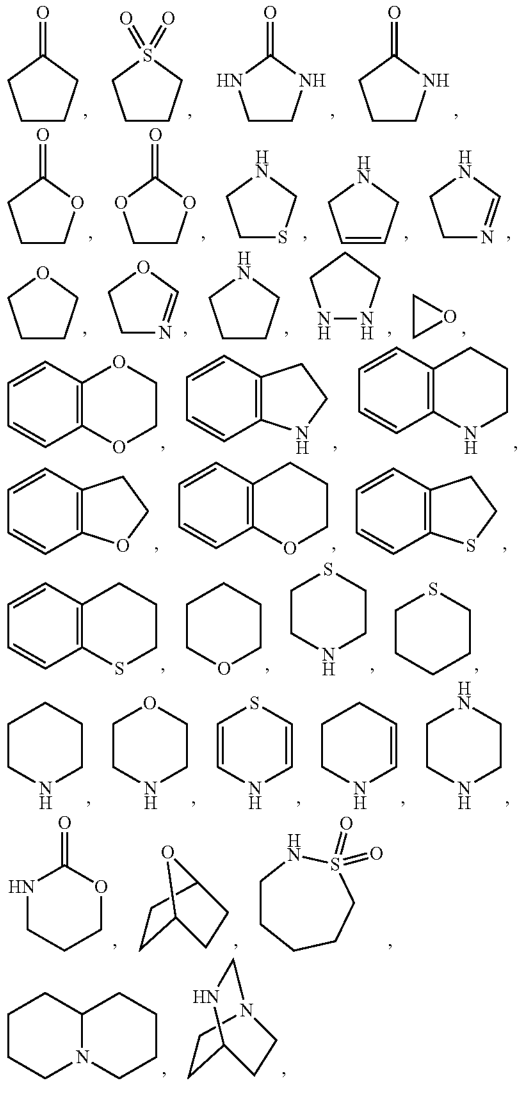

and the like.

The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The heterocyclyl ring systems can be heteroaryl ring systems having from 5 to 12 ring members, more usually from 5 to 10 ring members.

The term "heteroaryl" is used herein to denote a heterocyclyl ring system having aromatic character. The term "heteroaryl" embraces polycyclic (e.g. bicyclic) ring systems wherein one or more rings are non-aromatic, provided that at least one ring is aromatic. In such polycyclic systems, the ring system may be attached to the remainder of the compound by an aromatic ring or by a non-aromatic ring.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. The heteroaryl ring system may contain up to about five heteroatoms typically selected from nitrogen, oxygen and sulphur. Typically, the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

Examples of five membered heteroaryl groups include but are not limited to pyrrolyl, furanyl, thienyl, imidazolyl, oxazolyl, oxadiazolyl, oxatriazole, isoxazolyl, thiazolyl, thiadiazolyl, isothiazolyl, pyrazolyl, triazolyl and tetrazolyl groups. In particular, examples of five membered heteroaryl groups include but are not limited to pyrrolyl, furanyl, thienyl, imidazolyl, oxazolyl, oxadiazolyl, isoxazolyl, thiazolyl, thiadiazolyl, isothiazolyl, pyrazolyl and triazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from: a benzene ring fused to a 5- or 6-membered ring containing 1, 2 or 3 ring heteroatoms; a pyridine ring fused to a 5- or 6-membered ring containing 0, 1, 2 or 3 ring heteroatoms; a pyrimidine ring fused to a 5- or 6-membered ring containing 0, 1 or 2 ring heteroatoms; a pyrrole ring fused to a 5- or 6-membered ring containing 0, 1, 2 or 3 ring heteroatoms; a pyrazole ring fused to a 5- or 6-membered ring containing 0, 1 or 2 ring heteroatoms; an imidazole ring fused to a 5- or 6-membered ring containing 0, 1 or 2 ring heteroatoms; an oxazole ring fused to a 5- or 6-membered ring containing 0, 1 or 2 ring heteroatoms; an isoxazole ring fused to a 5- or 6-membered ring containing 0, 1 or 2 ring heteroatoms; a thiazole ring fused to a 5- or 6-membered ring containing 0, 1 or 2 ring heteroatoms; an isothiazole ring fused to a 5- or 6-membered ring containing 0, 1 or 2 ring heteroatoms; a thiophene ring fused to a 5- or 6-membered ring containing 0, 1, 2 or 3 ring heteroatoms; a furan ring fused to a 5- or 6-membered ring containing 0, 1, 2 or 3 ring heteroatoms; a cyclohexyl ring fused to a 5- or 6-membered aromatic ring containing 1, 2 or 3 ring heteroatoms; and a cyclopentyl ring fused to a 5- or 6-membered aromatic ring containing 1, 2 or 3 ring heteroatoms.

Particular examples of bicyclic heteroaryl groups containing a five membered ring fused to another five membered ring include but are not limited to imidazothiazolyl (e.g. imidazo[2,1-b]thiazole) and imidazoimidazolyl (e.g. imidazo[1,2-a]imidazole).

Particular examples of bicyclic heteroaryl groups containing a six membered ring fused to a five membered ring include but are not limited to benzofuranyl, benzothiophenyl, benzimidazolyl, benzoxazolyl, isobenzoxazolyl, benzisoxazolyl, benzthiazolyl, benzisothiazolyl, isobenzofuranyl, indolyl, isoindolyl, indolizinyl, indolinyl, isoindolinyl, purinyl, indazolyl, pyrazolopyrimidinyl (e.g. pyrazolo[1,5-a]pyrimidine), triazolopyrimidinyl (e.g. [1,2,4]triazolo[1,5-a]pyrimidine), benzodioxolyl, imidazopyrazinyl, imidazopyridazinyl, imidazopyridinyl and pyrazolopyridinyl (e.g. pyrazolo[1,5-a]pyridine) groups.

Particular examples of bicyclic heteroaryl groups containing two fused six membered rings include but are not limited to quinolizinyl, quinolinyl, isoquinolinyl, cinnolinyl, chromanyl, isochromanyl, thiochromanyl, benzopyranyl, benzodioxanyl, benzoxazinyl, pyridopyridinyl, quinoxalinyl, quinazolinyl, phthalazinyl, naphthyridinyl and pteridinyl groups.

Particular examples of bicyclic heteroaryl groups containing two fused six membered rings include but are not limited to quinolizinyl, quinolinyl, isoquinolinyl, benzopyranyl, benzodioxanyl, benzoxazinyl, pyridopyridinyl, quinoxalinyl, quinazolinyl, phthalazinyl, naphthyridinyl, and pteridinyl groups.

Examples of polycyclic heteroaryl groups containing an aromatic ring and a non-aromatic ring include, tetrahydroisoquinolinyl, tetrahydroquinolinyl, dihydrobenzothienyl, dihydrobenzofuranyl, 2,3-dihydro-benzo[1,4]dioxinyl, benzo[1,3]dioxolyl, 4,5,6,7-tetrahydrobenzofuranyl, tetrahydrotriazolopyrazinyl (e.g. 5,6,7,8-tetrahydro-[1,2,4]triazolo[4,3-a]pyrazinyl), and indolinyl.

A nitrogen-containing heteroaryl ring must contain at least one ring nitrogen atom. Each ring may, in addition, contain up to about four other heteroatoms typically selected from nitrogen, sulphur and oxygen. Typically, the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazolyl, benzthiazolyl and benzisothiazole, indolyl, 3H-indolyl, isoindolyl, indolizinyl, isoindolinyl, purinyl, indazolyl, quinolizinyl, benzoxazinyl, pyridopyridinyl, quinoxalinyl, quinazolinyl, cinnolinyl, phthalazinyl, naphthyridinyl, and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), and combinations thereof (e.g. thiomorpholine).

Particular examples include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), azetidinyl, pyranyl(2H-pyranyl or 4H-pyranyl), dihydrothiophenyl, dihydropyranyl, dihydrofuranyl, dihydrothiazolyl, tetrahydrofuranyl, tetrahydrothiophenyl, dioxanyl, dioxolanyl, tetrahydropyranyl, imidazolinyl, oxazolinyl, oxazolidinyl, oxetanyl, thiazolinyl, 2-pyrazolinyl, pyrazolidinyl and piperazinyl. In general, preferred non-aromatic heterocyclyl groups include saturated groups such as piperidinyl, pyrrolidinyl, azetidinyl, morpholinyl and piperazinyl. In general, preferred non-aromatic heterocyclyl groups include saturated groups such as piperidinyl, pyrrolidinyl, azetidinyl, morpholinyl and piperazinyl.

In a nitrogen-containing non-aromatic heterocyclyl ring the ring must contain at least one ring nitrogen atom.

Particular examples of nitrogen-containing non-aromatic heterocyclyl groups include aziridinyl, morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), dihydrothiazolyl, imidazolinyl, oxazolinyl, thiazolinyl, 2-pyrazolinyl, 3-pyrazolinyl, pyrazolidinyl and piperazinyl.

Particular examples of 3 to 6 membered monocyclic saturated heterocyclyls include morpholinyl, thiomorpholinyl, dioxanyl, piperidinyl (e.g. 1-piperidinyl, 2-piperidinyl, 3-piperidinyl and 4-piperidinyl), piperazinyl, pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, tetrahydrofuranyl, tetrahydrothiophenyl, tetrahydropyranyl (e.g. 4-tetrahydro pyranyl), dithianyl, trioxanyl, trithianyl, aziridinyl, oxiranyl, thiiranyl, diaziridinyl, dioxarinyl, oxetanyl, azetidinyl, thietanyl, dioxetanyl ring systems.

Particular examples of 3 to 6 membered monocyclic heterocyclyls include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, piperazinyl, tetrahydrofuranyl, tetrahydrothiophenyl, dioxanyl, tetrahydropyranyl (e.g. 4-tetrahydro pyranyl), dithianyl, trioxanyl, trithianyl, aziridinyl, oxiranyl, thiiranyl, diaziridinyl, dioxarinyl, oxetanyl, azetidinyl, thietanyl, dioxetanyl, azirinyl, azetyl, 1,2-dithietyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl ring systems.

Particular examples of 3 to 12 membered heterocycles include morpholinyl, thiomorpholinyl, piperidinyl (e.g. 1-piperidinyl, 2-piperidinyl, 3-piperidinyl and 4-piperidinyl), pyrrolidinyl (e.g. 1-pyrrolidinyl, 2-pyrrolidinyl and 3-pyrrolidinyl), imidazolidinyl, pyrazolidinyl, oxazolidinyl, isoxazolidinyl, thiazolidinyl, isothiazolidinyl, dioxolanyl, dithiolanyl, piperazinyl, tetrahydrofuranyl, tetrahydrothiophenyl, dioxanyl, tetrahydropyranyl (e.g. 4-tetrahydropyranyl), dithianyl, trioxanyl, trithianyl, aziridinyl, oxiranyl, thiiranyl, diaziridinyl, dioxarinyl, oxetanyl, azetidinyl, thietanyl, dioxetanyl, azirinyl, azetyl, 1,2-dithietyl, pyrrolyl, furanyl, thiophenyl, imidazolyl, pyrazolyl, oxazolyl, thiazolyl, isothiazolyl, triazolyl, oxadiazolyl, thiadiazolyl, dithiazolyl, pyridinyl, pyranyl, thiopyranyl, pyrimidinyl, thiazinyl, oxazinyl, triazinyl, azepanyl, oxepanyl, thiepanyl, 1,2-diazepanyl, 1,4-diazepanyl, diazepinyl, thiazepinyl, azocanyl, azocinyl, imidazothiazolyl (e.g. imidazo[2,1-b]thiazolyl), imidazo-imidazolyl (e.g. imidazo[1,2-a]imidazolyl), benzofuranyl, benzothiophenyl, benzimidazolyl, benzoxazolyl, isobenzoxazolyl, benzisoxazolyl, benzthiazolyl, benzisothiazolyl, isobenzofuranyl, indolyl, isoindolyl, indolizinyl, indolinyl, isoindolinyl, purinyl, indazolyl, pyrazolopyrimidinyl (e.g. pyrazolo[1,5-a]pyrimidinyl), triazolopyrimidinyl (e.g. [1,2,4]triazolo[1,5-a]pyrimidinyl), benzodioxolyl, imidazopyridinyl and pyrazolopyridinyl (e.g. pyrazolo[1,5-a]pyridinyl), quinolinyl, isoquinolinyl, chromanyl, thiochromanyl, isochromanyl, benzodioxanyl, quinolizinyl, benzoxazinyl, pyridopyridinyl, quinoxalinyl, quinazolinyl, cinnolinyl, phthalazinyl, naphthyridinyl, pteridinyl, tetrahydroisoquinolinyl, tetrahydroquinolinyl, dihydrobenzothienyl, dihydrobenzofuranyl, 2,3-dihydrobenzo[1,4]dioxinyl, benzo[1,3]dioxolyl, 4,5,6,7-tetrahydrobenzofuranyl, tetrahydrotriazolopyrazinyl (e.g. 5,6,7,8-tetrahydro-[1,2,4]triazolo[4,3-a]pyrazinyl), 8-oxa-3-azabicyclo-[3.2.1]octanyl, 2-oxa-5-azabicyclo[2.2.1]heptanyl, 3-oxa-8-azabicyclo[3.2.1]octanyl, 3,6-diazabicyclo[3.1.1]heptanyl ring systems.

Particular examples of 5 to 6 membered aromatic heterocycles include but are not limited to pyrrolyl, furanyl, thiophenyl, imidazolyl, furazanyl, oxazolyl, oxadiazolyl, oxatriazolyl, isoxazolyl, thiazolyl, thiadiazolyl, isothiazolyl, pyrazolyl, triazolyl, tetrazolyl, pyridinyl, pyrazinyl, pyridazinyl, pyrimidinyl and triazinyl ring systems.

The heterocyclyl and carbocyclyl rings also include bridged ring systems such as for example bridged cycloalkanes, such as for example norbornane (1,4-endo-methylene-cyclohexane), adamantane, oxa-adamantane; bridged morpholine rings such as for example 8-oxa-3-azabicyclo[3.2.1]octane, 2-oxa-5-azabicyclo[2.2.1]heptane, 3-oxa-8-azabicyclo[3.2.1]octane; bridged piperazine rings such as for example 3,6-diazabicyclo[3.1.1]heptane; bridged piperidine rings such as for example 1,4-ethylenepiperidine. For an explanation of the distinction between fused and bridged ring systems, see *Advanced Organic Chemistry*, by Jerry March, 4$^{th}$ Edition, Wiley Interscience, pages 131-133, 1992.

Lines drawn into ring systems indicate that the bond may be attached to any of the suitable and available ring atoms.

The term "optional" or "optionally" means the event described subsequent thereto may or may not happen. This term encompasses the cases that the event may or may not happen.

In the compounds of the present disclosure the carbon atom indicated with a "*" in the drawn formula, is a chiral center. When the carbon atom is indicated with "(R*)", it means that it is a pure enantiomer but that it is unknown whether is it an R or S enantiomer. Similarly, when the carbon atom is indicated with "(S*)", it means that it is a pure enantiomer but that it is unknown whether is it an R or S enantiomer.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted", if not explicitly defined, means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkynyl, $C_{1-6}$alkylalkynyl, halo, acyl, acyloxy, $—CO_2H$, $—CO_2$-alkyl, nitro, haloalkyl, fluoroalkyl, and amino, including mono- and di-substituted amino groups (e.g. $—NH_2$, —NHR, $—N(R)_2$), and the protected derivatives thereof. In some embodiments, optional substituents are independently selected from halogen, —CN, $—NH_2$, $—NH(CH_3)$, $—N(CH_3)_2$, —OH, $—CO_2H$, $—CO_2$alkyl, —C(═O) $NH_2$, —C(═O)NH(alkyl), —C(═O)N(alkyl)$_2$, —S(═O)$_2$NH$_2$, —S(═O)$_2$NH(alkyl), —S(═O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, —CN, $—NH_2$, —OH, $—NH(CH_3)$, $—N(CH_3)_2$, $—CH_3$, $—CH_2CH_3$, $—CF_3$, $—OCH_3$, and $—OCF_3$, In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (═O).

The term a "therapeutically effective amount" as used herein refers to the amount of active compound or pharmaceutical agent that, when administered to a mammal in need, is effective to at least partially ameliorate or to at least partially prevent diseases, disorders or conditions described herein.

As used herein, the term "composition" is intended to encompass a product comprising specified ingredients in specified amounts, as well as any product which results, directly or indirectly, from combinations of the specified ingredients in the specified amounts.

As used herein, the term "expression" includes the process by which polynucleotides are transcribed into mRNA and translated into peptides, polypeptides, or proteins.

The term "activator" is used in this specification to denote any molecular species that results in activation of the indicated receptor, regardless of whether the species itself binds to the receptor or a metabolite of the species binds to the receptor. Thus, the activator can be a ligand of the receptor or it can be an activator that is metabolized to the ligand of the receptor, i.e., a metabolite that is formed in tissue and is the actual ligand.

The term "antagonist" as used herein, refers to a small-molecule agent that binds to a receptor and subsequently decreases the agonist induced transcriptional activity of the receptor.

The term "agonist" as used herein, refers to a small-molecule agent that binds to a receptor and subsequently increases receptor transcriptional activity in the absence of a known agonist.

The term "inverse agonist" as used herein, refers to a small-molecule agent that binds to a receptor and subsequently decreases the basal level of receptor transcriptional activity that is present in the absence of a known agonist.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. Those skilled in the art recognize that a therapy which reduces the severity of a pathology in one species of mammal is predictive of the effect of the therapy on another species of mammal.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "proliferative disease" refers to a disease that occurs due to abnormal growth or extension by the multiplication of cells. A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

As used herein, the term "cancer" refers to a malignant neoplasm. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behçet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

Isomers, Salts, N-Oxides, Solvates, Polymorphs, Prodrugs, Isotopically Labeled Derivatives Hereinbefore and hereinafter, the term "compound of formula (I), (II), (IIIa), (IIIb), (IVa), (IVb), (Va), (Vb)", "compounds of the present disclosure or invention", "compounds presented herein", or similar terms, is meant to include the addition salts, the solvates and the stereoisomers thereof.

In certain embodiments, the compounds presented herein possess one or more stereocenters and each center independently exists in either the R or S configuration. The compounds presented herein include all diastereomeric, enantiomeric, atropisomers, and epimeric forms as well as the appropriate mixtures thereof. Stereoisomers are obtained, if desired, by methods such as, stereoselective synthesis and/or the separation of stereoisomers by chiral chromatographic columns. In some embodiments, a compound of the present disclosure is used as a single enantiomer. In some embodiments, a compound of the present disclosure is used as a racemic mixture. In some embodiments, a compound of the present disclosure possesses hindered rotation about a single bond resulting in atropisomers.

In some situations, compounds may exist as tautomers. All tautomers are included within the scope of the compounds presented herein.

For the avoidance of doubt, where a compound can exist in one of several geometric isomeric or tautomeric forms and only one is specifically described or shown, all others are nevertheless embraced. Examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

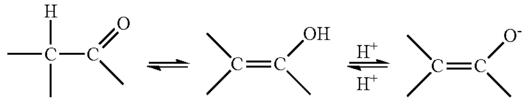

keto enol enolate

Such forms in so far as they may exist, are intended to be included within the scope of the compounds presented herein. It follows that a single compound may exist in both stereoisomeric and tautomeric form.

Where compounds described herein contain one or more chiral centres, and can exist in the form of two or more optical isomers, references to the compounds described herein include all optical isomeric forms thereof (e.g. enantiomers, epimers and diastereoisomers), either as individual optical isomers, or mixtures (e.g. racemic mixtures) of two or more optical isomers, unless the context requires otherwise. When a compound has more than one chiral centre, and one chiral centre is indicated as having an absolute stereoconfiguration, the other chiral centre(s) include all optical isomeric forms, either as individual optical isomers, or mixtures (e.g. racemic mixtures) of two or more optical isomers, thereof, unless the context requires otherwise. The optical isomers may be characterized and identified by their optical activity (i.e. as + and − isomers depending on the direction in which they rotate plane polarized light, or d and l isomers) or they may be characterized in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog (1966) *Angew. Chem. Int. Ed. Engl.,* 5, 385-415. For instance, resolved enantiomers whose absolute configuration is not known can be designated by (+) or (−) depending on the direction in which they rotate plane polarized light.

Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds exist as two or more isomeric forms, one isomeric form, e.g. one enantiomer in a pair of enantiomers, may exhibit advantages over the other isomeric form, e.g. over the other enantiomer, for example, in terms of biological activity. Thus, in certain circumstances, it may be desirable to use as a therapeutic agent only one of a pair of enantiomers, or only one of a plurality of diastereoisomers.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound described herein is for instance specified as(S), this means that the compound is substantially free of the (R) isomer; when a compound described herein is for instance specified as E, this means that the compound is substantially free of the Z isomer; when a compound described herein is for instance specified as cis, this means that the compound is substantially free of the trans isomer.

As used herein, any chemical formula with bonds shown only as solid lines and not as solid wedged or hashed wedged bonds, or otherwise not indicated as having a particular configuration (e.g. R, S) around one or more atoms, contemplates each possible stereoisomer, or mixture of two or more stereoisomers.

The terms "stereoisomers", "stereoisomeric forms" or "stereochemically isomeric forms" hereinbefore or hereinafter are used interchangeably.

Enantiomers are stereoisomers that are non-superimposable mirror images of each other. A 1:1 mixture of a pair of enantiomers is a racemate or racemic mixture.

Atropisomers (or atropisomers) are stereoisomers which have a particular spatial configuration, resulting from a restricted rotation about a single bond, due to large steric hindrance. All atropisomeric forms of the compounds described herein are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the present disclosure includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The methods and formulations described herein include the use of N-oxides (if appropriate), crystalline forms (also known as polymorphs), solvates and hydrates (also known as pseudo-polymorphs), pharmaceutically acceptable salts, and combinations thereof, of compounds having the structures presented herein, as well as active metabolites of these compounds having the same type of activity.

In some embodiments, compounds described herein, are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

In specific embodiments, the compounds described herein exist in solvated forms with pharmaceutically acceptable solvents such as water, ethanol, and the like. In other embodiments, the compounds described herein exist in unsolvated form.

In some embodiments, the compounds described herein include solvent addition forms or crystal forms thereof, particularly solvates or polymorphs. As used herein, the term "solvate" means a physical association of the compounds of the present invention with one or more solvent molecules, as well as pharmaceutically acceptable addition salts thereof. This physical association involves varying degrees of ionic and covalent bonding, including hydrogen bonding. In certain instances, the solvate will be capable of isolation, for example when one or more solvent molecules are incorporated in the crystal lattice of the crystalline solid. The term "solvate" is intended to encompass both solution-phase and isolatable solvates. Solvates contain either stoichiometric or non-stoichiometric amounts of a solvent, and may be formed during the process of crystallization with pharmaceutically acceptable solvents such as water, ethanol, isopropanol, methanol, DMSO, ethyl acetate, acetic acid, ethanolamine and the like. Hydrates are formed when the solvent is water, or alcoholates are formed when the solvent is alcohol. The compounds described herein may exert their biological effects whilst they are in solution.

The salt forms of the compounds presented herein are typically pharmaceutically acceptable salts, and examples of pharmaceutically acceptable salts are discussed in Berge et al. (1977) "Pharmaceutically Acceptable Salts," J. Pharm. Sci., Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The pharmaceutically acceptable salts include pharmaceutically acceptable acid and base addition salts and are meant to comprise the therapeutically active non-toxic acid and base addition salt forms that the compounds described herein are able to form.

The salts of the present disclosure can be synthesized from the parent compound that contains a basic or acidic moiety by conventional chemical methods such as methods described in "Pharmaceutical Salts: Properties, Selection, and Use", P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

The pharmaceutically acceptable acid addition salts can conveniently be obtained by treating the base form with such appropriate inorganic acid (such as hydrochloric acid, hydrobromic acid, sulfuric acid, nitric acid, phosphoric acid and the like) or organic acids such (as acetic acid, methanesulfonic acid, maleic acid, tartaric acid, citric acid and the like) in an anion form.

Appropriate anions comprise, for example, acetate, 2,2-dichloroacetate, adipate, alginate, ascorbate (e.g. L-ascorbate), L-aspartate, benzenesulfonate, benzoate, 4-acetamidobenzoate, butanoate, bicarbonate, bitartrate, bromide, (+) camphorate, camphor-sulphonate, (+)-(1S)-camphor-10-sulphonate, calcium edetate, camsylate, caprate, caproate, caprylate, carbonate, chloride, cinnamate, citrate, cyclamate, dihydrochloride, dodecylsulphate, edetate, estolate, esylate, ethane-1,2-disulphonate, ethanesulphonate, formate, fumarate, galactarate, gentisate, glucoheptonate, gluceptate, gluconate, D-gluconate, glucuronate (e.g. D-glucuronate), glutamate (e.g. L-glutamate), α-oxoglutarate, glycolate, glycollylarsanilate, hexylresorcinate, hippurate, hydrabamine, hydrobromide, hydrochloride, hydriodate, 2-hydroxyethane-sulphonate, hydroxynaphthoate, iodide, isethionate, lactate (e.g. (+)-L-lactate, (±)-DL-lactate), lactobionate, malate, (−)-L-malate, maleate, malonate, mandelate, (±)-DL-mandelate, mesylate, methanesulfonate, methylbromide, methylnitrate, methylsulfate, mucate, naphthalenesulphonate (e.g. naphthalene-2-sulphonate), naphthalene-1,5-disulphonate, 1-hydroxy-2-naphthoate, napsylate, nicotinate, nitrate, oleate, orotate, oxalate, palmitate, pamoate (embonate), pantothenate, phosphate/diphosphate, propionate, polygalacturonate, L-pyroglutamate, pyruvate, salicylate, 4-amino-salicylate, sebacate, stearate, subacetate, succinate, sulfate, tannate, tartrate, (+)-L-tartrate, teoclate, thiocyanate, toluenesulphonate (e.g. p-toluenesulphonate), tosylate, triethiodide, undecylenate, valeric acids, as well as acylated amino acids and cation exchange resins. Conversely said salt forms can be converted by treatment with an appropriate base into the free base form.

The compounds of the present disclosure containing an acidic proton may also be converted into their nontoxic metal or amine addition salt forms by treatment with appropriate organic and inorganic bases in a cation form. Appropriate basic salts comprise those formed with organic cations such as arginine, benzathine, benzylamine, butylamine, chloroprocaine, choline, diethanolamine, dicyclohexylamine, diethanolamine, diethylamine, ethanolamine, ethylamine, ethylenediamine, lysine, meglumine, phenylbenzylamine, piperazine, procaine, triethylamine, tromethamine, and the like; those formed with ammonium ion (i.e., $NH_4^+$), quaternary ammonium ion $N(CH_3)_4^+$, and substituted ammonium ions (e.g., $NH_3R^+$, $NH_2R_2^+$, $NHR_3^+$, $NR_4^+$); and those formed with metallic cations such as aluminum, calcium, lithium, magnesium, potassium, sodium, zinc, and the like. Where the compounds described herein contain an amine function, these may form quaternary ammonium salts, for example by reaction with an alkylating agent according to methods well known to the skilled person. Such quaternary ammonium compounds are within the scope of the compounds presented herein.

Conversely said salt forms can be converted by treatment with an appropriate acid into the free form.

The screening and characterization of the pharmaceutically acceptable salts, polymorphs and/or solvates may be accomplished using a variety of techniques including, but not limited to, thermal analysis, X-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravimetric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). Solid State NMR (SS-NMR) is also known as Magic Angle Spinning NMR or MAS-NMR. The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Vivekkumar K. and Bari S. "Prodrug Design", Academic Press, 2016; Rautio, J. and Laine, K. "Prodrugs in Drug Design and Development" in "Textbook of Drug Design and Development", Strømgaard, Krogsgaard-Larsen, and Madsen, Ed. 5, 2017, Chapter 10; and Di and Kerns, "Prodrugs" in "Drug-Like Properties", 2016, $2^{nd}$. Ed. 471-485, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like.

Prodrug forms of the herein described compounds, wherein the prodrug is metabolized in vivo to produce a compound of the present disclosure, as set forth herein, are included within the scope of the claims. In some cases, some of the herein-described compounds may be a prodrug for another derivative or active compound.

In some embodiments, sites on the compounds disclosed herein are susceptible to various metabolic reactions. Therefore, incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

The compounds of the present disclosure include compounds that are isotopically labeled, i.e., with one or more isotopic substitutions. These compounds are identical to those recited in the various formulae and structures presented herein, but for the fact that one or more atoms are replaced by an atom having an atomic mass or mass number different from the atomic mass or mass number usually found in nature. A reference to a particular element includes within its scope all isotopes of the element, either naturally occurring or synthetically produced, either with natural abundance or in an isotopically enriched form. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment of the invention, the compounds contain no radioactive isotopes. In another embodiment, the compound may contain one or more radioisotopes. Compounds containing such radioisotopes may also be useful in a diagnostic context. Radiolabeled compounds described herein may comprise a radioactive isotope selected from the group of $^{2}H$, $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$. In particular, deuterated compounds are intended to be included within the scope of the present invention. In some embodiments, metabolic sites on the compounds described herein are deuterated.

Throughout the specification, groups and substituents thereof can be chosen to provide stable moieties and compounds.

Synthesis of Compounds

In this section, as in all other sections of this application unless the context indicates otherwise, references to formula (I) also include all other sub-groups and examples thereof as defined herein.

The synthesis of compounds described herein are accomplished using means described in the chemical literature, using the methods described herein, or by a combination thereof. In addition, solvents, temperatures and other reaction conditions presented herein may vary. Techniques and materials recognized in the field are described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein.

The starting materials and reagents used for the synthesis of the compounds described herein may be synthesized or obtained from commercial sources, such as, but not limited to, Sigma-Aldrich, FischerScientific (Fischer Chemicals), and AcrosOrganics.

In the reactions described herein, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyl dimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as acetyl, trifluoroacetyl, t-butoxycarbonyl (Boc), benzyloxycarbonyl (CBz), and 9-fluorenylmethyleneoxycarbonyl (Fmoc). Carboxylic acid reactive moieties may be protected by conversion to simple ester compounds as exemplified herein, which include conversion to alkyl esters, or they may be blocked with oxidativelyremovable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a $Pd^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

Me

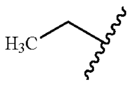
Et

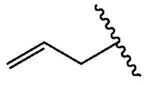
allyl

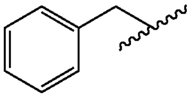
Bn

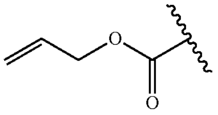
alloc

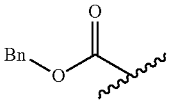
Cbz

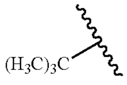
t-butyl

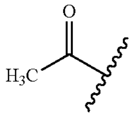
acetyl

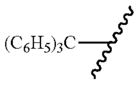
trityl

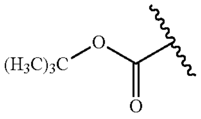
Boc

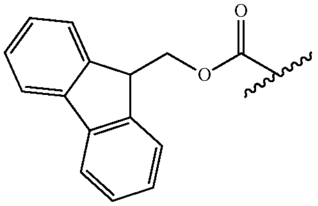
Fmoc

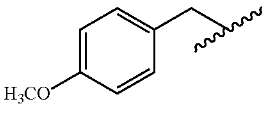
PMB

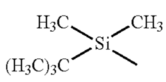
TBDMS

Other protecting groups, plus a detailed description of techniques applicable to the creation of protecting groups and their removal are described in T. W. Greene and P. G. M. Wuts, Protective Groups in Organic Synthesis, 4th ed., Wiley, Hoboken, New Jersey, 2007, which is incorporated herein by reference for such disclosure.

Schemes of Synthesis

Compounds of Formula (I) and intermediates thereof, wherein all variables are as defined in the present disclosure, may be prepared according to the reaction schemes presented in the Figures, where LG represents a leaving group, such as for example ester, acyl chloride; and PG represents a suitable protecting group, as exemplified herein above.

In scheme 1 (see FIG. 1), the following definition applies: $A^4$ represents a nitrogen.

The conditions of each of the reactions depicted in Scheme 1 may be the following:

Reaction 1: an intermediate of formula (X) may be reacted with a Bredereck's reagent in a suitable solvent, such as toluene. The resulting compound may be cyclized in the presence of 2-Methyl-2-thiopseudourea hemisulfate, a suitable base, such as for example sodium ethoxide in a suitable solvent, such as for example EtOH. The resulting compound may be oxidized in the presence of meta-chloroperbenzoic acid in a suitable solvent, such as DCM, resulting in a compound of formula (XI).

Reaction 2: an intermediate of formula (XI) may be deprotected in the presence of Trifluoroacetic acid in a suitable solvent, such as DCM, resulting in a compound of formula (XII).

Reaction 3: an intermediate of formula (XII) may be reacted with an intermediate of formula (XIII) in the presence of a suitable base such as for example triethylamine and a suitable solvent, such as for example DCM, resulting in a compound of formula (XV).

Reaction 4: an intermediate of formula (XII) may be reacted with diphosgene in the presence of a suitable base, such as for example triethylamine, and a suitable solvent, such as for example DCM. The resulting intermediate may be reacted with intermediate of formula (XIV), in the presence of a suitable base, such as for example triethylamine and a suitable solvent, such as for example DCM, resulting in a compound of formula (XV).

Reaction 5: an intermediate of formula (XV) may be reacted with an intermediate of formula (XVI), resulting in a compound of formula (I).

Reaction 6: an intermediate of formula (XI) may be reacted with an intermediate of formula (XVI), followed by deprotection in the presence of Trifluoroacetic acid in a suitable solvent, such as DCM, resulting in a compound of formula (XVIII).

Reaction 7: an intermediate of formula (X) may be reacted with a Bredereck's reagent in a suitable solvent, such as toluene. The resulting compound may be cyclized with an intermediate of formula (XVI) in the presence of a suitable base, such as sodium ethoxide and a suitable solvent, such as for example EtOH, providing a compound of formula (XVII).

Reaction 8: an intermediate of formula (XVII) may be converted into an intermediate of formula (XVIII) in the presence of HCl 4M and a suitable solvent or solvent mixture such as for example Dioxane and MeOH.

Reaction 9: an intermediate of formula (XVIII) may be reacted with an intermediate of formula (XIX) in the presence of HBTU (2-(1H-Benzotriazole-1-yl)-1,1,3,3-tetramethyluronium hexafluorophosphate), a suitable base, such as for example diisopropylethylamine, and a suitable solvent, such as for example DMF, resulting in a compound of formula (I).

Reaction 10: an intermediate of formula (XVIII) may be reacted with an intermediate of formula (XIII), in the presence of a suitable base, such as for example triethylamine and a suitable solvent, such as for example DCM, resulting in a compound of formula (I).

Figure 2:
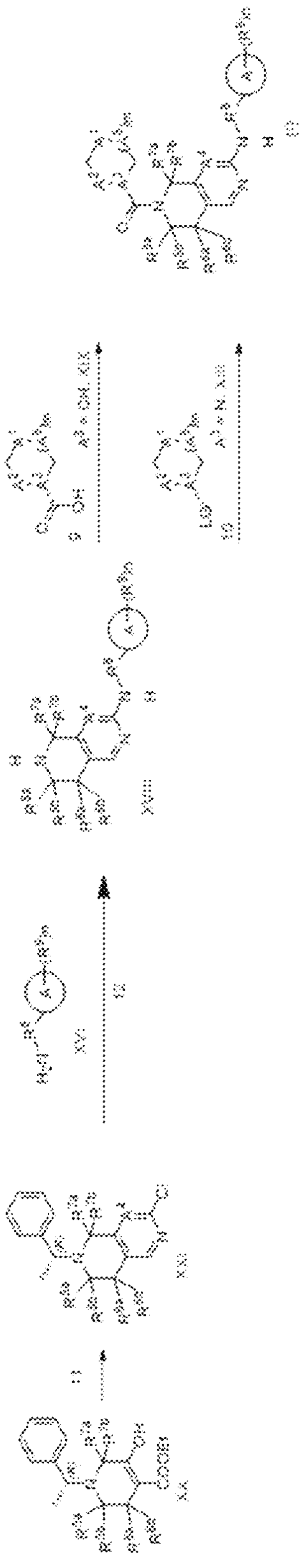
FIG. 2. Scheme 2.

In scheme 2 (see FIG. 2), the following definition applies: $A^4$ represents a nitrogen.

The conditions of each of the reactions depicted in Scheme 2 may be the following:

Reaction 11: an intermediate of formula (XX) may be reacted with urea in the presence of a suitable base, such as sodium methoxide and a suitable solvent, such as for example MeOH. The resulting compound may be reacted with $POCl_3$ and finally converted into an intermediate of formula (XXI) in the presence of Zinc activated, ammonia, $NH_3$ (28% in $H_2O$) and a suitable solvent, such as for example EtOH.

Reaction 12: an intermediate of formula (XXI) may be reacted with an intermediate of formula (XVI) in the presence of a suitable catalyst, such as for example RuPhos Pd G3, a suitable base, such as sodium tert-butoxide and a suitable solvent, such as for example toluene. The resulting compound may be deprotected in the presence of hydrogen and 10% Pd/C in a suitable solvent, such as for example, MeOH, resulting in a compound of formula (XVIII).

Figure 3:
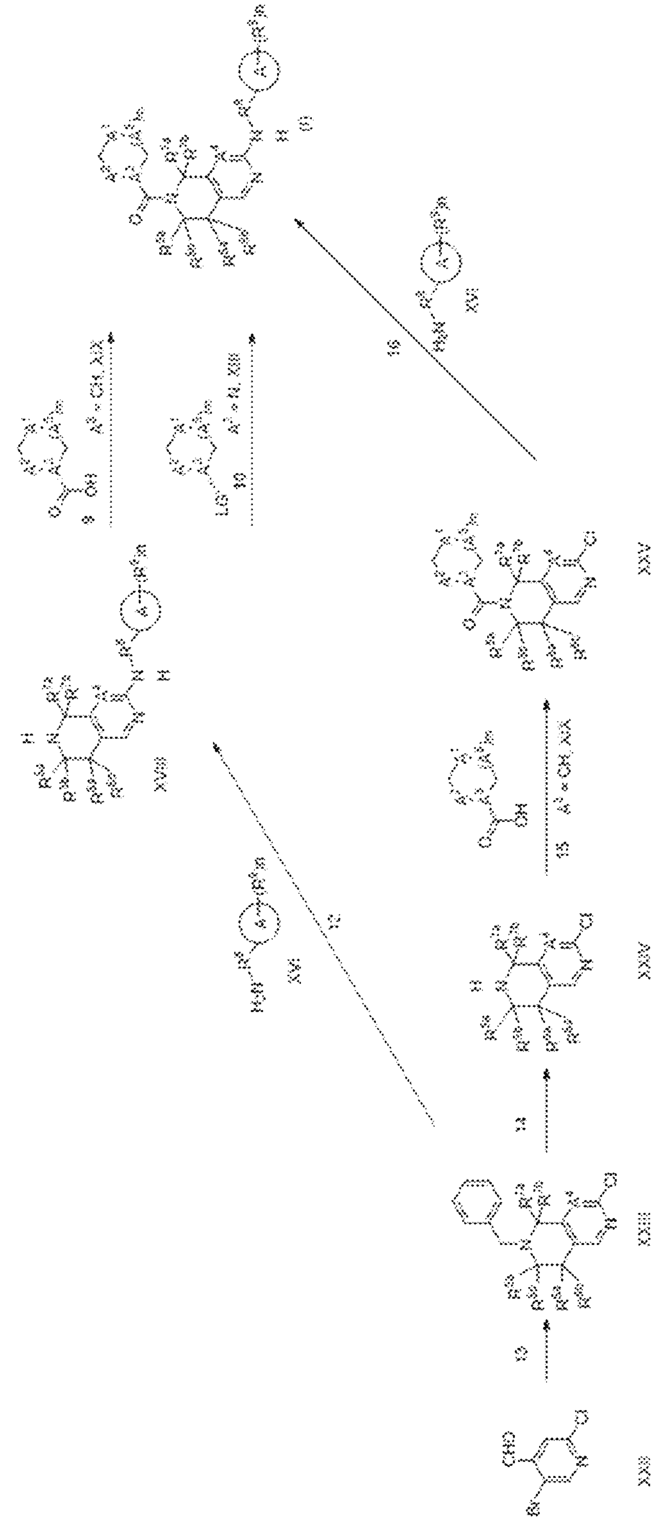
FIG. 3. Scheme 3.

In scheme 3 (see FIG. 3), the following definition applies: $A^4$ represents CH.

The conditions of each of the reactions depicted in Scheme 3 may be the following:

Reaction 13: an intermediate of formula (XXII) may be reacted in the presence of propyne, a suitable catalyst, such as for example $PdCl_2(TPP)_2$, Copper Iodide, a suitable base, such as for example triethylamine, and a suitable solvent, such as for example DMF. The resulting intermediate may be reacted with tert-Butylamine in a suitable solvent, such as for example water. The resulting intermediate may be cyclized with copper iodide in a suitable solvent, such as for example DMF. The resulting intermediate may be alkylated with benzyl bromide in a suitable solvent, such as for example $CH_3CN$. The resulting intermediate may be reduced with sodium Borohydride in a suitable solvent, such as for example MeOH, resulting in a compound of formula (XXIII).

Reaction 14: an intermediate of formula (XXIII) may be deprotected with 1-Chloroethyl chloroformate, in a suitable base, such as for example potassium carbonate, in a suitable solvent, such as for example dichloroethane, resulting in compound of formula (XXIV).

Reaction 15: an intermediate of formula (XXIV) may be reacted with an intermediate of formula (XIX) in the presence of HBTU (2-(1H-Benzotriazole-1-yl)-1,1,3,3-tetramethyluronium hexafluorophosphate), a suitable base, such as for example diisopropylethylamine, and a suitable solvent, such as for example DMF, resulting in a compound of formula (XXV).

Reaction 16: an intermediate of formula (XXV) may be reacted in the presence of an intermediate of formula (XVI), a suitable catalyst, such as for example RuPhos Pd G3, a suitable base, such as for example Sodium tert-butoxide, and a suitable solvent, such as for example toluene, resulting in compound of formula (I).

Figure 4:
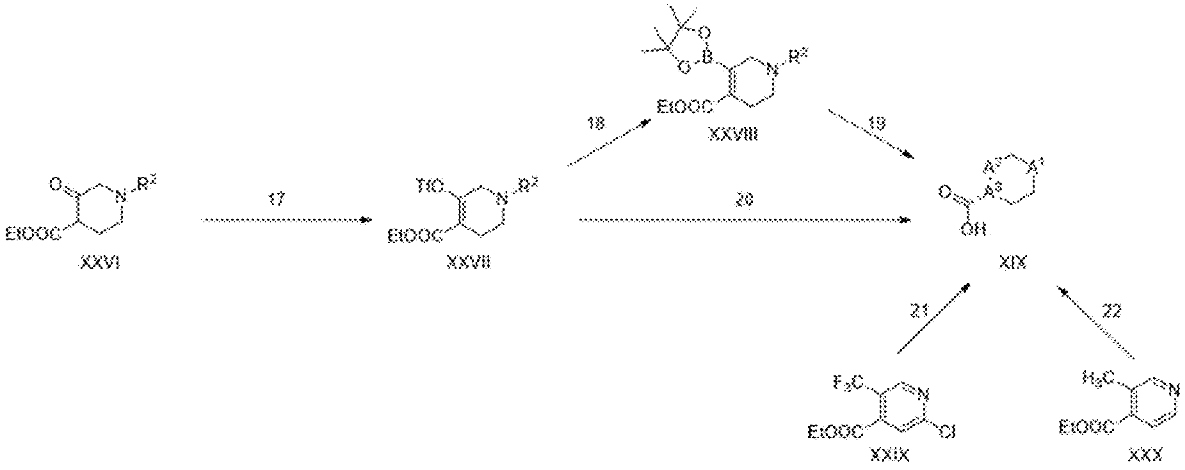
FIG. 4. Scheme 4.

In scheme 4 (see FIG. 4), the following definitions apply: $A^1$=$NR^2$, $A^2$=$CR^{3a}R^{3b}$, $A^3$=CH.

The conditions of each of the reactions depicted in Scheme 4 may be the following:

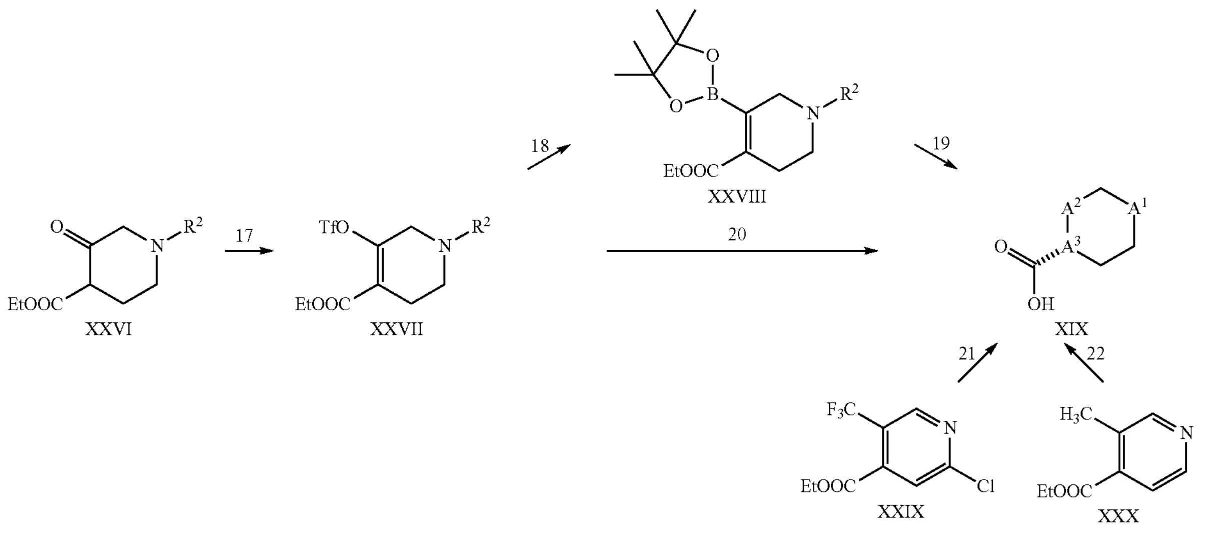

Reaction 17: an intermediate of formula (XXVI) may be converted into an intermediate of formula (XXVII) in the presence of Trifluoromethanesulfonic anhydride, a suitable base, such as for example diisopropylethylamine, and a suitable solvent, such as for example toluene.

Reaction 18: an intermediate of formula (XXVII) may be reacted with Bis(pinacolato)diboron, a suitable catalyst, such as for example Pd(dppf)$Cl_2$·$CH_2Cl_2$, a suitable base, such as for example potassium acetate, and a suitable solvent, such as for example Dioxane, resulting in a compound of formula (XXVIII).

Reaction 19: an intermediate of formula (XXVIII) may be reacted in the presence of an arylbromide, a suitable catalyst, such as for example bis(triphenylphosphine)palladium(II) dichloride, a suitable base, such as sodium carbonate 1M, and a suitable solvent, such as for example dioxane. The resulting intermediate may be converted into an intermediate of formula (XIX) in the presence of HCl 6M and water.

Reaction 20: an intermediate of formula (XXVII) may be reacted in the presence of an arylboronic acid, pinacol ester, a suitable catalyst, such as for example bis(triphenylphosphine)palladium(II) dichloride, a suitable base, such as sodium carbonate 1M, and a suitable solvent, such as for example dioxane. The resulting intermediate may be converted into an intermediate of formula (XIX) in the presence of HCl 6M and water.

Reaction 21: 4-Pyridinecarboxylic acid, 2-chloro-5-(trifluoromethyl)-, ethyl ester may be hydrogenated with 10% Pd/C, in 37% HCl and a suitable solvent, such as for example MeOH. The resulting intermediate may be reacted with aqueous formaldehyde 37% and Sodium triacetoxyborohydride in a suitable solvent, such as for example THF, resulting in a compound of formula (XIX).

Reaction 22: 4-Pyridinecarboxylic acid, 3-methyl-, ethyl ester may be hydrogenated with 10% Pd/C, in 37% HCl and a suitable solvent, such as for example MeOH. The resulting intermediate may be reacted with aqueous formaldehyde 37% and Sodium triacetoxyborohydride in a suitable solvent, such as for example THF, resulting in a compound of formula (XIX).

The skilled person will realize that another sequence of the chemical reactions shown in the Schemes below, may also result in the desired compound of formula (I).

The skilled person will realize that intermediates and final compounds shown in the schemes below may be further functionalized according to methods well-known by the person skilled in the art.

The compounds of formula (I) may also be converted into each other via art-known reactions or functional group transformations. For instance, substituents like —C(=O)—O—$C_{1-6}$alkyl or $C_{1-6}$alkyl-O—C(=O)—, can be converted into HOOC—$C_{1-6}$alkyl or carboxyl in the presence of lithium hydroxide, and in the presence of a suitable solvent, such as for example tetrahydrofuran or an alcohol, e.g. methanol.

The skilled person will realize that in the reactions described in the Schemes, in certain cases it may be advisable or necessary to perform the reaction under an inert atmosphere, such as for example under $N_2$-gas atmosphere.

It will be apparent for the skilled person that it may be necessary to cool the reaction mixture before reaction work-up, meaning those series of manipulations required to isolate and purify the product(s) of a chemical reaction such as for example quenching, column chromatography, or extraction.

The skilled person will realize that heating the reaction mixture under stirring may enhance the reaction outcome. In some reactions microwave heating may be used instead of conventional heating to shorten the overall reaction time.

The compounds of the invention as prepared in the processes described herein may be synthesized in the form of mixtures of enantiomers, in particular racemic mixtures of enantiomers, that can be separated from one another following art-known resolution procedures. Racemic compounds of formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I), and the pharmaceutically acceptable addition salts and solvates thereof, involves liquid chromatography using a chiral stationary phase e.g. by supercritical fluid chromatography. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In all these preparations, the reaction products may be isolated from the reaction medium and, if necessary, further purified according to methodologies generally known in the art such as, for example, extraction, crystallization, trituration and chromatography. The purity of the reaction products may be determined according to methodologies generally known in the art such as for example LC-MS, TLC, HPLC.

Methods of Treatment and Medical Uses, Pharmaceutical Compositions and Combinations The present invention also provides methods for the treatment or prevention of a proliferative disease (e.g., cancer, benign neoplasm, angiogenesis, inflammatory disease, autoinflammatory disease, or autoimmune disease) or an infectious disease (e.g., a viral disease) in a subject. Such methods comprise the step of administering to the subject in need thereof an effective amount of a compound of the present disclosure, or a pharmaceutically acceptable salt, solvate, hydrate, tautomer, stereoisomer, or isotopically labeled derivative thereof, or a pharmaceutical composition thereof.

The subject being treated is a mammal. The subject may be a human. The subject may be a domesticated animal, such as a dog, cat, cow, pig, horse, sheep, or goat. The subject may be a companion animal such as a dog or cat. The subject may be a livestock animal such as a cow, pig, horse, sheep, or goat. The subject may be a zoo animal. The subject may be a research animal such as a rodent, dog, or non-human primate. The subject may be a non-human transgenic animal such as a transgenic mouse or transgenic pig.

The proliferative disease to be treated or prevented using the compounds of Formula (I) or Formula (II) will typically be associated with aberrant activity of CDK7. Aberrant activity of CDK7 may be an elevated and/or an inappropriate (e.g., abnormal) activity of CDK7. In certain embodiments, CDK7 is not overexpressed, and the activity of CDK7 is elevated and/or inappropriate. In certain other embodiments, CDK7 is overexpressed, and the activity of CDK7 is elevated and/or inappropriate. The compounds of the present disclosure, and pharmaceutically acceptable salts, solvates, hydrates, tautomers, stereoisomers, isotopically labeled derivatives, and compositions thereof, may inhibit the activity of CDK7 and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Inhibition of the activity of CDK7 is expected to cause cytotoxicity via induction of apoptosis. The compounds of the present disclosure, and pharmaceutically acceptable salts, solvates, hydrates, tautomers, stereoisomers, isotopically labeled derivatives, and compositions thereof, may induce apoptosis, and therefore, be useful in treating and/or preventing proliferative diseases.

In certain embodiments, the proliferative disease to be treated or prevented using the compounds of the present disclosure is cancer. All types of cancers disclosed herein or known in the art are contemplated as being within the scope of the invention.

The compounds of the present invention may be useful in the treatment of a variety of cancers, including but not limited to carcinoma, including that of the breast, liver, lung, colon, kidney, bladder, including small cell lung cancer, non-small cell lung cancer, head and neck, thyroid, esophagus, stomach, pancreas, ovary, gall bladder, cervix, prostate and skin, including squamous cell carcinoma; hematopoietic tumors of lymphoid lineage, including leukemia, acute lymphoblastic leukemia, acute lymphocytic leukemia, Hodgkin's lymphoma, non-Hodgkin's lymphoma, B-cell lymphoma, T-cell lymphoma, hairy cell lymphoma, myeloma, mantle cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including seminoma, melanoma, osteosarcoma, teratocarcinoma, keratoctanthoma, xenoderoma pigmentosum, thyroid follicular cancer and Kaposi's sarcoma.

The proliferative disease may be a cancer associated with dependence on BCL-2 anti-apoptotic proteins (e.g., MCL-1 and/or XIAP). The proliferative disease may be a cancer associated with overexpression of MYC (a gene that codes for a transcription factor). The proliferative disease may be a hematological malignancy. The proliferative disease may be a blood cancer. The proliferative disease may be leukemia. The proliferative disease may be chronic lymphocytic leukemia (CLL). The proliferative disease may be acute lymphoblastic leukemia (ALL). The proliferative disease may be T-cell acute lymphoblastic leukemia (T-ALL). The proliferative disease may be chronic myelogenous leukemia (CML). The proliferative disease may be acute myelogenous leukemia (AML). The proliferative disease may be lymphoma. The proliferative disease may be melanoma. The proliferative disease may be multiple myeloma. The proliferative disease may be a bone cancer. The proliferative disease may be osteosarcoma. The proliferative disease may be Ewing's sarcoma. The proliferative disease may be triple-negative breast cancer (TNBC). The proliferative disease may be a brain cancer. The proliferative disease may be neuroblastoma. The proliferative disease may be a lung cancer, small cell lung cancer (SCLC), or large cell lung cancer. The proliferative disease may be a benign neoplasm. All types of benign neoplasms disclosed herein or known in the art are contemplated as being within the scope of the invention.

The proliferative disease may be associated with angiogenesis. All types of angiogenesis disclosed herein or known in the art are contemplated as being within the scope of the invention.

The proliferative disease may be an inflammatory disease. All types of inflammatory diseases disclosed herein or known in the art are contemplated as being within the scope of the invention. The inflammatory disease may be rheumatoid arthritis. The proliferative disease may be an autoinflammatory disease. All types of autoinflammatory diseases disclosed herein or known in the art are contemplated as being within the scope of the invention. The proliferative disease may be an autoimmune disease. All types of autoimmune diseases disclosed herein or known in the art are contemplated as being within the scope of the invention.

The cell described herein may be an abnormal cell. The cell may be in vitro or in vivo. The cell may be a proliferative cell. The cell may be a blood cell. The cell may be a lymphocyte. The cell may be a cancer cell. The cell may be a leukemia cell. The cell may be a CLL cell. The cell may be a melanoma cell. The cell may be a multiple myeloma cell. The cell may be a benign neoplastic cell. The cell may be an endothelial cell. The cell may be an immune cell.

In another aspect, the present invention provides methods of downregulating the expression of CDK7 in a biological sample or subject.

In yet another aspect, the present invention provides the compounds of the present disclosure, and pharmaceutically acceptable salts, solvates, hydrates, tautomers, stereoisomers, isotopically labeled derivatives, and compositions thereof, for use in the treatment of a proliferative disease in a subject. The compounds described herein, and pharmaceutically acceptable salts and compositions thereof, may be used in inhibiting cell growth. The compounds described herein, and pharmaceutically acceptable salts and compositions thereof, may be used in inducing apoptosis in a cell. The compounds described herein, and pharmaceutically acceptable salts and compositions thereof, may be used in inhibiting transcription.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount may be from about 0.005 mg/kg to 50 mg/kg body weight. The amount of a compound according to the present invention, also referred to here as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment, the compounds according to the invention are preferably formulated prior to administration. As described herein below, suitable pharmaceutical formulations are prepared by known procedures using well known and readily available ingredients.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18th ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, or a nose spray. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The exact dosage and frequency of administration depends on the particular compound used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The methods described herein may also comprise the additional step of administering one or more additional pharmaceutical agents in combination with the compound of the present invention, a pharmaceutically acceptable salt thereof, or compositions comprising such compound or pharmaceutically acceptable salt thereof. Such additional pharmaceutical agents include, but are not limited to, anti-proliferative agents, anti-cancer agents, anti-diabetic agents, anti-inflammatory agents, immunosuppressant agents, and a pain-relieving agent. The additional pharmaceutical agent(s) may synergistically augment inhibition of CDK7 or CDK12 and/or CDK13 induced by the inventive compounds or compositions of this invention in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetrocarcin A;
- glucocorticoids, for example prednisone or prednisolone;
- antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, carminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, venetoclax, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- farnesyltransferase inhibitors for example tipifarnib;
- histone deacetylase (HDAC) inhibitors for example sodium butyrate, suberoylanilide hydroxamic acid (SAHA), depsipeptide (FR 901228), NVP-LAQ824, R306465, quisinostat, trichostatin A, vorinostat;
- Inhibitors of the ubiquitin-proteasome pathway for example PS-341, Velcade (MLN-341) or bortezomib;
- Yondelis;
- Telomerase inhibitors for example telomestatin;
- Matrix metalloproteinase inhibitors for example batimastat, marimastat, prinostat or metastat;
- Recombinant interleukins for example aldesleukin, denileukin diftitox, interferon alfa 2a, interferon alfa 2b, peginterferon alfa 2b;
- MAPK inhibitors;
- Retinoids for example alitretinoin, bexarotene, tretinoin;
- Arsenic trioxide;
- Asparaginase;
- Steroids for example dromostanolone propionate, megestrol acetate, nandrolone (decanoate, phenpropionate), dexamethasone;
- Gonadotropin releasing hormone agonists or antagonists for example abarelix, goserelin acetate, histrelin acetate, leuprolide acetate;
- Thalidomide, lenalidomide;
- Mercaptopurine, mitotane, pamidronate, pegademase, pegaspargase, rasburicase;
- BH3 mimetics for example ABT-199;
- MEK inhibitors for example PD98059, AZD6244, CI-1040;
- colony-stimulating factor analogs for example filgrastim, pegfilgrastim, sargramostim; erythropoietin or analogues thereof (e.g. darbepoetin alfa); interleukin 11;

oprelvekin; zoledronate, zoledronic acid; fentanyl; bisphosphonate; palifermin;

a steroidal cytochrome P450 17alpha-hydroxylase-17,20-lyase inhibitor (CYP17), e.g. abiraterone, abiraterone acetate;

mTOR inhibitors such as rapamycins and rapalogs, and mTOR kinase inhibitors;

PI3K inhibitors and dual mTOR/PI3K inhibitors; PI3K delta inhibitors for example idelalisib and duvelisib;

BTK inhibitors for example Ibrutinib, ONO-4059, ACP-196;

R-CHOP (Rituxan added to CHOP-Cyclophosphamide, Doxorubicin, Vincristine and Prednisolone);

Daratumumab.

Therefore, an embodiment of the present invention relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

EXAMPLES

The following examples are offered for purposes of illustration, and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific.

When a stereocenter is indicated with 'RS' this means that a racemic mixture was obtained.

For intermediates that may be used in a next reaction step as a crude or as a partially purified intermediate, theoretical mol amounts may be indicated in the reaction protocols described below.

Hereinafter, "DCM" and "$CH_2Cl_2$" means dichloromethane; "r.t." means room temperature; "Boc" means tert-butoxycarbonyl; "$CH_3CN$" and "ACN" means acetonitrile; "MeOH" means methanol; "EtOH" means ethanol; "iPrOH" means isopropanol; "DMF" means dimethylformamide; "$iPrNH_2$" means isopropylamine; "$SOCl_2$" means thionylchloride; "$Et_3N$" means triethylamine; "$NH_4OAc$" means ammonium acetate; "$NH_4OH$" means ammonium hydroxide; "$NH_4Cl$" means ammonium chloride; "$NaBH(OAc)_3$" means sodium triacetoxyborohydride; "$POCl_3$" means phosphorus oxychloride; "RuPhos Pd G3" means (2-Dicyclohexylphosphino-2',6'-diisopropoxy-1,1'-biphenyl)(2-(2'-amino-1,1'-biphenyl))palladium(II) methanesulfonate; "$Na_2CO_3$" means sodium carbonate; "$KHSO_4$" means potassium hydrogenasulfate, "HBTU" means 2-(1H-Benzotriazole-1-yl)-1,1,3,3-tetramethyluronium hexafluorophosphate; "EA" means ethylamine; "$NH_4HCO_3$" means ammonium bicarbonate; "TFA" means trifluoroacetic acid; "THF" means tetrahydrofuran; "h" means hours; "RM" means reaction mixture; "SFC" means Supercritical fluid chromatography; "Bredereck's reagent" means tert-Butoxy bis(dimethylamino)methane; "AcOEt" means ethyl acetate; "$K_2CO_3$" means potassium carbonate; "$MgSO_4$" means magnesium sulfate; "$Boc_2O$" means di-tert-butyl decarbonate.

Example A: Preparation of the Intermediates and the Final Compounds, and Characterization Thereof Synthesis of Intermediate 1:

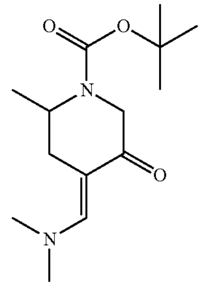 [SMILES: CC1C/C(=C\N(C)C)C(=O)CN1C(=O)OC(C)(C)C]

Bredereck's reagent (43 mL, 0.208 mol) was added slowly to a solution of 1-boc-2-methyl-piperidin-5-one (37 g, 0.173 mol) in toluene (370 mL) at room temperature. The reaction was stirred for 15 hours. The mixture was evaporated until dryness and the residue was used without purification for the next step.

Synthesis of Intermediate 2:

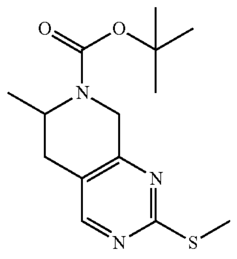

Sodium ethoxide (150 mL, 382.6 mmol) was added slowly to a mixture of intermediate 1 (46.6 g, 173.6 mmol) and 2-Methyl-2-thiopseudourea hemisulfate (48.3 g, 347.3 mmol) in EtOH (340 mL) at room temperature. The reaction was heated at 90° C. for 8 hours.

The reaction mixture was allowed to cool to room temperature, poured into $H_2O$ and NaCl, and extracted with AcOEt. The organic layer was dried over $MgSO_4$, filtered and evaporated until dryness. The residue was purified by flash chromatography (dryload:DCM/MeOH gradient from 100:0 to 98:2). The pure fractions were collected and evaporated yielding intermediate 2 (18.1 g, 35%).

Synthesis of Intermediate 3a and 3b:

3a

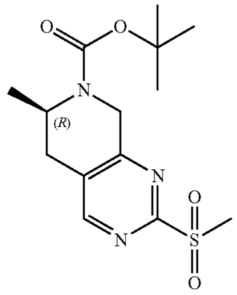

3b

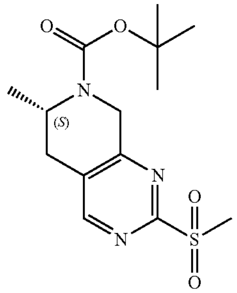

Meta-chloroperbenzoic acid (17.5 g, 71 mmol) was added portionwise to a solution of intermediate 2 (7.1 g, 24 mmol) in DCM (120 mL) at 5° C. The reaction was stirred for 2 hours. $H_2O$ was added and the mixture basified with $K_2CO_3$, stirred for 1 hour then the organic layer was extracted, dried over $MgSO_4$, filtered and evaporated, the residue was purified by flash chromatography ($DCM/MeOH/NH_4OH$ gradient from 100:0:0 to 95:5:0.2). The pure fractions were collected and evaporated yielding 5.68 g (72%) of both enantiomers.

Both enantiomers were separated by chiral SFC (Stationary phase: Chiralpak IG 5 µm 250*20 mm, Mobile phase: 70% $CO_2$, 30% mixture of EtOH/iPrOH 50/50 v/v) yielding intermediate 3b (2.48 g, 31%, enantiomer(S), $[\alpha]_d$: −70.2° (589 nm, c 0.32 w/v %, DMF, 20° C.)) and intermediate 3a (2.72 g, 34%, enantiomer (R), $[\alpha]_d$: +77.3° (589 nm, c 0.22 w/v %, DMF, 20° C.).

Synthesis of Intermediate 4:

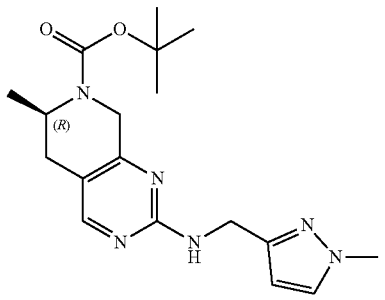

(1-Methyl-1H-pyrazol-3-yl)methylamine (5 g, 45 mmol) in a sealed tube was heated to 100° C. then intermediate 3a (1.8 g, 5.5 mmol) was added and the mixture was heated at 110° C. for 5 hours. The residue was purified without work up by flash chromatography ($DCM/MeOH/NH_4OH$ gradient from 100:0:0 to 95:5:0.2) yielding intermediate 4 (1.87 g, 83%).

Synthesis of Intermediate 5:

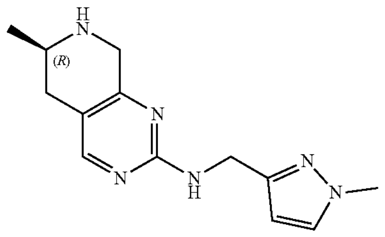

Trifluoroacetic acid (15 mL, 0.196 mol) was added slowly to a solution of intermediate 4 (7.18 g, 20 mmol) in dichloromethane (110 mL) at room temperature. The reaction was stirred for 15 hours. $H_2O$ was added and the mixture was basified with $K_2CO_3$. The organic layer was extracted, dried over $MgSO_4$, filtered and evaporated until dryness, yielding intermediate 5 (5.2 g, 100%).

Synthesis of Intermediate 6:

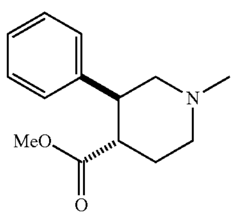 [SMILES: COC(=O)[C@H]1CCN(C)C[C@@H]1c1ccccc1]

NaH (16.3 g, 407.2 mmol) was added slowly to MeOH (300 mL) at room temperature under $N_2$. The mixture was stirred for 10 min at room temperature. Then 4-Piperidinecarboxylic acid, 1-methyl-3-phenyl-methyl ester (95 g, 407.2 mmol) in MeOH (500 mL) was added and the mixture was stirred at 80° C. under nitrogen atmosphere for 16 hours. MeOH was removed in vacuo. Aqueous $K_2CO_3$ was added and the mixture was extracted with DCM, the organic layer was dried over $MgSO_4$, filtered and evaporated until dryness, yielding intermediate 6 (88 g, 93%).

Synthesis of Intermediate 7a and 7b:

7a

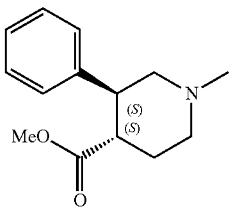

7b

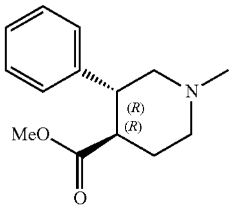

Intermediate 6 (74.7 g, 320.3 mmol) was purified by chiral SFC (Stationary phase: CHIRALPAK IC 5 μm 250*30 mm, Mobile phase: 94% $CO_2$, 6% iPOH (0.6% $iPrNH_2$)) yielding intermediate 7b (36.3 g, 48.5%) and of intermediate 7a (32.1 g, 42.9%).

Synthesis of Intermediate 8:

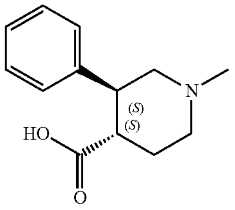

Intermediate 7a (32 g, 0.137 mol) in HCl 6M (470 ml) was heated at 100° C. overnight in a sealed tube. The reaction mixture was evaporated, taken up in toluene 3 times and dried, yielding intermediate 8 (30 g, 100%, $[\alpha]_d$: +56° (589 nm, c 0.55 w/v %, DMF, 20° C.).

Synthesis of Intermediate 9:

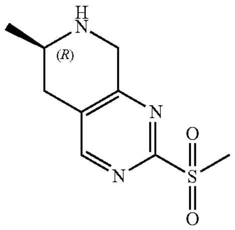

HCl 4M in dioxane (38 mL, 152 mmol) was added dropwise to a solution of intermediate 3a (5 g, 15.3 mmol) in dioxane (50 mL) at room temperature. The reaction mixture was stirred for 8 hours. The mixture was evaporated until dryness. The residue was taken up with $H_2O$, $K_2CO_3$ and DCM. The organic layer was extracted, dried over $MgSO_4$, filtered and evaporated until dryness, yielding intermediate 2 (3.4 g, 98%).

Synthesis of Intermediate 10:

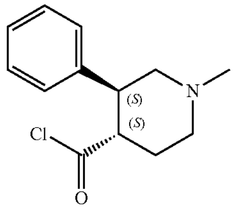

Intermediate 8 (5.4 g, 21.1 mmol) in $SOCl_2$ (108 mL, 1.64 g/mL, 1489 mmol) was stirred at 80° C. for 3 hours and cooled at room temperature. The solvent was removed, the compound was put into $N_2$ atmosphere and used without purification.

Synthesis of Intermediate 11:

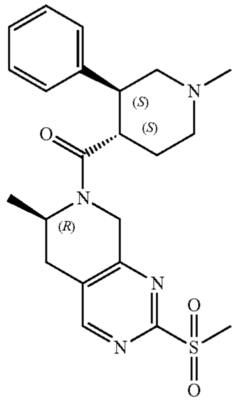

Intermediate 10 (5.7 g, 21.12 mmol) in DCM (45 mL) was added dropwise to a stirred solution of intermediate 2 (4 g, 17.6 mmol) and $Et_3N$ (9 mL, 65.12 mmol) in DCM (92 mL) at rt. The reaction mixture was stirred at rt for 2 hours, water was added and the organic layer was extracted (twice) with DCM, dried over $MgSO_4$, filtered and evaporated until dryness. The residue was purified by flash chromatography ($DCM/MeOH/NH_4OH$ gradient from 100:0:0 to 88:12:0.2). The pure fractions were collected and evaporated. The residue was purified by flash chromatography (Heptane/AcOEt gradient from 60:40 to 70:30). The pure fractions were collected and evaporated, yielding intermediate compound 10 (5 g, 66%).

Synthesis of Intermediate 12:

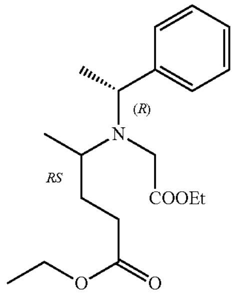

To a solution of Pentanoic acid, 4-[[(1R)-1-phenylethyl]amino]-, ethyl ester (70 g, 0.28 mol) and $NaBH(OAc)_3$ (116.2 g, 0.83 mol) in DCM (1 L) was added ethyl glyoxylate 50% toluene (116 mL, 0.55 mol) at rt. The resulting mixture was stirred at rt for 24 hours. Ethyl glyoxylate 50% toluene (59 mL, 0.28 mol) then $NaBH(OAc)_3$ (60 g, 0.283 mol) were added again and the reaction mixture was stirred for 20 hours and 2 days. The mixture was poured into a saturated solution of $NaHCO_3$. The organic layer was extracted, dried over $MgSO_4$, filtered and evaporated until dryness. The residue was purified by flash chromatography (Heptane/AcOEt gradient from 90:10 to 60:40), yielding intermediate 12 (59.2 g, 62%).

Synthesis of Intermediate 13:

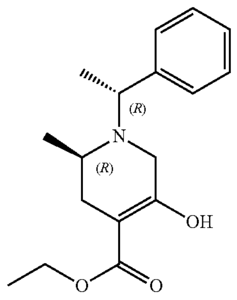

The reaction was performed in 2 batches in parallel:

Potassium tert-butylate (22.5 g; 0.2 mol) was added portionwise to a solution of intermediate 12 (29.6 g; 0.088 mol) in toluene (300 mL) at room temperature. The reaction was stirred for 8 hours, poured into $H_2O+NH_4Cl$ and extracted with AcOEt. The organic layer was dried over $MgSO_4$, filtered and evaporated. The residue was purified by flash chromatography (Heptane/AcOEt gradient from 100:0 to 95:5). The fractions were collected and evaporated until dryness, yielding intermediate 13 (23.1 g, 45%) and a mixture of the 2 diastereoisomers (3.6 g, 22:78 (R,R):(R,S)).

Synthesis of Intermediate 14:

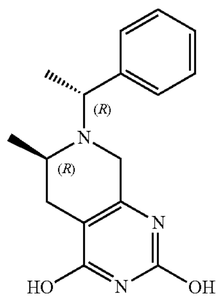

Sodium methoxide (29.5 mL, 160 mmol) was added slowly to a solution of intermediate 13 (23 g, 79.5 mmol), urea (19 g, 316 mmol) in MeOH at room temperature. The reaction was stirred for 23 hours to reflux, then heated again at 120° C. for 2 hours. MeOH was evaporated and the residue was taken up with a minimum volume of $H_2O$. The pH was adjusted around 8 with HCl 3M then 1M. The precipitate was filtered, washed with $H_2O$ and dried, yielding intermediate 14 (19.4 g, 85%).

Synthesis of Intermediate 15:

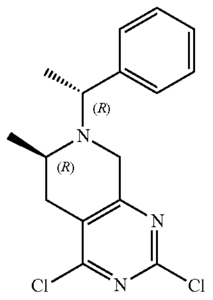

A mixture of intermediate 14 (17.4 g, 61 mmol) in $POCl_3$ (200 mL) was heated to 100° C. for 15 hours, then cooled to room temperature. $POCl_3$ was evaporated until dryness, the crude mixture was taken up into DCM and was poured onto ice and water under stirring (control of temperature below 40° C.). The organic layer was decanted and dried over $MgSO_4$, filtered then the solvent was evaporated until dryness. This mixture was purified by flash chromatography (DCM/MeOH gradient from 100:0 to 90:10). The fractions were collected and evaporated until dryness, yielding intermediate 15 (21.9 g, 100%).

Synthesis of Intermediate 16:

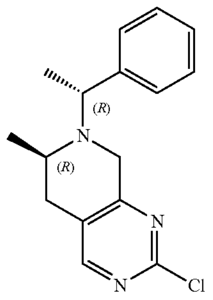

Intermediate 15 (21 g, 65.2 mmol), Zn activated (34.3 g, 0.524 mol), $NH_3$ (28% in $H_2O$) (21 mL, 0.333 mol) in EtOH (400 mL) were stirred in a round flask. The mixture was heated to reflux for 15 hours, cooled to room temperature then filtered. The insoluble was washed with DCM and the filtrate was evaporated until dryness, poured into $NH_4Cl+H_2O$, extracted with DCM. The organic layer was dried over $MgSO_4$, filtered and evaporated until dryness. The residue was purified by flash chromatography (DCM/MeOH gradient from 100:0 to 95:5). The fractions were collected and evaporated, yielding intermediate 16 (11.1 g, 59%).

Synthesis of Intermediate 17:

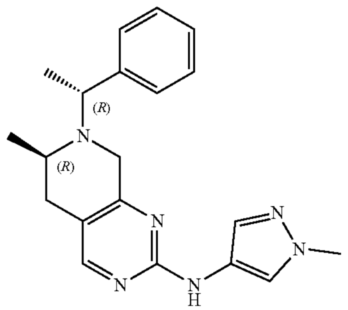

In a sealed vessel, 1-Methyl-1H-pyrazol-4-amine (1.2 g, 12.4 mmol) was added to a mixture of intermediate 16 (2.5 g, 8.7 mmol), RuPhos Pd G3 (371 mg, 0.44 mmol) and sodium tert-butoxide (2.1 g, 21.9 mmol) in toluene (110 mL) under $N_2$. The reaction was degassed under $N_2$ for 5 min. The reaction mixture was stirred at 120° C. for 2 hours. The mixture was poured into water and EtOAc, the organic layer was separated, dried over $MgSO_4$, filtered and evaporated. A purification was performed by flash chromatography (DCM/MeOH/$NH_4OH$ gradient from 100:0:0 to 95:5:0.2), yielding intermediate 17 (2.54 g, 84%).

Synthesis of Intermediate 18:

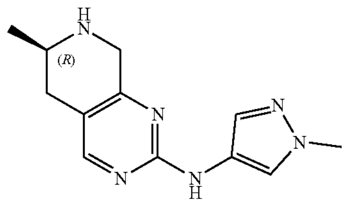

Intermediate 17 (2.54 g, 7.3 mmol) was hydrogenated at room temperature in MeOH (110 mL) with Pd/C (2 g, 1.9 mmol) as a catalyst at atmospheric pressure for 18 h. The catalyst was filtered through a pad of Celite®. The Celite® was washed twice with MeOH. The filtrate was evaporated to give intermediate 18 (1.73 g, 97%), used as it for next step.

Synthesis of Intermediate 19:

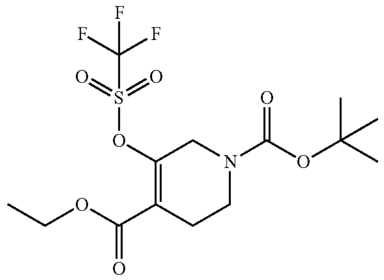 [SMILES: CCOC(=O)C1=C(OS(=O)(=O)C(F)(F)F)CN(C(=O)OC(C)(C)C)CC1]

Trifluoromethanesulfonic anhydride (13.6 mL, 81.1 mmol) was added to a solution of Ethyl 1-Boc-3-oxopiperidine-4-carboxylate (20 g, 73.7 mmol) and Diidopropylethylamine (19.3 mL, 110.6 mmol) in 180 mL of toluene at 0° C. The mixture was stirred at 0° C. for 16 h. Water was added and the mixture was extracted with AcOEt. The organic layer was separated, dried over $MgSO_4$, filtered and evaporated to afford intermediate 19 (32.8 g, 81.3 mmol, >100%) which was used without further purification.

Synthesis of Intermediate 20:

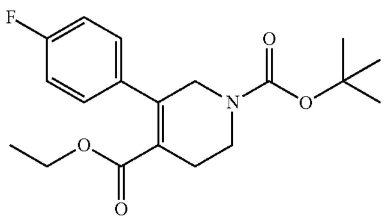 [SMILES: CCOC(=O)C1=C(c2ccc(F)cc2)CN(C(=O)OC(C)(C)C)CC1]

Intermediate 19 (4.4 g, 9.9 mmol), bis(triphenylphosphine)palladium(II) dichloride (696 mg, 1 mmol), 4-fluorophenylboronic acid, pinacol ester (3.3 g, 14.9 mmol) and sodium carbonate 1M (19.8 mL, 19.8 mmol) were taken in dioxane (100 mL), the mixture was bubbling with $N_2$ for 15 minutes and then it was heated at 80° C. for 2 hours. The mixture was filtered through a short pad of celite. $H_2O$ and AcOEt were added, the organic layer was washed with brine, dried over $MgSO_4$ and evaporated. The crude was purified by flash column chromatography (silica gel, AcOEt/Heptane, from 0/100 to 40/60). The desired fractions were collected, evaporated in vacuo and dried under high vacuum to give intermediate 20 (3 g, 87%) as a yellow oil.

Synthesis of Intermediate 21:

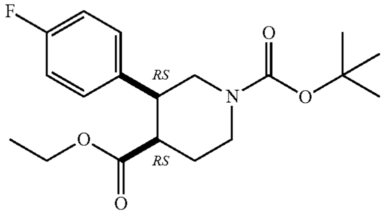 [SMILES: CCOC(=O)[C@@H]1CCN(C(=O)OC(C)(C)C)C[C@@H]1c1ccc(F)cc1]

Intermediate 20 (3.1 g, 8.4 mmol) was taken in MeOH. 10% Pd/C (540 mg, 5 mmol) was added and the reaction vessel was connected to a balloon filled with hydrogen. The mixture was stirred under atmosphere of hydrogen overnight at room temperature. The mixture was filtered through a pad of celite and the cake was washed with MeOH (5×10 mL) and concentrated to dryness, yielding intermediate 21 (3 g, 93%). The product was used as such for the next step.

Synthesis of Intermediate 22:

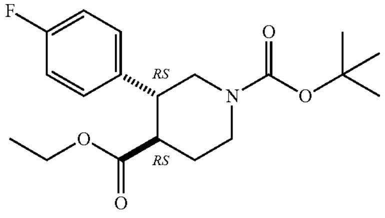 [SMILES: CCOC(=O)[C@@H]1CCN(C(=O)OC(C)(C)C)C[C@H]1c1ccc(F)cc1]

To a solution of intermediate 21 in 60 mL of EtOH under $N_2$ atmosphere, sodium ethylate (3.4 mL, 9 mmol) was added. The reaction mixture was heated at reflux for 3 hours. The reaction mixture was poured into an aqueous ammonium chloride solution, and the resultant mixture was extracted with ethyl acetate. The organic layer was dried over $MgSO_4$, filtered and concentrated under reduced pressure. The crude mixture was purified by flash column chromatography on silica gel using eluents Heptane/AcOEt (0:100 to 50:50), yielding intermediate 22 (2 g, 59%).

Synthesis of Intermediate 23:

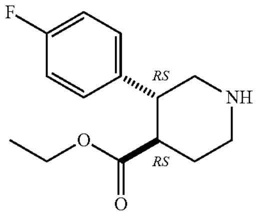 [SMILES: CCOC(=O)[C@@H]1CCNC[C@H]1c1ccc(F)cc1]

Trifluoroacetic acid (4.3 mL, 56 mmol) was added to solution of intermediate 22 (2 g, 5.6 mmol) in DCM (60 mL). The mixture was stirred overnight and was concentrated to dryness. The crude mixture was washed with toluene twice and concentrated to dryness. 1M $Na_2CO_3$ (15 mL) and DCM (75 mL) were added. The organic layer was separated, and the aqueous phase extracted once more with DCM. The combined organic layers were dried over MgSO4, filtered and concentrated in vacuo. Intermediate 23 was used as such for the next step (1.3 g, 95%).

Synthesis of Intermediate 24:

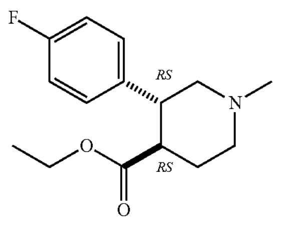

Intermediate 23 was taken in THF (15 mL) and treated with 37% aqueous formaldehyde (0.3 mL, 4 mmol) at room temperature. Sodium triacetoxyborohydride (0.8 g, 4 mmol) was then added after 15 minutes. The reaction mixture was stirred overnight. $Na_2CO_3$ was added and the mixture was extracted with DCM (2×50 mL). The combined organic layers were dried over $MgSO_4$, filtered and concentrated. The crude mixture was purified by chromatography over silica gel (25 g column, gradient of MeOH in DCM from 100:0 to 0:100) affording intermediate 24 (0.42 g, 80%).

Synthesis of Intermediate 25:

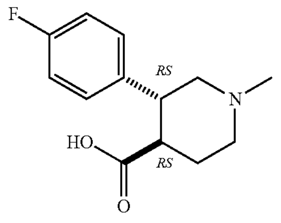

Intermediate 24, HCl 6M (0.7 mL, 1.6 mmol) and $H_2O$ (2 mL) were stirred at reflux overnight. The mixture was dried, at room temperature under high vacuum and used as such in the next synthetic step (438 mg, 1.6 mmol, 100%).

Synthesis of Intermediate 26a and 26b:

26a

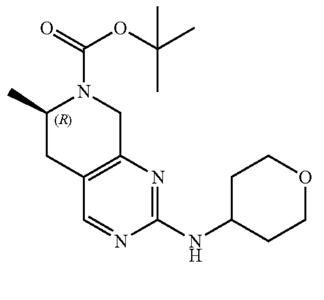

-continued

26b

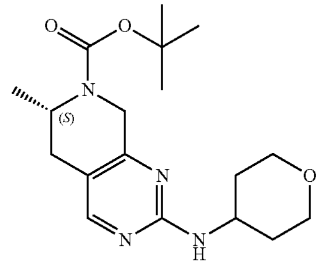

1-(tetrahydro-2H-pyran-4-yl) guanidine (22 g, 153.6 mmol) and Intermediate 1 (31.4 g, 117 mmol) were taken in EtOH (500 mL). Sodium ethoxide (100 mL, 255.7 mmol) was added and the resulting mixture was heated at 50° C. for 5.5 hours. The solution was partially evaporated and the residue was poured into $H_2O$+DCM. The organic layer was extracted, dried over $MgSO_4$, filtered and evaporated until dryness. The residue was purified by preparative LC (SiOH 35-40 μm Buchi, gradient from 100% DCM to 90% DCM 10% $CH_3OH$). The fractions were collected and evaporated until dryness to give 30.6 g. A purification was performed via chiral SFC (Stationary phase: CHIRALPAK AD-H 5 μm 250*30 mm, Mobile phase: 65% CO2, 35% EtOH) yielding Intermediate 26a (13 g, 32%, $[\alpha]_d$: +99.3° (589 nm, c 0.45 w/v %, DMF, 20° C.)) and Intermediate 26b (13.1 g, 32%, $[\alpha]_d$: −101.6° (589 nm, c 0.43 w/v %, DMF, 20° C.)).

Synthesis of Intermediate 27:

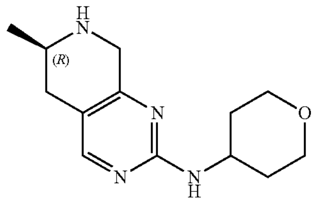

HCl 4M in Dioxane (91 mL, 364 mmol) was added to a solution of intermediate 26a (13 g, 37.3 mmol) in Dioxane (14 5 mL) and MeOH (45 mL) at room temperature. The reaction was stirred for 15 hours. The solvents were evaporated until dryness and the residue was taken up with DCM+$H_2O$+$K_2CO_3$. The organic layer was extracted, dried over $MgSO_4$, filtered and dried. The residue was purified by preparative LC (80 g of SiOH 35-40 μm Buchi, gradient from 100% DCM to 80% DCM 20% $CH_3OH$ 0.2% $NH_4OH$). The fractions were collected and evaporated until dryness, yielding intermediate 27 (8.2 g, 88%).

Synthesis of Intermediate 28:

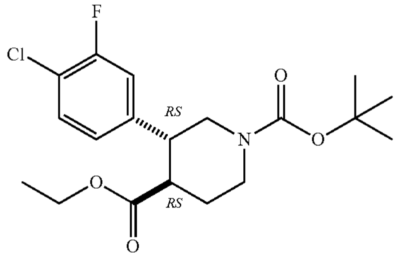

Intermediate 28 was prepared following the same procedure as for intermediate 22 replacing 4-fluorophenylboronic acid, pinacol ester by 3-fluoro4-chlorophenylboronic acid, pinacol ester.

Synthesis of Intermediate 29:

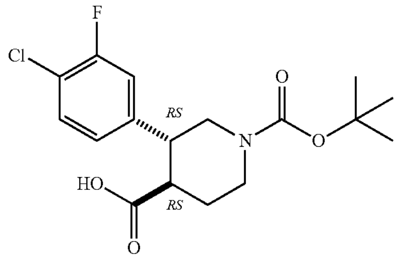

Sodium hydroxide 1M (19.5 mL, 19.5 mmol) was added to a solution of intermediate 28 (3.8 g, 9.8 mmol) in MeOH (50 mL). The mixture was stirred overnight at room temperature for 24 hours. The pH was brought to 2-3 with $KHSO_4$ 1M and the mixture was concentrated to dryness. The product (solid) was used as such for the next step (1.6 g, 47%).

Synthesis of Intermediate 30:

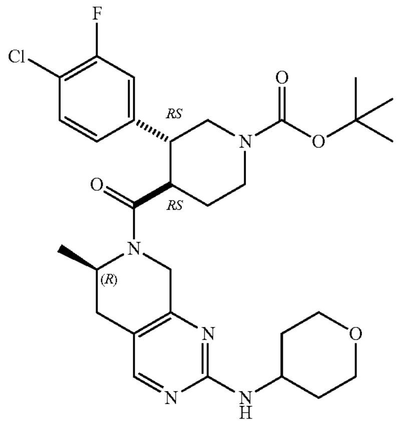

HBTU (2-(1H-Benzotriazole-1-yl)-1,1,3,3-tetramethyluronium hexafluorophosphate) (0.9 g, 2.4 mmol) was added to a solution of intermediate 29 (0.9 g, 2.6 mmol), intermediate 27 (0.5 g, 2 mmol) and diisopropylethylamine (0.7 ml, 4 mmol) in DMF (20 ml). The reaction was stirred overnight at room temperature for 8 hours. $Na_2CO_3$ (50 ml, 1M) was added and the reaction was extracted with ethylacetate (3×20 ml). The combined organic layers were washed with brine (50 ml), dried over $MgSO_4$, filtered and concentrated to afford the crude. Chromatography over silica gel (DCM/MeOH 100:0 to 0:100) afforded intermediate 30 (1.2 g, 98%).

Synthesis of Intermediate 31:

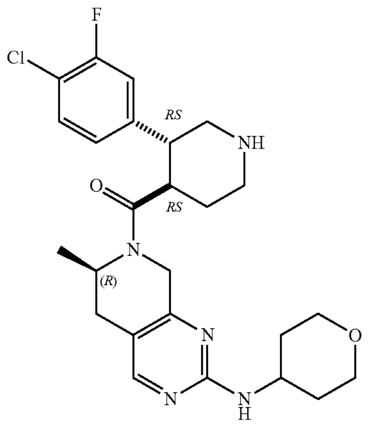

Trifluoroacetic acid (4.7 mL, 61.6 mmol) was added to a solution of intermediate 30 (1.2 g, 1.9 mmol) in DCM (20 mL) at room temperature. The mixture was stirred for 4 hours. Then, the solvent was evaporated under vacuum. The crude mixture was taken in DCM (20 mL) and the solution was washed with 1M $Na_2CO_3$ (30 mL). The organic layer was dried over $MgSO_4$, filtered and concentrated under vacuum. The crude mixture was purified by chromatography over silica gel (gradient of DCM/MeOH/$NH_4OH$, 9.0/0.9/0.1, v/v/v in DCM from 0 to 100%) affording the colourless oil intermediate 31 (0.6 g, 67%).

Synthesis of Intermediate 32a and 32b:

32a

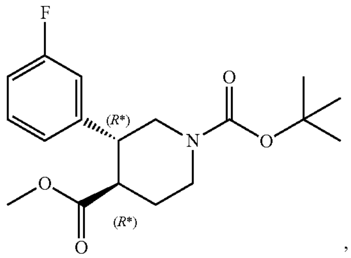

,

32b

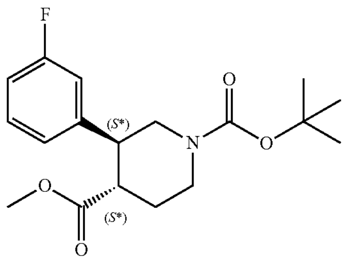

Same procedure as for Intermediate 22, replacing 4-fluorophenylboronic acid, pinacol ester by 3-fluorophenylboronic acid, pinacol ester. Both trans enantiomers were separated via chiral SFC (Stationary phase: CHIRACEL OJ-H 5 μm 250*30 mm, Mobile phase: 88% $CO_2$, 12% MeOH) yielding intermediate 32a (0.59 g, 21%, $[\alpha]_d$: +9° (589 nm, c 0.468 w/v %, DMF, 20° C.) and intermediate 32b (0.61 g, 22%, $[\alpha]_d$: −8° (589 nm, c 0.98 w/v %, DMF, 20° C.).

Synthesis of Intermediate 33:

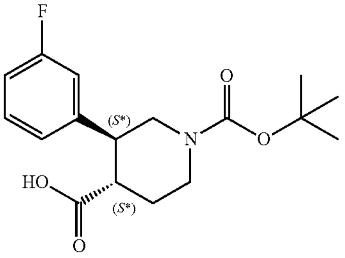 [SMILES: CC(C)(C)OC(=O)N1CC[C@H](C(=O)O)[C@@H](c2cccc(F)c2)C1]

Intermediate 32b (613 mg, 1.8 mmol) and Lithium hydroxide monohydrate (404 mg, 9.6 mmol) in THF/$H_2O$ (50/50) (10 mL) were stirred at rt for a weekend. HCl 3M (3.2 mL, 9.6 mmol) was added, and the reaction mixture was extracted. The organic layer was separated, dried over $MgSO_4$, filtered and evaporated yielding intermediate 33 (423 mg, 72%).

Synthesis of Intermediate 34:

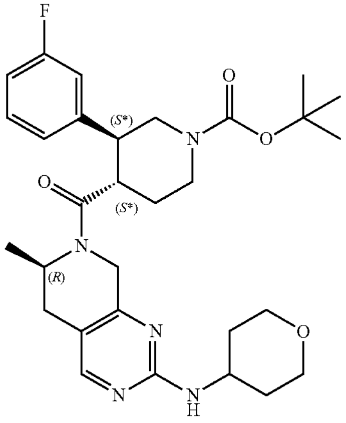

Intermediate 27 (200 mg, 0.8 mmol), intermediate 33 (434 mg, 1.2 mmol), HBTU (2-(1H-Benzotriazole-1-yl)-1, 1,3,3-tetramethyluronium hexafluorophosphate) (610 mg, 1.6 mmol), and diisopropylamine (0.8 mL, 4.8 mmol) were stirred in DMF (15 mL) at rt overnight.

$H_2O$ and DCM were added, the reaction mixture was extracted, and the organic layer was separated, dried over $MgSO_4$, filtered and evaporated. A purification was performed via preparative LC (Stationary phase: irregular SiOH 40 μm 25 g, Mobile phase: 98/2 to 90/10/0.1 DCM/MeOH/$NH_4OH$) yielding 450 mg (100%) of intermediate 34.

Synthesis of Intermediate 35:

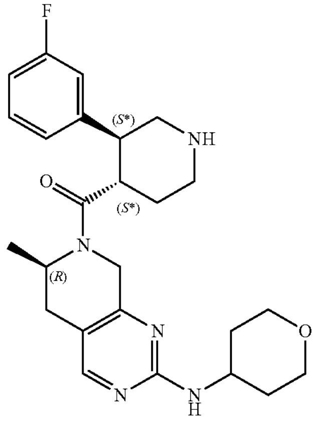

Intermediate 34 (380 mg, 0.81 mmol) and trifluoroacetic acid (0.93 mL, 12.2 mmol) were stirred in DCM (10 mL) at rt for 8h. Trifluoroacetic acid was evaporated. $H_2O$, DCM and $K_2CO_3$ were added, the reaction mixture was extracted, the organic layer was separated, dried over $MgSO_4$, filtered and evaporated yielding intermediate 35 (0.5 g, 95%).

Synthesis of Intermediate 36:

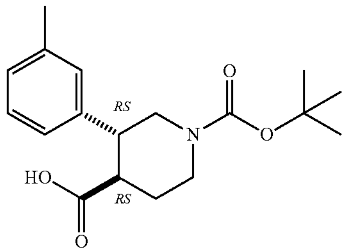

Intermediate 36 (3.49 g, 89%) was prepared following the same procedure as for intermediate 29.

Synthesis of Intermediate 37a and 37b:

37a

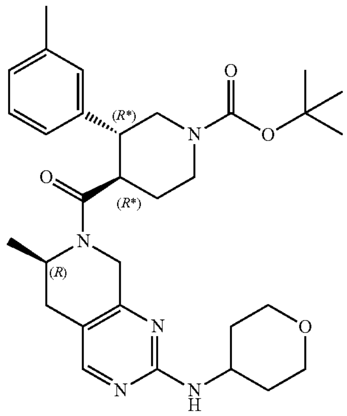

-continued

37b

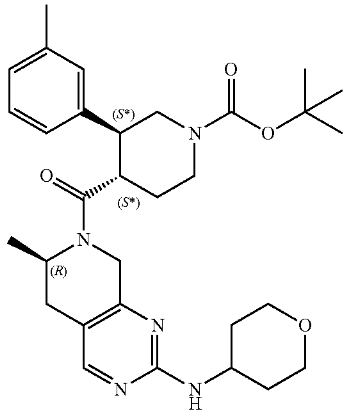

A mixture of intermediate 36 (1.54 g, 4.8 mmol), intermediate 27 (1 g, 4 mmol) and diisopropylethylamine (1.37 mL, 8.0 5 mmol) were taken in DMF (40 mL). HBTU (2-(1H-Benzotriazole-1-yl)-1,1,3,3-tetramethyluronium hexafluorophosphate) (1.8 g, 4.8 mmol) was added at room temperature. The reaction mixture was stirred overnight. AcOEt (200 mL) and 1M $Na_2CO_3$ (100 mL) were added. The aqueous phase was extracted once more with AcOEt (50 mL). The combined organic layers were washed with brine (50 mL), dried over $MgSO_4$, filtered and evaporated to dryness. The crude mixture was purified by chromatography over silica gel (gradient of MeOH in DCM from 0 to 5%) affording an amorphous solid. Separation of diastereoisomers was performed by reverse phase: Method MMP5-AC-ACN: gradient of ACN in 65 mM $NH_4OAc$ in water/ACN 9/1 from 28 to 64%. The two diastereoisomers were collected separately. The pH of both fractions was brought to 8 with 1M $Na_2CO_3$. Intermediates 37a and 37b were extracted with DCM (3 times). The organic layers were dried over $MgSO_4$, filtered and concentrated to white amorphous solids; yielding intermediate 37a (1.02 g, 46%) and intermediate 37b (0.65 g, 29%).

Synthesis of Intermediate 38:

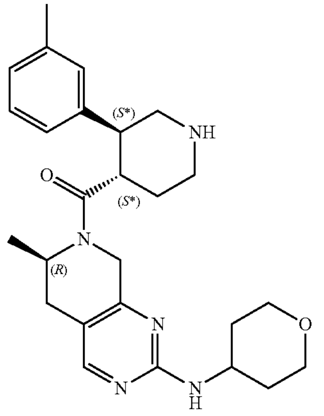

TFA (3.04 g, 39.4 mmol) was added to a solution of intermediate 37b (652 mg, 1.2 mmol) in DCM (20 mL) at room temperature. The mixture was stirred for 4 hours. The reaction mixture was concentrated to dryness. The crude mixture was taken in DCM (100 mL) and a solution 1M $Na_2CO_3$ (50 mL) was added. The organic layer was dried over $MgSO_4$, filtered and concentrated to the crude sticky solid. Flash chromatography over silica gel (gradient of DCM/MeOH/$NH_4OH$, 9.0/0.9/0.1 in DCM from 0 to 100%) gave intermediate 38 (552 mg, 94%) as an amorphous white solid.

Synthesis of Intermediate 39:

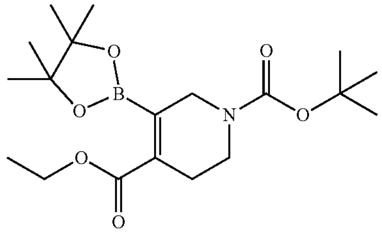 [SMILES: CCOC(=O)C1=C(B2OC(C)(C)C(C)(C)O2)CN(C(=O)OC(C)(C)C)CC1]

Intermediate 19 (10 g, 25 mmol), Bis(pinacolato)diboron (9.5 g, 37.5 mmol), Pd(dppf)$Cl_2$·$CH_2Cl_2$ (0.6 g, 0.75 mmol) and potassium acetate (7.3 g, 75 mmol) were suspended in dioxane (100 mL). The mixture was degassed by bubbling nitrogen for 15 minutes and then heated at 90° C. for 5 hours. The reaction mixture was allowed to cool to room temperature. Water (50 mL) and AcOEt (50 mL) were added. The organic layer was separated. The aqueous phase was extracted once more with AcOEt (25 mL). The combined organic layers were washed with saturated NaCl (25 mL), dried over $MgSO_4$, filtered and evaporated in vacuo. The residue was purified by flash column chromatography (silica gel; AcOEt in heptane 0/100 to 50/50) yielding an oil (7.5 g, 79%) which was used as such for the next step.

Synthesis of Intermediate 40:

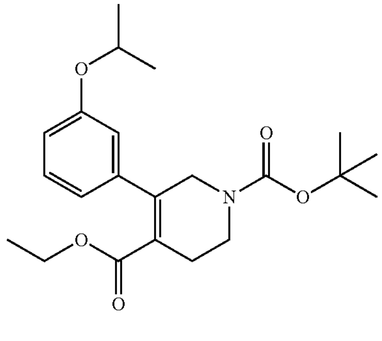 [SMILES: CCOC(=O)C1=C(c2cccc(OC(C)C)c2)CN(C(=O)OC(C)(C)C)CC1]

Intermediate 39 (7.5 g, 16.7 mmol), 3-Bromophenyl isopropyl ether (2 mL, 12.4 mmol), Bis(triphenylphosphine) palladium(II) dichloride (0.4 g, 0.6 mmol) and sodium carbonate 1M (18.5 mL, 18.5 mmol) were taken in dioxane (50 mL), the mixture was bubbling with $N_2$ for 15 minutes and then it was heated at 100° C. for 2 hours. The mixture was filtered through a short pad of celite. $H_2O$ and AcOEt were added, the organic layer was washed with brine, dried over $MgSO_4$ and evaporated. The residue was purified by flash column chromatography (silicagel; eluent: AcOEt in heptane 0/100 to 25/75). The product was obtained as an oil (3.9 g, 71%).

Synthesis of Intermediate 41:

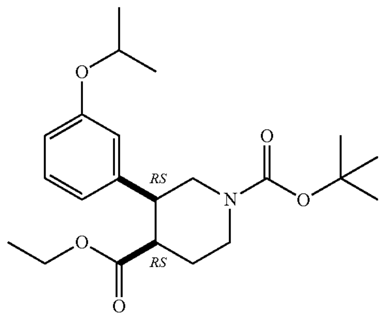

Intermediate 40 (7.9 g, 20.2 mmol) was taken in MeOH (80 mL) and cooled in an ice bath under a nitrogen stream. 10% Pd/C (0.9 g, 8.3 mmol) was added and the reaction vessel connected to a balloon filled with $H_2$. The mixture was stirred under an atmosphere of $H_2$ overnight at room temperature. The mixture was filtered through a pad of celite and the cake was washed with MeOH (5×30 mL) and concentrated to dryness. Intermediate 41 (oil) was used as such for the next step (7.2 g, 91%).

Synthesis of Intermediate 42:

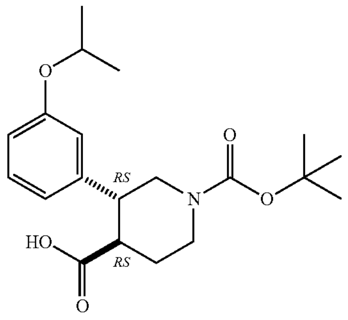

To a solution of intermediate 41 (7.2 g, 18.5 mmol) in EtOH (25 mL) under a $N_2$ atmosphere, sodium ethylate (7.2 mL, 19.4 mmol) was added. The reaction mixture was heated to reflux overnight. $H_2O$ and DCM were added and the organic layer were separated, dried over $MgSO_4$, filtered and concentrated to dryness. The aqueous layer was acidified with $KHSO_4$ 1M until pH=5-6. AcOEt was added and the organic layer was separated, dried over $MgSO_4$, filtered and concentrated to dryness to give intermediate 42 (0.9 g, 13%).

Synthesis of Intermediate 43:

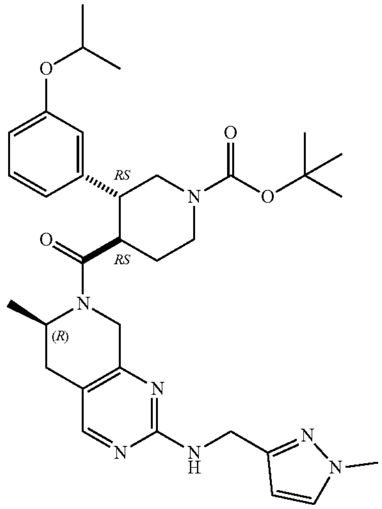

HBTU (2-(1H-Benzotriazole-1-yl)-1,1,3,3-tetramethyluronium hexafluorophosphate) (0.7 g, 1.9 mmol) was added to a solution of intermediate 42 (0.7 g, 1.9 mmol), intermediate 5 (0.4 g, 1.6 mmol), and diisopropylethylamine (0.8 mL, 4.8 mmol) in DMF (20 mL). The reaction was stirred two days at room temperature. 1M $Na_2CO_3$ (20 mL) and AcOEt (50 mL) were added. The phases were separated. The combined organic layers were dried over $MgSO_4$, filtered and evaporated in vacuo. The residue was purified by flash column chromatography (silica gel; eluent: DCM/MeOH (9:1) in DCM 0/100 to 100/0). The desired fractions were collected and concentrated in vacuo to give intermediate 43 (0.3 g, 33%).

Synthesis of Intermediate 44:

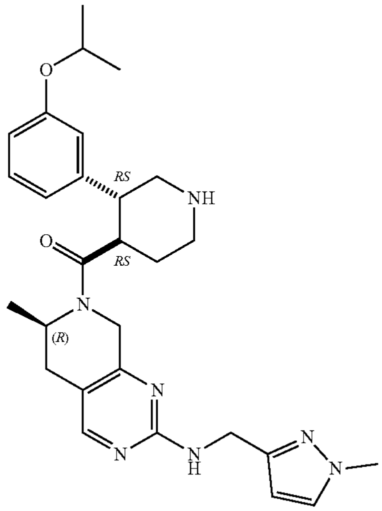

Trifluoroacetic acid (0.4 mL, 5.4 mmol) was added to a solution of intermediate 43 (0.3 g, 0.5 mmol) in DCM (15 mL). The mixture was stirred overnight and was concentrated to dryness. The crude mixture was washed with toluene twice and concentrated to dryness; neutralized with 1M $Na_2CO_3$ 1M. The mixture was extracted with DCM, the organic layer was dried over $MgSO_4$, filtered and concentrated to dryness. The intermediate 44 was used as such for the next step (0.2 g, 88%).

Synthesis of Intermediate 45:

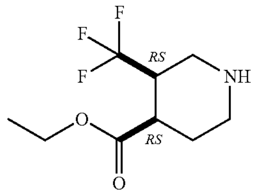

A solution of 4-Pyridinecarboxylic acid, 2-chloro-5-(trifluoromethyl)-, ethyl ester (9.6 g, 37.8 mmol) in MeOH (150 mL) was treated with 37% HCl (0.3 ml, 3.8 mmol). To the mixture was added 10% Pd/C (4 g, 3.7 mmol) and the resulting suspension was stirred under 100 psi of hydrogen at 50° C. for 20 hours. The catalyst was filtered off through a pad of Celite. The filtrate was concentrated to give intermediate 45 as a white solid (9.6 g, 100%).

Synthesis of Intermediate 46:

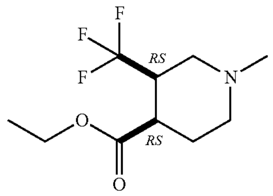 [SMILES: CCOC(=O)[C@@H]1CCN(C)C[C@@H]1C(F)(F)F]

Intermediate 45 (4.4 g, 19.6 mmol) was taken in THF (50 mL) and treated with aqueous formaldehyde 37% (2.2 mL, 29.4 mmol) at room temperature. Sodium triacetoxyborohydride (6.2 g, 29.4 mmol) was then added after 15 minutes. The reaction was continued for 2 hours. The reaction mixture was diluted with DCM (150 mL) and washed with 1M $Na_2CO_3$ (150 mL). The aqueous phase was extracted once more with DCM (100 mL). The combined organic layers were dried over $MgSO_4$, filtered and concentrated. Chromatography over silica gel (80 g column, gradient of AcOEt in heptane from 0 to 100 afforded intermediate 46 (2.9 g, 62%).

Synthesis of Intermediate 47:

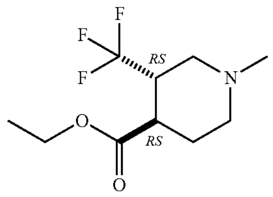 [SMILES: CCOC(=O)[C@@H]1CCN(C)C[C@H]1C(F)(F)F]

To a solution of intermediate 46 (2.2 g, 9.4 mmol) in 100 mL of EtOH under N2 atmosphere, sodium ethylate (3.7 g, 9.8 mmol) was added. The reaction mixture was heated to reflux overnight. Water was added and the organic layer was separated, dried over $MgSO_4$, filtered and concentrated to dryness to give intermediate 47 (1.4 g, 63%). The product was used as such for the next step.

Synthesis of Intermediate 48:

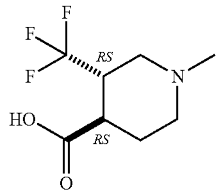

HCl 6M (3 mL, 6.7 mmol) was added to a solution of intermediate 47 (0.8 g, 3.3 mmol) and water (2 mL). The mixture was stirred at 110° C. overnight and concentrated to dryness. The product was used as such for the next step.

Synthesis of Intermediate 49a and 49b:

49a

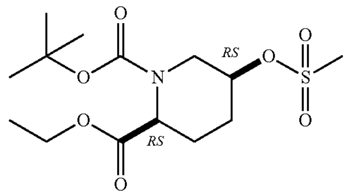

,

49b

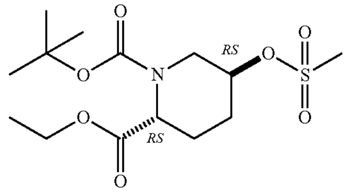

1,2-Piperidinedicarboxylic acid, 5-hydroxy-1-(1,1-dimethylethyl) 2-ethyl ester (2.2 g, 8.3 mmol) and triethylamine (2.9 mL, 20.8 mmol) were dissolved in DCM (25 mL) and cooled to 0° C. under nitrogen atmosphere. Methanesulfonyl chloride (0.7 mL, 8.7 mmol) was added. The reaction mixture was allowed to come to room temperature and stirred for 1.5 additional hours. The reaction mixture was diluted with DCM (20 mL) and washed with water (10 mL). The phases were separated and the aqueous layer was extracted once more with DCM (10 mL). The combined organic layers were dried over $MgSO_4$, filtered and evaporated in vacuo. The residue was purified by flash column chromatography (silica gel; eluent: AcOEt in heptane 0/100 to 100/0). The product fractions containing 49a and 49b were collected and concentrated in vacuo. Intermediate 49a was obtained pure by reverse phase chromatography [start (70% $H_2O$-30% $CH_3CN$—$CH_3OH$)-end (27% $H_2O$-73% $CH_3CN$—$CH_3OH$)]-[$H_2O$: 25 mM $NH_4HCO_3$] (1.61 g, 55%). Intermediate 49b was obtained pure by reverse phase chromatography [start (70% $H_2O$-30% $CH_3CN$—$CH_3OH$)-end (27% $H_2O$-73% $CH_3CN$—$CH_3OH$)]-[$H_2O$: 25 mM $NH_4HCO_3$] (0.35 g, 12%).

Synthesis of Intermediate 50:

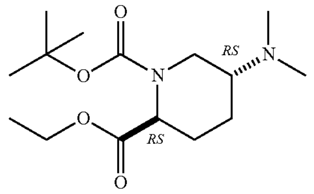 [SMILES: CCOC(=O)[C@@H]1CC[C@@H](N(C)C)CN1C(=O)OC(C)(C)C]

Intermediate 49a (1.6 g, 4.1 mmol) and DMF (4 mL) were taken in a sealed tube. A Dimethylamine solution (8.5 mL, 62.2 mmol) was added. The mixture was heated at 70° C. for 60 hours. After concentration under vacuum, the residue was purified by flash column chromatography (silica gel; $CH_2Cl_2/CH_3OH$, 9/1, v/v in $CH_2Cl_2$ 0/100 to 100/0). The desired fractions were collected and concentrated in vacuo. Intermediate 50 was obtained pure by reverse phase chromatography [start (95% $H_2O$-5% $CH_3CN$—$CH_3OH$)-end (63% $H_2O$-37% $CH_3CN$—$CH_3OH$)]-[$H_2O$: 0.1% HCOOH] (0.4 g, 31%).

Synthesis of Intermediate 51:

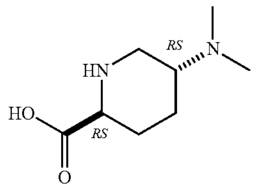

Intermediate 50 (0.4 g, 1.3 mmol) and $H_2O$ (2.7 ml) were taken in a sealed tube. HCl 12M (0.9 mL, 3.8 mmol) was added. The mixture was refluxed overnight. The mixture was concentrated to dryness and co-evaporated with diethyl ether (2×5 mL). The crude intermediate 51 was dried, at 50° C., under high vacuum and used as such for the next step (0.3 g, 100%).

Synthesis of Intermediate 52:

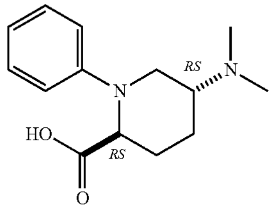 [SMILES: CN(C)[C@@H]1CC[C@@H](C(=O)O)N(c2ccccc2)C1]

Intermediate 51 (0.3 g, 1.3 mmol) and DMF (3.8 mL) were taken in a sealed tube and bubbled with nitrogen for ca. 15 minutes. Cesium carbonate (0.8 g, 2.6 mmol), iodobenzene (0.15 mL, 1.3 mmol) and copper iodide (0.03 g, 0.15 mmol) were then added and the resulting mixture was heated at 140° C., under nitrogen atmosphere, overnight. The reaction was allowed to cool to room temperature. Water (5 mL) and AcOEt (10 mL) were added. The phases were separated and the organic layer was discarded. The aqueous layer was brought to pH 6 with the addition of 1 M HCl and then concentrated in vacuo. The residue was washed, several times, with $CH_2Cl_2/CH_3OH$, 9/1, v/v and the washes filtered through a syringe filter (0.45 μm). Solvents were evaporated in vacuo and the residue was purified by reverse phase chromatography [start (95% $H_2O$-5% $CH_3CN$—$CH_3OH$)-end (63% $H_2O$-37% $CH_3CN$—$CH_3OH$)]-[$H_2O$: 25 mM $NH_4HCO_3$] yielding intermediate 52 (0.14 g, 43%).

Synthesis of Intermediate 53:

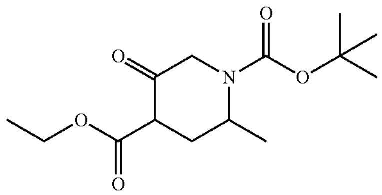 [SMILES: CCOC(=O)C1CC(C)N(C(=O)OC(C)(C)C)CC1=O]

4-Piperidinecarboxylic acid, 2-methyl-5-oxo-1-(1-phenylethyl)-, ethyl ester (2 g, 6.5 mmol) was taken in EtOH (50 mL), cooled in an ice bath under a nitrogen stream. $H_2$ and Di-tert-butyl dicarbonate (4.5 mL, 19.7 mmol) were added and the reaction vessel connected to a balloon filled with $H_2$. The mixture was stirred under an atmosphere of $H_2$ overnight at room temperature. The mixture was filtered through a pad of celite and the cake was washed with MeOH (5×10 mL), the filtrate was concentrated to dryness. The residue was purified by flash column chromatography (silica gel; Heptane/AcOEt, 5/1, v/v in Heptane 0/100 to 100/0). The desired fractions were collected and concentrated in vacuo to give 1.8 g (99%) of intermediate 53.

Synthesis of Intermediate 54:

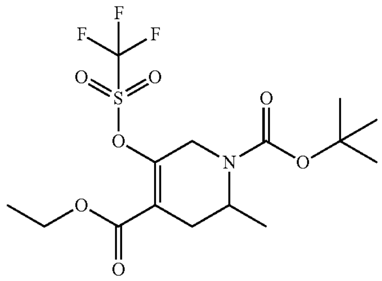 [SMILES: CCOC(=O)C1=C(OS(=O)(=O)C(F)(F)F)CN(C(=O)OC(C)(C)C)C(C)C1]

To a solution of intermediate 53 (1.9 g, 6.5 mmol) and diisopropylethylamine (1.7 mL, 9.8 mmol) in 30 mL of toluene at 0° C., trifluoromethanesulfonic anhydride (1.3 mL, 7.9 mmol) was added. The mixture was allowed to stir at 0° C. for 16 h. Water was added and the mixture was extracted with AcOEt. The organic layer was separated, dried over $MgSO_4$, filtered and evaporated. The residue was purified by flash column chromatography (silica gel; AcOEt in Heptane 0/100 to 100/0). The desired fractions were collected and concentrated in vacuo to give 1.3 g, (47%) of intermediate 54 as a red gum.

Synthesis of Intermediate 55:

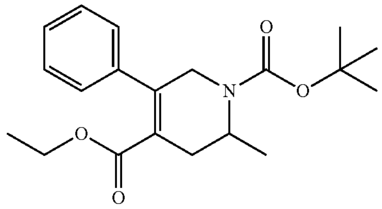 [SMILES: CCOC(=O)C1=C(c2ccccc2)CN(C(=O)OC(C)(C)C)C(C)C1]

Intermediate 54 (3.5 g, 8.4 mmol), Bis(triphenylphosphine)palladium(II) dichloride (587 mg, 0.8 mmol), phenylboronic acid (1.5 g, 12.5 mmol) and sodium carbonate 1M (16.7 mL, 16.7 mmol) were taken in dioxane (100 mL), the mixture was bubbling with $N_2$ for 15 minutes and then it was heated at 80° C. overnight. The mixture was filtered through a short pad of celite. Water and AcOEt were added, the organic layer was washed with brine, dried over $MgSO_4$ and evaporated. The crude mixture was purified by flash column chromatography (silica gel, AcOEt/Heptane, from 0/100 to 40/60). The desired fractions were collected, evaporated in vacuo and dried under high vacuum to give intermediate 55 (2.9 g, 100%).

Synthesis of Intermediate 56:

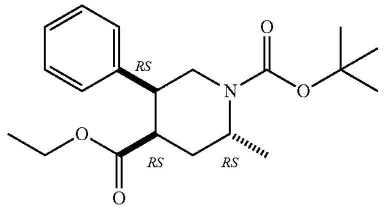 [SMILES: CCOC(=O)[C@@H]1C[C@@H](C)N(C(=O)OC(C)(C)C)C[C@@H]1c1ccccc1]

Intermediate 55 (2.9 g, 8.4 mmol) was taken in MeOH (70 mL) and cooled in an ice bath under a nitrogen stream. 10% Pd/C (0.5 g, 4.9 mmol) was added and the reaction vessel was connected to a balloon filled with $H_2$. The mixture was stirred under an atmosphere of $H_2$ overnight at room temperature. The mixture was filtered through a pad of celite and the cake was washed with MeOH (5×10 mL) and concentrated to dryness. Intermediate 56 was used as such for the next step (2.8 g, 95%).

Synthesis of Intermediate 57:

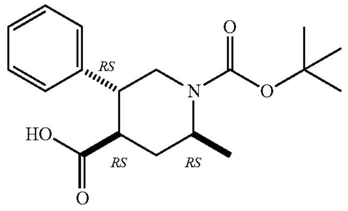 [SMILES: C[C@H]1C[C@@H](C(=O)O)[C@H](c2ccccc2)CN1C(=O)OC(C)(C)C]

To a solution of intermediate 56 in 60 mL of EtOH under a $N_2$ atmosphere, sodium ethylate (3.1 mL, 8.4 mmol) was added. The reaction mixture was heated to reflux for 3 hours. The reaction mixture was poured into an aqueous ammonium chloride solution, and the resultant product was extracted with ethyl acetate. The organic layer was dried over $MgSO_4$, filtered and concentrated under reduced pressure. The crude mixture was purified by flash column chromatography on silica gel using as eluents Heptane/AcOEt (0:100 to 50:50). The product was purified by reverse phase chromatography [start (47% $H_2O$-53% ACN: MeOH 1:1)-end (18% $H_2O$-82% ACN: MeOH 1:1)]-[65 mM $NH_4OAc$+ACN (90:10)] to give intermediate 57 (1.8 g, 71%).

Synthesis of Intermediate 58:

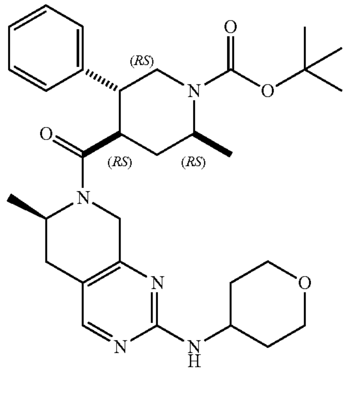 [SMILES: C[C@@H]1Cc2cnc(NC3CCOCC3)nc2CN1C(=O)[C@@H]1C[C@H](C)N(C(=O)OC(C)(C)C)C[C@H]1c1ccccc1]

Intermediate 57 (0.2 g, 0.86 mmol), intermediate 27 (0.3 g, 0.9 mmol) and diisopropylethylamine (0.4 mL, 2.6 mmol) were taken in DMF (15 mL) at room temperature. HBTU (0.4 g, 1 mmol) was added and the mixture was stirred for 20 minutes. 1M $Na_2CO_3$ (10 mL) and $CH_2Cl_2$ (35 mL) were added. The organic layer was separated, and the aqueous phase extracted once more with $CH_2Cl_2$ (30 mL). The combined organic layers were dried over $MgSO_4$, filtered and concentrated in vacuo. The residue was purified by flash column chromatography (silica gel; $CH_2Cl_2$/$CH_3OH$, 9/1, v/v in $CH_2Cl_2$ 0/100 to 100/0). The desired fractions were collected and concentrated in vacuo to give intermediate 58 (0.3 g, 64%).

Synthesis of Intermediate 59:

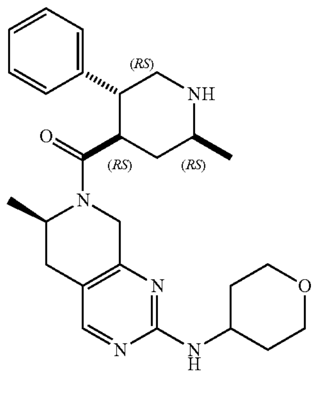 [SMILES: C[C@@H]1Cc2cnc(NC3CCOCC3)nc2CN1C(=O)[C@@H]1C[C@H](C)NC[C@H]1c1ccccc1]

Trifluoroacetic acid (0.4 mL, 5.5 mmol) was added to a solution of intermediate 58 (0.3 g, 0.5 mmol) in DCM (40 mL). The mixture was stirred overnight. The mixture was concentrated to dryness. The crude mixture was washed with toluene twice and concentrated to dryness. 1M $Na_2CO_3$ (35 mL) and $CH_2Cl_2$ (150 mL) were added. The organic layer was separated, and aqueous phase extracted once more with $CH_2Cl_2$ (30 mL). The combined organic layers were dried over $MgSO_4$, filtered and concentrated in vacuo. The crude intermediate 59 was used as such in the next step (0.24 g, 96%).

Synthesis of Intermediate 60:

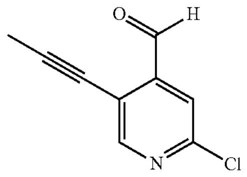

Propyne (2.7 g, 67.4 mmol) was bubbled in DMF (75 mL) at −10/−15° C. 5-bromo-2-chloro-4-Pyridinecarboxaldehyde (12.4 g, 56.2 mmol), $PdCl_2(TPP)_2$ (1.5 g, 2.2 mmol), CuI (321 mg, 1.7 mmol) and triethylamine (23.5 mL, 168.5 mmol) were added and the reaction vessel closed tight. The mixture was stirred at room temperature for 2.5 hours. The reaction mixture was then poured onto iced water (200 mL)/saturated $NH_4Cl$ (20 mL). The organics were extracted with AcOEt (250 mL and 150 mL). The combined organic layers were washed with sat. $NaHCO_3$ (100 mL). The aqueous phase was extracted back with AcOEt (50 mL). The combined organic layers were dried over $MgSO_4$, filtered and concentrated. Chromatography over silica gel (gradient of AcOEt in heptane from 0 to 35%) afforded a yellowish solid intermediate 60 (5.1 g, 50%).

Synthesis of Intermediate 61:

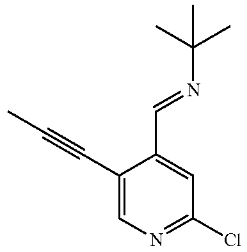 [SMILES: CC#Cc1cnc(Cl)cc1/C=N/C(C)(C)C]

To a suspension of intermediate 60 (9 g, 50.3 mmol) in water (100 mL), was added tert-Butylamine (25 mL, 238 mmol). The reaction was stirred at room temperature for 48 hours. The excess of tert-Butylamine was removed by rotary evaporation. The resulting residue was partitioned between AcOEt (200 mL) and water (100 mL). The organic layer was washed with brine (50 mL), dried over $MgSO_4$, filtered and concentrated to afford the crude intermediate 61 (11.9 g, 100%) used in the next step without further purification.

Synthesis of Intermediate 62:

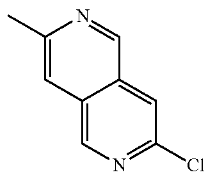

Intermediate 61 (2.7 g, 11.4 mmol) was taken in DMF (150 mL) and degassed by bubbling nitrogen for 15 minutes. The catalyst copper iodide (0.2 g, 1.1 mmol) was added and the resulting mixture was heated at 100° C. for 2 hours. The mixture was allowed to cool to room temperature and quenched with water (10 mL). Most of solvent was removed in vacuo. The residue was taken in AcOEt (200 mL) and washed with saturated $NH_4Cl$ (70 mL), dried over $MgSO_4$, filtered and concentrated to dryness. Chromatography over silica gel (gradient of AcOEt in heptane from 0 to 30%) afforded intermediate 62 (1.7 g, 81%).

Synthesis of Intermediate 63:

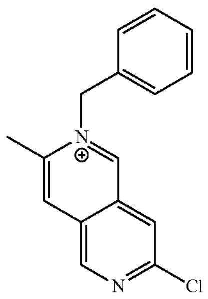 [SMILES: Cc1cc2cnc(Cl)cc2c[n+]1Cc1ccccc1]

Intermediate 62 (1.5 g, 8.4 mmol) and benzyl bromide (1.6 mL, 13.6 mmol) were taken in acetonitrile (30 mL) in a sealed tube. The mixture was stirred at 80° C. for 48 hours. The mixture was allowed to cool to room temperature and poured onto diethyl ether (200 mL). The precipitate was filtered through sintered funnel and washed with diethyl ether (2×15 mL). Intermediate 63 was collected and dried under high vacuum (2.3 g, 75%).

Synthesis of Intermediate 64:

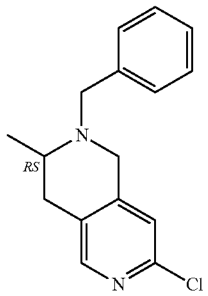 [SMILES: CC1Cc2cnc(Cl)cc2CN1Cc1ccccc1]

Sodium Borohydride (1.2 g, 32.6 mmol) was added portion-wise to a solution of intermediate 63 (2.3 g, 6.5 mmol) in MeOH (60 mL) over 30 minutes. The mixture was then stirred for another 2 hours. The reaction mixture was quenched with water (150 mL) and 1M NaOH (50 mL). The organics were extracted with DCM (3×100 mL), dried over $MgSO_4$, filtered and concentrated to dryness. Chromatography over silica gel (gradient of MeOH in DCM from 0 to 5%) afforded intermediate 64 (1.5 g, 82%).

Synthesis of Intermediate 65:

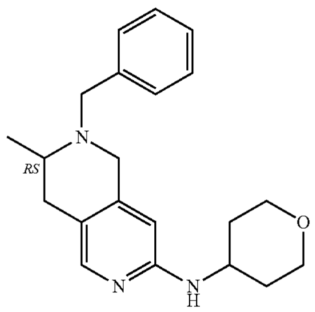 [SMILES: CC1Cc2cnc(NC3CCOCC3)cc2CN1Cc1ccccc1]

Intermediate 64 (1.5 g, 5.5 mmol), 4-aminotetrahydropyran (1.1 mL, 11 mmol), RuPhosPdG3 (230 mg, 0.3 mmol) and Sodium tert-butoxide (1 g, 11 mmol) were taken in toluene (50 mL) while bubbling nitrogen in a reaction tube. Degassing was continued for 5 minutes and reaction vessel closed tight with a screw cap. The mixture was heated to 120° C. for 2 hours. The mixture was allowed to cool to room temperature, diluted with AcOEt (100 mL) and washed once with water (100 mL). The organic layer was dried over $MgSO_4$, filtered and concentrated. Chromatography over silica gel (gradient of MeOH in DCM from 0 to 5%) gave intermediate 65 (1.6 g, 82%).

Synthesis of Intermediate 66:

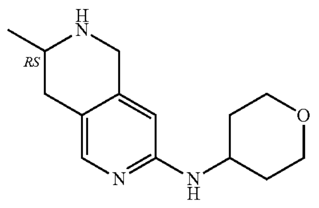 [SMILES: CC1Cc2cnc(NC3CCOCC3)cc2CN1]

The hydrogenolysis of the benzyl group of intermediate 65 (1.6 g, 4.7 mmol) was performed over Pd/C 10% (569 mg, 0.5 mmol) under atmospheric pressure of Hydrogen over 2.5 hours. The catalyst was filtered off through a pad of Celite that was further washed with MeOH (3×20 mL). The filtrate was concentrated. Flash chromatography over silica gel (gradient of a mixture DCM/MeOH/$NH_4OH$, 9.0/0.9/0.1, v/v/v, in DCM from 0 to 50%) afforded intermediate 66 (843 mg, 70%).

Synthesis of Intermediate 67a and 67b:

67a

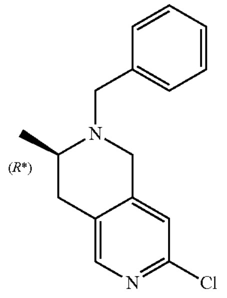

67b

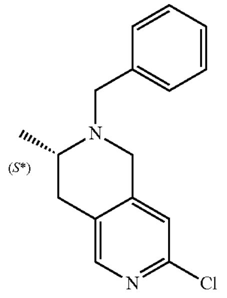

Both enantiomers of intermediate 64 (3.5 g, 9.9 mmol) were separated using Chiral SFC 20% 2-Propanol, 80% $CO_2$, Column Lux-Amylose-1 yielding intermediate 67a (1.2 g, 45%) and intermediate 67b (1.2 g, 45%).

Synthesis of Intermediate 68:

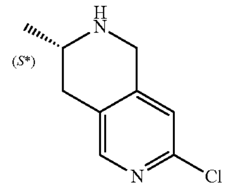

1-Chloroethyl chloroformate (1.5 mL, 13.5 mmol) was added dropwise to a suspension of intermediate 67b (1.2 g, 4.5 mmol) and potassium bicarbonate (5 g, 49.6 mmol) in dichloroethane (40 mL). The mixture was refluxed for 3 hours. The mixture was filtered through a sintered funnel and the filtrate was concentrated to dryness. The residue was taken in MeOH (50 mL) and refluxed for 1 hour. The reaction mixture was concentrated under reduced pressure. The residue was triturated with diethyl ether (50 mL). The resulting powdered solid was filtered through a sintered funnel and washed with diethyl ether (2×15 mL) to give intermediate 68 as hydrochloride salt (1 g, 84%).

Synthesis of Intermediate 69:

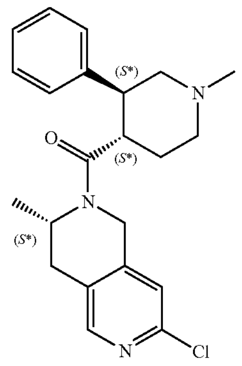 [SMILES: C[C@H]1Cc2cnc(Cl)cc2CN1C(=O)[C@H]1CCN(C)C[C@@H]1c1ccccc1]

HBTU (1.9 g, 5.2 mmol) was added to a solution of intermediate 68 (1 g, 1.7 mmol), intermediate 8 (1.1 g, 5.2 mmol) and diisopropylethylamine (3.2 mL, 18.8 mmol) in DMF (25 mL) at room temperature. The reaction was continued for 20 hours. The mixture was concentrated to dryness. The residue was taken in AcOEt (200 mL) and washed with 1M $Na_2CO_3$ (150 mL). The aqueous phase was extracted with AcOEt (100 mL). The combined organic layers were washed with brine (100 mL), dried over $MgSO_4$, filtered and concentrated to dryness. Chromatography over silica gel (gradient of DCM/MeOH/$NH_4OH$ (9.0/0.9/0.1, v/v/v) in DCM from 0 to 50%) afforded intermediate 69 (760 mg, 38%).

Synthesis of Intermediate 70:

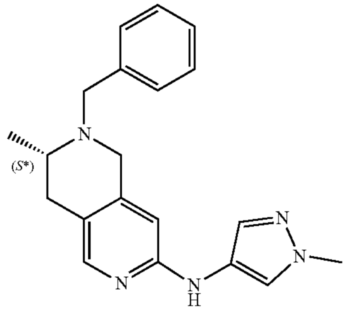

Intermediate 67b (331 mg, 1.2 mmol), 1-methyl-1H-pyrazol-4-amine hydrochloride (0.24 g, 1.8 mmol), RuPhos-PdG3 (51 mg, 0.06 mmol) and potassium carbonate (0.4 g, 3 mmol) were taken in tBuOH (25 mL) while bubbling nitrogen in a reaction tube. Degassing was continued for 5 minutes and reaction vessel closed tight with a screw cap. The mixture was heated to 120° C. 12 hours. The mixture was allowed to cool to room temperature, diluted with AcOEt (80 mL) and washed once with water (20 mL). The organic layer was dried over $MgSO_4$, filtered and concentrated. Chromatography over silica gel (gradient of MeOH in DCM from 0 to 5%) gave intermediate 70 (268 mg, 52%).

Synthesis of Intermediate 71:

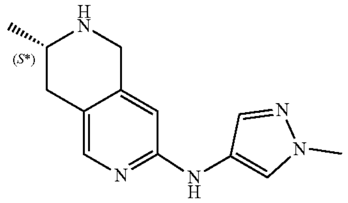

Intermediate 70 (268 mg, 0.8 mmol) was taken in MeOH (30 mL) and cooled in an ice bath under a nitrogen stream. Pd/C 10% (22 mg, 0.2 mmol) was added and the reaction vessel was connected to a balloon filled with Hydrogen. The mixture was stirred under an atmosphere of hydrogen overnight at room temperature. The mixture was filtered through a pad of celite and the cake was washed with MeOH (5×10 mL) and concentrated to dryness. Intermediate 71 (0.209 g, >100%) was used as such for the next step.

Synthesis of Intermediate 72:

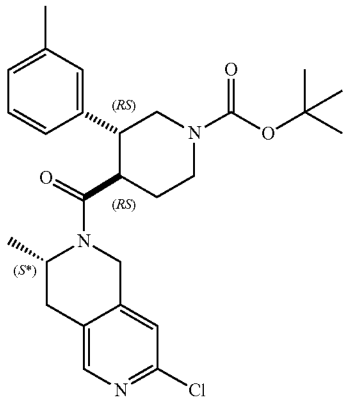

HBTU (2.2 g, 5.9 mmol) was added to a solution of intermediate 68 (0.9 g, 4.9 mmol), intermediate 36 (1.8 g, 5.6 mmol) and diisopropylethylamine (2.5 mL, 14.8 mmol) in DMF (40 mL). The reaction was stirred two days at room temperature. 1M $Na_2CO_3$ (20 mL) and $CH_2Cl_2$ (150 mL) were added. The phases were separated. The aqueous layer was extracted with $CH_2Cl_2$ (5 mL). The combined organic layers were dried over $MgSO_4$, filtered and evaporated in vacuo. The residue was purified by flash column chromatography (silica gel; AcOEt in Heptane 0/100 to 15/85). The desired fractions were collected and concentrated in vacuo to give intermediate 72 (2.1 g, 84%).

Synthesis of Intermediate 73:

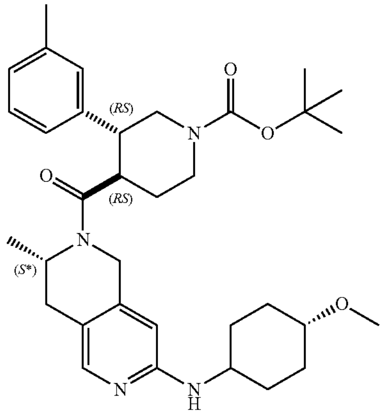

Intermediate 72 (712 mg, 1.4 mmol), trans-4-Methoxy-cyclohexylamine (0.4 g, 2.7 mmol), RuPhosPdG3 (58 mg, 0.07 mmol) and Sodium tert-butoxide (0.2 g, 2.1 mmol) were taken in toluene (20 mL) while bubbling nitrogen in a reaction tube. Degassing was continued for 5 minutes and the reaction vessel was closed tight with a screw cap. The mixture was heated to 100° C. for 20 hours. The mixture was allowed to cool to room temperature, diluted with ethyl acetate (50 mL) and washed once with water (20 mL). The organic layer was dried over $MgSO_4$, filtered and concentrated to dryness. Chromatography over silica gel (gradient of DCM/MeOH (9.0/1.0, v/v) in DCM from 0 to 80%) gave intermediate 73 (663 mg, 81%).

Synthesis of Intermediate 74:

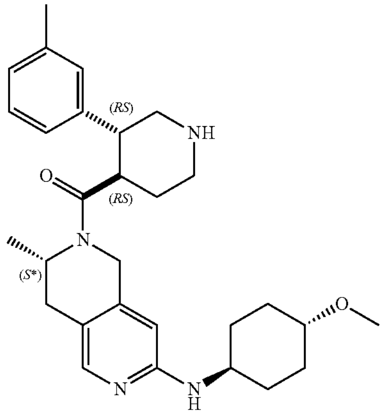

Trifluoroacetic acid (0.9 mL, 11.5 mmol) was added to solution of intermediate 73 (663 mg, 1.1 mmol) in DCM (15 mL). The mixture was stirred overnight. The mixture was concentrated to dryness. The crude mixture was washed with toluene twice and concentrated to dryness. The crude was treated with Amberlyst A26 hydroxide until pH=7. The resin was filtered off through a sintered funnel and washed successively with MeOH (40 mL) and then DCM (40 mL) and was concentrated to dryness. The residue was purified by flash column chromatography (silica gel; $CH_2Cl_2/CH_3OH/NH_3$, 9/0.9/0.1, v/v in $CH_2Cl_2$ 0/100 to 100/0) yielding intermediate 74 as an oil (492 mg, 88%).

Synthesis of Intermediate 75:

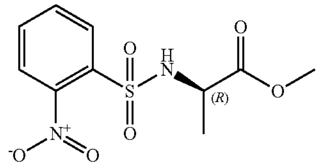

D-Alanine methyl ester hydrochloride (2 g, 14.3 mmol), triethylamine (4.4 mL, 31.5 mmol) were taken in DCM (30 mL) with stirring. Then, 2-Nitrobenzenesulfonyl chloride (3.5 g, 15.7 mmol) in DCM (20 mL) was then added slowly to the mixture at RT and the mixture was stirred for 3 hours. Water (60 mL) was added to the mixture. The organics were extracted with DCM (10 mL). The organic layer was dried over $MgSO_4$, filtered and concentrated to the crude. Chromatography over silica gel (gradient of AcOEt in heptane from 0 to 60%) to give intermediate 75 (3.7 g, 88%) as a solid.

Synthesis of Intermediate 76:

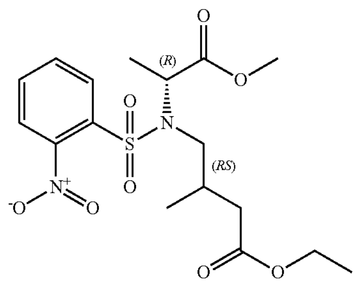

Cesium carbonate (5.1 g, 15.8 mmol) was added to a mixture of Intermediate 75 (3.8 g, 13.2 mmol) and Butanoic Acid, 4-Iodo-3-Methyl-, Ethyl Ester (4 g, 15.8 mmol) in DMF (50 mL). The reaction mixture was stirred at room temperature for 1 hour at room temperature. Then was stirred at 50° C. overnight. $H_2O$ and AcOEt were added and the organics were separated, the organic layer was dried over $MgSO_4$, filtered and concentrated to dryness. The residue was purified by flash column chromatography (silica gel; Heptane in AcOEt from 100/0 to 40/60), yielding 4.6 g of a mixture of intermediate 76 and 75, used crude for the next step.

Synthesis of Intermediate 77:

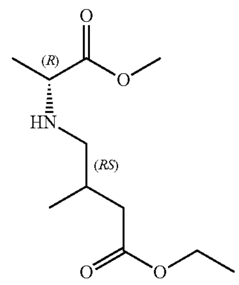

Thiophenol (0.8 mL, 8.3 mmol) was added to a mixture of intermediates 76 and 75 (4.6 g) and cesium carbonate (4.9 g, 15.1 mmol) in DMF (30 mL). The reaction was stirred at rt for 3 hours. The mixture was diluted with diethyl ether (50 mL) and water (50 mL). The organic layer was separated and washed one more time with water (30 mL) and then brine (30 mL). Drying over $MgSO_4$, filtration and removal of solvents gave the crude which was purified by chromatography over silica gel (gradient of AcOEt in heptane from 0 to 100%) yielding intermediate 77 (1.6 g, 86%).

Synthesis of Intermediate 78:

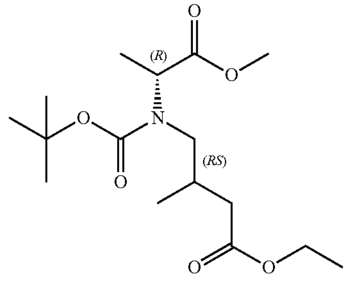

Intermediate 77 (1.6 g, 6.5 mmol) and Di-tert-butyl decarbonate (1.7 mL, 11 mmol) in DCM (20 mL) were stirred at room temperature overnight. The mixture was partitioned between water (25 mM) and DCM (50 mL). The aqueous layer was extracted again with DCM (30 mL). The combined organic layers were dried over $MgSO_4$, filtered and concentrated to dryness. The residue was chromatographed over silica gel (AcOEt/Heptane, from 0/100 to 35/65). Intermediate 78 was obtained as an oil (1.9 g, 91%).

Synthesis of Intermediate 79a and 79b:

79a

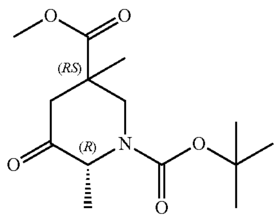

-continued

79b

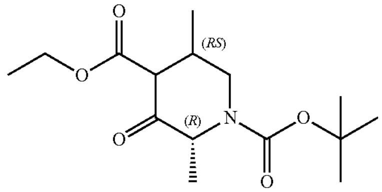

Intermediate 78 (1.9 g, 6 mmol) was stirred in THF (50 mL) for 10 min. Potassium tert-butoxide (1 g, 9 mmol) was added and the reaction mixture was stirred for 2 hours. Water was added and the mixture was extracted with AcOEt. The organic layer was separated, dried over $MgSO_4$, filtered and evaporated to dryness. Chromatography (silica gel, AcOEt/Heptane, from 0/100 to 50/50) gave a mixture of 79a and 79b (1.3 g).

Synthesis of Intermediate 80:

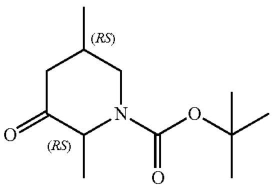

Intermediates 79a and 79b (1.3 g) and sodium chloride (0.26 g, 4.4 mmol) were stirred overnight at 140° C. in a mixture of DMSO (10 mL) and $H_2O$ (5 mL). The mixture was allowed to cool to room temperature and diluted with water (25 mL). Organics were extracted with AcOEt (2×40 mL), washed with brine, dried over $MgSO_4$, filtered and concentrated. The residue was purified by flash column chromatography (silica gel; AcOEt in Heptane from 0/100 to 100/0). Intermediate 80 was obtained as an oil (0.5 g, 90%).

Synthesis of Intermediate 81:

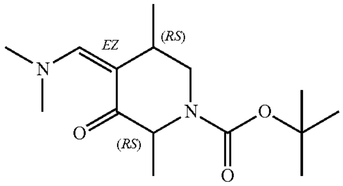

Tert-Butoxybis(dimethylamino)methane (2.2 mL, 10.9 mmol) was added to a solution of intermediate 80 (495 mg, 2.2 mmol) in toluene (10 mL) at room temperature. The mixture was stirred overnight. 2 additional equivalents of Tert-Butoxybis(dimethylamino)methane were added and the reaction mixture was stirred at 80° C. for 5 hours. The reaction mixture was concentrated to dryness. The crude residue was dried at room temperature under high vacuum and finally used as such in the next step.

Synthesis of Intermediate 82:

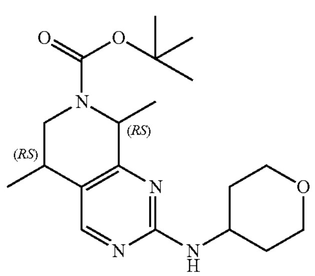

Sodium ethylate (1.6 mL, 4.3 mmol) was added to a mixture of intermediate 81 (0.61 g, 2.2 mmol) and 1-(tetrahydro-2H-pyran-4-yl) guanidine (11 g, 7.4 mmol) in EtOH (20 mL). The resulting mixture was heated to 90° C. over the weekend. The mixture was allowed to cool to room temperature, quenched with water (20 mL) and extracted with DCM (60 mL). The organic layer was dried over $MgSO_4$, filtered and concentrated. Chromatography over silica gel (gradient of AcOEt in Heptane from 0 to 100%) gave intermediate 82 (0.6 g, 71%).

Synthesis of Intermediate 83:

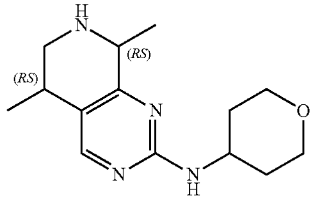

Trifluoroacetic acid (1.2 mL, 15.9 mmol) was added to a solution of intermediate 82 (578 mg, 1.6 mmol) in DCM (10 mL). The reaction mixture was stirred overnight. The mixture was concentrated to dryness, washed with toluene twice and concentrated to dryness. The crude mixture was treated with Amberlyst $A^{26}$ hydroxide until pH=7. The resin was filtered off through a sintered funnel and washed successively with MeOH (40 mL) and then DCM (40 mL) and the mixture was concentrated to dryness. Compound 83 (0.42 g, 98%) was obtained as an oil and was used as such for the next step.

Synthesis of Intermediate 84a and 84b:

84a

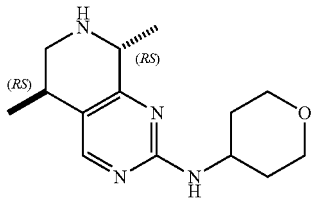

-continued

84b

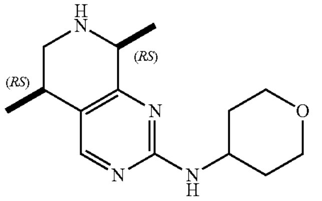

Intermediate 83 (732 mg, 2.8 mmol) was purified by reverse phase chromatography [Start (95% $H_2O$-5% ACN-MeOH)-End (63% $H_2O$-37% ACN-MeOH]-[0.1% TFA]. The solution was neutralized with $Na_2CO_3$ solid, extracted with DCM, dried over $MgSO_4$, filtered, concentrated to dryness yielding 84a (315 mg, 42%) and 84b (133 mg, 18%).

Synthesis of Intermediate 85:

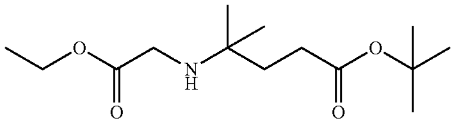 [SMILES: CCOC(=O)CNC(C)(C)CCC(=O)OC(C)(C)C]

Tert-butyl 4-amino-4-methylpentanoate (19.4 g, 104 mmol) was taken in DCE (200 mL) and treated with Ethyl 2-oxoacetate (30.8 mL, 156 mmol) at RT and the mixture was stirred for 45 minutes. Triacetoxyborohydride (33 g, 156 mmol) was then added portion-wise over 15 minutes and the reaction was allowed to stir overnight. The reaction was quenched with 1M $Na_2CO_3$ (150 mL) and the organics were extracted with DCE (2×60 mL). The combined organic layers were dried over $MgSO_4$, filtered and concentrated to dryness. Chromatography over silica gel (gradient of MeOH in DCM from 0 to 40%) afforded intermediate 85 (11.2 g, 39%).

Synthesis of Intermediate 86:

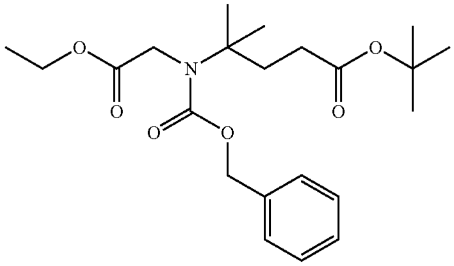 [SMILES: CCOC(=O)CN(C(=O)OCc1ccccc1)C(C)(C)CCC(=O)OC(C)(C)C]

Benzyl chloroformate (23.4 mL, 164 mmol) was added to a solution of intermediate 85 (11.2 g, 41 mmol) in a saturated solution of $NaHCO_3$ (70 mL) and DCM (100 mL) at 0° C. The mixture was allowed to come to RT and stirred overnight. The mixture was diluted with DCM (100 mL) and 25% $NH_4OH$ (30 mL) was added with stirring. After 15 minutes, the organic layer was separated, dried over $MgSO_4$, filtered and concentrated. Chromatography over silica gel (gradient of AcOEt in heptane from 0 to 30%) afforded intermediate 86 (3.8 g, 82%).

Synthesis of Intermediate 87:

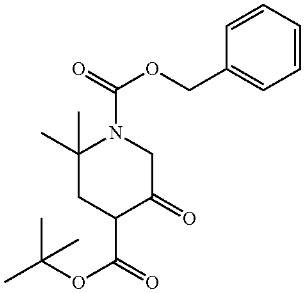 [SMILES: CC(C)(C)OC(=O)C1CC(C)(C)N(C(=O)OCc2ccccc2)CC1=O]

Potassium tert-butoxide (5.7 g, 50.7 mmol) was added to a solution of intermediate 86 (13.8 g, 33.8 mmol) in THF (120 mL) and the mixture was allowed to stir for 1 hour at RT. The reaction was diluted with DCM (250 mL) and $H_2O$ (50 mL). $KHSO_4$ 1M (30 mL) was added with stirring. The organic layer was separated and the aqueous phase was extracted once with more DCM (50 mL). The combined organic layers were dried over $MgSO_4$, filtered and concentrated to the crude oil. Chromatography over silica gel (gradient of AcOEt in heptane from 0 to 20%) afforded intermediate 87 (9.5 g, 78%).

Synthesis of Intermediate 88:

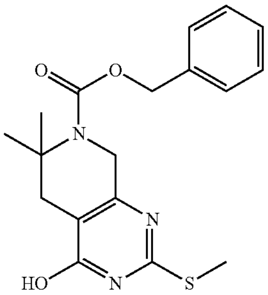 [SMILES: CSc1nc(O)c2c(n1)CN(C(=O)OCc1ccccc1)C(C)(C)C2]

Sodium ethoxide in EtOH (29.6 mL, 79.3 mmol) was added to a mixture of intermediate 87 (9.5 g, 26.4 mmol) and S-Methylisothiourea (11 g, 79.3 mmol) in EtOH (120 mL). The resulting mixture was heated to 90° C. and stirred overnight. The mixture was allowed to cool to room temperature and diluted with AcOEt (100 mL) and $H_2O$ (40 mL). The pH was brought to 2-3 with 1M HCl. The organic layer was separated (brine was added in order to separate the phases), dried over $MgSO_4$, filtered and concentrated under vacuum. Acetonitrile was added in order to remove impurities and the solution was filtered under vacuum. Intermediate 88 was dried to get 828 mg (9%) as a white solid. The filtered solution was concentrated under vacuum and purified by flash chromatography over silica gel (gradient of AcOEt in heptane from 0 to 40%) to afford intermediate 88 (5.3 g, 49%) as a yellow solid.

Synthesis of Intermediate 89:

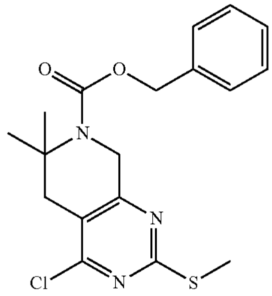 [SMILES: CSc1nc(Cl)c2c(n1)CN(C(=O)OCc1ccccc1)C(C)(C)C2]

Intermediate 88 (5.3 g, 14.8 mmol) was heated at 80° C. in $POCl_3$ (44 mL) for 1 hour. The reaction mixture was poured onto crushed ice (200 g). $H_2O$ (100 mL) and DCM (100 mL) were added with stirring. $Na_2CO_3$ was slowly added to pH 7-8. The organic layer was separated and the aqueous phase was extracted once more with DCM (50 mL). The combined organic layers were dried over $MgSO_4$, filtered and concentrated to dryness. The crude mixture was purified by flash column chromatography over silica gel (gradient of AcOEt in heptane from 0 to 35%) to yield intermediate 89 (2.5 g, 44%).

Synthesis of Intermediate 90:

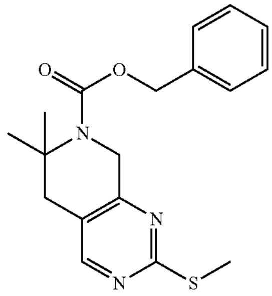 [SMILES: CSc1ncc2c(n1)CN(C(=O)OCc1ccccc1)C(C)(C)C2]

Intermediate 89 (2.5 g, 6.8 mmol), Zn (3.5 g, 54 mmol) and Ammonia (2.5 mL, 34 mmol) were taken in EtOH (60 mL). The mixture was refluxed (80° C.) overnight, cooled to RT and filtered through a pad of celite and the cake was washed with EtOH. The crude mixture was purified by flash column chromatography over silica gel (gradient of AcOEt in heptane from 0 to 25%) to yield intermediate 90 (1.9 g, 81%).

Synthesis of Intermediate 91:

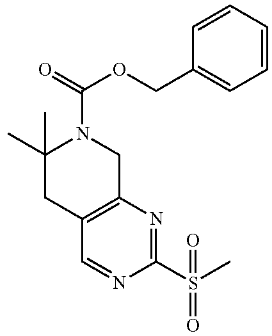 [SMILES: CC1(C)Cc2cnc(S(C)(=O)=O)nc2CN1C(=O)OCc1ccccc1]

3-Chloroperbenzoic acid (3.3 g, 14.9 mmol) was added portion-wise to a solution of intermediate 90 (1.7 g, 5 mmol) in DCM (70 mL). The reaction was allowed to stir at RT for 7 hours. 1M $Na_2CO_3$ (40 mL) was added to the mixture with stirring. DCM (30 mL) was added and the organic layer was separated and washed once more with 1M $Na_2CO_3$ (20 mL). The organic layer was dried over $MgSO_4$, filtered and concentrated under vacuum. Chromatography over silica gel (gradient of MeOH in DCM from 0 to 40%) afforded intermediate 91 as a colorless oil (1.4 g, 71%).

Synthesis of Intermediate 92:

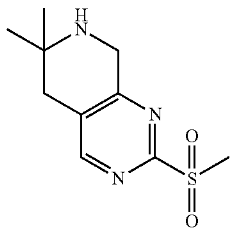

Intermediate 91 (1.3 g, 3.6 mmol) and triethylamine (126 μl, 0.9 mmol) were taken in MeOH (60 mL) and the mixture was reduced over Pd/C 10% (142 mg, 0.1 mmol) under 1 atmosphere of $H_2$ for 1 hour. The catalyst was filtered off through a short pad of celite. Then, the filtrate was concentrated to dryness. The crude intermediate 92 (865 mg, 96%) was obtained as a yellow sticky solid and it was used as such in the next synthetic step without further purification.

Synthesis of Intermediate 93:

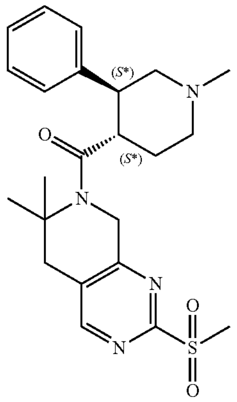

Intermediate 93 (147 mg, 18%) has been prepared by a similar reaction protocol as for intermediate 11, starting from intermediate 92.

Synthesis of Intermediate 94:

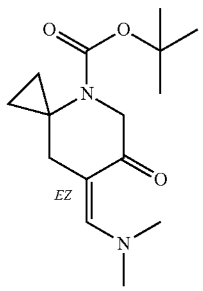 [SMILES: CN(C)/C=C1/CC2(CC2)N(C(=O)OC(C)(C)C)CC1=O]

Tert-Butoxybis(dimethylamino)methane (1.6 mL, 7.7 mmol) was added to a solution of 4-Azaspiro[2.5]octane-4-carboxylic acid, 6-oxo-, 1,1-dimethylethyl ester (1.4 g, 6.4 mmol) in toluene (21 mL) at room temperature. The reaction mixture was stirred for 20 hours, concentrated to dryness. The crude intermediate 94 was dried, at room temperature, under high vacuum and used as such in the next synthetic step (1.8 g, 100%).

Synthesis of Intermediate 95:

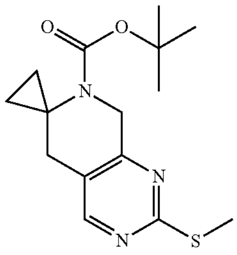 [SMILES: CSc1ncc2c(n1)CN(C(=O)OC(C)(C)C)C1(CC1)C2]

2-Methyl-2-thiopseudourea hemisulfate (1.8 g, 12.9 mmol) and intermediate 94 (1.8 g, 6.4 mmol) were taken in EtOH (51 mL). Sodium ethoxide (6 mL, 16 mmol) was added and the resulting mixture was heated at 85° C. for 12 hours. The reaction mixture was taken in AcOEt (50 mL) and $H_2O$ (50 mL) was added. The organic layer was separated, and the aqueous phase was extracted with more AcOEt (2×20 mL). The combined organic layers were dried over $MgSO_4$, filtered and evaporated in vacuo. The residue was purified by flash column chromatography (silica; Heptane/AcOEt, 2/1, v/v in Heptane 0/100 to 100/0). The desired fractions were collected and evaporated in vacuo to yield intermediate 95 as a brown foam (1.1 g, 58%).

Synthesis of Intermediate 96:

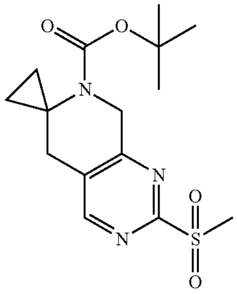 [SMILES: CC(C)(C)OC(=O)N1Cc2nc(S(C)(=O)=O)ncc2CC12CC2]

3-Chloroperbenzoic acid (2.5 g, 11.1 mmol) was added portion-wise to a solution of intermediate 95 in DCM (35 mL). The reaction mixture was stirred, at room temperature, overnight. The reaction mixture was diluted with DCM (40 mL) and washed with 1M $Na_2CO_3$ (30 mL). The organic layer was separated and washed once more with saturated NaCl (20 mL). The organic layer was dried over $MgSO_4$, filtered and evaporated in vacuo. The residue was purified by flash column chromatography (silica; AcOEt in Heptane 0/100 to 60/40). The desired fractions were collected and evaporated in vacuo to yield intermediate 96 as a colorless foam (1 g, 83%).

Synthesis of Intermediate 97:

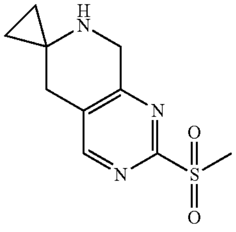 [SMILES: CS(=O)(=O)c1ncc2c(n1)CNC1(CC1)C2]

Intermediate 96 (1 g, 3.1 mmol) was taken in DCM (35 mL) and treated with Trifluoroacetic acid (3.4 mL, 46.2 mmol) at room temperature. The reaction mixture was stirred overnight. The reaction mixture was evaporated in vacuo and then co-evaporated with Toluene (10 mL). The residue was taken in DCM (40 mL) and 1M $Na_2CO_3$ (20 mL) was added. The organic layer was separated, and the aqueous phase was extracted with more DCM (2×10 mL). The combined organic layers were dried over $MgSO_4$, filtered and evaporated in vacuo. The residue was purified by flash column chromatography (silica; DCM/MeOH, 9/1, v/v in DCM 0/100 to 100/0). The desired fractions were collected and concentrated in vacuo yielding intermediate 97 (0.6 g, 87%).

Synthesis of Intermediate 98:

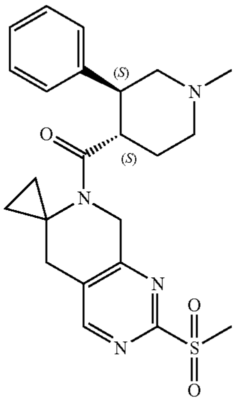

Intermediate 27 (0.5 g, 2.2 mmol), Intermediate 8 (0.6 g, 2.2 mmol), 2-Chloro-1-methylpyridin-1-ium iodide (1.1 g, 4.5 mmol) and triethylamine (1.9 mL, 11.3 mmol) were taken in THF (26 mL) while a stream nitrogen was bubbled through the solution. The vial was sealed and the resulting solution was stirred at 55° C. for 20 hours. AcOEt (80 mL) and 1M $Na_2CO_3$ (60 mL) were added. The phases were separated. The organic layer was dried over $MgSO_4$, filtered and concentrated in vacuo. The residue was purified by flash column chromatography (silica; DCM/MeOH, 9/1, v/v in DCM 0/100 to 100/0). The fractions containing the desired product were collected together and evaporated in vacuo yielding intermediate 98 (0.8 g, 84%).

Synthesis of Intermediate 99:

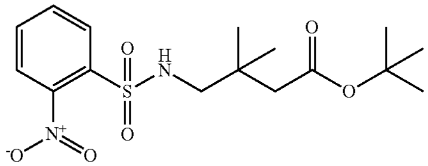

tert-butyl 4-amino-3,3-dimethylbutanoate (3.7 g, 19.9 mmol) and triethylamine (6.1 mL, 43.8 mmol) were taken in DCM (40 mL) with stirring. 2-Nitrobenzenesulfonyl chloride (5.3 g, 23.9 mmol) in DCM (30 mL) was then added dropwise with ice cooling over 15 minutes. The mixture was then allowed to warm up to room temperature. Stirring was maintained for 4 hours. Water (100 mL) was added to the mixture. The organics were extracted with DCM (50 mL). The organic layer was washed with sat. $NaHCO_3$ (100 mL), dried over $MgSO_4$, filtered and concentrated to the crude. Chromatography over silica gel (gradient of AcOEt in heptane from 0 to 50%) afforded the yellowish solid intermediate 99 (7.9 g, 99%).

Synthesis of Intermediate 100:

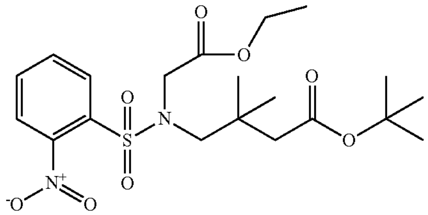

Intermediate 99 (7.4 g, 19.9 mmol) and ethyl bromoacetate (8.8 mL, 79.4 mmol) were taken in DMF (100 mL). Potassium carbonate (8.2 g, 59.6 mmol) was added at room temperature and the reaction was stirred overnight. The reaction mixture was diluted with AcOEt (200 mL) and water (500 mL). The organic layer was separated, washed with brine (100 mL), dried over $MgSO_4$, filtered and concentrated to the crude. Chromatography over silica gel (gradient of AcOEt in heptane from 0 to 30%) afforded intermediate 100 as a viscous colorless oil (7.6 g, 82%).

Synthesis of Intermediate 101:

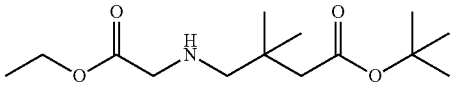 [SMILES: CCOC(=O)CNCC(C)(C)CC(=O)OC(C)(C)C]

Thiophenol (1.5 g, 14.5 mmol) was added to a mixture of intermediate 100 (6 g, 13.1 mmol) and cesium carbonate (8.6 g, 26.3 mmol) in DMF (60 mL). The reaction was monitored by TLC (heptane/EA, 2/1, v/v) and appeared to be complete within 45-60 minutes. The mixture was diluted with diethyl ether (200 mL) and water (200 mL). The organic layer was separated and washed one more time with water (70 mL) and then brine (50 mL). Drying over $MgSO_4$, filtration and removal of solvents gave a crude mixture. Chromatography over silica gel (gradient of AcOEt in heptane from 0 to 30%) afforded intermediate 101 as a clear oil (3.6 g, 52%).

Synthesis of Intermediate 102:

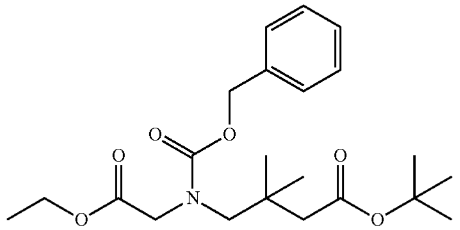 [SMILES: CCOC(=O)CN(CC(C)(C)CC(=O)OC(C)(C)C)C(=O)OCc1ccccc1]

Benzyl chloroformate (3.9 mL, 27.8 mmol) was added to a solution of intermediate 101 (1.9 g, 6.9 mmol) in saturated $NaHCO_3$ (20 mL) and DCM (25 mL) at 0° C. The mixture was allowed to come to room temperature and stirred overnight. The mixture was diluted with DCM (100 mL) and 25% $NH_4OH$ (25 mL) was added with stirring. After 15 minutes, the organic layer was separated, dried over $MgSO_4$, filtered and concentrated to dryness. Chromatography over silica gel (gradient of AcOEt in heptane from 0 to 30%) afforded intermediate 102 as a clear oil (2.6 g, 92%).

Synthesis of Intermediate 103a and 103b:

103a

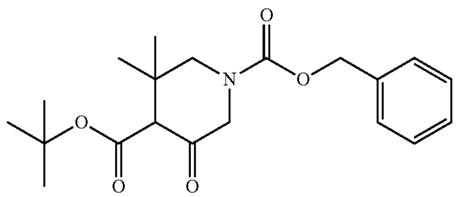

, and

103b

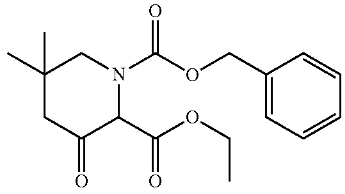

Potassium tert-butoxide (1 g, 9.6 mmol) was added to a solution of intermediate 102 (2.6 g, 6.4 mmol) in THF (50 mL). TLC (Heptane/AcOEt, 2/1, v/v) after 2 hours showed complete conversion. The reaction was diluted with AcOEt (100 mL) and water (25 mL). Sat. $NH_4Cl$ (20 mL) was added with stirring. The organic layer was separated, and the aqueous phase was extracted once more with AcOEt (50 mL). The combined organic layers were dried over $MgSO_4$, filtered and concentrated to dryness. Chromatography over silica gel (gradient of AcOEt in heptane from 0 to 15%) afforded intermediate 103a (272 mg, 11%) and 103b (1.2 g, 54%).

Synthesis of Intermediate 104:

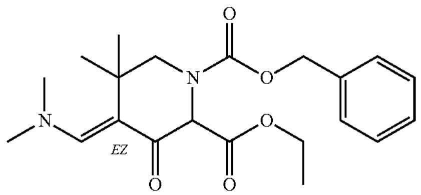 [SMILES: CCOC(=O)C1C(=O)/C(=C/N(C)C)C(C)(C)CN1C(=O)OCc1ccccc1]

Intermediate 103b (750 mg, 2.2 mmol) and N,N-DimethylFormamide Dimethyl acetal (1 ml, 7.5 mmol) were stirred at 90° C. for 2 hours. The reaction mixture was concentrated to dryness. The crude intermediate 104 was dried at room temperature under high vacuum and finally used as such in the next step (901 mg, >100%).

Synthesis of Intermediate 105:

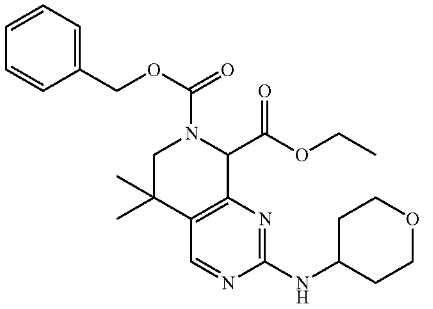 [SMILES: CCOC(=O)C1c2nc(NC3CCOCC3)ncc2C(C)(C)CN1C(=O)OCc1ccccc1]

Intermediate 104 (0.8 g, 2.2 mmol) and 1-(tetrahydro-2H-pyran-4-yl) guanidine (483 mg, 3.4 mmol) were taken in DMF (15 mL). Sodium acetate (369 mg, 4.5 mmol) was added and the resulting mixture was heated to 90° C. for 45 minutes. The mixture was allowed to cool to room temperature and concentrated to dryness. The residue was taken in AcOEt (50 mL) and washed with water (50 mL), 0.5M HCl (50 mL) and brine (15 mL). The organic layer was dried over $MgSO_4$, filtered and concentrated to dryness. Chromatography over silica gel (gradient of MeOH in DCM from 0 to 5%) afforded intermediate 105 as a yellowish oil (122 mg, 11%).

Synthesis of Intermediate 106:

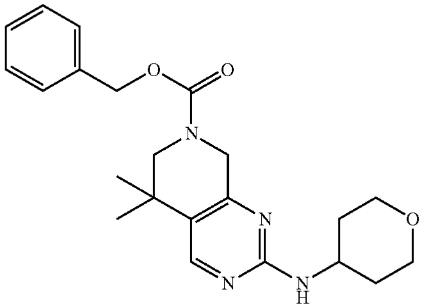 [SMILES: CC1(C)CN(C(=O)OCc2ccccc2)Cc2nc(NC3CCOCC3)ncc21]

1M Sodium hydroxide (2 mL, 2 mmol) was added to a solution of intermediate 105 (122 mg, 0.26 mmol) in THF (2 mL). The mixture was stirred at room temperature for 6 hours. 1M sulfuric acid (1.1 mL, 1.1 mmol) was added to the mixture that was then heated to 80° C. for 1 hour. The mixture was allowed to cool to room temperature and diluted with AcOEt (20 mL) and brine (20 mL). The organic layer was separated, dried over $MgSO_4$, filtered and concentrated to dryness. Chromatography over silica gel (gradient of MeOH in DCM from 0 to 5%) afforded intermediate 106 (92 mg, 85%).

Synthesis of Intermediate 107:

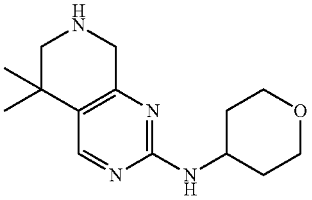 [SMILES: CC1(C)CNCc2nc(NC3CCOCC3)ncc21]

The hydrogenolysis of intermediate 106 (92 mg, 0.23 mmol) in MeOH (10 mL) over Pd/C 10% (61 mg, 0.06 mmol) was performed under atmospheric pressure of $H_2$ at room temperature over 45 minutes. The catalyst was filtered off through a short pad of Celite that was further rinsed with MeOH (3×10 mL). The filtrate was concentrated to dryness yielding intermediate 107 (51 mg, 80%).

Synthesis of Intermediate 108:

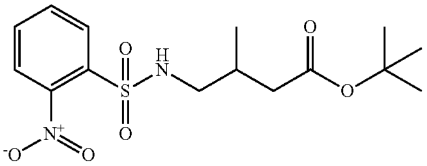

Triethylamine (22.6 mL, 162 mmol) was added to a cold (ice-bath) solution of tert-butyl 4-amino-3-methylbutanoate (23.5 g, 135.5 mmol) and DCM (300 mL). Then 2-Nitrobenzenesulfonyl chloride (36 g, 162.5 mmol) in DCM (100 mL) was added dropwise. The reaction mixture was allowed to warm to room temperature and the stirring was maintained overnight. Sat. $NaHCO_3$ (100 mL) was added to the mixture. The phases were separated, and the organic layer was dried over $MgSO_4$, filtered and concentrated in vacuo. The residue was purified by flash column chromatography (silica; heptane/AcOEt, 2/1, v/v in heptane 0/100 to 100/0) yielding intermediate 108 (27.5 g, 57%) used directly in the next step.

Synthesis of Intermediate 109:

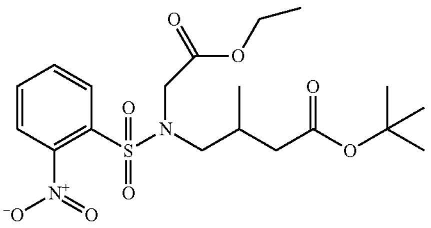

Intermediate 108 (27.5 g, 76.7 mmol) and bromoacetate (34 mL, 307 mmol) were taken in DMF (385 mL). Potassium carbonate (21.2 g, 153 mmol) was added at room temperature and the reaction mixture continued overnight. The mixture was diluted with AcOEt (300 mL) and washed with water (900 mL). The aqueous layer was washed twice more with AcOEt (2×200 mL). The combined organic layers were washed with saturated NaCl (100 mL), dried over $MgSO_4$, filtered and concentrated in vacuo. The residue was purified by flash column chromatography (silica; Heptane/AcOEt, 2/1, v/v in heptane 0/100 to 100/0) yielding intermediate 109 (28.6 g, 83%).

Synthesis of Intermediate 110:

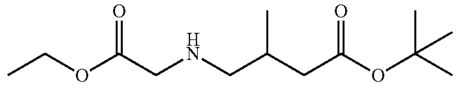 [SMILES: CCOC(=O)CNCC(C)CC(=O)OC(C)(C)C]

Thiophenol (9.9 ml, 96 mmol) was added to a mixture of intermediate 109 (28.6 g, 64.3 mmol) and cesium carbonate (41.9 g, 128.7 mmol) in DMF (350 mL). The reaction mixture was stirred, at room temperature for 24 hours. The mixture was diluted with AcOEt (200 mL) and water (500 mL). The aqueous layer was extracted with AcOEt (3×200 mL and 2×100 mL). The combined organic layers were washed with saturated NaCl (100 mL), dried over $MgSO_4$, filtered and concentrated in vacuo. The residue was purified by flash column chromatography (silica; Heptane/AcOEt, 1/1, v/v in heptane 0/100 to 100/0) yielding intermediate 110 (12.3 g, 73%).

Synthesis of Intermediate 111:

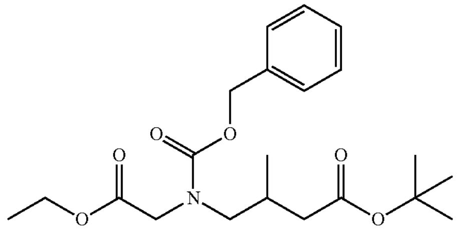 [SMILES: CCOC(=O)CN(CC(C)CC(=O)OC(C)(C)C)C(=O)OCc1ccccc1]

Benzyl chloroformate (17.3 mL, 121.3 mmol) was added to a solution of intermediate 110 (12.3 g, 47.4 mmol) in sodium bicarbonate (120 mL) and DCM (160 mL) at 0° C. The mixture was allowed to come to room temperature and stirred overnight. The mixture was diluted with DCM (60 mL). The organic layer was dried over $MgSO_4$, filtered and concentrated in vacuo. The residue was purified by flash column chromatography (silica; Heptane/AcOEt, 2/1, v/v in heptane 0/100 to 100/0) yielding intermediate 111 (17.9 g, 96%).

Synthesis of Intermediate 112:

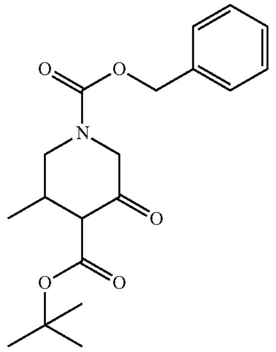 [SMILES: CC1CN(C(=O)OCc2ccccc2)CC(=O)C1C(=O)OC(C)(C)C]

Potassium tert-butoxide (7.6 g, 68.2 mmol) was added to a solution of intermediate 111 (17.9 g, 45.4 mmol) in THF (136 mL) under nitrogen atmosphere. The reaction was diluted with DCM (30 mL) and water (20 mL). Sat. $NH_4Cl$ (50 mL) was added with stirring. The organic layer was separated, and the aqueous phase was extracted once more with DCM (20 mL). The combined organic layers were dried over $MgSO_4$, filtered and concentrated in vacuo. The residue was purified by flash column chromatography (silica; heptane/AcOEt, 2/1, v/v in heptane 0/100 to 100/0) yielding intermediate 112 (9 g, 57%).

Synthesis of Intermediate 113:

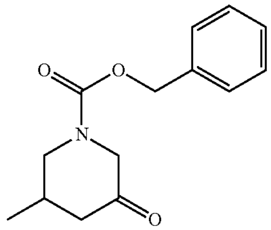 [SMILES: CC1CC(=O)CN(C(=O)OCc2ccccc2)C1]

Trifluoroacetic acid (38.5 mL, 518.1 mmol) was added to a solution of intermediate 112 (9 g, 25.9 mmol) in DCM (90 mL). The mixture was stirred for 3 hours to complete tert-Butyl ester cleavage. The mixture was concentrated dry to a residue that was taken in $MeOH/H_2O$ (175 mL/70 mL) and refluxed overnight. The mixture was allowed to cool to room temperature and MeOH was removed in vacuo. DCM (50 mL) and 1M $Na_2CO_3$ (50 mL) were added with stirring. The organic layer was separated, dried over $MgSO_4$, filtered and evaporated in vacuo. The residue was purified by flash column chromatography (silica; heptane/AcOEt, 2/1, v/v in heptane 0/100 to 100/0) yielding intermediate 113 (5.2 g, 81%).

Synthesis of Intermediate 114:

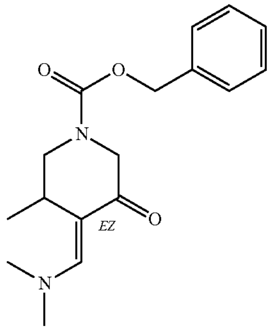 [SMILES: CC1CN(C(=O)OCc2ccccc2)CC(=O)/C1=C/N(C)C]

Tert-Butoxybis(dimethylamino)methane (1 mL, 4.8 mmol) was added to a solution of intermediate 113 (1 g, 4 mmol) in toluene (10 mL) at room temperature. The mixture was stirred for 20 hours. The reaction mixture was concentrated to dryness. The crude intermediate 114 was dried, at room temperature, under high vacuum and used as such in the next synthetic step (1.2 g, 100%).

Synthesis of Intermediate 115:

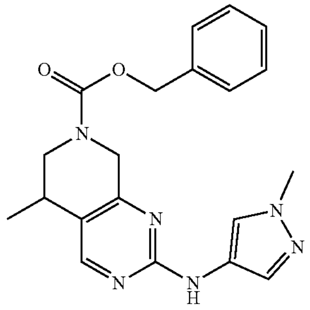 [SMILES: CC1CN(C(=O)OCc2ccccc2)Cc2nc(Nc3cnn(C)c3)ncc21]

N-(1-methyl-1H-pyrazol-4-yl) guanidine (0.7 g, 4.8 mmol) and intermediate 114 (1.2 g, 4 mmol) were taken in EtOH (31 mL). Sodium ethoxide (3 mL, 8.1 mmol) was added and the resulting mixture was heated at 45° C. overnight. The reaction mixture was diluted with DCM (50 mL) and the organics were washed with water (20 mL). The organic layer was dried over $MgSO_4$, filtered and concentrated to dryness. The residue was purified by flash column chromatography (silica; AcOEt in heptane 0/100 to 100/0), yielding intermediate 115 (0.3 g 69% Purity).

Synthesis of Intermediate 116:

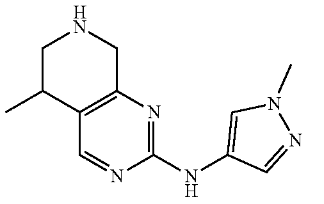 [SMILES: CC1CNCc2nc(Nc3cnn(C)c3)ncc21]

The hydrogenolysis of intermediate 115 (0.3 g, 0.8 mmol) in MeOH (5 mL) over Pd/C 10% (0.2 g, 0.2 mmol) was performed under atmosphere of $H_2$ at room temperature overnight. The catalyst was filtered off through a short pad of celite that was further rinsed with MeOH (3×10 mL). The filtrate was concentrated in vacuo. The residue was purified by flash column chromatography (silica; DCM/MeOH, 9/1, v/v in DCM 0/100 to 100/0), yielding intermediate 116 (0.019 g, 9%).

Synthesis of Intermediate 117:

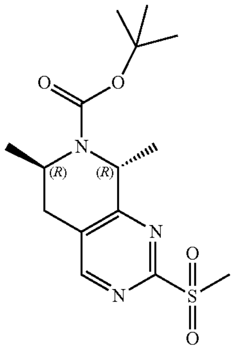

NaH (60% dispersion in mineral oil) (195 mg, 4.9 mmol) was added portion-wise to a solution intermediate 3a (800 mg, 2.4 mmol) and iodomethane (456 μL, 7.3 mmol) in DMF (8.8 mL, 113.7 mmol) at 0° C. The reaction mixture was stirred at 0° C. for 30 minutes. The reaction mixture was quenched with a $NH_4Cl$ aqueous solution and extracted with AcOEt three times. The organic layer was washed with brine, dried over $MgSO_4$, filtered and the solvent was evaporated. The residue was purified by chromatography over silica gel ($SiO_2$, Grace, 40 g; eluent: 90% heptane, 10% EtOAc to 40% Heptane, 60% AcOEt). The pure fractions were collected, and the solvent was evaporated to give intermediate 117 (410 mg, 49%).

Synthesis of Intermediate 118:

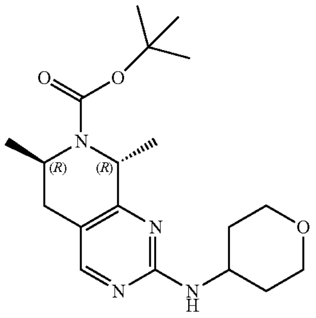

Intermediate 117 (410 mg, 1.2 mmol) and Tetrahydro-2H-pyran-4-amine (0.75 g, 7.2 mmol) were stirred at 110° C. for 5 h. The crude mixture was purified by chromatography over silica gel ($SiO_2$, Grace, 40 g; eluent: 90% heptane, 10% AcOEt to 40% Heptane, 50% AcOEt, 10% MeOH (2% $NH_4OH$)). The pure fractions were collected, and the solvent was evaporated to give intermediate 118 (310 mg, yield 71%).

Synthesis of Intermediate 119:

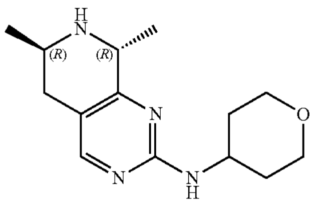

HCl 4M in Dioxane (2.1 mL, 4 M, 8.4 mmol) was added to a solution of intermediate 118 (310 mg, 0.86 mmol) in 1,4-dioxane (3.1 mL, 37.2 mmol) and MeOH (1 mL, 26 mmol) at room temperature. The reaction was stirred for 3 hours. The volatiles were evaporated, and the residue was taken up in water, basified with $K_2CO_3$ and the aqueous phase was extracted with DCM. The organic layer was dried over $MgSO_4$, filtered and evaporated until dryness to give intermediate 119 (180 mg, yield 80%).

Synthesis of Intermediate 120a and 120b:

120a

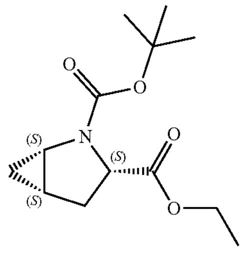

and

-continued

120b

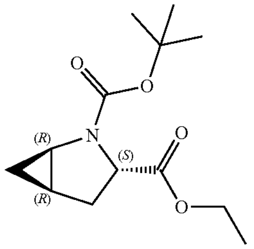

A mixture of 1M diethyl Zinc in hexane (165.8 mL, 165.8 mmol) and DCM (160 mL) was cooled to 0° C. under nitrogen atmosphere. Trifluoroacetic acid (12.7 mL, 165.8 mmol) in DCM (70 mL) was then added dropwise over ca.30 minutes. After another 30 minutes, a solution of Diiodomethane (13.3 mL, 165.8 mmol) in DCM (70 mL) was also added dropwise over ca.15 minutes to the white suspension. After another 10 minutes, the resulting mixture was treated with a solution of Ethyl N-Boc-L-proline-4-ene (20 g, 82.8 mmol) in DCM (50 mL) (slow addition over 30 minutes). The reaction was maintained at 0° C. for 5 minutes and then allowed to warm to room temperature and stirred for another 2.5 hours. Finally, the mixture was again cooled at 0° C. and triethylamine (28.9 mL, 207.2 mmol) was slowly added. The mixture was allowed to come to room temperature and reaction continued overnight at room temperature. The insolubles were filtered through a plug of Celite that was further washed with DCM (3×100 mL). The organic layer was separated, and the aqueous phase was extracted once more with DCM (250 mL). The combined organic layers were dried over $MgSO_4$ and filtered. To overcome the partial Boc-cleavage, di-tert-butyl dicarbonate (9 g, 41.4 mmol) was added to the solution and the mixture was stirred for 3 hours. The mixture was concentrated to dryness. Chromatography over silica gel (gradient of AcOEt in heptane from 0 to 15%) afforded the pure diastereoisomers 120a (15 g, 71%) and 120b (749 mg, 3.5%).

Synthesis of Intermediate 121:

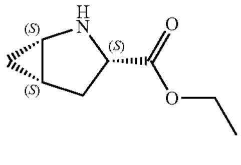

Intermediate 120a (15 g, 58.7 mmol) was taken in AcOEt (150 mL) and treated with 4N HCl in Dioxane (100 mL, 400 mmol) at room temperature. The mixture was stirred for 5 hours. The mixture was concentrated to the crude that was further dried under high vacuum at 60° C. Intermediate 121 (15.2 g, >100%) was used as such in the next step.

Synthesis of Intermediate 122:

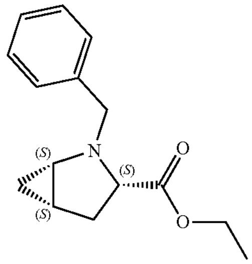

Intermediate 121 (11.3 g, 58.7 mmol), benzyl bromide (8.4 mL, 70.5 mmol) and potassium carbonate (12.1 g, 88.1 mmol) were taken in DMF (200 mL) and stirred at room temperature for 6 hours. The mixture was diluted with AcOEt (250 mL), water (50 mL) and brine (50 mL) were added. The organic layer was separated and washed once more with water (100 mL), dried over $MgSO_4$, and filtered. Removal of solvent gave a crude oil. Flash chromatography over silica gel (gradient of AcOEt in heptane from 0 to 25%) afforded intermediate 122 as a clear oil (11.6 g, 80%).

Synthesis of Intermediate 123:

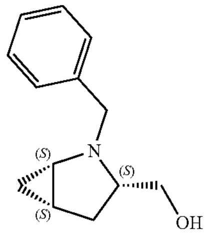

A solution of intermediate 122 (11.6 g, 47.3 mmol) in THF (100 mL) was added dropwise to a suspension of $LiAlH_4$ (2.7 g, 70.9 mmol) in THF (50 mL) under a nitrogen stream. The mixture was stirred at 0° C. for 2 hours. The reaction was quenched with water (15 mL) at 0° C. The mixture was diluted with DCM (100 mL) and insolubles were filtered through a pad of Celite that was further rinsed with DCM (3×50 mL). The filtrate was transferred to a separation funnel and was washed with brine (50 mL). The organic layer was dried over $MgSO_4$, filtered and concentrated to dryness to yield intermediate 123 (8.3 g, 85%).

Synthesis of Intermediate 124:

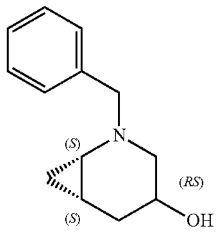

Trifluoroacetic anhydride (11.5 mL, 82.6 mmol) was added to a solution of intermediate 123 (11.2 g, 55.1 mmol) in THF (100 mL) at −78° C. The mixture was stirred at the same temperature for 3 hours and then triethylamine (15.3 mL, 110.2 mmol) was added dropwise and the reaction was continued for 15 minutes at −78° C., allowed to come to room temperature and finally refluxed overnight. 2.5M sodium hydroxide (220.4 mL, 551 mmol) was added and the mixture was stirred at room temperature for 3 hours. Most of the organic solvent was then removed in vacuo. DCM (200 mL) and brine were added to the residue. The organic layer was separated and the aqueous phase was extracted once more with DCM (100 mL). The combined DCM-extracts were dried over $MgSO_4$, filtered and concentrated to dryness. Chromatography over silica gel (gradient of AcOEt in heptane from 0 to 80%) gave intermediate 124 (9.8 g, 87%)

Synthesis of Intermediate 125:

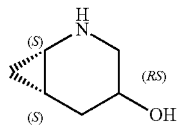

Intermediate 124 (9.8 g, 48 mmol) and 4N HCl in dioxane (13.2 mL, 52.8 mmol) were stirred in EtOH (165 mL). 10% Pd/C (2.1 g, 2 mmol) was added and the reaction was placed under an atmosphere of $H_2$ (balloon filled with $H_2$). The mixture was stirred for 5 hours at room temperature. The catalyst was filtered off through a pad of Celite that was further washed with MeOH (2×20 mL). The filtrate was concentrated to dryness to yield intermediate 125 as a crude solid (8.3 g, >100%).

Synthesis of Intermediate 126:

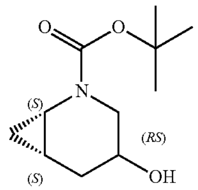

Intermediate 125 (8.3 g, 38.6 mmol) was taken in DCM (125 mL). 1M sodium hydroxide (126.3 mL, 126.3m mol) was added with stirring. Di-tert-butyl dicarbonate (10.1 g, 46.3 mmol) in DCM (75 mL) was then added slowly. The turbid mixture was vigorously stirred overnight. The mixture was diluted with DCM (20 mL) and a saturated solution of $NaHCO_3$ was added. The organic layer was separated and dried over $MgSO_4$. Filtration and solvent removal gave the crude. Chromatography over silica gel (gradient of AcOEt in heptane from 0 to 50%) afforded intermediate 126 (4.3 g, 52%).

Synthesis of Intermediate 127:

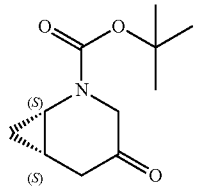

Dess martin periodinane (12.4 g, 29.4 mmol) was added to a solution of intermediate 126 (4.2 g, 19.6 mmol) in DCM (300 mL) at room temperature. The mixture was stirred for 3 hours. 1M $Na_2CO_3$ (200 mL) and a saturated solution of $Na_2S_2O_3$ (10 mL) were added with vigorous stirring. After 10 minutes, DCM (100 mL) was added and the organic layer was separated. Drying over $MgSO_4$, filtration and removal of solvent gave the crude. Chromatography over silica gel column (gradient of AcOEt in heptane from 0 to 50%) afforded a colorless oil that crystallized upon standing yielding intermediate 127 (3.6 g, 87%).

Synthesis of Intermediate 128:

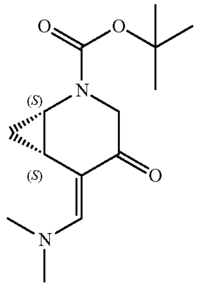

tert-Butoxybis(dimethylamino)methane (2.9 mL, 14.2 mmol) was added to a solution of intermediate 127 (1.5 g, 7.1 mmol) in toluene (50 mL) at room temperature. The mixture was stirred overnight. The reaction mixture was concentrated to dryness. The crude residue was dried at room temperature under high vacuum yielding intermediate 128 used as such in the next step (2.3 g, >100%).

Synthesis of Intermediate 129:

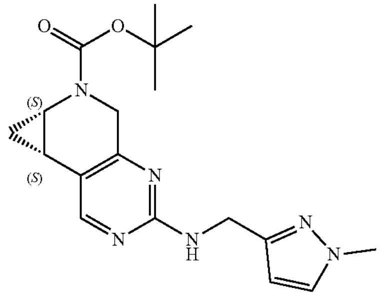

Intermediate 128 (517 mg, 1.9 mmol) and N-[(1-methyl-1H-pyrazol-3-yl)methyl] guanidine (0.6 g, 3.9 mmol) were taken in EtOH (20 mL). Sodium ethoxide (1.4 mL, 3.9 mmol) was added and the resulting mixture was heated to 70° C. for 18 hours. The mixture was allowed to cool to room temperature and DCM (100 mL) was added followed by water (20 mL) and brine (20 mL). The organic layer was separated, dried over $MgSO_4$, filtered and concentrated to dryness. Chromatography over silica gel (gradient of MeOH in DCM from 0 to 5%) afforded a yellowish stick intermediate 129 (527 mg, 75%).

Synthesis of Intermediate 130:

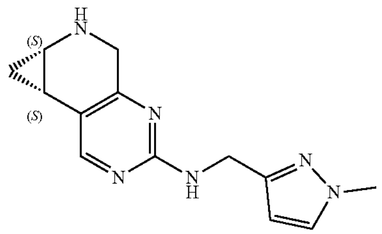

Trifluoroacetic acid (3.2 mL, 42 mmol) was added to a solution of intermediate 129 (522 mg, 1.4 mmol) in DCM (10 mL) and the mixture was stirred at room temperature for 2 hours. The reaction mixture was concentrated to dryness. The residue was taken in DCM (30 mL) and washed with 1M $Na_2CO_3$ (15 mL). The aqueous phase was extracted exhaustively with DCM/MeOH (9/1, v/v). The combined organic layers were dried over $MgSO_4$, filtered and concentrated to the crude. Chromatography over silica a gel (gradient of a mixture DCM/MeOH/$NH_4OH$ (9.0/0.9/0.1, v/v/v) in DCM from 0 to 50%) afforded intermediate 130 (347 mg, 91%) as a sticky solid.

Synthesis of Intermediate 131:

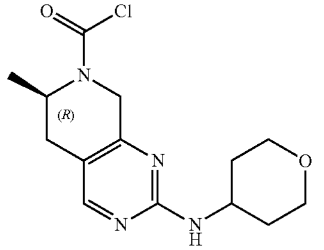

A mixture of intermediate 27 (0.88 g, 3.5 mmol), triethylamine (0.62 mL, 4.4 mmol) and DCM (12 mL) was added to a cold solution (ice-bath) of Diphosgene (0.52 mL, 4.3 mmol) in DCM (10 mL). The reaction mixture was stirred, at 0° C., for 90 minutes. $H_2O$ and DCM were added, the RM was extracted, the organic layer was separated, dried over $MgSO_4$, filtered and evaporated yielding to intermediate 131 used as it for next step.

Synthesis of Intermediate 132a and 132b:

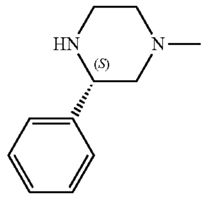

132a

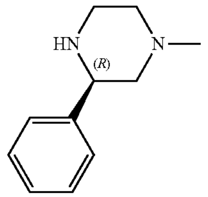

132b

1-Methyl-3-phenylpiperazine (13.3 g, 75.7 mmol) was separated via chiral SFC (Stationary phase: CHIRALPAK AD-H 5 μm 250*30 mm, Mobile phase: 92% CO2, 8% mixture of MeOH/iPrOH 50/50 v/v (+3.0% $iPrNH_2$)) to give intermediate 132a (5.9 g, 33.3 mmol). $[\alpha]_d$=+49.1° (589 nm, c 0.33 w/v %, CHCl3, 20° C.) ((S) enantiomer) and intermediate 132b (6.4 g, 36.1 mmol) $[\alpha]_d$=−56.9° (589 nm, c 0.32 w/v %, CHCl3, 20° C.) ((R) enantiomer).

Synthesis of Intermediate 133:

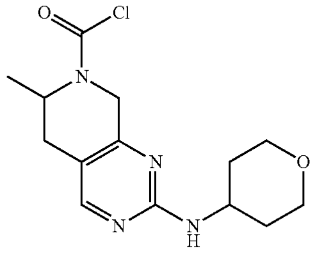 [SMILES: CC1Cc2cnc(NC3CCOCC3)nc2CN1C(=O)Cl]

A mixture of intermediate 66 (850 mg, 3.4 mmol), triethylamine (504 μl, 3.6 mmol) and DCM (10 mL) was added to a cold solution (ice-bath) of diphosgene (437 μl, 3.6 mmol) in DCM (5 mL). The reaction mixture was stirred, at 0° C., for 90 minutes. Water and DCM were added, the RM was extracted, the organic layer was separated, dried over $MgSO_4$, filtered and evaporated yielding intermediate 133 used as it for next step.

Synthesis of Intermediate 134:

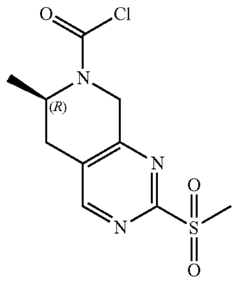

A mixture of intermediate 2 (0.5 g, 1.9 mmol), triethylamine (0.7 mL, 5 mmol) and DCM (10 mL) was added to a cold solution (ice-bath) of diphosgene (0.27 mL, 2.2 mmol) in DCM (5 mL). The reaction mixture was stirred, at 0° C., for 90 minutes. Water and DCM were added, the RM was extracted, the organic layer was separated, dried over $MgSO_4$, filtered and evaporated yielding used as it for next step.

Synthesis of Intermediate 135:

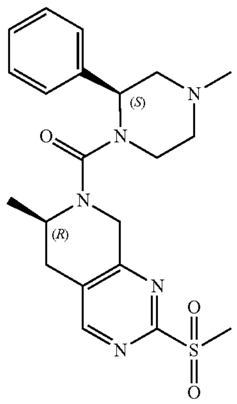

Intermediate 134 (549 mg, 1.9 mmol), intermediate 132a (434 mg, 2.5 mmol), triethylamine (0.34 mL, 2.4 mmol) in DCM (5 mL). The RM was stirred at rt 2 days. Water and DCM were added, the RM was extracted, the organic layer was separated, dried over $MgSO_4$, filtered and evaporated. A purification was performed via preparative LC (Stationary phase: irregular SiOH 35-40 μm 24 g Buchi, Mobile phase: DCM 100% to 95/5/0.1 CMA). The pure fractions were collected and evaporated until dryness to give 589 mg (72%) of intermediate 135. $[\alpha]_d$=+28.3° (589 nm, c 0.36 w/v %, DMF, 20° C.).

Synthesis of Intermediate 136:

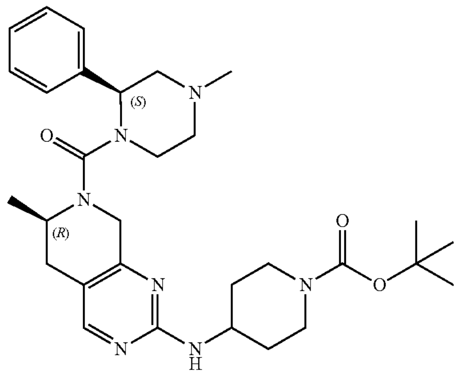

Intermediate 135 (500 mg, 1.16 mmol) and 4-Amino-1-Boc-piperidine (1.6 g, 8 mmol) were stirred at 110° C. in a sealed tube overnight. The residue was purified by preparative LC (Stationary phase: irregular SiOH 35-40 μm 40 g Buchi, gradient from 100% DCM to 90% DCM 10% $CH_3OH$ 0.1% $NH_4OH$) yielding intermediate 136 (575 mg, 90% yield). $[\alpha]_d$=+68.4° (589 nm, c 0.22 w/v %, DMF, 20° C.).

Synthesis of Intermediate 137:

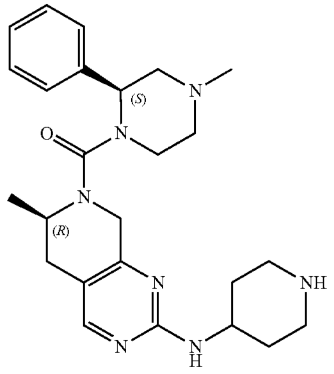

Intermediate 136 (575 mg, 1 mmol) and trifluoroacetic acid (1.2 mL, 15.7 mmol) were stirred in DCM (20 mL) at rt for 15 hours. Water was added and the mixture was basified with $K_2CO_3$. The organic layer was extracted and the aqueous layer was saturated with $K_2CO_3$ and extracted with AcOEt. Both organic layers were put together, dried over $MgSO_4$, filtered and evaporated until dryness to give intermediate 137 (429 mg, 91%).

Synthesis of Intermediate 138:

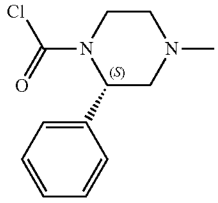

A mixture of intermediate 132a (150 mg, 0.85 mmol), triethylamine (142 μl, 1 mmol) and DCM (3.5 mL) was added to a cold solution (ice-EtOH) of triphosgene (303 mg, 1 mmol) in DCM (2.5 mL). Temperature was allowed to increase to rt and the reaction was stirred for 1h. Water and DCM were added, the RM was extracted, the organic layer was separated, dried over $MgSO_4$ filtered and evaporated. The crude intermediate 138 was used as it for the next step.

Synthesis of Intermediate 139:

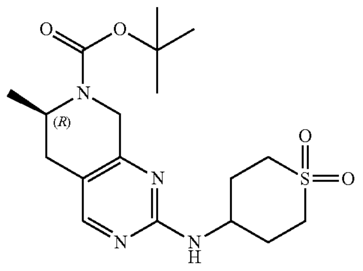

Intermediate 3a (580 mg, 1.77 mmol) and 1,1-Dioxo-tetrahydrothiopyran-4-amine (2 g, 13.4 mmol) in a sealed tube were heated at 110° C. for 6 hours. DCM and water were added, the organic layer was extracted, dried over $MgSO_4$, filtered and evaporated until dryness. The residue was purified by preparative LC (SiOH 35-40 μm Buchi, gradient from 100% DCM to 90% DCM 10% $CH_3OH$ 0.1% $NH_4OH$). The fractions were collected and evaporated until dryness to give intermediate 139 (350 mg, 50%).

Synthesis of Intermediate 140:

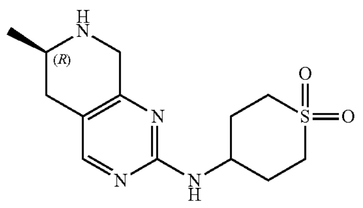

Trifluoroacetic acid (2.2 mL, 8.8 mmol) was added dropwise to a solution of intermediate 139 (350 mg, 0.88 mmol) in dioxane (3.5 mL) and MeOH (1 mL) at room temperature. The reaction was stirred for 2 days, poured into water, basified with $K_2CO_3$ and extracted with DCM. The organic layer was dried over $MgSO_4$, filtered and evaporated until dryness to give intermediate 140 (249 mg, 95%).

Synthesis of Intermediate 141:

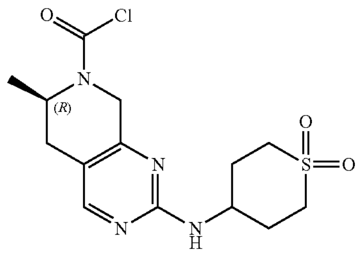

A mixture of intermediate 140 (249 mg, 0.84 mmol), pyridine (0.102 mL, 1.26 mmol) and DCM (3 mL) was added at −5° C. to a solution of diphosgene (0.12 mL, 1 mmol) in DCM (3 mL). The reaction mixture was stirred, at 0° C., for 90 minutes. Water and DCM were added, the mixture was extracted, the organic layer was separated, dried over $MgSO_4$, filtered and evaporated yielding intermediate 141 used as it for the next step.

Synthesis of Compound 1:

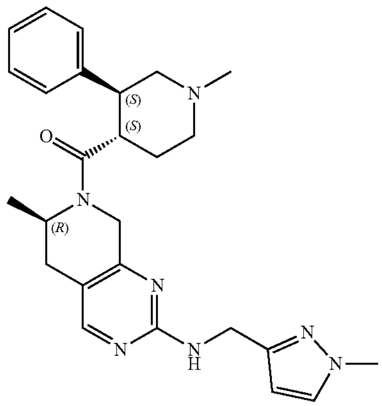

A mixture of intermediate 5 (5.2 g, 20.1 mmol), intermediate 8 (7.7 g, 30.1 mmol), HBTU (2-(1H-Benzotriazole-1-yl)-1,1,3,3-tetramethyluronium hexafluorophosphate) (15.5 g, 40.9 mmol), diisopropylethylamine (20 mL, 0.121 mol) in DMF (140 mL) was stirred at room temperature for 20 hours. The solvent was removed and the residue was taken up with DCM and $H_2O$. The organic layer was extracted, dried over $MgSO_4$, filtered and evaporated. The crude mixture was purified by flash chromatography (DCM/MeOH gradient from 100:0 to 80:20) followed by achiral SFC (Stationary phase: 2-Ethylpyridine 5 μm 150*30 mm, Mobile phase: 90% CO2, 10% MeOH (0.6% $iPrNH_2$)). The pure fractions were collected and evaporated, yielding Compound 1, which was crystallized in diethylether, filtered and dried, yielding 4.24 g (44%) $[\alpha]_d$: +59.4° (589 nm, c 0.18 w/v %, DMF, 20° C.). m.p.=178° C. (DSC).

The compounds listed in the table below have been prepared by an analogous reaction protocol:

| Compound | Structure | Quantity | Yield |
|---|---|---|---|
| Compound 2 | 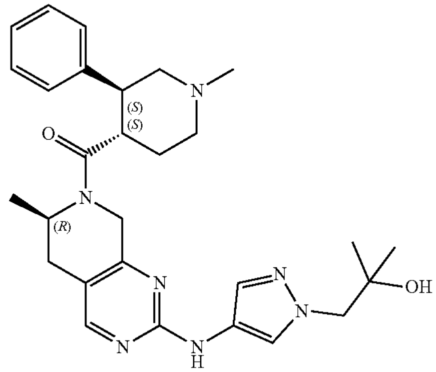 | 0.021 g | 75% |
| Compound 3 | 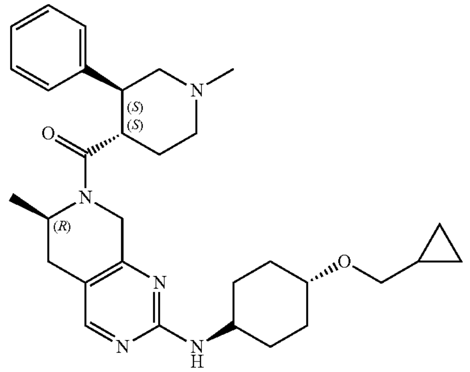 $[\alpha]_d$: +47.0° (589 nm, c 0.12 w/v, MeOH, 23° C.) | 0.170 g | 38% |

-continued
| Compound | Structure | Quantity | Yield |
|---|---|---|---|
| Compound 4 | 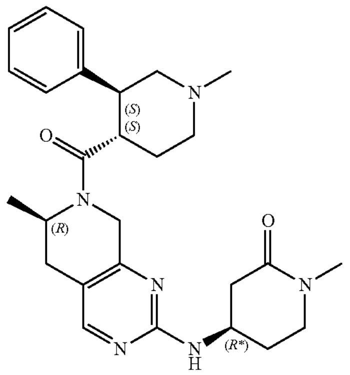 [α]$_d$: +32.4° (589 nm, c 0.12 w/v, MeOH, 23° C.) | 0.052 g | 17% |
| Compound 5 | 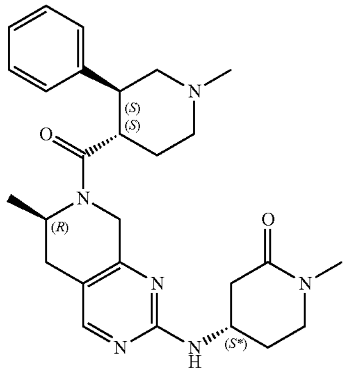 [α]$_d$: +78.8° (589 nm, c 0.12 w/v, MeOH, 23° C.) | 0.044 g | 15% |
| Compound 6 | 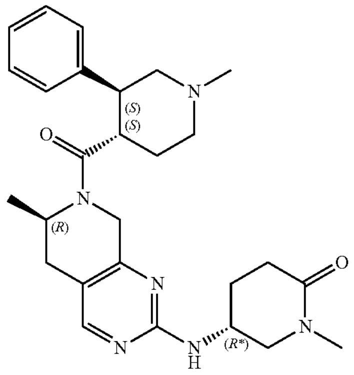 | 0.030 g | 37% |
| Compound 7 | 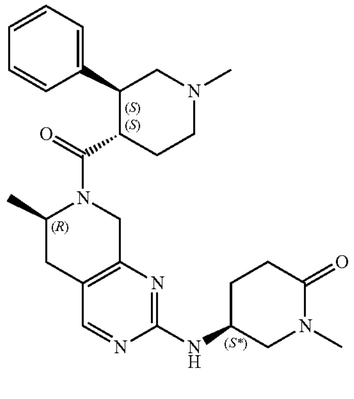 | 0.024 g | 30% |

-continued
| Compound | Structure | Quantity | Yield |
|---|---|---|---|
| Compound 8 | 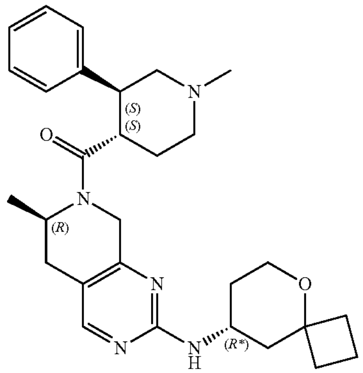 | 0.041 g | 31% |
| Compound 9 | 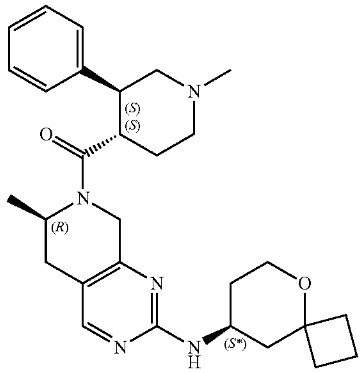 | 0.041 g | 31% |
| Compound 10 | 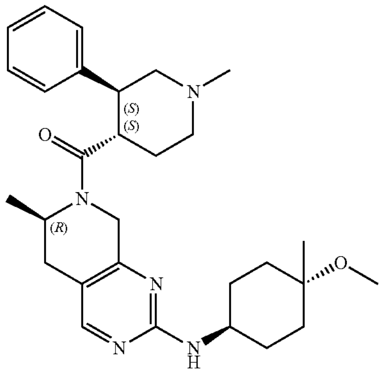 [α]$_d$: +50.1° (589 nm, c 0.12 w/v, MeOH, 23° C.) | 0.087 g | 18% |
| Compound 11 | 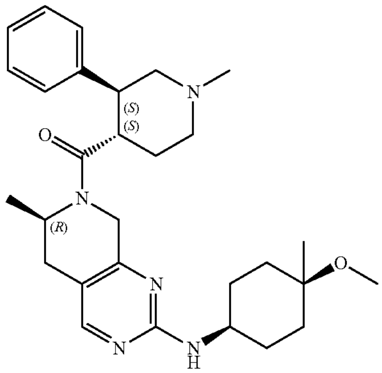 [α]$_d$: +54.7° (589 nm, c 0.12 w/v, MeOH, 23° C.) | 0.130 g | 28% |

-continued
| Compound | Structure | Quantity | Yield |
| --- | --- | --- | --- |
| Compound 12 | 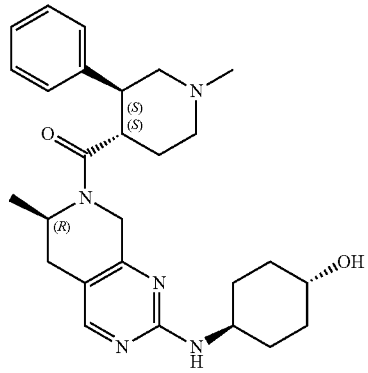 | 0.075 g | 42% |
| Compound 13 | 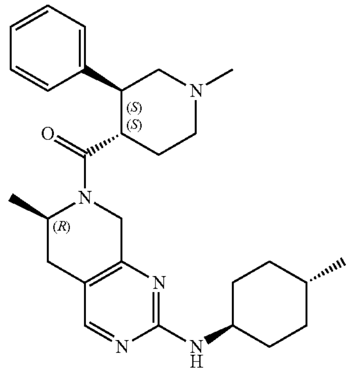 | 0.111 g | 29% |
| Compound 14 | 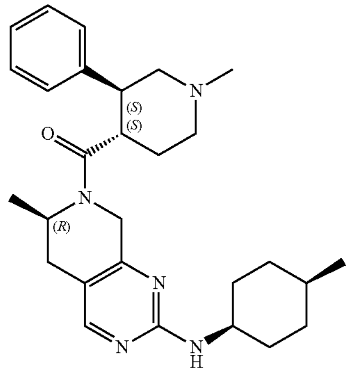 | 0.156 g | 38% |
| Compound 15 | 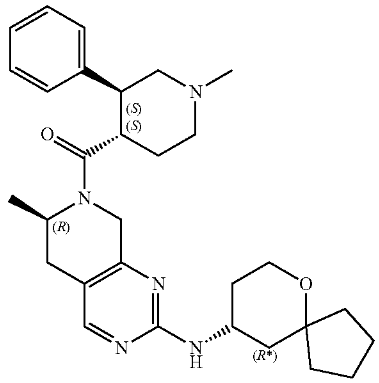 [α]$_d$: +51.1° (589 nm, c 0.11 w/v, MeOH, 23° C.) | 0.030 g | 13% |

-continued
| Compound | Structure | Quantity | Yield |
|---|---|---|---|
| Compound 16 | 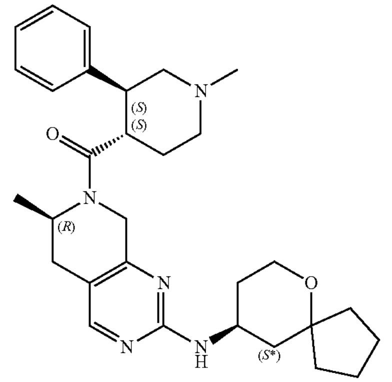 [α]$_d$: +65.3° (589 nm, c 0.093 w/v, MeOH, 23° C.) | 0.020 g | 9% |
| Compound 17 | 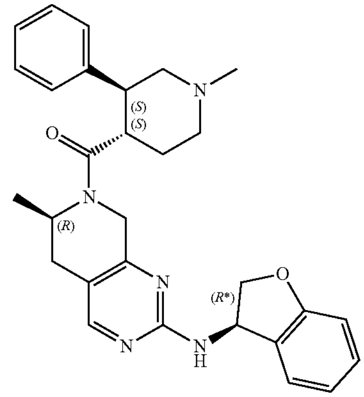 | 0.069 g | 18% |
| Compound 18 | 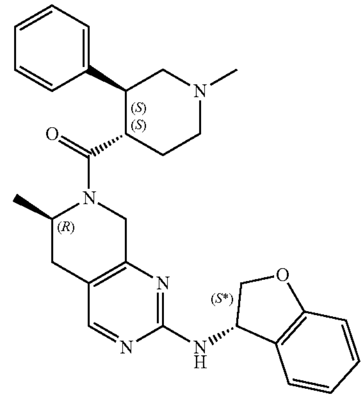 | 0.057 g | 15% |
| Compound 19 | 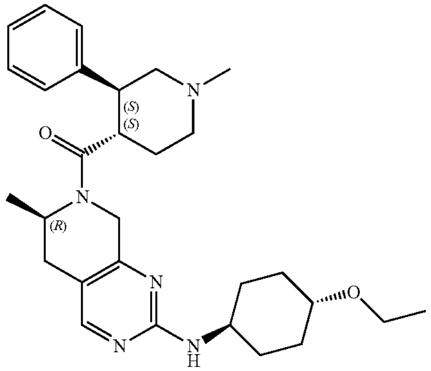 | 0.16 g | 39% |

-continued
| Compound | Structure | Quantity | Yield |
| --- | --- | --- | --- |
| Compound 20 | 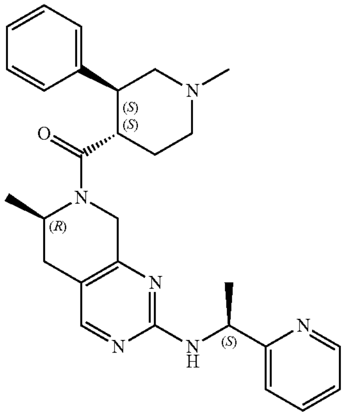 | 0.25 g | 46% |
| Compound 21 | 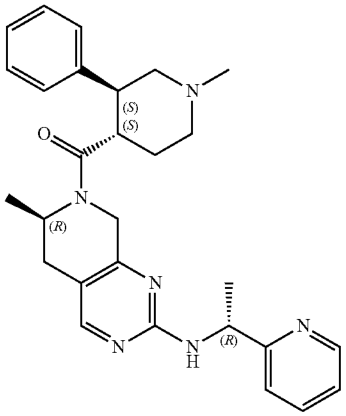 | 0.25 g | 34% |
| Compound 22 | 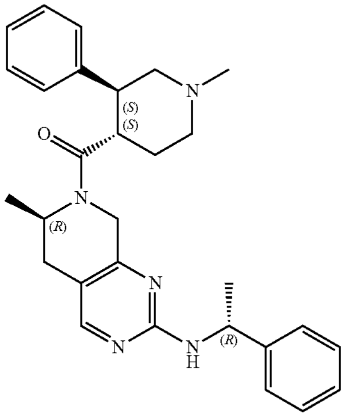 | 0.12 g | 55% |

-continued
| Compound | Structure | Quantity | Yield |
| --- | --- | --- | --- |
| Compound 23 | 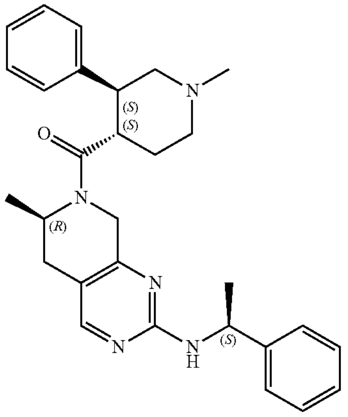 | 0.034 g | 13% |
| Compound 24 | 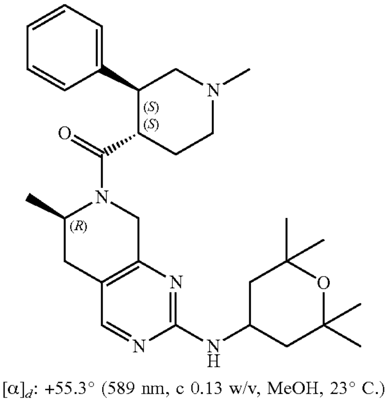 [α]$_d$: +55.3° (589 nm, c 0.13 w/v, MeOH, 23° C.) | 0.088 g | 56% |
| Compound 25 | 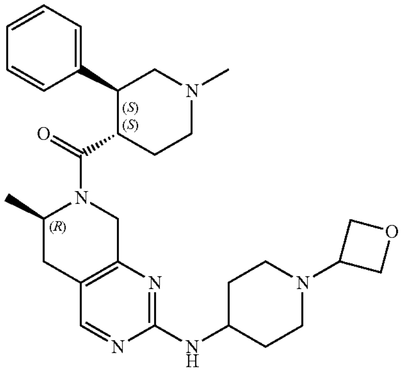 [α]$_d$: +54.4° (589 nm, c 0.11 w/v, MeOH, 23° C.) | 0.1 g | 46% |

-continued
| Compound | Structure | Quantity | Yield |
|---|---|---|---|
| Compound 26 | 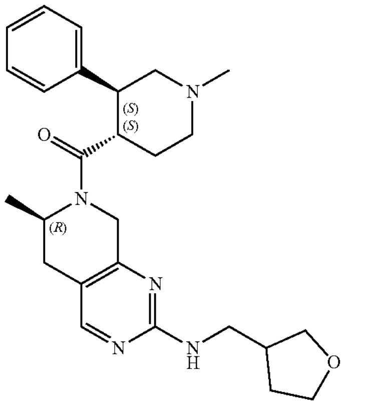<br>[α]$_d$: +62.3° (589 nm, c 0.14 w/v, MeOH, 23° C.) | 0.136 g | 45% |
| Compound 27 | 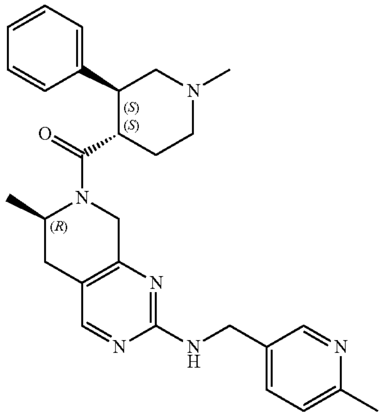 | 0.148 g | 32% |
| Compound 28 | 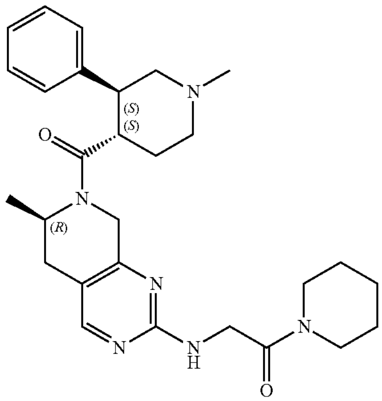 | 0.078 g | 45% |

-continued
| Compound | Structure | Quantity | Yield |
| --- | --- | --- | --- |
| Compound 29 | 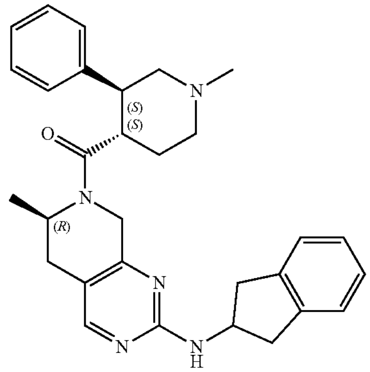 | 0.17 g | 35% |
| Compound 30 | 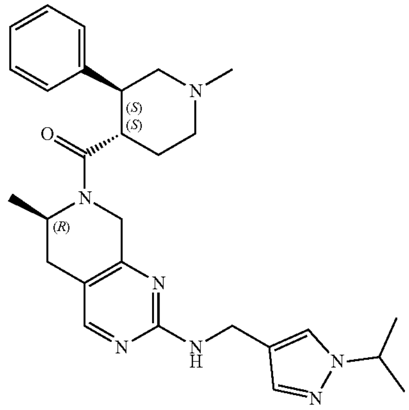 | 0.133 g | 43% |
| Compound 31 | 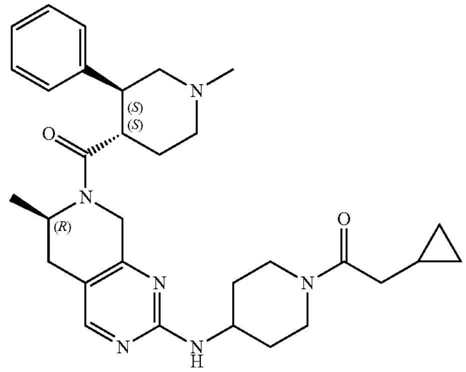 | 0.06 g | 25% |
| Compound 32 | 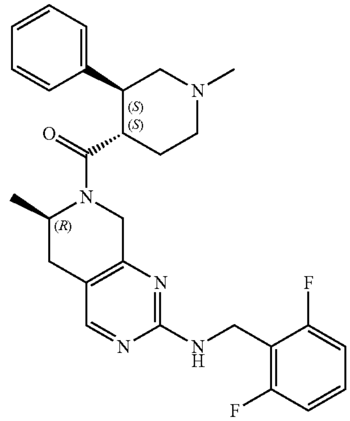 | 0.07 g | 23% |

-continued
| Compound | Structure | Quantity | Yield |
| --- | --- | --- | --- |
| Compound 33 | 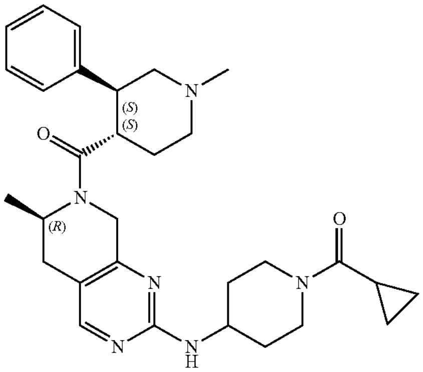 | 0.101 g | 31% |
| Compound 34 | 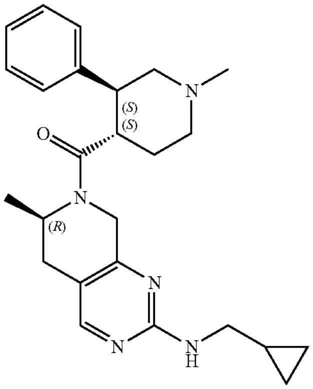 | 0.082 g | 35% |
| Compound 35 | 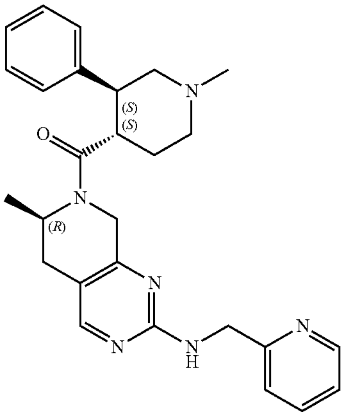 | 0.09 g | 24% |
| Compound 36 | 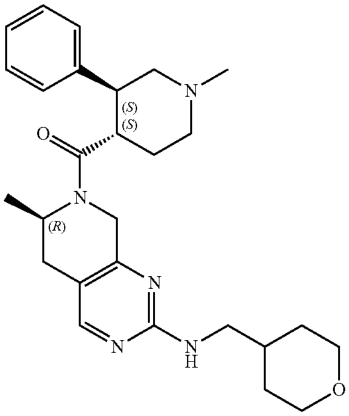 | 0.08 g | 40% |

-continued
| Compound | Structure | Quantity | Yield |
| --- | --- | --- | --- |
| | [α]$_d$: +62.5° (589 nm, c 0.14 w/v, MeOH, 23° C.) | | |
| Compound 37 | 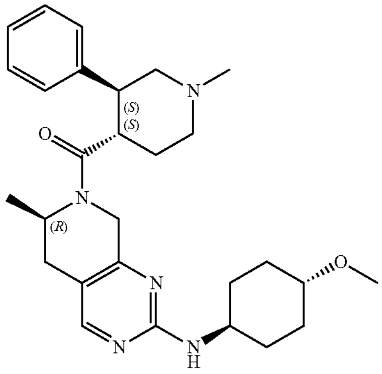 | 0.191 g | 36% |
| Compound 38 | 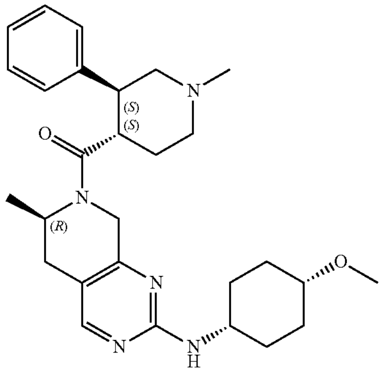 | 0.274 g | 25% |
| Compound 39 | 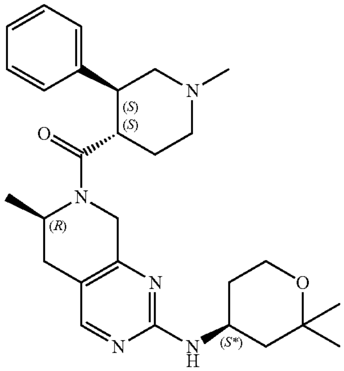 [α]$_d$: +53.5° (589 nm, c 0.17 w/v, DMF, 20° C.) | 0.125 g | 33% |
| Compound 40 | 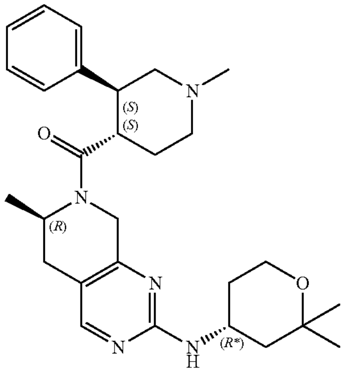 [α]$_d$: +66.3° (589 nm, c 0.16 w/v, DMF, 20° C.) | 0.185 g | 35% |

-continued
| Compound | Structure | Quantity | Yield |
|---|---|---|---|
| Compound 41 | 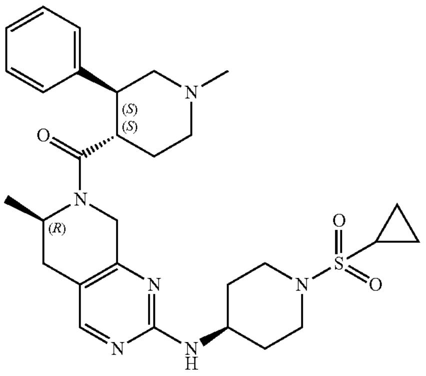 | 0.041 g | 22% |
| Compound 42 | 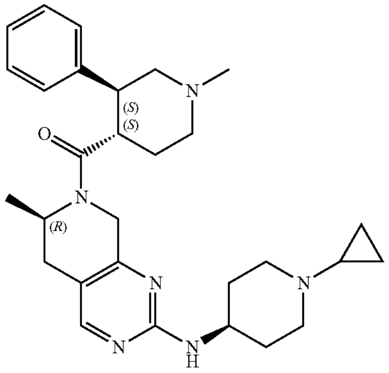 | 0.097 g | 31% |
| Compound 43 | 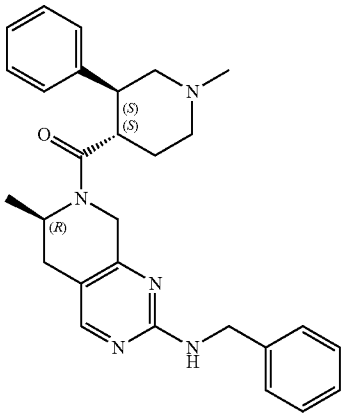 | 0.077 g | 34% |
| Compound 44 | 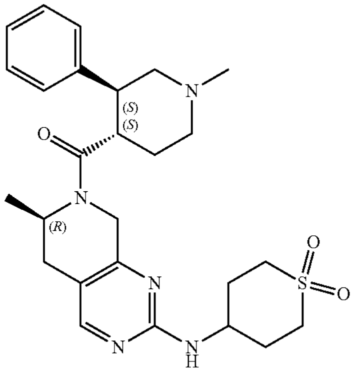 | 0.035 g | 17% |

-continued
| Compound | Structure | Quantity | Yield |
|---|---|---|---|
| Compound 45 | 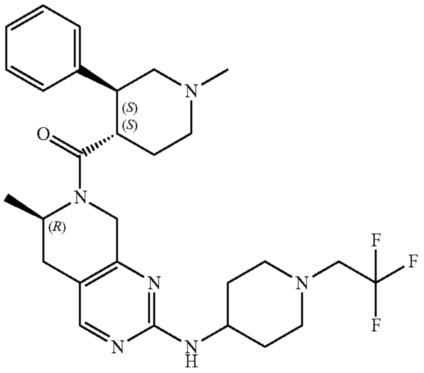 | 0.234 g | 44% |
| Compound 46 | 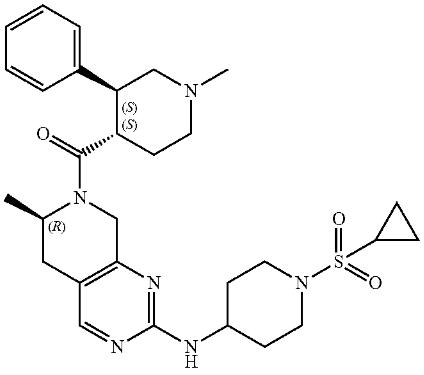 | 0.041 g | 15% |
| Compound 47 | 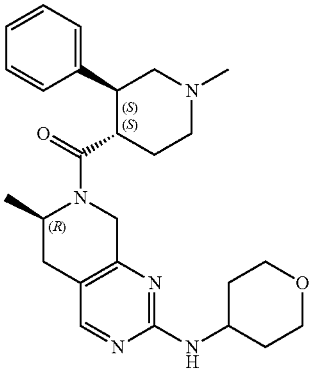<br>[α]$_d$: +58.18° (589 nm, c 0.11 w/v %, DMF, 20° C.)<br>m.p. = 162.7° C. (DSC) | 0.763 g | 42% |

Synthesis of Compound 1:

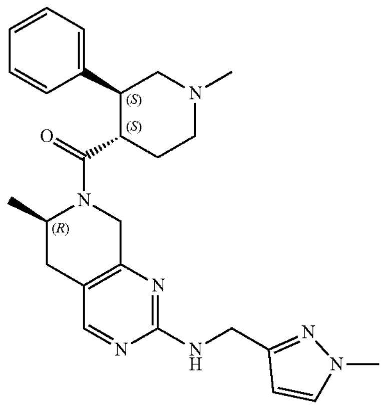

Second Synthesis (1-Methyl-1H-pyrazol-3-yl)methylamine (1 g, 9 mmol) was heated to 110° C. in a sealed tube, then intermediate 11 (425 mg, 0.99 mmol) was added and the reaction mixture was heated at 110° C. for 5 hours. The residue was dissolved in DCM and purified by flash chromatography (DCM/MeOH/$NH_4OH$ gradient from 100:0:0 to 90:10:0.2). The pure fractions were collected and evaporated, yielding Compound 1 which was crystallized in $Et_2O$, filtered and dried (177 mg, 39%). m.p.=178° C. (DSC).

The compounds listed in the table below have been prepared by an analogous reaction protocol:

| Compound | Structure | Quantity | Yield |
|---|---|---|---|
| Compound 48 | 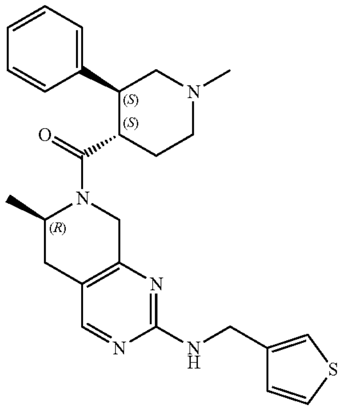 | 0.051 g | 32% |
| Compound 49 | 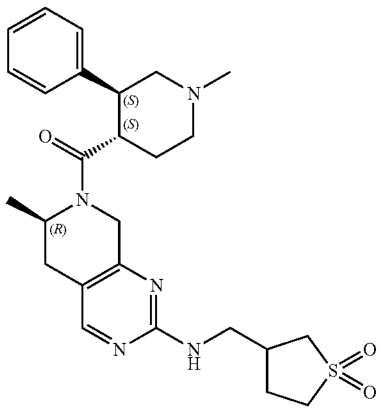 | 0.071 g | 41% |

-continued
| Compound | Structure | Quantity | Yield |
| --- | --- | --- | --- |
| Compound 50 | 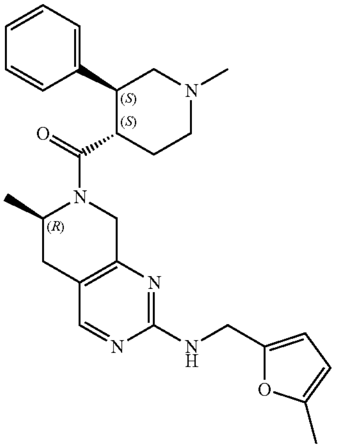 | 0.084 g | 52% |
| Compound 51 | 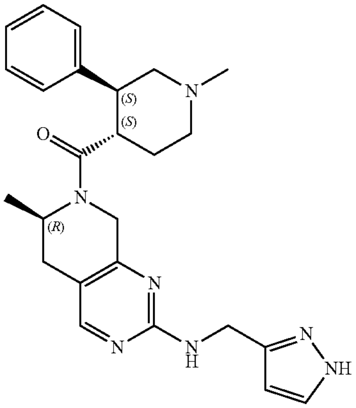 | 0.054 g | 17% |
| Compound 52 | 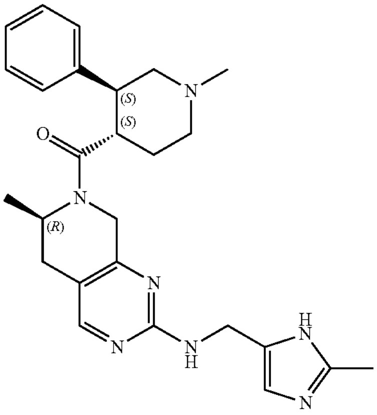 | 0.122 g | 38% |

-continued
| Compound | Structure | Quantity | Yield |
|---|---|---|---|
| Compound 53 | 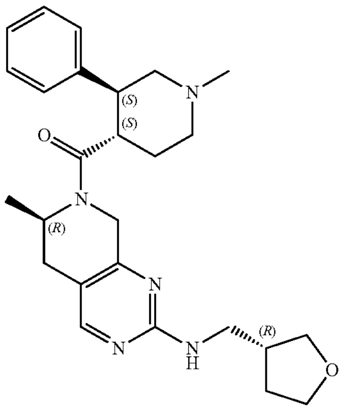 | 0.09 g | 43% |
| Compound 54 | 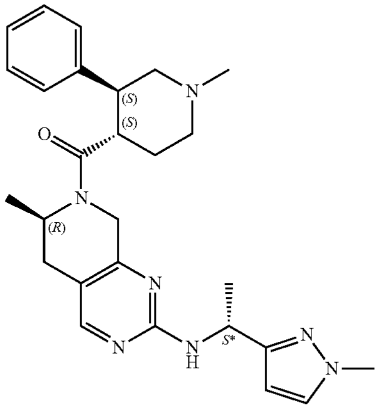 | 0.09 g | 41% |
| Compound 55 | 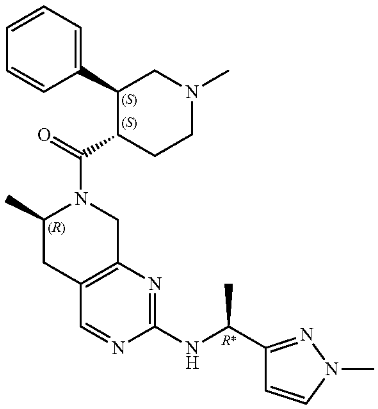 | 0.065 g | 29% |

-continued
| Compound | Structure | Quantity | Yield |
|---|---|---|---|
| Compound 56 | 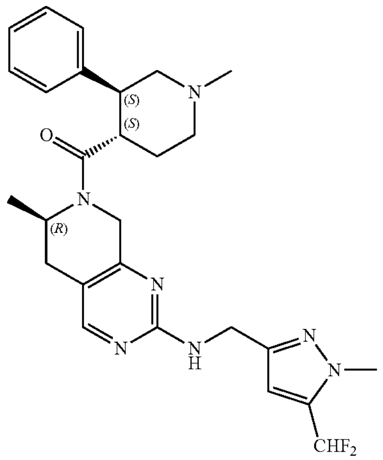 | 0.08 g | 34% |
| Compound 57 | 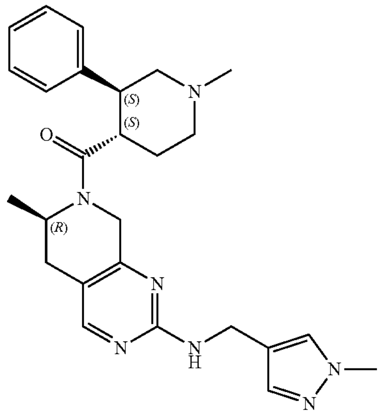 | 0.108 g | 63% |
| Compound 58 | 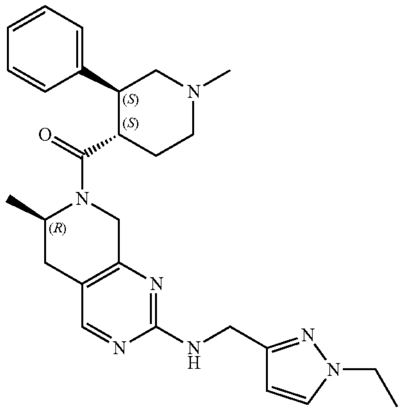 | 0.05 g | 23% |

-continued
| Compound | Structure | Quantity | Yield |
|---|---|---|---|
| Compound 59 | 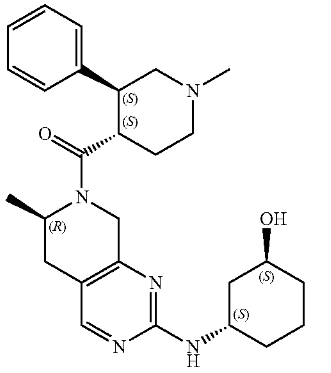 | 0.075 g | 35% |
| Compound 60 | 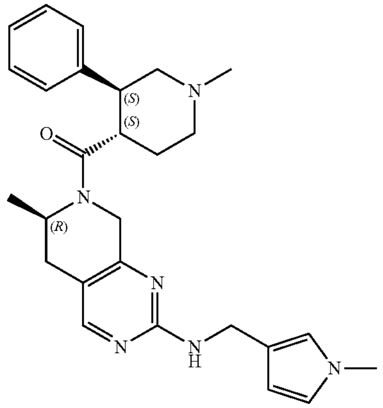 | 0.113 g | 53% |
| Compound 61 | 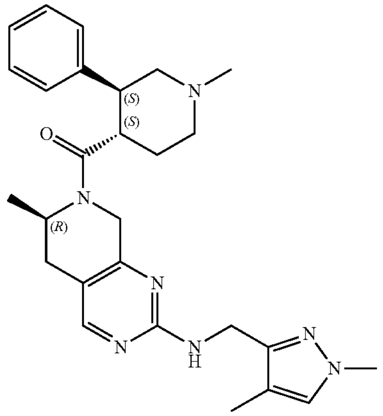 | 0.129 g | 58% |
| Compound 62 | 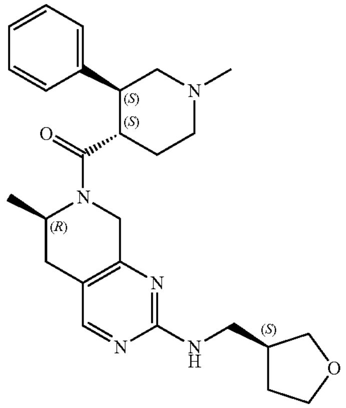 | 0.082 g | 39% |

-continued
| Compound | Structure | Quantity | Yield |
|---|---|---|---|
| Compound 63 | 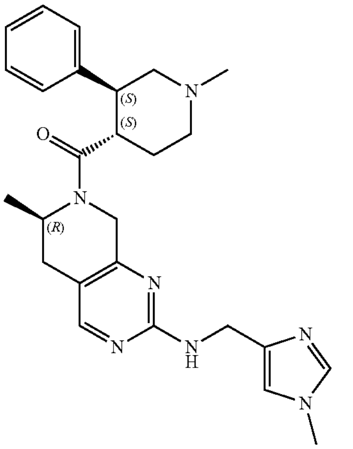 | 0.079 g | 37% |
| Compound 64 | 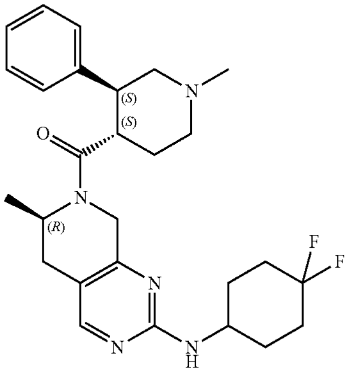 | 0.032 g | 19% |
| Compound 65 | 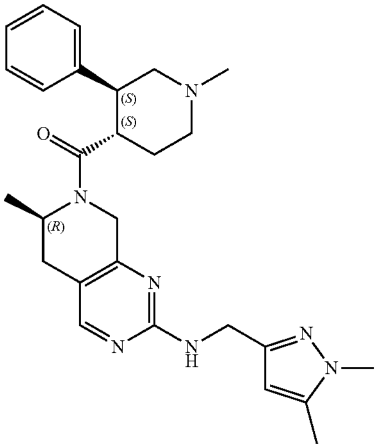 | 0.056 g | 34% |

-continued
| Compound | Structure | Quantity | Yield |
| --- | --- | --- | --- |
| Compound 66 | 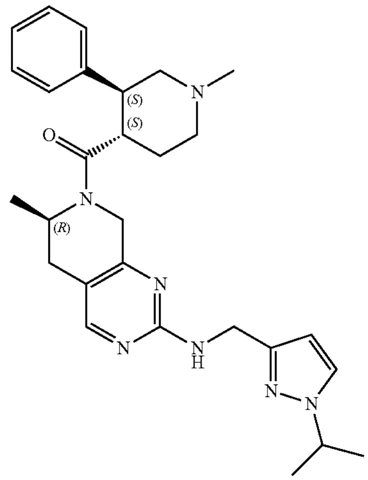 | 0.052 g | 30% |
| Compound 67 | 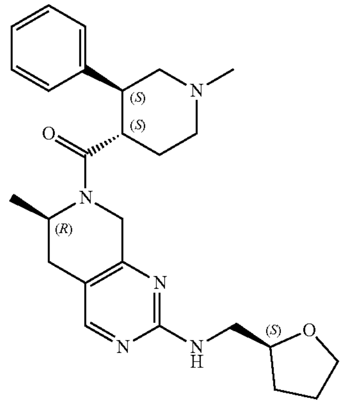 | 0.082 g | 43% |
| Compound 68 | 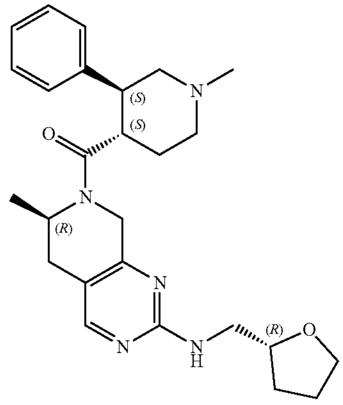 | 0.078 g | 41% |

-continued
| Compound | Structure | Quantity | Yield |
|---|---|---|---|
| Compound 69 | 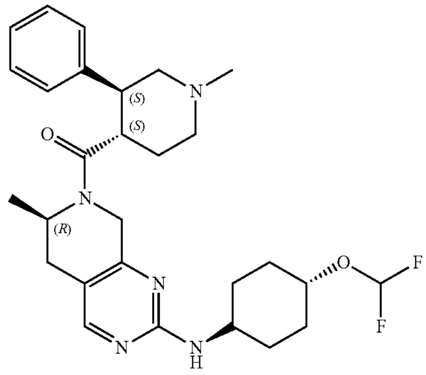 | 0.114 g | 31% |
| Compound 70 | 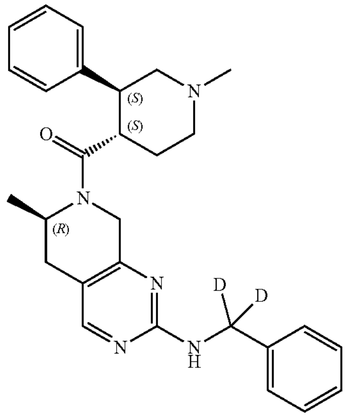 | 0.08 g | 35% |
| Compound 71 | 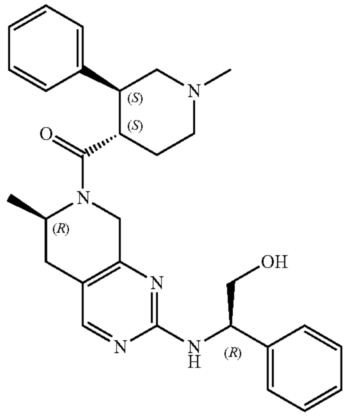 | 0.125 g | 46% |

-continued

| Compound | Structure | Quantity | Yield |
|---|---|---|---|
| Compound 72 | 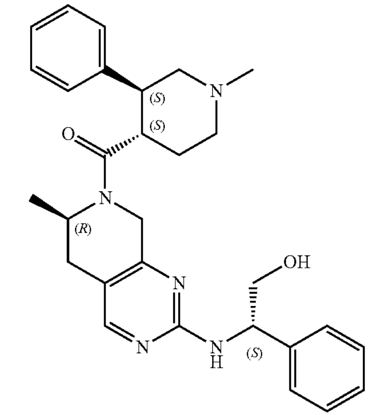 | 0.167 g | 49% |

Synthesis of Compound 91:

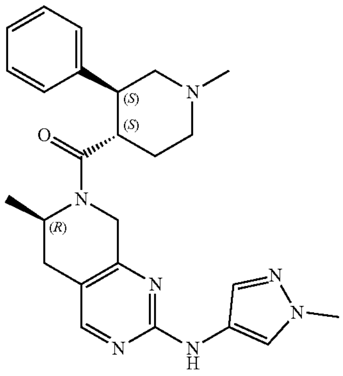

A mixture of intermediate 18 (250 mg, 1 mmol), intermediate 8 (400 mg, 1.6 mmol), HBTU (2-(1H-Benzotriazole-1-yl)-1,1,3,3-tetramethyluronium hexafluorophosphate) (590 mg, 1.6 mmol), diisopropylethylamine (1.1 mL, 6.6 mmol) in DMF (10 mL) was stirred for 15 hours at room temperature. The solvent was removed by evaporation and the residue was taken up with DCM+$H_2O$. The organic layer was extracted, dried over $MgSO_4$, filtered and evaporated until dryness. This fraction was purified by flash chromatography (DCM/MeOH/$NH_4OH$ gradient from 100:0:0 to 90:10:0.2). The pure fractions were collected and evaporated until dryness. The residue was washed with an aqueous solution of $K_2CO_3$ and $CH_2Cl_2$ was added. The mixture was stirred for 20 min then the organic layer was extracted, dried over $MgSO_4$, filtered and evaporated until dryness, yielding compound 91 (190 mg, 41%). This fraction was freeze-dried with acetonitrile/water 20/80 to give Compound 91 (177 mg, 39%). $[\alpha]_d$: +67.7° (589 nm, c 0.08 w/v, MeOH, 23° C.).

The compounds listed in the table below have been prepared by an analogous reaction protocol:

| Compound | Structure | Quantity | Yield |
|---|---|---|---|
| Compound 73 | 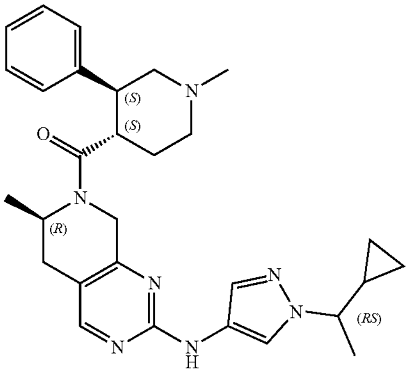 | 0.124 g | 33% |
| Compound 74 | 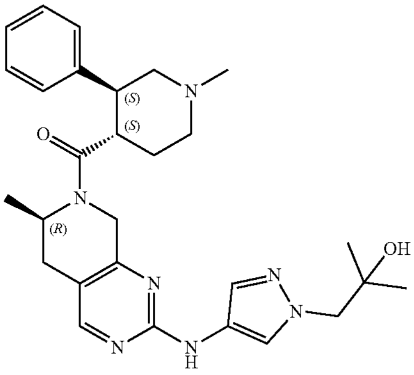 | 0.021 g | 18% |

-continued
| Compound | Structure | Quantity | Yield |
|---|---|---|---|
| Compound 75 | 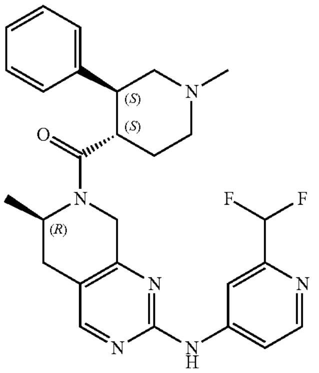 | 0.044 g | 22% |
| Compound 76 | 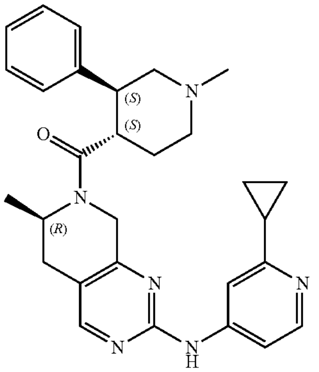 | 0.059 g | 21% |
| Compound 77 | 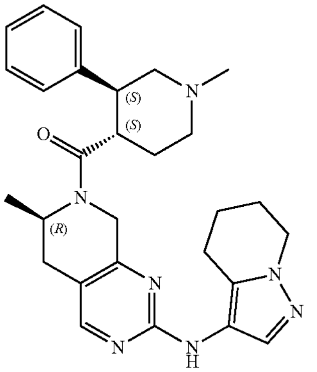 | 0.015 g | 9% |
| Compound 78 | 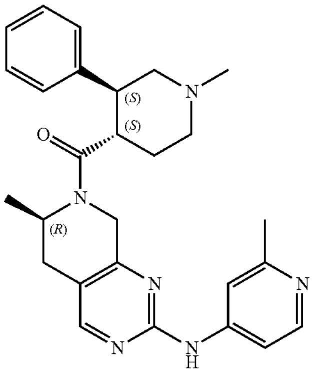 | 0.083 g | 27% |
-continued
| Compound | Structure | Quantity | Yield |
|---|---|---|---|
| Compound 79 | 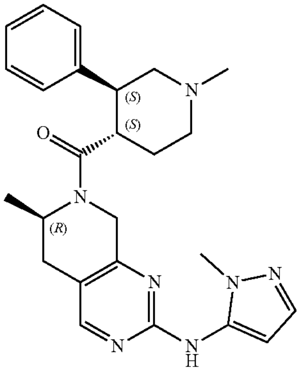 | 0.153 g | 44% |
| Compound 80 | 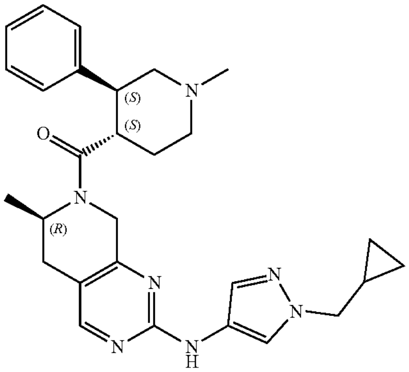 | 0.109 g | 36% |
| Compound 81 | 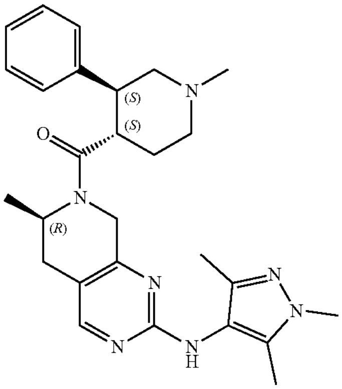 | 0.099 g | 38% |
| Compound 82 | 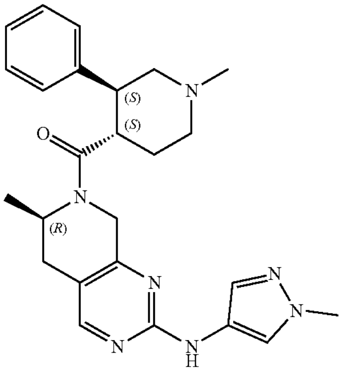 | 0.177 g | 39% |

-continued
| Compound | Structure | Quantity | Yield |
|---|---|---|---|
| Compound 83 | 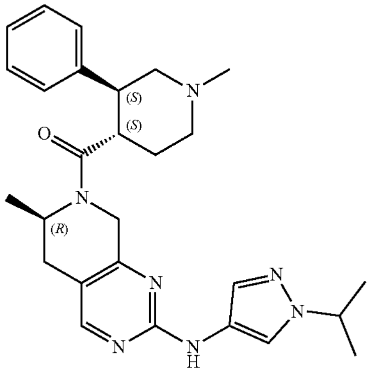<br>[α]$_d$: +71.1° (589 nm, c 0.09 w/v, MeOH, 23.00° C.) | 0.208 g | 30% |
| Compound 84 | 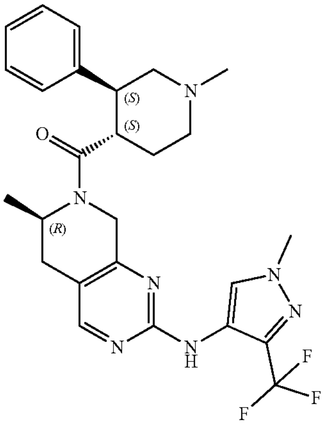 | 0.030 g | 15% |
| Compound 85 | 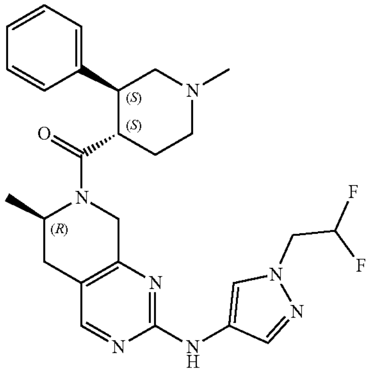 | 0.042 g | 21% |
| Compound 86 | 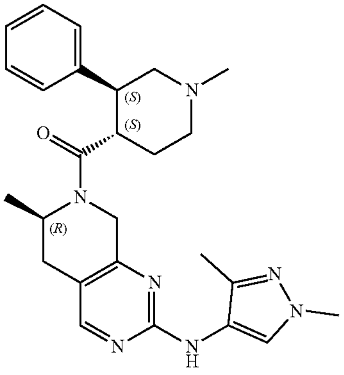 | 0.029 g | 11% |
-continued
| Compound | Structure | Quantity | Yield |
|---|---|---|---|
| Compound 87 | 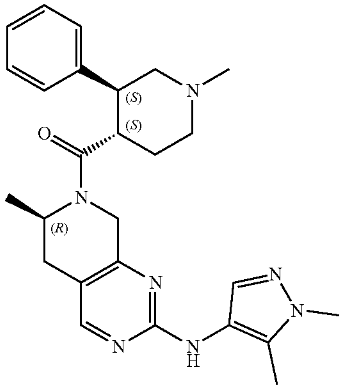 | 0.020 g | 16% |
| Compound 88 | 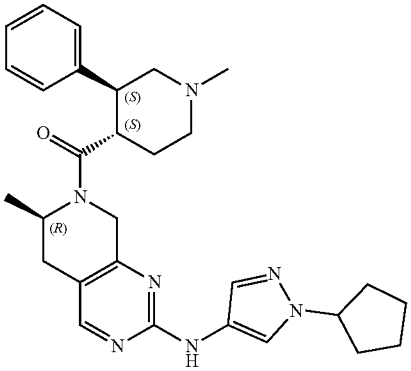<br>[α]$_d$: +67.5° (589 nm, c 0.11 w/v, MeOH, 23.00° C.) | 0.125 g | 33% |
| Compound 89 | 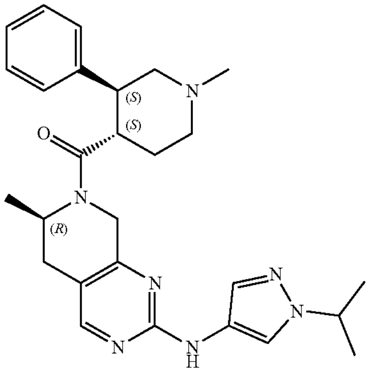 | 0.204 g | 59% |

-continued

| Compound | Structure | Quantity | Yield |
| --- | --- | --- | --- |
| Compound 90 | 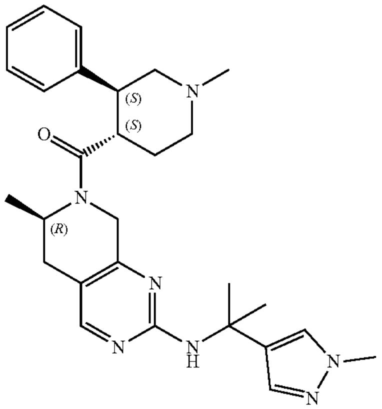 | 0.046 g | 42% |

Synthesis of Compound 92a and 92b:

92a

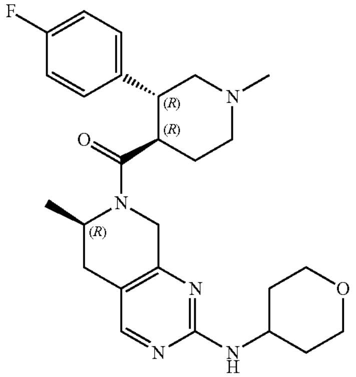

-continued

92b

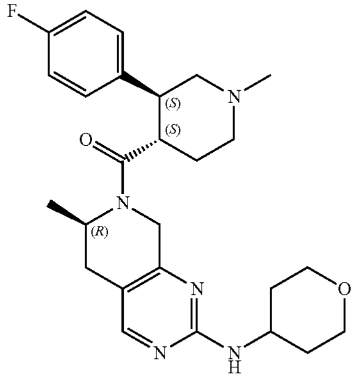

HBTU (2-(1H-Benzotriazole-1-yl)-1,1,3,3-tetramethyluronium hexafluorophosphate) (0.6 g, 1.6 mmol) was added to a solution of intermediates 25 (0.44 g, 1.6 mmol), 27 (0.36 g, 1.4 mmol) and diisopropylethylamine (1 mL, 5.8 mmol) in DMF (20 mL). The reaction was stirred overnight at room temperature. 1M $Na_2CO_3$ (10 mL) and DCM (25 mL) were added. The phases were separated. The aqueous layer was extracted with more DCM (5 mL). The combined organic layers were dried over $MgSO_4$, filtered and evaporated in vacuo. The residue was purified by flash column chromatography (silica; DCM/$CH_3OH$, 9/1, v/v in DCM 0/100 to 100/0). The desired fractions were collected and concentrated in vacuo to give a residue which was purified by reverse phase chromatography [start (90% $H_2O$-10% ACN: MeOH 1:1)-end (54% $H_2O$-46% ACN: MeOH 1:1)]-[65 mM $NH_4OAc$+ACN (90:10)]. The desired fractions were collected and concentrated in vacuo to give Compound 92a (180 mg, 26%) and Compound 92b (152 mg, 22%).

The compounds listed in the table below have been prepared by an analogous reaction protocol:

| Compound | Structure | Quantity | Yield |
| --- | --- | --- | --- |
| Compound 93 | 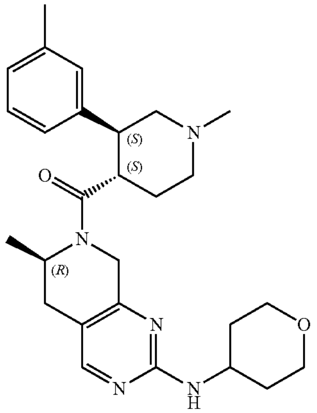 | 0.028 g | 7% |

-continued
| Compound | Structure | Quantity | Yield |
| --- | --- | --- | --- |
| Compound 97 | 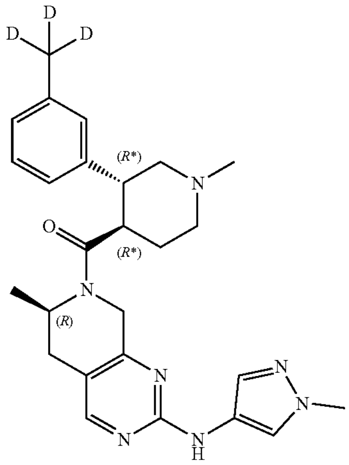 [α]$_d$: +30° (589 nm, c 0.09 w/v, MeOH, 23° C.) | 0.026 g | 7% |
| Compound 98 | 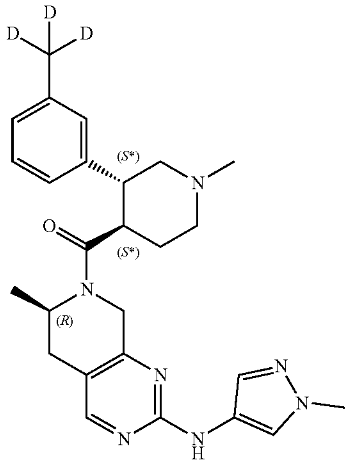 [α]$_d$: +62.5° (589 nm, c 0.08 w/v, MeOH, 23° C.) | 0.015 g | 4% |
| Compound 99 | 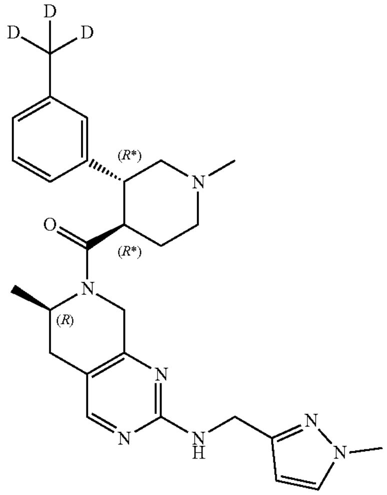 [α]$_d$: +114.8° (589 nm, c 0.08 w/v, MeOH, 23° C.) | 0.101 g | 31% |

-continued
| Compound | Structure | Quantity | Yield |
| --- | --- | --- | --- |
| Compound 100 | 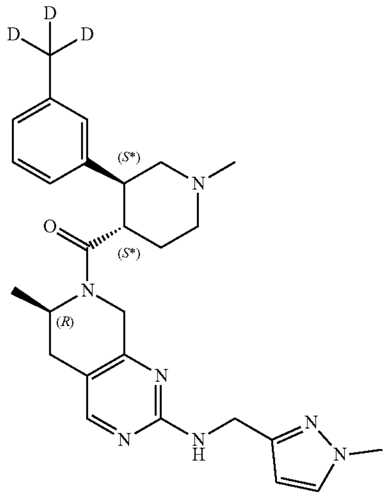 [α]$_d$: +50.6° (589 nm, c 0.13 w/v, MeOH, 23° C.) | 0.063 g | 19% |
| Compound 101 | 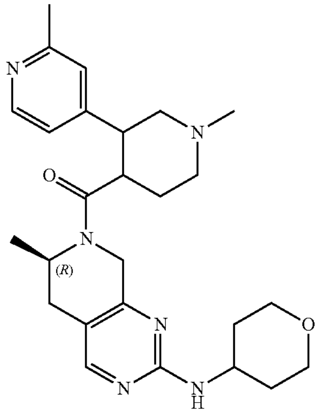 | 0.815 g | 58% |
| Compound 102 | 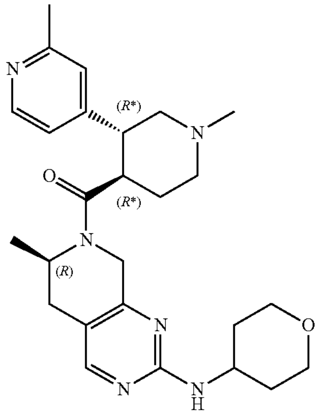 [α]$_d$: +62.6° (589 nm, c 0.02 w/v, MeOH, 23° C.) | 0.212 g | 15% |

-continued
| Compound | Structure | Quantity | Yield |
| --- | --- | --- | --- |
| Compound 103 | 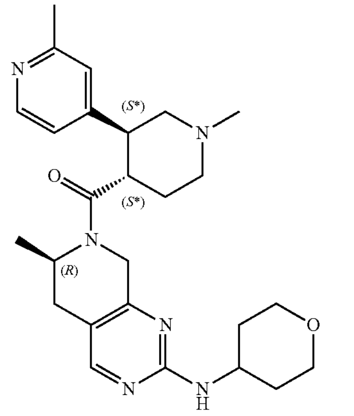 [α]$_d$: +113.3° (589 nm, c 0.14 w/v, MeOH, 23° C.) | 0.28 g | 20% |
| Compound 104 | 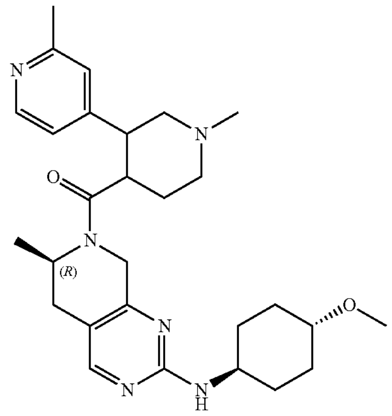 | 0.4 g | 51% |
| Compound 105 | 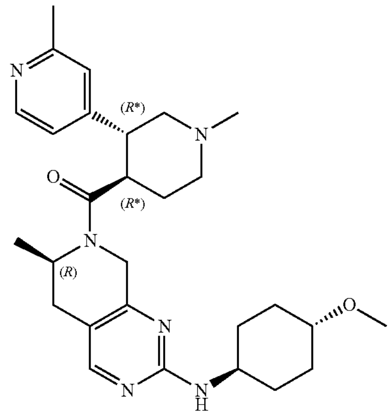 [α]$_d$: +61.1° (589 nm, c 0.14 w/v, MeOH, 23° C.) | 0.1 g | 13% |

-continued
| Compound | Structure | Quantity | Yield |
|---|---|---|---|
| Compound 106 | 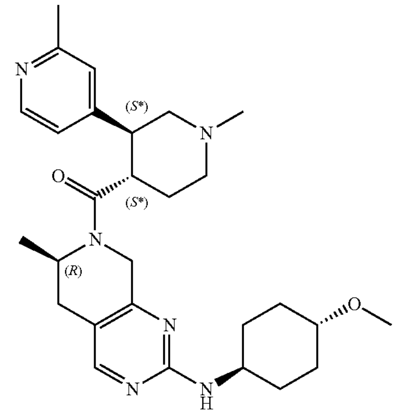 [α]$_d$: +104.9° (589 nm, c 0.15 w/v, MeOH, 23° C.) | 0.13 g | 17% |
| Compound 107 | 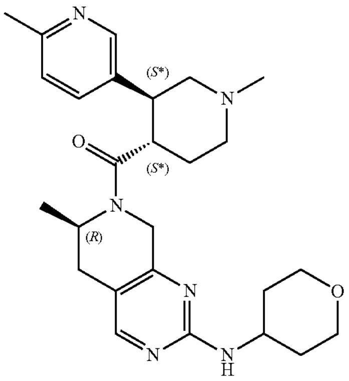 [α]$_d$: +73.2° (589 nm, c 0.14 w/v, MeOH, 23° C.) | 0.26 g | 23% |
| Compound 108 | 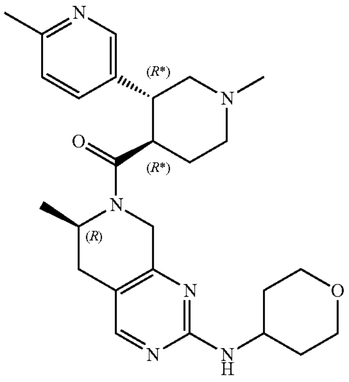 [α]$_d$: +104.9° (589 nm, c 0.15 w/v, MeOH, 23° C.) | 0.21 g | 19% |

-continued
| Compound | Structure | Quantity | Yield |
|---|---|---|---|
| Compound 109 | 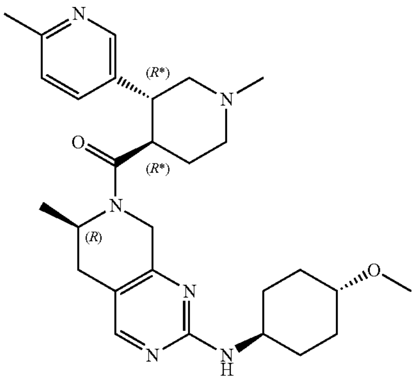 | 0.172 g | 24% |
| | $[\alpha]_d$: +109.0° (589 nm, c 0.14 w/v, MeOH, 23° C.) | | |
| Compound 110 | 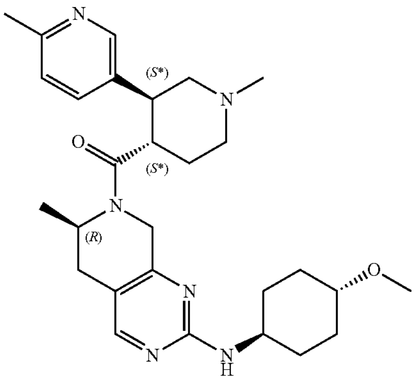 | 0.140 g | 20% |
| | $[\alpha]_d$: +123.5° (589 nm, c 0.16 w/v, MeOH, 23° C.) | | |
| Compound 111 | 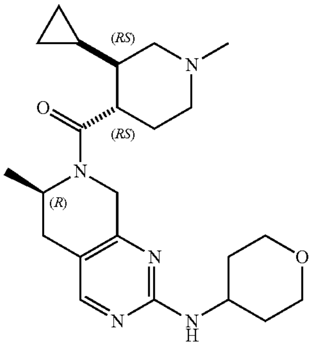 | 0.435 g | 33% |
| Compound 112 | 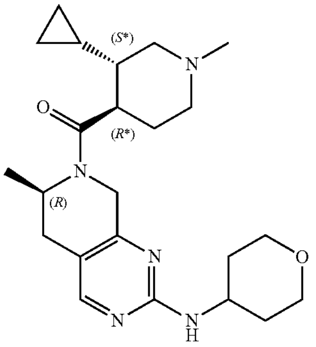 | 0.135 g | 10% |
| | $[\alpha]_d$: +77.9° (589 nm, c 0.18 w/v, MeOH, 23° C.) | | |

-continued
| Compound | Structure | Quantity | Yield |
| --- | --- | --- | --- |
| Compound 113 | 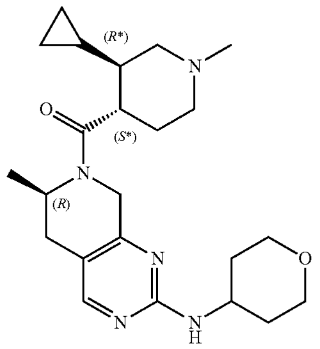 [α]$_d$: +138.8° (589 nm, c 0.17 w/v, MeOH, 23° C.) | 0.140 g | 10% |
| Compound 114 | 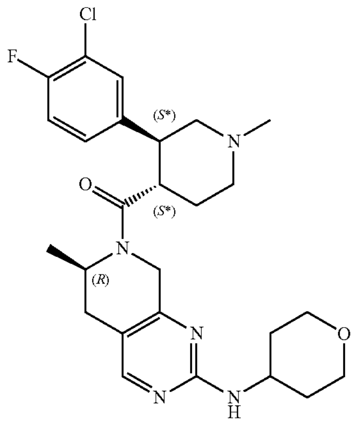 [α]$_d$: +44.6° (589 nm, c 0.07 w/v, MeOH, 23.0° C.) | 0.024 g | 5% |
| Compound 115 | 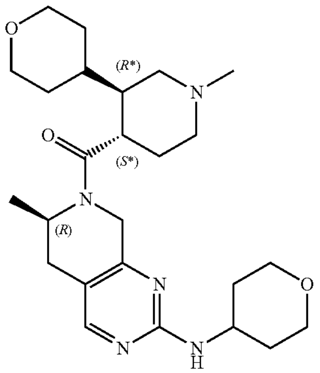 [α]$_d$: +142.3° (589 nm, c 0.16 w/v, MeOH, 23° C.) | 0.187 g | 16% |

-continued
| Compound | Structure | Quantity | Yield |
|---|---|---|---|
| Compound 116 | 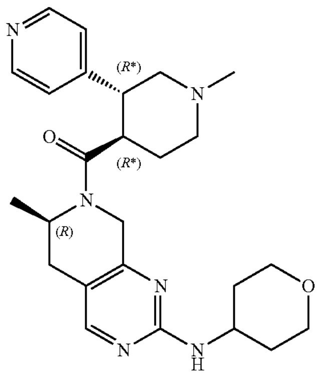 [α]$_d$: +81.9° (589 nm, c 0.12 w/v, MeOH, 23° C.) | 0.142 g | 16% |
| Compound 117 | 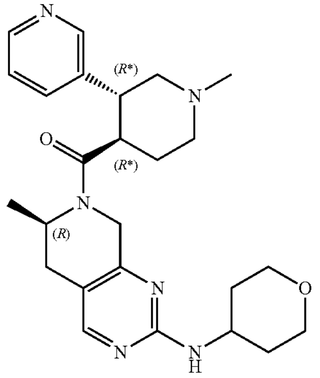 [α]$_d$: +92.1° (589 nm, c 0.13 w/v, MeOH, 23° C.) | 0.17 g | 19% |
| Compound 118 | 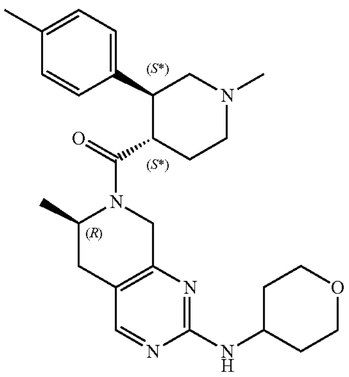 [α]$_d$: +57.8° (589 nm, c 0.11 w/v, MeOH, 23° C.) | 0.156 g | 22% |

-continued
| Compound | Structure | Quantity | Yield |
|---|---|---|---|
| Compound 119 | 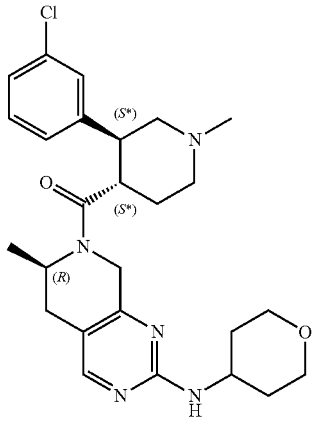 | 0.04 g | 8% |
| Compound 120 | 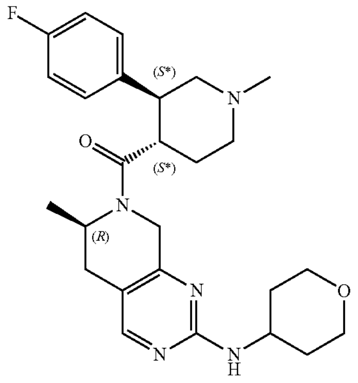<br>[α]$_d$: +74.5° (589 nm, c 0.21 w/v, MeOH, 23° C.) | 0.152 g | 22% |
| Compound 121 | 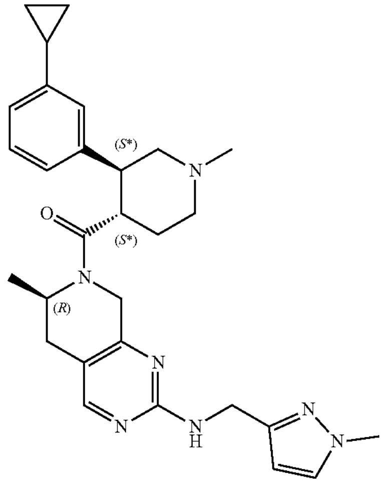<br>[α]$_d$: +33.1° (589 nm, c 0.12 w/v, MeOH, 23° C.) | 0.066 g | 7% |

Synthesis of Compound 122a and 122b:

122a

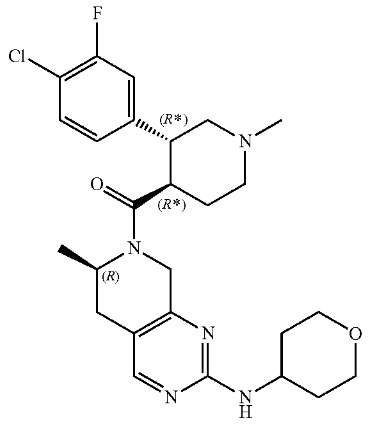

122b

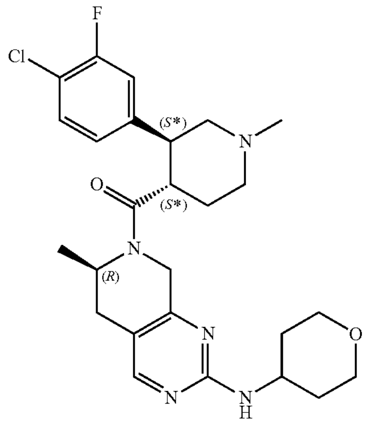

Intermediate 31 (0.38 g, 0.78 mmol) was taken in THF (10 mL) and treated with 37% aqueous formaldehyde (116 μl, 1.6 mmol) at room temperature. Sodium Triacetoxyborohydride (0.33 g, 1.6 mmol) was then added after 15 minutes. The reaction was stirred at rt overnight. $Na_2CO_3$ was added and the reaction was extracted with DCM (2×20 mL). The combined organic layers were dried over $MgSO_4$, filtered and concentrated. Chromatography over silica gel (gradient of DCM/MeOH/$NH_4$OH (9.0/0.9/0.1) afforded a mixture of diastereoisomers. The mixture was purified by reverse phase chromatography [start (81% $H_2$O-19% MeCN-MeOH)-end (45% $H_2$O-55% MeCN-MeOH)]-[65 mM $NH_4$OAc+ACN (90:10. The desired fractions were combined and pH brought to 8 with 1M $Na_2CO_3$. Compound was extracted with DCM (2×15 mL), dried over $MgSO_4$, filtered and concentrated to give 89 mg of first diastereoisomer and 71 mg of second diastereoisomer. The first diastereoisomer was purified by reverse phase chromatography [start (90% $H_2$O-10% MeCN-MeOH)-end (54% $H_2$O-46% MeCN-MeOH)]-[25 mM $NH_4HCO_3$]. Desired fractions were concentrated in vacuo at 60° C. and dried under vacuum to give the Compound 122a as a white solid (30 mg, 8%). The second diastereoisomer was purified by reverse phase chromatography [start (90% $H_2$O-10% MeCN-MeOH)-end (54% $H_2$O-46% MeCN-MeOH)]-[25 mM $NH_4HCO_3$]. Desired fractions were concentrated in vacuo at 60° C. and dried under vacuum to give Compound 122b as a white solid (29 mg, 7%).

The compounds listed in the table below have been prepared by an analogous reaction protocol:

| Compound | Structure | Quantity | Yield |
|---|---|---|---|
| Compound 123 | 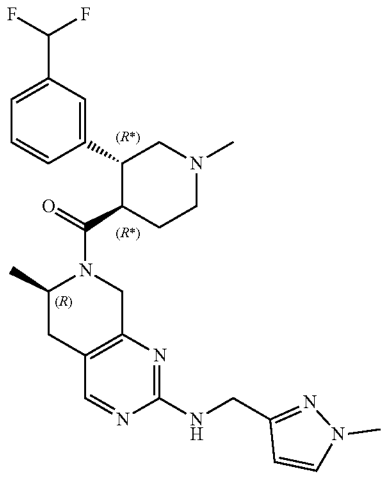 [α]$_d$: +89.2° (589 nm, c 0.12 w/v, MeOH, 23° C.) | 0.053 g | 25% |

-continued
| Compound | Structure | Quantity | Yield |
|---|---|---|---|
| Compound 124 | 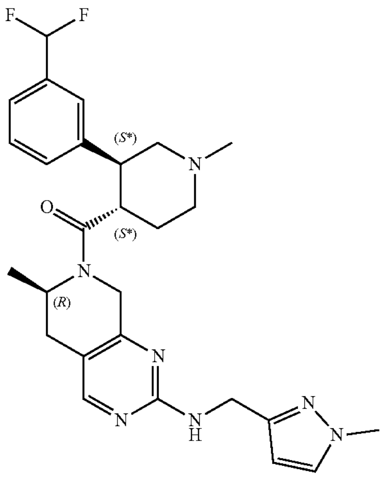 [α]$_d$: +49.7° (589 nm, c 0.13 w/v, MeOH, 23° C.) | 0.041 g | 20% |
| Compound 125 | 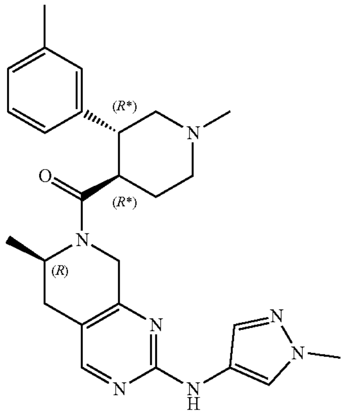 [α]$_d$: +113.4° (589 nm, c 0.14 w/v, MeOH, 23° C.) | 0.103 g | 32% |
| Compound 126 | 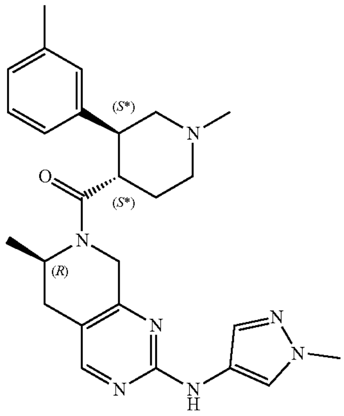 [α]$_d$: +62.1° (589 nm, c 0.17 w/v, MeOH, 23° C.) | 0.084 g | 26% |

-continued
| Compound | Structure | Quantity | Yield |
|---|---|---|---|
| Compound 127 | 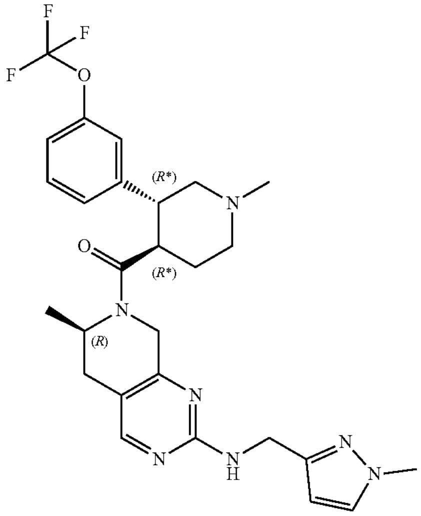<br>[α]$_d$: +80.9° (589 nm, c 0.10 w/v, MeOH, 23° C.) | 0.046 g | 6% |
| Compound 128 | 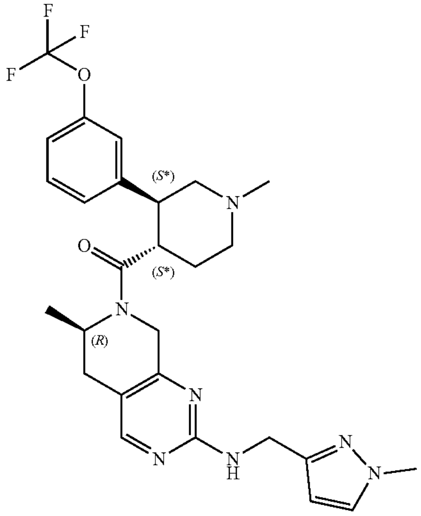<br>[α]$_d$: +46.9° (589 nm, c 0.11 w/v, MeOH, 23° C.) | 0.047 g | 6% |
| Compound 129 | 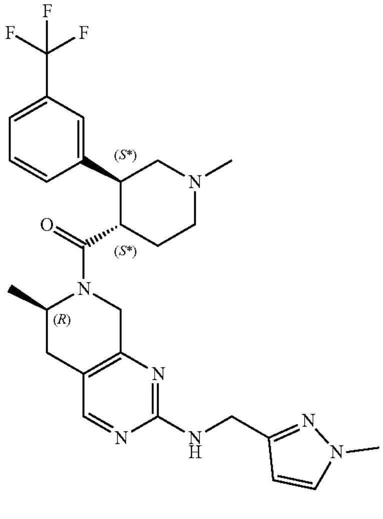 | 0.117 g | 15% |

-continued
| Compound | Structure | Quantity | Yield |
|---|---|---|---|
| Compound 130 | 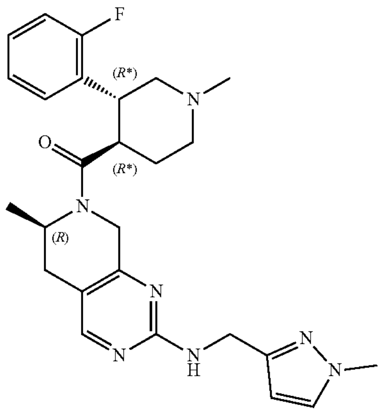 [α]$_d$: +102.1° (589 nm, c 0.11 w/v, MeOH, 23° C.) | 0.1 g | 14% |
| Compound 131 | 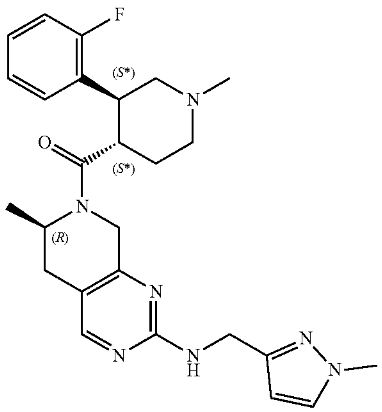 [α]$_d$: +55.0° (589 nm, c 0.12 w/v, MeOH, 23° C.) | 0.067 g | 9% |
| Compound 132 | 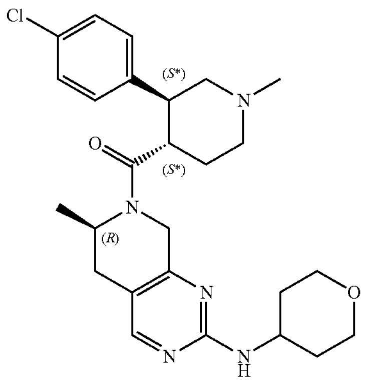 [α]$_d$: +70.1° (589 nm, c 0.14 w/v, MeOH, 23° C.) | 0.101 g | 19% |

-continued
| Compound | Structure | Quantity | Yield |
|---|---|---|---|
| Compound 133 | 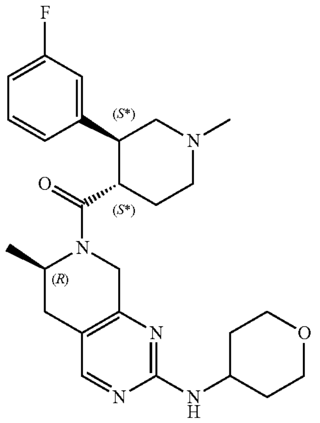 | 0.09 g | 25% |
| Compound 134 | 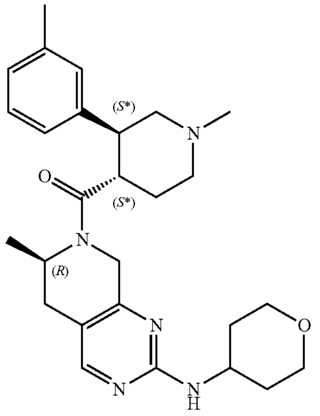<br>[α]$_d$: +66.2° (589 nm, c 0.14 w/v, Methanol, 23.0° C.) | 0.492 g | 90% |
| Compound 135 | 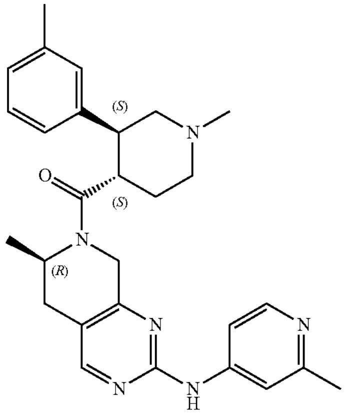 | 0.023 g | 28% |

-continued
| Compound | Structure | Quantity | Yield |
| --- | --- | --- | --- |
| Compound 136 | 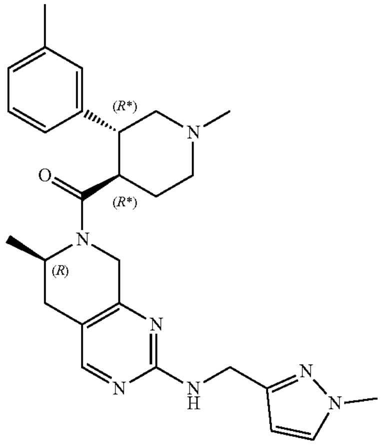 | 0.07 g | 29% |
| Compound 137 | 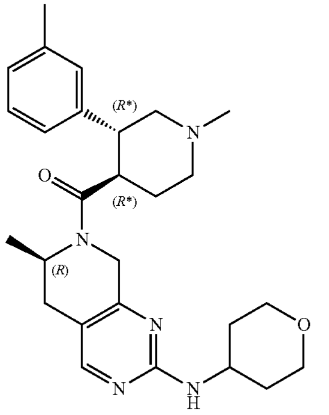<br>[α]$_d$: +74.6° (589 nm, c 0.24 w/v %, DMF, 20° C.) | 0.085 g | 65% |
| Compound 138a | 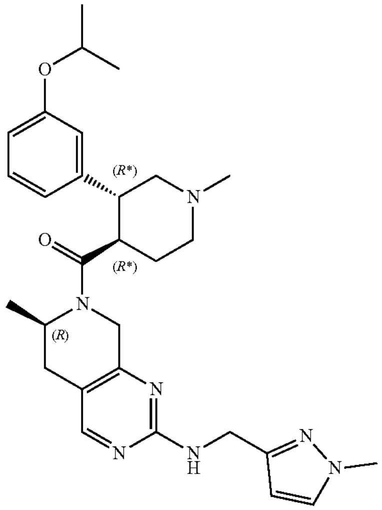<br>[α]$_d$: +93.5° (589 nm, c 0.1 w/v, MeOH, 23° C.) | 0.026 g | 10% |

-continued
| Compound | Structure | Quantity | Yield |
|---|---|---|---|
| Compound 138b | 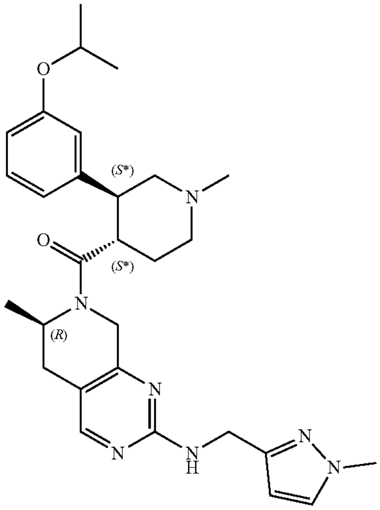 [α]$_d$: +41.6° (589 nm, c 0.11 w/v, MeOH, 23° C.) | 0.018 g | 7% |
| Compound 139 | 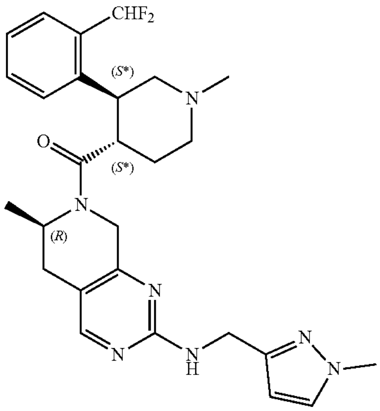 [α]$_d$: +17.2° (589 nm, c 0.093 w/v, MeOH, 23° C.) | 0.012 g | 3% |

Synthesis of Compound 140a

140a

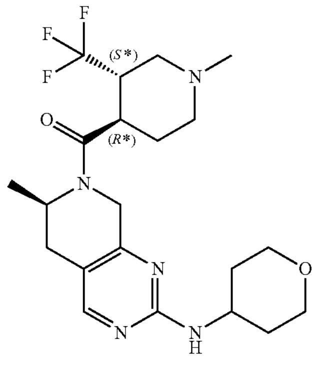

140b

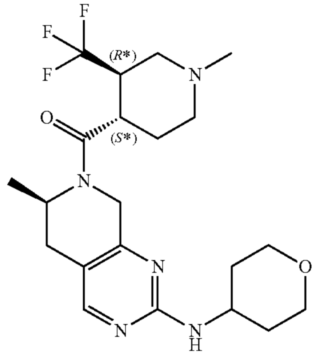

HBTU (2-(1H-Benzotriazole-1-yl)-1,1,3,3-tetramethyluronium hexafluorophosphate) (1.2 g, 3.2 mmol) was added to a solution of intermediate 47 (0.8 g, 3.2 mmol), intermediate 27 (0.7 g, 2.9 mmol) and diisopropylethylamine (1.9 mL, 11.7 mmol) in DMF (20 mL). The reaction was stirred overnight at room temperature for 8 hours. $Na_2CO_3$ (50 mL, 1M) was added and the reaction was extracted with ACOEt (3×20 mL). The combined organic layers were washed with brine (50 mL), dried over $MgSO_4$, filtered and concentrated to dryness. The residue was purified by flash column chromatography (silica; DCM/$CH_3OH$, 9/1, v/v in DCM 0/100 to 100/0). The desired fractions were collected and concentrated in vacuo. The product was purified by reverse phase chromatography [start (90% water-10% MeCN-MeOH)-end (54% water-46% MeCN-MeOH)]-[65 mM $NH_4OAc$+MeCN (90:10)]. DCM was added, the phases were separated, and the organic layer was dried over $MgSO_4$, filtered and concentrated to dryness. The product was triturated to give a mixture of compounds 140a and 140b (600 mg, 46%). The mixture was submitted to chiral separation. Method: AMYLOSE_1 Q_M6: [75% [n-Heptane+0.1% DEA]-25% [2-Propanol+0.1% DEA] 0% [n-Heptane+0.1% DEA]-100% [2-Propanol+0.1% DEA]]. The products were concentrated to dryness to give Compound 140b (205 mg, 15%), $[\alpha]_d$: +114.3° (589 nm, c 0.13 w/v, MeOH, 23° C.) and Compound 140a (143 mg, 11%), $[\alpha]_d$: +80.1° (589 nm, c 0.13 w/v, MeOH, 23° C.).

The compounds listed in the table below have been prepared by an analogous reaction protocol:

| Compound | Structure | Quantity | Yield |
|---|---|---|---|
| Compound 141 | 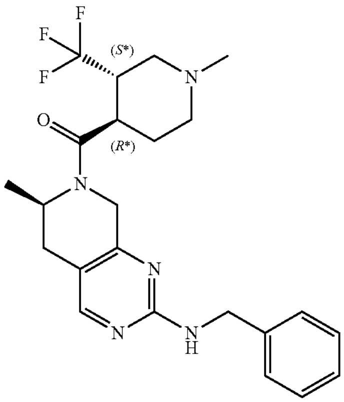 $[\alpha]_d$: +117.8° (589 nm, c 0.11 w/v, MeOH, 23° C.) | 0.072 g | 11% |
| Compound 142 | 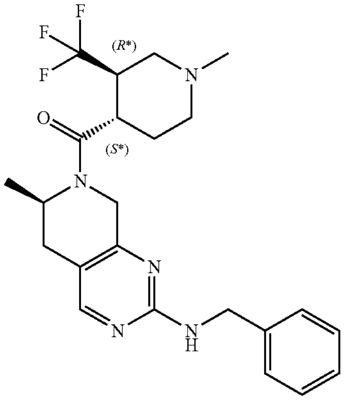 $[\alpha]_d$: +70.7° (589 nm, c 0.11 w/v, MeOH, 23° C.) | 0.06 g | 9% |
| Compound 143 | 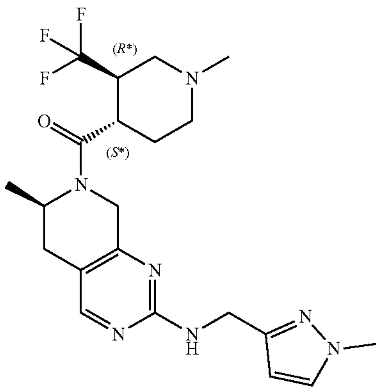 $[\alpha]_d$: +116.5° (589 nm, c 0.14 w/v, MeOH, 23° C.) | 0.063 g | 11% |

-continued

| Compound | Structure | Quantity | Yield |
|---|---|---|---|
| Compound 144 | 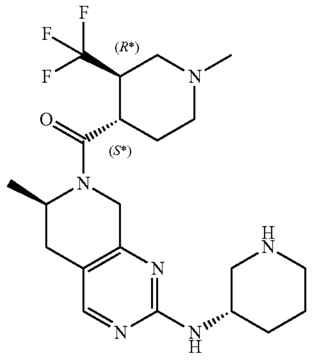 | 0.039 g | 10% |
| | [α]$_d$: +101.2° (589 nm, c 0.10 w/v, MeOH, 23° C.) | | |
| Compound 145 | 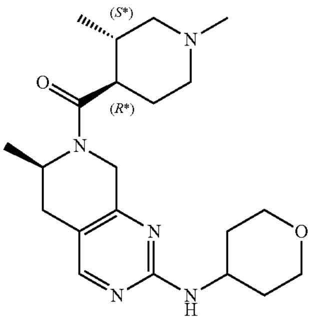 | 0.164 g | 21% |
| | [α]$_d$: +82.7° (589 nm, c 0.11 w/v, MeOH, 23° C.) | | |
| Compound 146 | 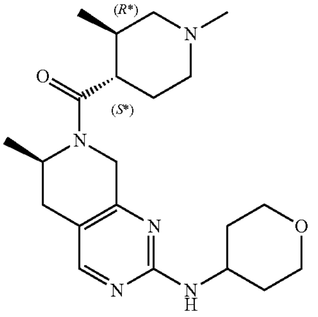 | 0.072 g | 9% |
| | [α]$_d$: +159.1° (589 nm, c 0.13 w/v, MeOH, 23° C.) | | |
| Compound 147 | 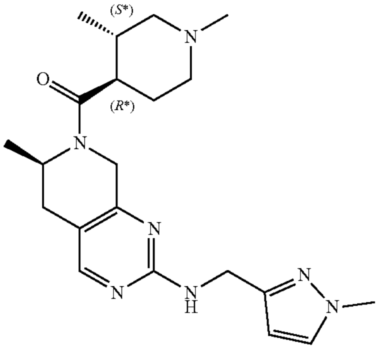 | 0.059 g | 8% |
| | [α]$_d$: +121.6° (589 nm, c 0.12 w/v, MeOH, 23° C.) | | |

Synthesis of Compound 166:

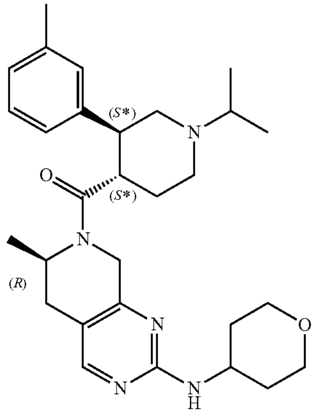

Intermediate 38 (156 mg, 0.347 mmol) was taken in dichloroethane and treated with acetone (0.139 mL, 0.694 mmol) and acetic acid (0.020 mL, 0.347 mmol) at room temperature. Triacetoxyborohydride (0.147 g, 0.694 mmol) was then added after 15 minutes. The reaction was continued overnight. The reaction was diluted with DCM (300 mL) and washed with 1M $Na_2CO_3$ (150 mL). The aqueous phase was extracted once more with DCM, (100 mL). The combined organic layers were dried over $MgSO_4$, filtered and concentrated to dryness. Chromatography over silica gel (gradient of DCM/MeOH/$NH_4OH$ (9.0/0.9/0.1) in DCM from 0 to 50%) afforded a mixture which was purified twice again by Prep LC: MMP4-AC: gradient of ACN/MeOH (1/1, v/v) in 25 mM Ammonium acetate from 19 to 55%) followed by a second Prep. LC: MMP5-$NH_4OH$-ACN: gradient of ACN in 0.4% aqueous ammonia from 28 to 64%. The pure fractions were collected and compound was extracted with DCM (100 mL), dried over $MgSO_4$, filtered and concentrated to the colorless stick compound which was triturated in pentane (2 mL) to give Compound 166 as a white solid (35 mg, 20%).

The compounds listed in the table below have been prepared by an analogous reaction protocol:

| Compound | Structure | Quantity | Yield |
|---|---|---|---|
| Compound 148 | 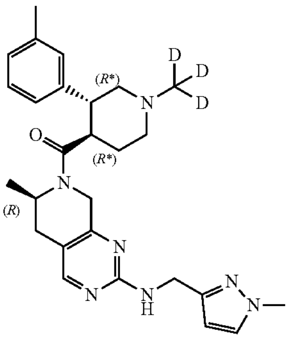 | 0.077 g | 32% |

-continued
| Compound | Structure | Quantity | Yield |
| --- | --- | --- | --- |
| Compound 149 | 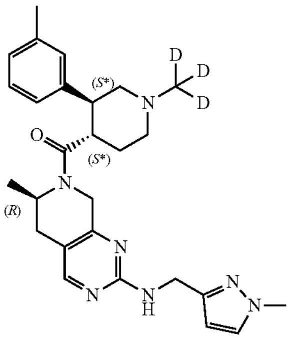 | 0.068 g | 26% |
| Compound 150 | 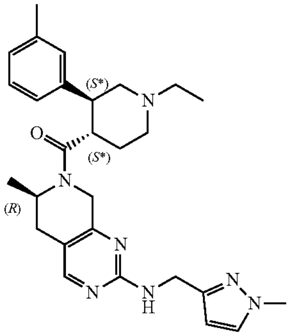 | 0.025 g | 24% |
| Compound 151 | 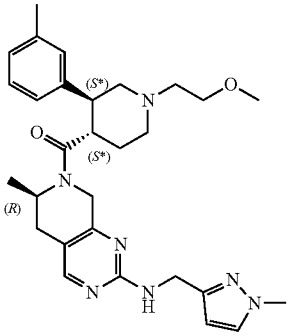 | 0.043 g | 38% |
| Compound 152 | 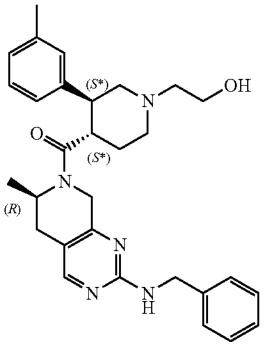 | 0.081 g | 37% |
-continued
| Compound | Structure | Quantity | Yield |
| --- | --- | --- | --- |
| Compound 153 | 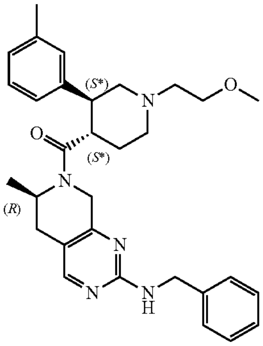 | 0.044 g | 19% |
| Compound 154 | 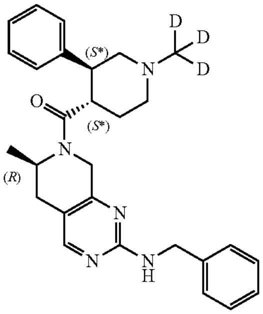 | 0.052 g | 25% |
| Compound 155 | 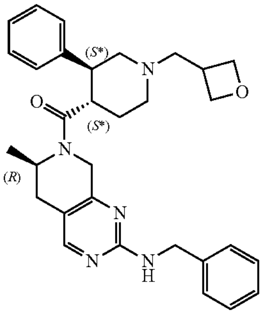 | 0.155 g | 67% |
| Compound 156 | 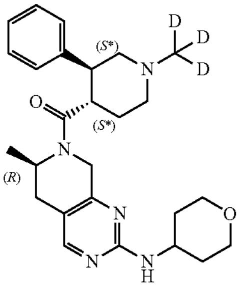 | 0.08 g | 38% |
| Compound 157 | 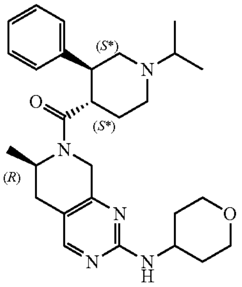 | 0.018g | 4% |

-continued
| Compound | Structure | Quantity | Yield |
|---|---|---|---|
| Compound 158 | 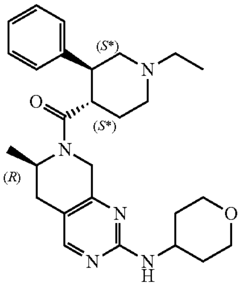 | 0.067 g | 16% |
| Compound 159 | 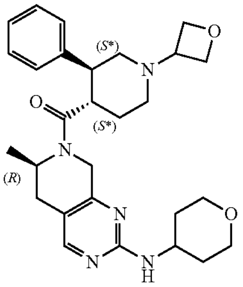 | 0.068 g | 55% |
| Compound 160 | 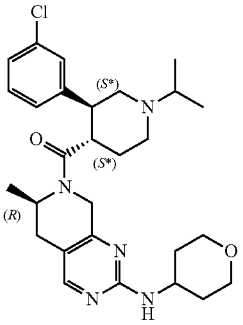 [α]$_d$: +4.3° (589 nm, c 0.12 w/v, Methanol, 23.0° C.) | 0.065 g | 15% |
| Compound 161 | 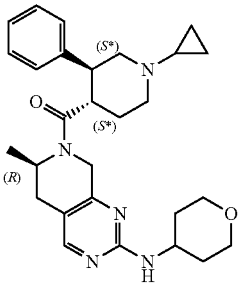 | 0.02 g | 40% |
| Compound 162 | 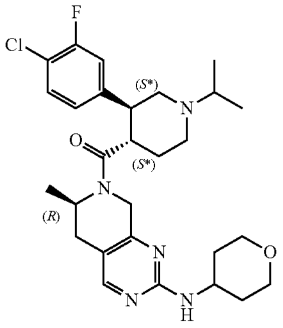 | 0.013 g | 3% |
-continued
| Compound | Structure | Quantity | Yield |
|---|---|---|---|
| Compound 163 | 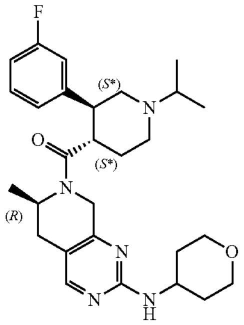 | 0.01 g | 2% |
| Compound 164 | 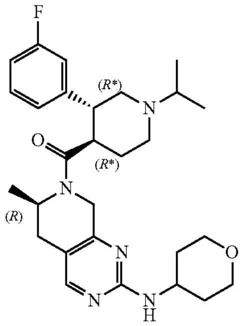 [α]$_d$: +116.3° (589 nm, c 0.12 w/v, MeOH, 23° C.) | 0.105 g | 18% |
| Compound 165 | 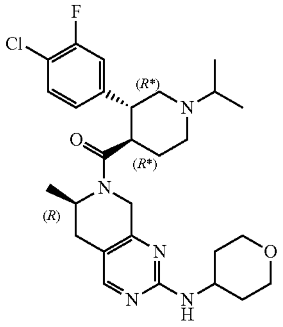 [α]$_d$: +114.6° (589 nm, c 0.08 w/v, MeOH, 23.0° C.) | 0.035 g | 8% |

Synthesis of Compound 167:

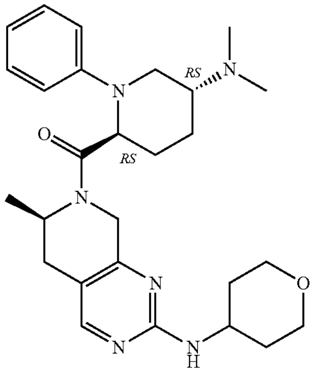

Intermediate 52 (0.276 g, 1.11 mmol), intermediate 27 (0.14 g, 0.55 mmol) and diisopropylethylamine (0.18 mL, 1.1 mmol) were dissolved in DMF (2 mL). The mixture was stirred at room temperature for 20 minutes before addition of HBTU (2-(1H-Benzotriazole-1-yl)-1,1,3,3-tetramethyluronium hexafluorophosphate) (0.25 g, 0.7 mmol). The mixture was stirred at rt overnight. The reaction was diluted with DCM (25 mL) and washed with 1M $Na_2CO_3$ (10 ml). The phases were separated, and the aqueous layer was extracted once more with DCM (10 mL). The combined organic layers were dried over $MgSO_4$, filtered and evaporated in vacuo. The residue was purified by flash column chromatography (silica; DCM/MeOH, 5/1, v/v in DCM 0/100 to 100/0). The desired fractions were collected and concentrated in vacuo. Compound 167 (0.073 g, 27%) was obtained pure by reverse phase chromatography [start (72% $H_2O$-28% $CH_3CN$—$CH_3OH$)-end (36% $H_2O$-64% $CH_3CN$—$CH_3OH$)]-[$H_2O$: 25 mM $NH_4HCO_3$] $[\alpha]_d$: +104.1° (589 nm, c 0.13 w/v, MeOH, 23° C.).

The compound listed in the table below has been prepared by an analogous reaction protocol:

| Compound | Structure | Quantity | Yield |
|---|---|---|---|
| Compound 168 | 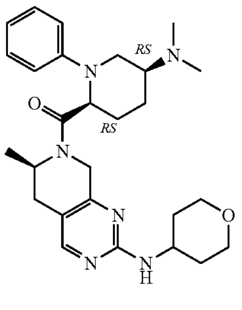 [SMILES: C[C@@H]1Cc2cnc(NC3CCOCC3)nc2CN1C(=O)[C@@H]1CC[C@H](N(C)C)CN1c1ccccc1] $[\alpha]_d$: +87.6° (589 nm, c 0.15 w/v, MeOH, 23° C.) | 0.017 g | 32% |

Synthesis of Compound 169a and 169b:

169a

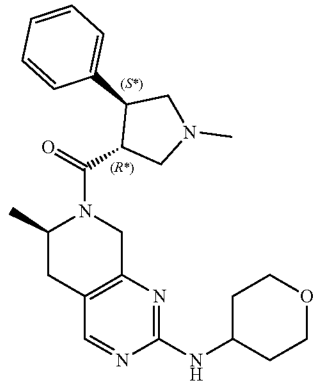

169b

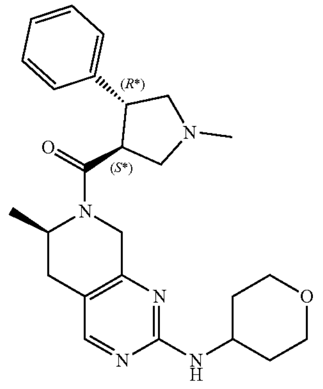

Intermediate 27 (0.5 g, 2 mmol), trans-3-Pyrrolidinecarboxylic acid, 1-methyl-4-phenyl-, hydrochloride (0.6 g, 2.4 mmol) and diisopropylethylamine (1 mL, 6 mmol) were dissolved in DMF (10 mL). The mixture was stirred, at room temperature, for 20 minutes before addition of HBTU (2-(1H-Benzotriazole-1-yl)-1,1,3,3-tetramethyluronium hexafluorophosphate) (0.9 g, 2.4 mmol). The resulting mixture was stirred at room temperature, for 1 additional hour. The reaction was diluted with DCM (5 mL) and washed with 1M $Na_2CO_3$ (40 mL). The phases were separated, and the aqueous layer was extracted once more with DCM (25 mL). The combined organic layers were dried over $MgSO_4$, filtered and evaporated in vacuo. The residue was purified by flash column chromatography (silica; DCM/MeOH/$NH_3$ (aqueous solution 25%), 9/0.95/0.05, v/v/v in DCM 0/100 to 100/0).

Compounds 169a and 169b were separated by reverse phase chromatography [start (90% water-10% $CH_3CN$)-end (54% water-46% $CH_3CN$)]-[water: 65 mM $NH_4OAc$+ACN (90:10)] yielding Compound 169b (0.2 g, 23%) $[\alpha]_d$: +73.9° (589 nm, c 0.18 w/v, MeOH, 23° C.) and Compound 169a (0.24 g, 27%) $[\alpha]_d$: +131.8° (589 nm, c 0.16 w/v, MeOH, 23° C.).

Synthesis of Compound 170a and 170b:

170a

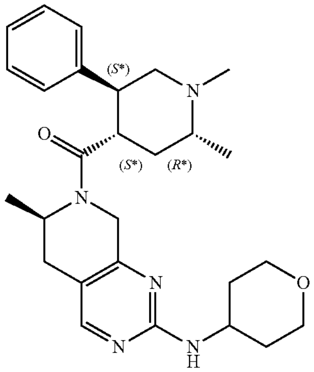

170b

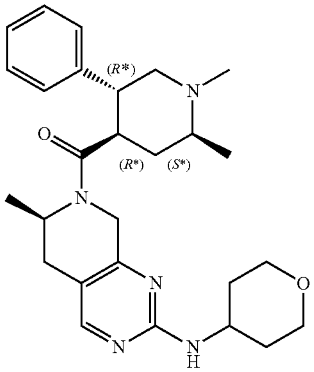

Intermediate 59 (0.24 g, 0.5 mmol) was taken in MeOH (15 mL) and treated with 37% aqueous formaldehyde (81 μl, 1.1 mmol) at room temperature. Sodium triacetoxyborohydride (172 mg, 0.8 mmol) was then added after 15 minutes. The reaction was allowed to stir overnight. $Na_2CO_3$ was added and the mixture was extracted with DCM (2×35 mL). The combined organic layers were dried over $MgSO_4$, filtered and concentrated. The residue was purified by reverse phase chromatography [start (81% water-19% ACN: MeOH 1:1)-end (45% water-55% ACN: MeOH 1:1)]-[65 mM $NH_4OAc$+ACN (90:10)]. The desired fractions were collected and extracted with DCM (2×35 mL). The combined organic layers were dried over $MgSO_4$, filtered and concentrated to give Compound 170a (52 mg, 20%). $[\alpha]_d$: +70.9° (589 nm, c 0.12 w/v, MeOH, 23° C.) and Compound 170b (61 mg, 24%) $[\alpha]_d$: +87° (589 nm, c 0.069 w/v, MeOH, 23° C.).

Synthesis of Compound 171a and 171b:

171a

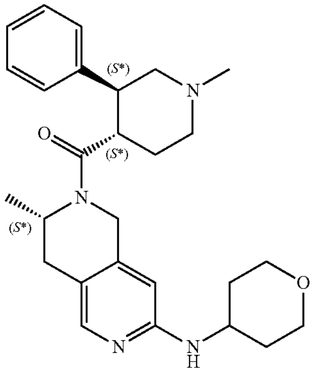

-continued

171b

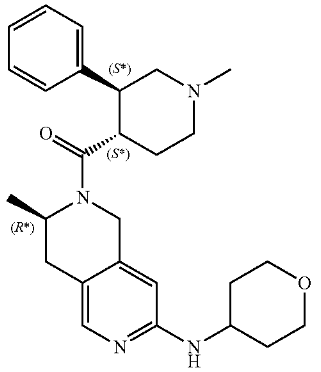

HBTU (2-(1H-Benzotriazole-1-yl)-1,1,3,3-tetramethyluronium hexafluorophosphate) (0.8 g, 2 mmol) was added to a solution of intermediate 66 (463 mg, 1.8 mol), intermediate 8 (526 mg, 2 mmol) and disopropylethylamine (1.3 mL, 7.5 mmol) in DMF (25 mL) at room temperature. The reaction was continued for 36 hours. The mixture was diluted with AcOEt (200 mL) and washed with 1M $Na_2CO_3$ (150 mL). The aqueous phase was extracted with AcOEt (3×100 mL). The combined organic layers were washed with brine (100 mL), dried over $MgSO_4$, filtered and concentrated. Chromatography over silica gel (gradient of a mixture DCM/MeOH/$NH_4OH$, 9.0/0.9/0.1, v/v/V, in DCM from 0 to 50%) afforded the mixture of compound 171a and 171b which were separated by chiral resolution (Column Amylose-1, Q-M5: gradient of (2-Propanol/Ethanol, 9/1, v/v+0.1% DEA) in (n-Heptane+0.1% DEA) from 5 to 70%, yielding Compound 171a (268 mg, 31%). $[\alpha]_d$: +34.5° (589 nm, c 0.13 w/v, Methanol, 23.0° C.) Compound 171b (220 mg, 26%) $[\alpha]_d$: −51.5° (589 nm, c 0.12 w/v, Methanol, 23.0° C.).

The compounds listed in the table below have been prepared by an analogous reaction protocol:

| Compound | Structure | Quantity | Yield |
|---|---|---|---|
| Compound 172 | 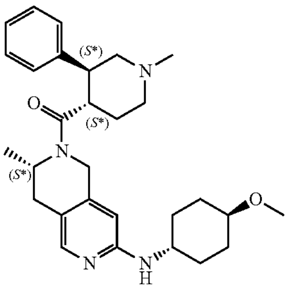 [SMILES: CO[C@H]1CC[C@H](Nc2cc3c(cn2)C[C@H](C)N(C(=O)[C@H]2CCN(C)C[C@@H]2c2ccccc2)C3)CC1] $[\alpha]_d$: +33.4° (589 nm, c 0.22 w/v, Methanol, 23.0° C.) | 0.179 g | 19% |

-continued

| Compound | Structure | Quantity | Yield |
|---|---|---|---|
| Compound 173 | 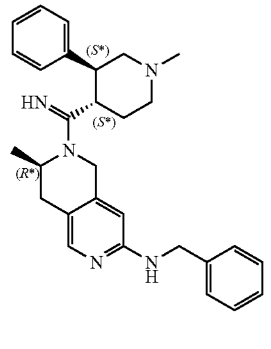 [SMILES: C[C@@H]1Cc2cnc(NCc3ccccc3)cc2CN1C(=N)[C@H]1CCN(C)C[C@@H]1c1ccccc1] [α]$_d$: +40.6° (589 nm, c 0.11 w/v, Methanol, 23.0° C.) | 0.12 g | 17% |

Synthesis of Compound 174:

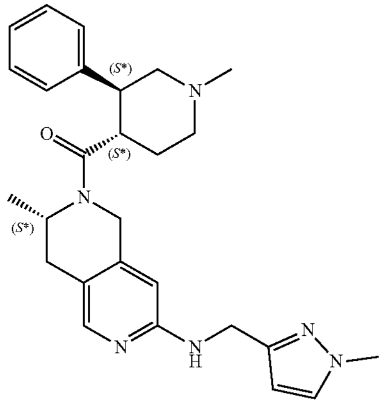

Intermediate 69 (300 mg, 0.8 mmol), (1-methyl-1H-pyrazol-3-yl) methanamine (0.2 g, 1.6 mmol), RuPhos Pd G3 (33 mg, 0.04 mmol) and Sodium tert-butoxide (0.15 g, 1.6 mmol) were taken in toluene (15 mL) while bubbling nitrogen in a reaction tube. Degassing was continued for 5 minutes and reaction vessel closed tight with a screw cap. The mixture was heated to 120° C. for 4 hours. The mixture was allowed to cool to room temperature, diluted with DCM/MeOH (100 ml, 5/1, v/v) and washed once with water (20 ml). The organic layer was dried over $MgSO_4$, filtered and concentrated. Chromatography over silica gel (gradient of DCM/MeOH/$NH_4OH$ (9.0/0.9/0.1, v/v/v) in DCM 0 to 50%) afforded an oily residue that crystallized upon standing, yielding Compound 174 (0.140 g, 39%) [α]$_d$: +43.7° (589 nm, c 0.17 w/v, Methanol, 23.0° C.).

The compound in the table below have been prepared by an analogous reaction protocol:

| Compound | Structure | Quantity | Yield |
|---|---|---|---|
| Compound 175 | 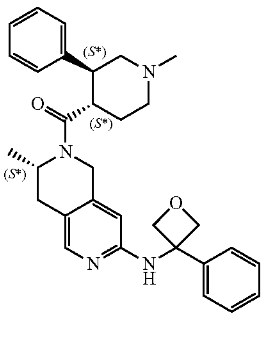 [SMILES: C[C@H]1Cc2cnc(NC3(c4ccccc4)COC3)cc2CN1C(=O)[C@H]1CCN(C)C[C@@H]1c1ccccc1] [α]$_d$: +24.8° (589 nm, c 0.11 w/v, Methanol, 23.0° C.) | 0.034 g | 8% |

Synthesis of Compound 176:

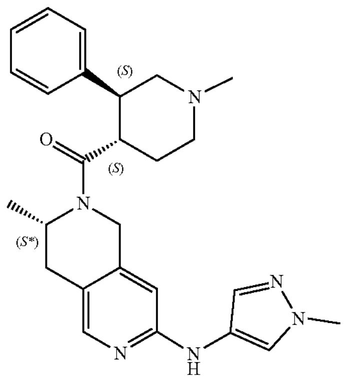

HBTU (2-(1H-Benzotriazole-1-yl)-1,1,3,3-tetramethyluronium hexafluorophosphate) (0.4 g, 1 mmol) was added to a solution of intermediate 71 (0.2 g, 0.8 mmol), intermediate 8 (0.26 g, 1 mmol) and diisopropylethylamine (0.4 ml, 2.6 mmol) in DMF (20 mL). The reaction was stirred two days at room temperature. 1M $Na_2CO_3$ (10 mL) and DCM (25 mL) were added. The aqueous layer was extracted with DCM (5 mL). The combined organic layers were dried over $MgSO_4$, filtered and evaporated in vacuo. The residue was purified by flash column chromatography (silica; DCM/$CH_3OH$, 9/1, v/v in DCM 0/100 to 100/0).

The desired fractions were collected and concentrated in vacuo. The residue was purified by reverse phase chromatography [start (81% $H_2O$-19% ACN: MeOH 1:1)-end (45% $H_2O$-55% ACN: MeOH 1:1)]-[25 mM $NH_4HCO_3$] and purified again by reverse phase chromatography [start (90% $H_2O$-10% MeCN-MeOH)-end (54% $H_2O$-46% MeCN-MeOH)]-[65 mM $NH_4OAc$+MeCN (90:10)]. The desired fractions were collected and concentrated in vacuo. The residue was triturated in diethyl ether to give Compound 176 (82 mg, 21%) as an off-white solid. [α]$_d$: +8.2° (589 nm, c 0.07 w/v, MeOH, 23° C.).

Synthesis of Compounds 177a, 177b, 177c:

177a

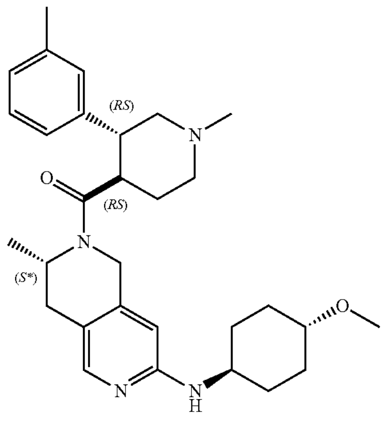

177b

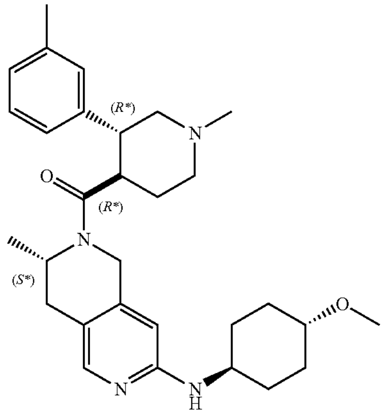

177c

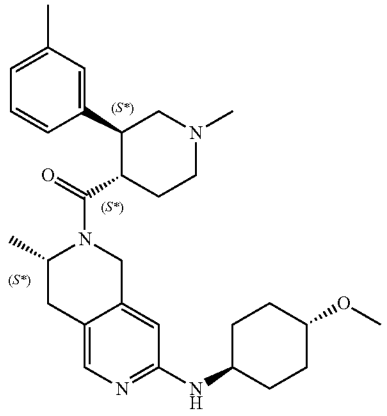

Intermediate 74 (0.49 g, 1 mmol) was taken in MeOH (15 mL) and treated with 37% aqueous formaldehyde (0.115 mL, 1.5 mmol) at room temperature. Triacetoxyborohydride (0.3 g, 1.5 mmol) was then added after 15 minutes. The reaction mixture was stirred overnight. The reaction was diluted with DCM (60 mL) and washed with 1M $Na_2CO_3$ (20 mL). The aqueous phase was extracted once more with DCM (50 mL). The combined organic layers were dried over $MgSO_4$, filtered and concentrated to the crude oil. The residue was purified by flash column chromatography (silica; DCM/$CH_3OH$, 9/1, v/v in DCM 0/100 to 100/0). The product was obtained as an oil. The impure product was purified by reverse phase chromatography [start (90% $H_2O$-10% MeCN-MeOH)-end (54% $H_2O$-46% MeCN-MeOH)]-[25 mM $NH_4HCO_3$]. Desired fractions were collected, concentrated at 60° C. and dried under high vacuum. The product was triturated in diethylether to give Compound 177a (343 mg, 67%). Chiral separation by SFC (Lux-Amylose-1 SFC isocratic Mode 20% Propanol) let to Compound 177b (116 mg, 23%). $[\alpha]_d$: +65.2° (589 nm, c 0.11 w/v, MeOH, 23° C.) and Compound 177c (72 mg, 14%) $[\alpha]_d$: +27.3° (589 nm, c 0.14 w/v, MeOH, 23° C.).

The compounds listed in the table below have been prepared by an analogous reaction protocol:

| Compound | Structure | Quantity | Yield |
|---|---|---|---|
| Compound 178 | 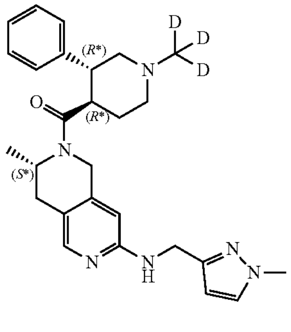 [SMILES: [2H]C([2H])([2H])N1CC[C@@H](C(=O)N2Cc3cc(NCc4ccn(C)n4)ncc3C[C@@H]2C)[C@H](c2ccccc2)C1] $[\alpha]_d$: +37.6° (589 nm, c 0.12 w/v, MeOH, 23° C.) | 0.044 g | 16% |
| Compound 179 | 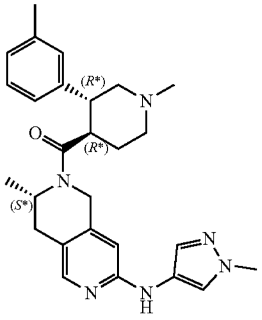 [SMILES: Cc1cccc([C@@H]2CN(C)CC[C@H]2C(=O)N2Cc3cc(Nc4cnn(C)c4)ncc3C[C@@H]2C)c1] $[\alpha]_d$: +24.5° (589 nm, c 0.09 w/v, MeOH, 23.00° C.) | 0.102 g | 20% |

Synthesis of Compounds 180a and 180b:

180a

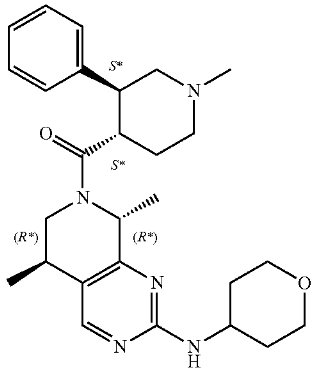

-continued

180b

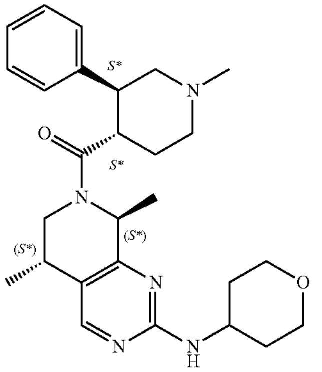

Intermediate 84a (0.3 g, 1.2 mmol), intermediate 8 (0.37 g, 1.44 mmol) and diisopropylamine (0.8 mL, 4.8 mmol) were taken in DMF (15 mL) at room temperature. HBTU (2-(1H-Benzotriazole-1-yl)-1,1,3,3-tetramethyluronium hexafluorophosphate) (0.55 g, 1.44 mmol) was added and the mixture was stirred overnight. 1M $Na_2CO_3$ (30 mL) and DCM (35 mL) were added. The organic layer was separated, and the aqueous phase was extracted once more with DCM (30 mL). The combined organic layers were dried over $MgSO_4$, filtered and concentrated in vacuo. The residue was purified by flash column chromatography (silica; DCM/$CH_3OH$, 9/1, v/v in DCM 0/100 to 100/0). The desired fractions were collected and concentrated in vacuo. The product was purified by reverse phase chromatography [start (72% $H_2O$-28% MeCN-MeOH)-end (36% $H_2O$-64% MeCN-MeOH)]-[65 mM $NH_4OAc$+MeCN (90:10)] and was triturated with diethyl ether to give a mixture of trans diastereoisomers (222 mg, 39%) as a foam. The residue was purified by chiral SFC (Lux-Amylose-1 SFC isocratic Mode 30% EtOH) to yield Compound 180a (0.061 g, 11%). $[\alpha]_d$: +100.8° (589 nm, c 0.21 w/v, MeOH, 23° C.) and Compound 180b (0.052 g, 9%) $[\alpha]_d$: −80.7° (589 nm, c 0.15 w/v, MeOH, 23° C.).

The compounds listed in the table below have been prepared by an analogous reaction protocol:

| Compound | Structure | Quantity | Yield |
|---|---|---|---|
| Compound 181 | 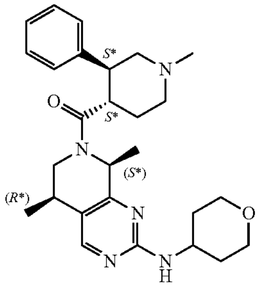<br>$[\alpha]_d$: +92.0° (589 nm, c 0.08 w/v, MeOH, 23° C.) | 0.034 g | 15% |

-continued

| Compound | Structure | Quantity | Yield |
|---|---|---|---|
| Compound 182 | 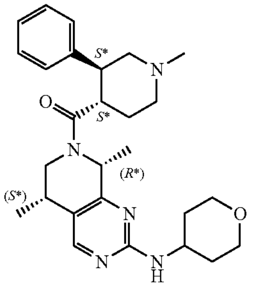 | 0.002 g | 0.9% |
| Compound 183 | 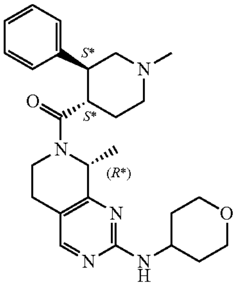<br>$[\alpha]_d$: −128.03° (589 nm, c 0.12 w/v, MeOH, 23° C.) | 0.081 g | 16% |
| Compound 184 | 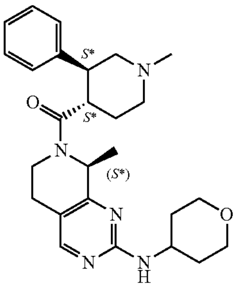<br>$[\alpha]_d$: +121.41° (589 nm, c 0.1 w/v, MeOH, 23° C.) | 0.103 g | 21 % |
| Compound 185 | 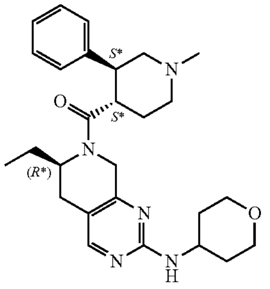<br>$[\alpha]_d$: +84.5° (589 nm, c 0.09 w/v, MeOH, 23° C.) | 0.099 g | 16% |

-continued

| Compound | Structure | Quantity | Yield |
| --- | --- | --- | --- |
| Compound 186 | 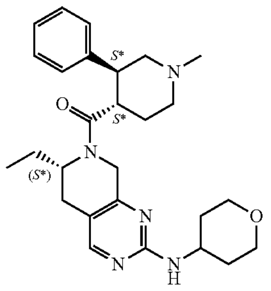<br>[α]$_d$: −108.6° (589 nm, c 0.11 w/v, MeOH, 23° C.) | 0.087 g | 14% |
| Compound 187 | 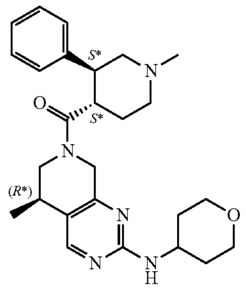<br>[α]$_d$: −55.6° (589 nm, c 0.11 w/v, Methanol, 23° C.) | 0.203 g | 31% |
| Compound 188 | 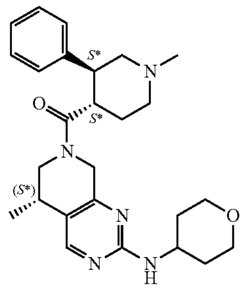<br>[α]$_d$: −41.2° (589 nm, c 0.11 w/v, Methanol, 23° C.) | 0.16 g | 24% |
| Compound 189 | 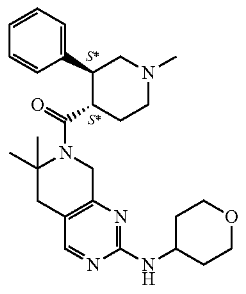 | 0.02 g | 20% |

Synthesis of Compound 190:

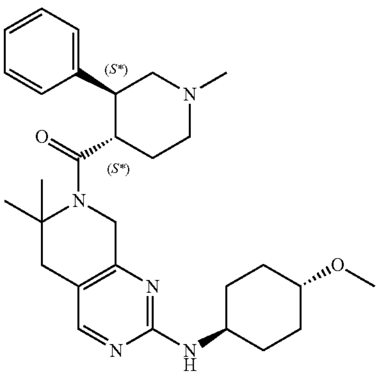 [SMILES: CO[C@H]1CC[C@H](Nc2ncc3c(n2)CN(C(=O)[C@H]2CCN(C)C[C@@H]2c2ccccc2)C(C)(C)C3)CC1]

(4-methoxycyclohexyl) amine (334 μl, 2.4 mmol) was added to a reaction tube with intermediate 93 (147 mg, 0.3 mmol) at 80° C. Then, the reaction mixture was heated at 100° C. for 15 min. $H_2O$ and DCM were added, and the organics were separated, dried over $MgSO_4$, filtered and concentrated. The crude was purified by chromatography over silica gel (gradient of MeOH in DCM from 0 to 100%) to afford a compound which was purified by reverse phase chromatography [start (70% $H_2O$-30% ACN: MeOH 1:1)-end (27% $H_2O$-73% ACN: MeOH 1:1)]-$H_2O$=[25 mM $NH_4HCO_3$, pH=8]. The residue was triturated in diethyl ether to give Compound 190 (43 mg, 26%) as a yellow solid. [α]$_d$: −41.6° (589 nm, c 0.08 w/v, MeOH, 23° C.).

The compound listed in the table below have been prepared by an analogous reaction protocol:

| Compound | Structure | Quantity | Yield |
| --- | --- | --- | --- |
| Compound 191 | 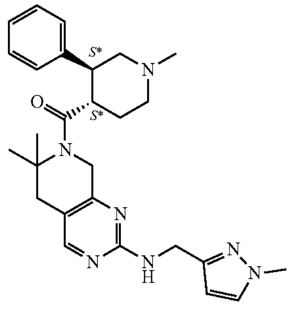 [SMILES: CN1CC[C@H](C(=O)N2Cc3nc(NCc4ccn(C)n4)ncc3CC2(C)C)[C@@H](c2ccccc2)C1]<br>[α]$_d$: −51.2° (589 nm, c 0.08 w/v, MeOH, 23° C.) | 0.02 g | 26% |

Synthesis of Compound 192:

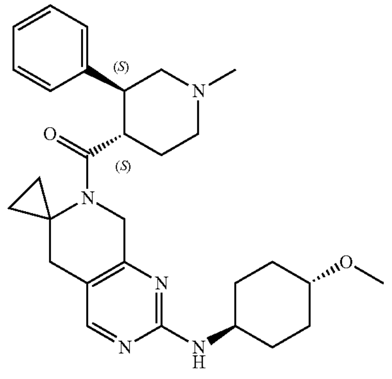

Compound 192 (0.12 g, 47%) $[\alpha]_d$: +32.9° (589 nm, c 0.18 w/v, MeOH, 23° C.) has been prepared by an analogous reaction protocol as for Compound 190 starting from intermediate 98.

Synthesis of Compound 193:

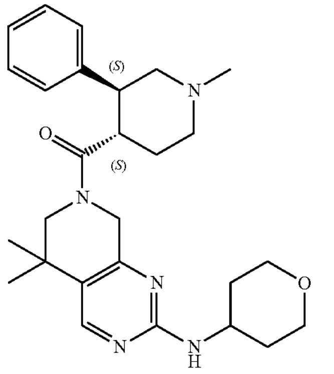

HBTU (2-(1H-Benzotriazole-1-yl)-1,1,3,3-tetramethyluronium hexafluorophosphate) (81 mg, 0.21 mmol) was added to a solution of intermediate 107 (51 mg, 0.2 mmol), intermediate 8 (55 mg, 0.2 mmol) and Diisopropylethylamine (132 μl, 0.8 mmol) in DMF (5 mL) at room temperature. The reaction was continued for 20 hours. The mixture was diluted with AcOEt (20 mL) and washed with 1M $Na_2CO_3$ (15 mL). The aqueous phase was extracted with AcOEt (10 mL). The combined organic layers were washed with brine (10 mL), dried over $MgSO_4$, filtered and concentrated dry to the crude. Chromatography over silica gel (DCM/MeOH/$NH_4OH$ (9.0/0.9/0.1, v/v/v) in DCM from 0 to 50%) afforded Compound 193 (49 mg, 54%) $[\alpha]_d$: −55.5° (589 nm, c 0.15 w/v, Methanol, 23° C.).

Synthesis of Compound 194:

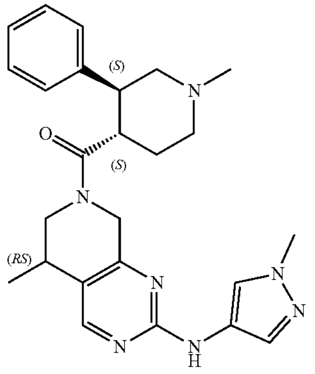

HBTU (2-(1H-Benzotriazole-1-yl)-1,1,3,3-tetramethyluronium hexafluorophosphate) (37 mg, 1 mmol) was added to a solution of intermediate 116 (0.022 g, 0.09 mmol), intermediate 8 (2 5 mg, 1 mmol) and diisopropylethylamine (61 μl, 0.36 mmol) in DMF (5 mL) at room temperature. The reaction was continued for 20 hours. The mixture was diluted with DCM (50 mL) and washed with 1M $Na_2CO_3$ (40 mL). The aqueous phase was extracted with DCM (50 mL). The combined organic layers were dried over $MgSO_4$, filtered and concentrated to dryness. Chromatography over silica gel (gradient of DCM/MeOH/$NH_4OH$ (9.0/0.9/0.1, v/v/v) in DCM from 0 to 50%) afforded Compound 194 (0.01 g, 23%).

Synthesis of Compound 195a and 195b:

195a

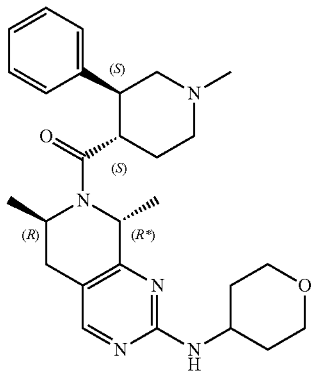

195b

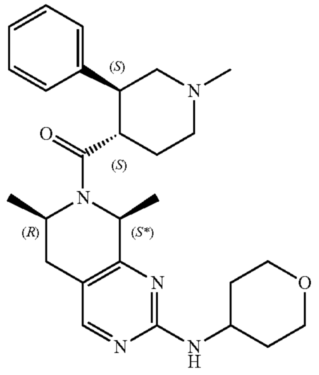

Oxalyl chloride (179 μL, 2 mmol) was added to a solution of intermediate 8 (526 mg, 2 mmol) in DCM (4 mL) at rt.

One drop of DMF was added and the reaction was stirred for 1 hour. Intermediate 119 (180 mg, 0.7 mmol) then triethylamine (572 μL, 4.1 mmol) were added. The reaction was stirred at rt for 14 hours. The reaction mixture was quenched with an aqueous solution of $NH_4Cl$ and extracted with EtOAc (3×). The organic layer was washed with brine, dried over $MgSO_4$, filtered and the solvent was evaporated. The residue was purified by chromatography over silica gel ($SiO_2$, Grace, 24 g; eluent: 100% DCM to 85% DCM, 15% MeOH (2% $NH_4OH$)). The pure fractions were collected and the solvent was evaporated to give two fractions which were combined to be purified by reverse phase (Stationary phase: YMC-actus Triart C18 10 μm 30*150 mm, Mobile phase: Gradient from 50% $NH_4HCO_3$ 0.2%, 50% MeOH to 15% $NH_4HCO_3$ 0.2%, 85% MeOH) followed by another purification which was performed via chiral SFC (Stationary phase: Lux Cellulose-2 5 μm 250*21.2 mm, Mobile phase: 50% CO2, 50% EtOH (0.3% $iPrNH_2$)): two fractions were freeze dried to give Compound 195a (6 mg, 2%) and Compound 195b (24 mg, 7%).

The compounds listed in the table below have been prepared by an analogous reaction protocol:

| Compound | Structure | Quantity | Yield |
|---|---|---|---|
| Compound 196 | 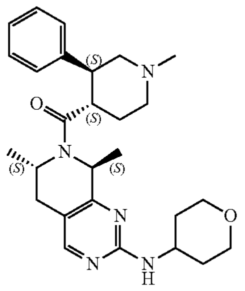 | 0.02 g | 5% |
| Compound 197 | 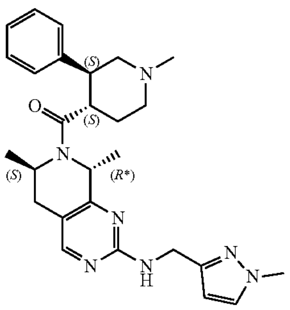 | 0.04 g | 5% |

Synthesis of Compound 198:

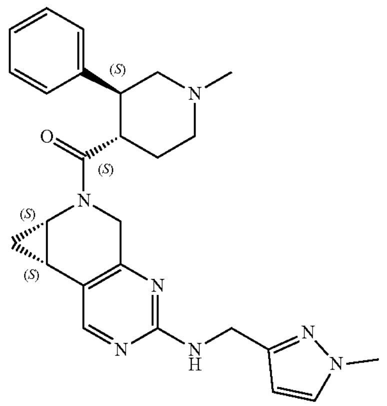

HBTU (2-(1H-Benzotriazole-1-yl)-1,1,3,3-tetramethyluronium hexafluorophosphate) (545 mg, 1.4 mmol) was added to a solution of intermediate 130 (335 mg, 1.3 mmol), intermediate 8 (367 mg, 1.4 mmol) and diisopropylethylamine (889 μl, 5.2 mmol) in DMF (30 mL) at room temperature. The reaction was continued for 20 hours. The mixture was diluted with AcOEt (150 mL) and washed with 1M $Na_2CO_3$ (100 mL). The aqueous phase was extracted with AcOEt (5×50 mL). The combined organic layers were dried over $MgSO_4$, filtered and concentrated to dryness. Chromatography over silica gel (DCM/MeOH/$NH_4OH$ (9.0/0.9/0.1, v/v/v) in DCM form 0 to 50%) afforded an amorphous solid (451 mg) which was crystallized from ACN (5 mL) to give Compound 198 as a white solid (136 mg, 22%). $[\alpha]_d$: +95.8° (589 nm, c 0.12 w/v, Methanol, 23° C.). The mother liquors were purified to give an additional batch of 160 mg (27%).

The compounds listed in the table below have been prepared by an analogous reaction protocol:

| Compound | Structure | Quantity | Yield |
|---|---|---|---|
| Compound 199 | 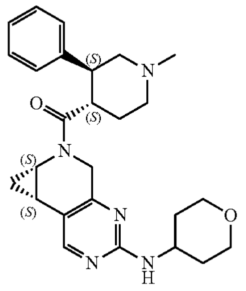 $[\alpha]_d$: +76.2° (589 nm, c 0.08 w/v, Methanol, 23° C.) | 0.024 g | 42% |
| Compound 200 | 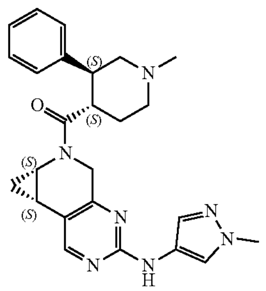 | 0.07 g | 39% |

-continued

| Compound | Structure | Quantity | Yield |
|---|---|---|---|
| | $[\alpha]_d$: +115.4° (589 nm, c 0.11 w/v, Methanol, 23° C.) | | |
| Compound 201 | 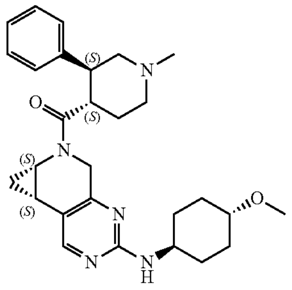<br>$[\alpha]_d$: +79.3° (589 nm, c 0.14 w/v, Methanol, 23° C.) | 0.105 g | 55% |
| Compound 202 | 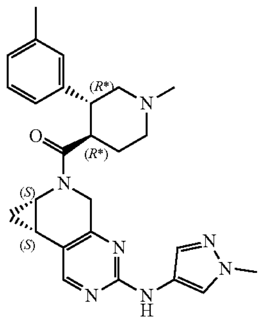<br>$[\alpha]_d$: +9.4° (589 nm, c 0.09 w/v, Methanol, 23° C.) | 0.067 g | 13% |
| Compound 203 | 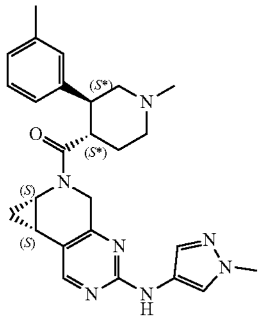<br>$[\alpha]_d$: +115.7° (589 nm, c 0.12 w/v, Methanol, 23° C.) | 0.097 g | 19% |

First Synthesis of Compound 204:

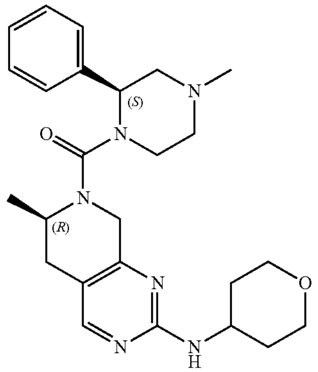

Intermediate 131 (1.1 g, 3.5 mmol), intermediate 132a (0.8 g, 4.5 mmol), triethylamine (0.7 mL, 5 mmol) in DCM (12 mL) were stirred at rt overnight. Water and DCM were added, the mixture was extracted, the organic layer was separated, dried over $MgSO_4$, filtered and evaporated to dryness. A purification was performed via preparative LC (Stationary phase: SiOH 35-40 μm 40 g Buchi, Mobile phase: DCM 100% to 90/10/0.1 CMA). The fractions were collected and evaporated until dryness. A second purification by preparative LC (24 g of SiOH 15 μm Interchim, gradient from 100% DCM to 90% DCM 10% $CH_3OH$ 0.2% $NH_4OH$) followed by a purification via achiral SFC (Stationary phase: 2-Ethylpyridine 5 μm 150*30 mm, Mobile phase: 88% CO2, 12% MeOH) gave Compound 204 (476 mg, 30%). $[\alpha]_d$: =+93.3° (589 nm, c 0.21 w/v %, DMF, 20° C.).

Second Synthesis of Compound 204a:

204a

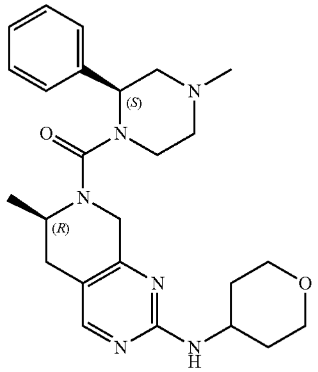

204b

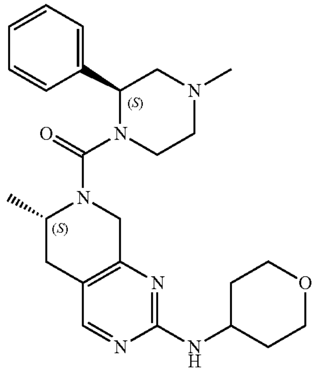

Intermediate 133 (1.06 g, 3.4 mmol), intermediate 132a (842 mg, 4.8 mmol), triethylamine (664 μl, 4.8 mmol) in DCM (10 mL) were stirred at rt overnight. Water and DCM were added, the mixture was extracted, and the organic layer was separated, dried over $MgSO_4$, filtered and evaporated. A purification was performed via preparative LC (Stationary phase: irregular SiOH 40 μm 40 g, Mobile phase: DCM 100% to 95/5/1 CMA) yielding the mixture of diastereoisomers which was separated by chiral SFC (Stationary phase: CHIRALPAK AD-H 5 μm 250*30 mm, Mobile phase: 65% $CO_2$, 35% MeOH (0.3% $iPrNH_2$)) yielding Compound 204b (255 mg), crystallized in diethylether (90 mg, 6%). $[\alpha]_d$: −115.7° (589 nm, c 0.35 w/v %, DMF, 20° C.) and Compound 204a (263 mg), crystallized in diethylether (70 mg, 4%). $[\alpha]_d$: +89.4° (589 nm, c 0.32 w/v %, DMF, 20° C.).

The compounds listed in the table below have been prepared by an analogous reaction protocol:

| Compound | Structure | Quantity | Yield |
|---|---|---|---|
| Compound 205 | 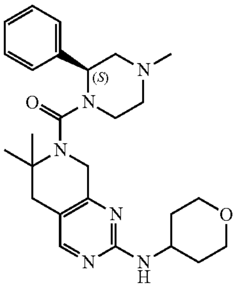 | 0.015 g | 7% |
| Compound 206 | 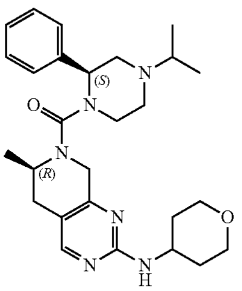<br>$[\alpha]_d$: = +96.9° (589 nm, c 0.23 w/v %, DMF, 20° C.) | 0.054 g | 47% |
| Compound 207 | 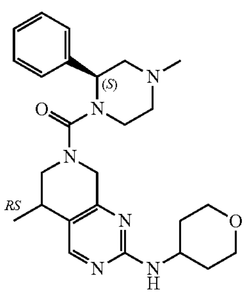 | 0.061 g | 16% |

-continued

| Compound | Structure | Quantity | Yield |
|---|---|---|---|
| Compound 208 | 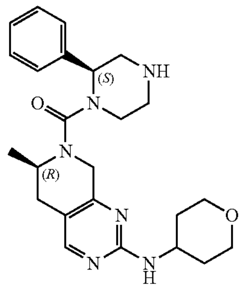<br>$[\alpha]_d$: = +96.67° (589 nm, c 0.18 w/v %, DMF, 20° C.) | 0.097 g | 14% |

Synthesis of Compound 209:

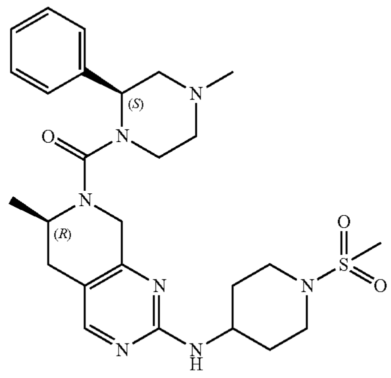

Methanesulfonyl chloride (52 μl, 0.67 mmol) was added dropwise to a solution of intermediate 137 (150 mg, 0.334 mmol), triethylamine (0.14 mL, 1 mmol) in DCM (2 mL) to 0° C. The reaction was stirred at room temperature for 15 hours. Water was added and the organic layer was extracted, dried over $MgSO_4$, filtered and evaporated until dryness. The residue was purified by preparative LC (12 g of SiOH 30 μm Interchim, gradient from 100% DCM to 80% DCM 20% $CH_3OH$ 0.1% $NH_4OH$). The fractions were collected and evaporated until dryness. The compound was crystallized in DIPE, filtered and dried to give Compound 209 (96 mg, 54%). $[\alpha]_d$: =+78.1° (589 nm, c 0.26 w/V %, DMF, 20° C.).

The compounds listed in the table below have been prepared by an analogous reaction protocol:

| Compound | Structure | Quantity | Yield |
|---|---|---|---|
| Compound 210 | 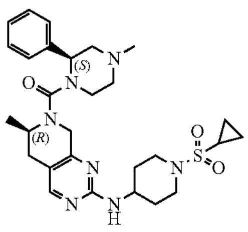<br>$[\alpha]_d$: = +84.4° (589 nm, c 0.25 w/v %, DMF, 20° C.) | 0.046 g | 25% |

-continued

| Compound | Structure | Quantity | Yield |
|---|---|---|---|
| Compound 211 | 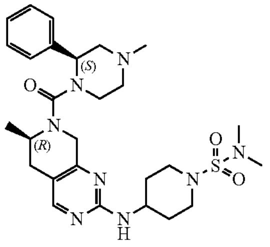 [α]$_d$: = +78.8° (589 nm, c 0.33 w/v %, DMF, 20° C.) | 0.065 g | 35% |
| Compound 212 | 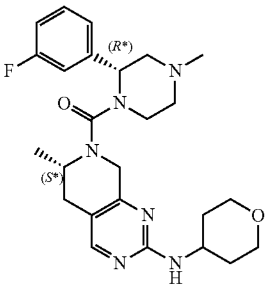 [α]$_d$: = +114.6° (589 nm, c 0.24 w/v %, DMF, 20° C.) | 0.04 g | 21% |

Synthesis of Compound 213:

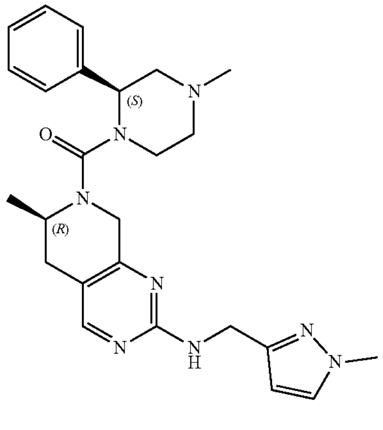

Intermediate 5 (130 mg, 0.503 mmol), intermediate 138 (144 mg, 0.6 mmol), triethylamine (0.105 mL, 0.755 mmol) were stirred in DCM (8.7 mL) at rt for 8h. Water and DCM were added, the mixture was extracted, the organic layer was separated, dried over $MgSO_4$, filtered and evaporated. A purification was performed via preparative LC (Stationary phase: irregular SiOH 40 μm 12 g, Mobile phase: 97/3/1 to 90/10/1 CMA) to give Compound 213 (70 mg, 30% yield).

Synthesis of Compound 214:

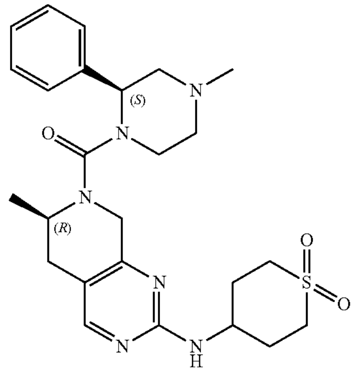

A mixture of intermediate 141 (252 mg, 0.7 mmol), intermediate 132a (140 mg, 0.79 mmol), triethylamine (0.15 mL, 1.1 mmol) in DCM (3.5 mL) was stirred at room temperature for 15 hours. The solvent was removed, and the residue was taken up with DCM and water. The organic layer was extracted, dried over $MgSO_4$, filtered and evaporated until dryness. The residue was purified by preparative LC (24 g of SiOH 35-40 μm Buchi, gradient from 100% DCM to 90% DCM 10% $CH_3OH$ 0.1% $NH_4OH$). The fractions were collected and evaporated until dryness to be purified by preparative LC (12 g of SiOH 15 μm Interchim, gradient from 100% DCM to 90% DCM 10% $CH_3OH$ 0.1% $NH_4OH$). The residue was crystallized in DIPE, filtered and dried to afford Compound 214 (96 mg, 27%). [α]$_d$: =+87.4° (589 nm, c 0.23 w/v %, DMF, 20° C.).

Example B: Analytical Characterization Methods of Intermediates and Compounds Optical Rotation (OR)

Optical rotations were measured at 20° C. or 23° C. on a Perkin Elmer 341 digital polarimeter at λ=589 nm (i.e., sodium D line), using a 0.2 mL cell (l=1 dm), and are given as [α]D (concentration in g/100 mL solvent).

Melting Points

For a number of compounds, melting points (m.p.) were determined with aDSC 1 STARe System from Mettler Toledo. Melting points were measured with a temperature gradient of 10° C./minute up to 350° C. Melting points are given by peak values LCMS General Procedure The High-Performance Liquid Chromatography (HPLC) measurement was performed using a LC pump, a diode-array (DAD) or a UV detector and a column as specified in the respective methods. If necessary, additional detectors were included (see table of methods below). Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "MSD" means Mass Selective Detector, "DAD" Diode Array Detector.

TABLE

LCMS Method codes (Flow expressed in mL/min; column temperature (T) in ° C.; Run time in minutes).

| Method code | Instrument | Column | Mobile phase | gradient | Flow Column T | Run time |
|---|---|---|---|---|---|---|
| 1 | Agilent: 1100-DAD and MSD | YMC: Pack ODS-AQ (3 μm, 4.6 × 50 mm) | A: HCOOH 0.1% in water, B: $CH_3CN$ | 95% A to 5% A in 4.8 min, held for 1 min, back to 95% A in 0.2 min. | 2.6 35 | 6 |
| 2 | Agilent 1260 Infinity DAD TOF-LC/MS G6224A | YMC-pack ODS-AQ C18 (50 × 4.6 mm, 3 μm) | A: 0.1% HCOOH in $H_2O$ B: $CH_3CN$ | From 95% A to 5% A in 4.8 min, held for 1.0 min, to 95% A in 0.2 min. | 2.6 35 | 6.8 |
| 3 | Agilent 1260 Infinity DAD TOF-LC/MS G6224A | YMC-pack ODS-AQ C18 (50 × 4.6 mm, 3 μm) | A: 0.1% HCOOH in $H_2O$ B: $CH_3CN$ | 100% A held for 0.2. From 100% A to 50% A in 4.5 min, and to 5% A in 0.1 min, held for 1.0 min, to 95% A in 0.2 min. | 2.6 35 | 6.8 |
| 4 | Waters: Acquity UPLC ® - DAD and Quattro Micro ™ | Waters: BEH C18 (1.7 μm, 2.1 × 100 mm) | A: 95% $CH_3COONH_4$ 7 mM / 5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |
| 5 | Waters: Acquity ® H-Class - DAD and SQD2 ™ | Waters BEH ® C18 (1.7 μm, 2.1 × 100 mm) | A: $CH_3COONH_4$ 7 mM 95%/ $CH_3CN$ 5%, B: $CH_3CN$ | From 84.2% A/15.8% B to 10.5% A in 2.18 min, held for 1.96 min, back to 84.2% A/15.8% B in 0.73 min, held for 0.49 min. | 0.343 40 | 6.1 |
| 6 | Waters: Acquity ® H-Class - DAD and SQD2 ™ | Waters BEH ® C18 (1.7 μm, 2.1 × 50 mm) | A: $CH_3COONH_4$ 7 mM 95%/ $CH_3CN$ 5%, B: $CH_3CN$ | From 95% A/5% B to 5% A in 1 min, held for 1.6 min, back to 95% A/5% B in 0.2 min, held for 0.5 min. | 0.5 40 | 3.5 |

Retention time ($R_t$) in min., $[M+H]^+$ peak (protonated molecule), LCMS method:

| Compound No. | Rt | [M + H]+ | LCMS Method | Compound No. | Rt | [M + H]+ | LCMS Method |
|---|---|---|---|---|---|---|---|
| 1 | 2 | 460.4 | 4 | 34 | 2.36 | 420.3 | 4 |
| 2 | 2.48 | 462.4 | 4 | 35 | 2.07 | 457.3 | 4 |
| 3 | 2.35 | 518 | 1 | 36 | 1.8 | 464 | 1 |
| 4 | 1.71 | 477 | 1 | 37 | 2.73 | 478 | 4 |
| 5 | 1.71 | 477 | 1 | 38 | 2.73 | 478 | 4 |
| 6 | 1.84 | 477.4 | 4 | 39 | 2.43 | 478 | 4 |
| 7 | 1.84 | 477.4 | 4 | 40 | 2.4 | 478 | 4 |
| 8 | 2.43 | 490.4 | 4 | 41 | 2.18 | 553.6 | 4 |
| 9 | 2.44 | 490.4 | 4 | 42 | 2.22 | 489.5 | 4 |
| 10 | 2.14 | 492 | 1 | 43 | 2.54 | 456.4 | 4 |
| 11 | 2.2 | 492 | 1 | 44 | 1.91 | 498.5 | 4 |
| 12 | 1.91 | 464.3 | 4 | 45 | 2.45 | 531.7 | 4 |
| 13 | 3.01 | 462.4 | 4 | 46 | 2.24 | 553.6 | 4 |
| 14 | 3.01 | 462.4 | 4 | 47 | 2.04 | 449.3 | 4 |
| 15 | 2.23 | 540 | 1 | 48 | 2.48 | 462.4 | 4 |
| 16 | 2.24 | 504 | 1 | 49 | 1.94 | 498.5 | 4 |
| 17 | 2.59 | 484.4 | 4 | 50 | 2.51 | 460.5 | 4 |
| 18 | 2.58 | 484.4 | 4 | 51 | 1.91 | 446.3 | 4 |
| 19 | 2.44 | 492.4 | 4 | 52 | 1.75 | 460.4 | 4 |
| 20 | 2.21 | 471.4 | 4 | 53 | 2.04 | 450.4 | 4 |

-continued

| Compound No. | Rt | [M + H]+ | LCMS Method | Compound No. | Rt | [M + H]+ | LCMS Method |
|---|---|---|---|---|---|---|---|
| 21 | 2.2 | 471.3 | 4 | 54 | 2.1 | 474.4 | 4 |
| 22 | 2.6 | 470.4 | 4 | 55 | 2.08 | 474.4 | 4 |
| 23 | 2.6 | 470.4 | 4 | 56 | 2.27 | 510.4 | 4 |
| 24 | 2.25 | 506 | 1 | 57 | 1.95 | 460.3 | 4 |
| 25 | 1.26 | 505 | 1 | 58 | 2.15 | 474.3 | 4 |
| 26 | 1.76 | 450 | 1 | 59 | 2.03 | 464.3 | 4 |
| 27 | 2.09 | 471.3 | 4 | 60 | 2.34 | 459.3 | 4 |
| 28 | 2.18 | 491.4 | 4 | 61 | 2.16 | 474.3 | 4 |
| 29 | 2.77 | 482.4 | 4 | 62 | 2.03 | 450.4 | 4 |
| 30 | 2.18 | 488.4 | 4 | 63 | 1.87 | 460.3 | 4 |
| 31 | 2.18 | 531.5 | 4 | 64 | 2.56 | 484.4 | 4 |
| 32 | 2.6 | 492.3 | 4 | 65 | 2.09 | 474.4 | 4 |
| 33 | 2.11 | 517.4 | 4 | 66 | 2.27 | 488.4 | 4 |
| 67 | 2.16 | 450.3 | 4 | 108 | 1.21 | 465 | 1 |
| 68 | 2.16 | 450.3 | 4 | 109 | 1.47 | 493 | 1 |
| 69 | 2.63 | 514.4 | 4 | 110 | 1.45 | 493 | 1 |
| 70 | 2.57 | 458.2 | 4 | 111 | 1.58 | 414 | 1 |
| 71 | 2.23 | 486.3 | 4 | 112 | 1.57 | 414 | 1 |
| 72 | 2.21 | 486.4 | 4 | 113 | 1.61 | 414 | 1 |
| 73 | 2.39 | 506 | 4 | 114 | 2.02 | 502.2 | 1 |
| 74 | 1.96 | 504.6 | 4 | 115 | 1.51 | 458 | 1 |
| 75 | 2.3 | 493.5 | 4 | 116 | 1.15 | 451 | 1 |
| 76 | 2.32 | 483.5 | 4 | 117 | 1.31 | 451 | 1 |
| 77 | 2.09 | 486.5 | 4 | 118 | 1.97 | 464.3 | 2 |
| 78 | 2.03 | 457.5 | 4 | 119 | 1.91 | 484.3 | 1 |
| 79 | 1.84 | 446.4 | 4 | 120 | 1.89 | 468.3 | 2 |
| 80 | 2.16 | 486.5 | 4 | 121 | 2.06 | 500 | 1 |
| 81 | 1.93 | 474.4 | 4 | 122a | 1.86 | 502.2 | 1 |
| 82 | 1.9 | 446.3 | 4 | 122b | 1.97 | 502.2 | 1 |
| 83 | 2.07 | 496.5 | 5 | 123 | 1.78 | 510 | 1 |
| 84 | 2.41 | 514.4 | 4 | 124 | 1.85 | 510 | 1 |
| 85 | 2.16 | 496.4 | 4 | 125 | 1.72 | 460 | 1 |
| 86 | 1.95 | 460.4 | 4 | 126 | 1.86 | 460 | 1 |
| 87 | 1.93 | 460.3 | 4 | 127 | 2.14 | 544 | 1 |
| 88 | 2.22 | 500.3 | 1 | 128 | 2.17 | 544 | 1 |
| 89 | 2.22 | 474.4 | 4 | 129 | 2.1 | 528 | 1 |
| 90 | 2.22 | 488.4 | 4 | 130 | 1.58 | 478 | 1 |
| 91 | 1.9 | 446.3 | 4 | 131 | 1.64 | 478 | 1 |
| 92a | 1.83 | 468.3 | 2 | 132 | 2.02 | 484.3 | 2 |
| 92b | 1.89 | 468.3 | 2 | 133 | 2.14 | 468.4 | 4 |
| 93 | 2.22 | 500.3 | 1 | 134 | 2.15 | 464.5 | 4 |
| 97 | 1.79 | 463.3 | 1 | 135 | 2.15 | 471.5 | 4 |
| 98 | 1.91 | 463.3 | 1 | 136 | 2.11 | 474.4 | 4 |
| 99 | 1.74 | 477 | 1 | 137 | 1.82 | 464.2 | 1 |
| 100 | 1.86 | 477 | 1 | 138a | 1.98 | 518 | 1 |
| 101 | 1.06 | 465 | 1 | 138b | 2.04 | 518 | 1 |
| 102 | 0.99 | 465 | 1 | 139 | 1.91 | 510 | 1 |
| 103 | 0.98 | 465 | 1 | 140a | 1.65 | 442 | 1 |
| 104 | 1.35 | 493 | 1 | 141 | 2.04 | 448 | 1 |
| 105 | 1.33 | 493 | 1 | 142 | 2.05 | 448 | 1 |
| 106 | 1.33 | 493 | 1 | 143 | 1.57 | 452 | 1 |
| 107 | 1.23 | 465 | 1 | 144 | 1.1 | 441 | 1 |
| 145 | 1.37 | 388 | 1 | 180a | 1.95 | 464 | 1 |
| 146 | 1.35 | 388 | 1 | 180b | 1.93 | 464 | 1 |
| 147 | 1.39 | 398 | 1 | 181 | 1.92 | 464 | 1 |
| 148 | 2.09 | 477.4 | 4 | 182 | 1.91 | 464 | 1 |
| 149 | 1.99 | 463.3 | 4 | 183 | 1.67 | 450 | 1 |
| 150 | 2.05 | 474.4 | 4 | 184 | 1.71 | 450 | 1 |
| 151 | 2.11 | 504.5 | 4 | 185 | 1.89 | 464.2 | 1 |
| 152 | 2.47 | 486.4 | 4 | 186 | 1.81 | 464.3 | 1 |
| 153 | 2.75 | 499.3 | 4 | 187 | 1.84 | 450.3 | 2 |
| 154 | 2.55 | 459.3 | 4 | 188 | 1.81 | 450.3 | 2 |
| 155 | 2.67 | 512.4 | 4 | 189 | 1.93 | 464.3 | 1 |
| 156 | 2.03 | 453.3 | 4 | 190 | 2.15 | 192.1 | 2 |
| 157 | 2.16 | 478.4 | 4 | 191 | 2.03 | 474.3 | 2 |
| 158 | 2.15 | 464.3 | 4 | 192 | 1.9 | 490.3 | 1 |
| 159 | 2.17 | 493.4 | 4 | 193 | 1.98 | 464.3 | 2 |
| 160 | 2.01 | 512.3 | 1 | 194 | 1.89 | 446.3 | 2 |
| 161 | 2.61 | 476.4 | 4 | 195a | 2.15 | 464.3 | 4 |
| 162 | 2.09 | 530.2 | 1 | 195b | 2.18 | 464.4 | 4 |
| 163 | 1.92 | 496.3 | 1 | 196 | 2.16 | 464.3 | 4 |
| 164 | 1.82 | 496.3 | 1 | 197 | 2.05 | 474.4 | 4 |
| 165 | 1.96 | 530.3 | 1 | 198 | 1.85 | 458.3 | 2 |
| 166 | 2.05 | 492.5 | 2 | 199 | 1.84 | 448.3 | 2 |
| 167 | 1.7 | 479.3 | 1 | 200 | 1.87 | 444.2 | 2 |
| 168 | 1.87 | 479.3 | 1 | 201 | 2.03 | 476.3 | 2 |

-continued

| Compound No. | Rt | [M + H]+ | LCMS Method | Compound No. | Rt | [M + H]+ | LCMS Method |
|---|---|---|---|---|---|---|---|
| 169a | 1.78 | 436.3 | 1 | 202 | 2.07 | 458.2 | 2 |
| 170a | 1.74 | 464.3 | 1 | 203 | 1.97 | 458.2 | 2 |
| 171a | 2.08 | 449.3 | 3 | 204a | 2.38 | 451.2 | 4 |
| 172 | 1.51 | 477.4 | 2 | 205 | 1.88 | 465.3 | 1 |
| 173 | 1.63 | 228.2160 (MH+/2) | 2 | 206 | 1.31 | 479.7 | 6 |
| 174 | 1.39 | 459.3 | 2 | 207 | 2.41 | 450.3 | 4 |
| 175 | 1.69 | 497.3 | 2 | 208 | 1.07 | 437.7 | 6 |
| 176 | 1.19 | 445.2 | 1 | 209 | 2.39 | 528.5 | 4 |
| 177a | 1.582 | 491 | 1 | 210 | 2.57 | 554.6 | 4 |
| 177b | 1.59 | 491 | 1 | 211 | 2.61 | 57.6 | 4 |
| 177c | 1.58 | 491 | 1 | 212 | 2.48 | 469.4 | 4 |
| 178 | 1.31 | 462 | 1 | 213 | 2.32 | 461.3 | 4 |
| 179 | 1.25 | 459.2 | 1 | 214 | 2.26 | 499.4 | 4 |

NMR

Some NMR experiments were carried out using a Bruker Avance 500 spectrometer equipped with a Bruker 5 mm BBFO probe head with z gradients and operating at 500 MHz for the proton and 125 MHz for carbon. Chemical shifts (d) are reported in parts per million (ppm). J values are expressed in Hz. Some NMR experiments were carried out using a Bruker Avance III 400 spectrometer at ambient temperature (298.6 K), using internal deuterium lock and equipped with reverse double-resonance (1H, 13C, SEI) probe head with z gradients and operating at 400 MHz for the proton. Chemical shifts (d) are reported in parts per million (ppm). J values are expressed in Hz.

$^1$H NMR Results

| Compound No. | $^1$H NMR results |
|---|---|
| 1 | Major rotamer (55%)<br>$^1$H NMR (500 MHz, DMSO-$d_6$) δ ppm 7.98 (s, 1H), 7.50 (s, 1H), 7.05-7.33 (m, 6H), 6.06 (s, 1H), 4.56-4.72 (m, 2H), 4.41 (br d, J = 6.0 Hz, 1H), 4.34 (br d, J = 4.7 Hz, 1H), 3.74-3.83 (m, 4H), 3.17 (td, J = 10.3, 5.0 Hz, 1H), 2.94-3.10 (m, 1H), 2.73-2.91 (m, 2H), 2.58 (br dd, J = 15.6, 5.3 Hz, 1H), 2.26-2.33 (m, 1H), 2.00-2.23 (m, 5H), 1.62-1.84 (m, 2H), 1.03 (br d, J = 6.4 Hz, 3H)<br>Minor rotamer (45%)<br>$^1$H NMR (500 MHz, DMSO-$d_6$) δ ppm 8.05 (s, 1H), 7.54 (s, 1H), 7.05-7.33 (m, 6H), 6.09 (br s, 1H), 4.81-4.92 (m, 1H), 4.56-4.72 (m, 1H), 4.41 (br d, J = 6.0 Hz, 1H), 4.34 (br d, J = 4.7 Hz, 1H), 3.64-3.83 (m, 4H), 2.94-3.10 (m, 2H), 2.73-2.91 (m, 2H), 2.58 (br dd, J = 15.6, 5.3 Hz, 1H), 2.26-2.33 (m, 1H), 2.00-2.23 (m, 5H), 1.62-1.84 (m, 2H), 0.43 (br d, J = 6.7 Hz, 3H) |
| 91 | Major rotamer (55%)<br>$^1$H NMR (500 MHz, DMSO-$d_6$) δ ppm 9.28 (s, 1H), 8.11 (s, 1H), 7.86 (s, 1H), 7.39 (s, 1H), 7.05-7.31 (m, 5H), 4.84-4.96 (m, 1H), 4.64 (quin, J = 6.0 Hz, 1H), 3.72-3.89 (m, 4H), 3.18 (td, J = 10.3, 5.6 Hz, 1H), 2.98-3.12 (m, 1H), 2.71-2.92 (m, 2H), 2.57-2.65 (m, 1H), 2.34-2.40 (m, 1H), 2.20 (s, 3H), 2.01-2.17 (m, 3H), 1.66-1.84 (m, 2H), 1.05 (d, J = 6.7 Hz, 3H)<br>Minor rotamer (45%)<br>$^1$H NMR (500 MHz, DMSO-$d_6$) δ ppm 9.28 (s, 1H), 8.17 (s, 1H), 7.83 (s, 1H), 7.52 (br s, 1H), 7.05-7.31 (m, 5H), 4.84-4.96 (m, 1H), 4.68-4.81 (m, 1H), 3.72-3.89 (m, 4H), 3.18 (td, J = 10.3, 5.6 Hz, 1H), 2.98-3.12 (m, 1H), 2.71-2.92 (m, 2H), 2.57-2.65 (m, 1H), 2.34-2.40 (m, 1H), 2.20 (s, 3H), 2.01-2.17 (m, 3H), 1.66-1.84 (m, 2H), 0.46 (d, J = 6.9 Hz, 3H) |
| 38 | Major rotamer (55%)<br>$^1$H NMR (500 MHz, DMSO-$d_6$) δ ppm 7.96 (s, 1H), 7.05-7.40 (m, 5H), 6.78 (br d, J = 7.9 Hz, 1H), 4.50-4.73 (m, 2H), 3.52-3.77 (m, 2H), 3.21 (s, 3H), 2.70-3.19 (m, 5H), 2.54-2.60 (m, 1H), 2.28 (br d, J = 15.1 Hz, 1H), 2.20 (s, 3H), 1.59-2.16 (m, 8H), 1.10-1.37 (m, 4H), 1.02 (d, J = 6.6 Hz, 3H)<br>Minor rotamer (45%)<br>$^1$H NMR (500 MHz, DMSO-$d_6$) δ ppm 8.02 (s, 1H), 7.05-7.40 (m, 5H), 6.78 (br d, J = 7.9 Hz, 1H), 4.79-4.91 (m, 1H), 4.50-4.73 (m, 1H), 3.52-3.77 (m, 2H), 3.24 (s, 3H), 2.70-3.19 (m, 5H), 2.54-2.60 (m, 1H), 2.28 (br d, J = 15.1 Hz, 1H), 2.20 (s, 3H), 1.59-2.16 (m, 8H), 1.10-1.37 (m, 4H), 0.44 (d, J = 6.9 Hz, 3H) |
| 47 | Major rotamer (60%)<br>$^1$H NMR (400 MHz, DMSO-$d_6$) δ ppm 7.98 (s, 1H), 6.88-7.35 (m, 6H), 4.52-4.74 (m, 2H), 3.60-4.01 (m, 4H), 3.36-3.45 (m, 1H), 2.59-3.23 (m, 5H), 2.30 (br d, J = 15.5 Hz, 1H), 1.99-2.24 (m, 6H), 1.64-1.89 (m, 4H), 1.36-1.60 (m, 2H), 1.03 (br d, J = 6.1 Hz, 3H)<br>Minor rotamer (40%) |

-continued

| Compound No. | $^1$H NMR results |
|---|---|
| | $^1$H NMR (400 MHz, DMSO-$d_6$) δ ppm 8.04 (s, 1H), 6.88-7.35 (m, 6H), 4.85 (br d, J = 4.5 Hz, 1H), 4.52-4.74 (m, 1H), 3.60-4.01 (m, 4H), 3.36-3.45 (m, 1H), 2.59-3.23 (m, 5H), 2.30 (br d, J = 15.5 Hz, 1H), 1.99-2.24 (m, 6H), 1.64-1.89 (m, 4H), 1.36-1.60 (m, 2H), 0.44 (br d, J = 6.5 Hz, 3H) |
| 201 | $^1$H NMR (400 MHz, CHLOROFORM-d) δ ppm 8.08 (s, 1H), 6.96 - 7.15 (m, 5H), 4.64-4.77 (m, 2H), 3.58-3.79 (m, 2H), 3.25-3.43 (m, 4H), 3.16-3.23 (m, 1H), 2.85-3.14 (m, 4H), 2.25 (s, 3H), 1.87-2.13 (m, 9H), 1.06-1.40 (m, 6H) |
| 174 | Major rotamer (60%)<br>$^1$H NMR (400 MHz, CHLOROFORM-d) δ ppm 7.66 (s, 1H), 6.99-7.18 (m, 6H, partially obscured by solvent peak), 6.08 (br s, 2H), 4.74 (br t, J = 5.4 Hz, 1H), 4.65 (d, J = 18.5 Hz, 1H), 4.31-4.47 (m, 2H), 4.05-4.20 (m, 1H), 3.92 (d, J = 18.5 Hz, 1H), 3.79 (s, 3H), 3.16-3.28 (m, 1H), 2.85-3.01 (m, 2H), 1.88-2.81 (m, 9H), 1.61-1.77 (m, 1H), 0.93 (d, J = 6.7 Hz, 3H)<br>Major rotamer (40%)<br>$^1$H NMR (400 MHz, CHLOROFORM-d) δ ppm 7.77 (s, 1H), 7.24 (d, J = 1.8 Hz, 1H), 6.99-7.18 (m, 5H), 6.12 (d, J = 2.0 Hz, 1H), 6.08 (br s, 1H), 4.90-5.00 (m, 1H), 4.76-4.82 (m, 1H), 4.31-4.47 (m, 3H), 3.83 (s, 3H), 3.71 (d, J = 16.6 Hz, 1H), 3.16-3.28 (m, 1H), 2.85-3.01 (m, 2H), 1.88-2.81 (m, 9H), 1.61-1.77 (m, 1H), 0.47 (d, J = 6.9 Hz, 3H) |

Example C: Pharmacological Assays

Expression and Purification of a Trimeric Complex of CDK7, Cyclin H, and MAT1

Human CDK7 (amino acids 1-346) containing an N-terminal $His_6$-tag followed by a tobacco etch virus (TEV) protease cleavage site, human MAT1 (amino acids 1-309) and human cyclin H (amino acids 1-323) were co-expressed in the baculovirus-SF9 insect cell expression system to generate a trimeric complex. Cell pellets were collected 72 h post-infection and were resuspended by Dounce homogenization in 20 mM Hepes-NaOH (pH 8.0), 300 mM NaCl, 10% glycerol, 2 mM dithiothreitol DTT), and 20 mM Imidazole supplemented with cOmplete™ Protease Inhibitor Cocktail (Roche) and 25 U/mL Benzonase® Nuclease HC according to the manufacturer's instructions. Cells were lysed by passing through a Microfluidics M110Y Microfluidizer 3 times at 600 kPa followed by centrifugation at 38,000×g at 4° C. for 1 hour. The supernatant was loaded onto a pre-equilibrated HisTrap HP column and eluted in 20 mM Hepes-NaOH (pH 8.0), 50 mM NaCl, 10% glycerol, 2 mM DTT, and 400 mM Imidazole. The eluate was further purified by gel filtration on a Superdex S200 16/60 column and eluted with 20 mM Hepes-NaOH (pH 7.5), 50 mM NaCl, 10% Glycerol, 2 mM DTT. Fractions containing a trimeric complex of CDK7, cyclin H, and MAT1 in a 1:1:1 ratio were pooled and concentrated to 3 mg/mL in a 10 kDa MWCO concentrator, and diluted to a final concentration of 1.6 mg/mL in 11.1 mM Hepes-NaOH (pH 8.0), 27.8 mM NaCl, 1.1 mM DTT and 50% glycerol.

In Vitro CDK7 Assay and Determination of Potency for Reversible Inhibitors

Inhibition potencies of compounds were studied using an absorbance kinetic assay as described below. Compounds with potencies approaching the limit of detection of the assay ($IC_{50}$≤10 nM) were further assessed in a more sensitive fluorescence end-point assay.

Absorbance Kinetic Assay (20 nM CDK7/Cyclin H/MAT-1 Complex)

CDK7 complex catalyzes the ATP-dependent phosphorylation of a peptide substrate CDK7/9-tide that is derived from RNA Pol II to produce phosphorylated peptide and ADP. The kinase reaction product ADP was converted to lactate and $NAD^+$ in the presence of phosphoenol pyruvate (PEP), NADH and coupling enzymes lactate dehydrogenase (LDH) and pyruvate kinase (PK). CDK7 complex catalytic activity was measured by following the absorbance intensity continuously at 340 nm that corresponds with the depletion of NADH.

Compound potencies were measured by a 12-point dose response manner under the assay conditions of 300 µM CDK7/9 tide ($K_M^{peptide}$=140.5±18.5 µM), 500 µM ATP ($K_M^{ATP}$=27.8±4.1 µM), 500 µM PEP, 100 µM NADH, 0.6-1 unit PK/0.9-1.4 unit and 20 nM CDK7/Cyclin H/MAT-1 complex in a buffer containing 20 mM Tris, pH 7.4, 10 mM $MgCl_2$ and 0.004% Triton X-100. Absorbance at 340 nm was followed kinetically at an interval of 2 minutes for 8 hours.

The assay was carried out with 100 µl reaction volume per well in a 384-well plate that was pre-spotted nanoliter volume of compounds by LabCyte Echo 555. Compound dilution plates were made by 2-fold (could vary upon necessity) dilution in DMSO for 11 concentrations plus a DMSO control of uninhibited reaction. 2× substrate and coupling reagent mixture was added to the assay plate followed by an addition of an equal volume of 40 nM CDK7/Cyclin H/MAT-1 complex. After mixing, assay plates were spun at 2000 rpm for 3 minutes and then transferred to the plate reader for data collection.

For reversible inhibitors, the absorbance reaction progress curves were linear. The steady-state rate was derived from the slope of the linear curves. The following equation is applied to determine percent inhibition.

$$\text{Percent Inhibition } (\%_{Inh}) = \left(\frac{v_o - v_i}{v_o}\right) \times 100$$

$v_o$=max rate (uninhibited rate)

$v_i$=inhibited rate

The $IC_{50}$ value is calculated by the following equation:

$$v_i = v_o + \frac{(v_{min} - v_o) * [I]^h}{IC_{50}^h + [I]^h}$$

where $v_o$ is the rate in the absence of inhibitor, $v_{min}$ is the rate at highest inhibitor concentration, and h is the Hill coefficient.

Flint Assay (5 nM CDK7/Cyclin H/MAT-1 Complex)

The continuous absorbance assay was converted to an end-point fluorescence assay following the NADH fluorescence signal decrease at the excitation and emission wavelengths of 340 nm and 440 nm, respectively.

Under the same concentrations of substrates and coupling reagents used in the absorbance assay, the fluorescence assay was performed at a reduced concentration of the CDK7/Cyclin H/MAT-1 complex of 5 nM (final concentration) with a reaction time of 24 hours. The percent of inhibition was calculated by the following equation.

$$\text{Percent of inhibition}=(\text{Sample}-\text{NC})/(\text{PC}-\text{NC})*100$$

where NC is the mean if negative control (reaction without inhibitor), and PC is the mean of positive control (reaction with complete inhibition).

Dosing curves were fitted using the following equation to obtain $IC_{50}$:

$$Y=\text{Bottom}+(\text{Top}-\text{Bottom})/(1+10\hat{}((\log IC_{50}-X)*\text{Hill slope}))$$

where $X=\log_{10}$ of the compound concentration; top and bottom can be defined by PC and NC respectively.

Imaging-Based Cellular RNA PolII Ser5 Phosphorylation Assay

To evaluate inhibition of CDK7 kinase activity, a 384-well automated imaging assay was used. This assay detects Serine 5 phosphorylation on a unique heptapeptide sequence in the C-terminal domain of Rpb1 subunit of RNA polymerase II, the downstream substrate of CDK7. This heptapeptide sequence is repeated up to 52 times in the CTD of Rpb1.

Materials

A549 adenocarcinoma human alveolar basal epithelial cells (ATCC, CCL-185), rabbit Phospho-Rpb1 CTD (Ser5) antibody (D9N51 (Cell Signaling Technology)), DMEM (Sigma), Fetal Bovine Serum (Biowest), L-glutamine (Sigma), Penicillin/Streptomycin (Life Technologies), Sodium Pyruvate (Sigma), Hepes (Sigma), poly-D-lysine coated µclear 384 black plates (Greiner), formaldehyde (PolySciences), D-PBS (Sigma), Methanol (Sigma), Alexa Fluor 488 goat anti rabbit IgG secondary antibody (Life Technologies), HCS CellMask™ Deep Red stain (Life Technologies), Hoechst 33258 (Invitrogen).

RNA Polymerase II Serine 5 phosphorylation was detected using a specific rabbit Phospho-Rpb1 CTD (Ser5) antibody. A549 adenocarcinoma human alveolar basal epithelial cells were seeded in 20 µl medium (DMEM supplemented with 1% Fetal Bovine Serum (heat inactivated 30' 56° C.), 2 mM L-glutamine, 50 U/ml penicillin 50 µg/ml streptomycin, 1 mM sodium pyruvate and 50 mM hepes) at 1000 cells/well and cultured in poly-D-lysine coated µclear 384 black plates for 20 hours at 37° C. and 5% $CO_2$.

After incubation cells were challenged with compound for 3 hours at 37° C. and 5% $CO_2$. DMSO was used as high control and as low control 10 µM of LDC4297 reference compound was used. 40 nl of test compounds and controls were spotted in cell plates using Echo Liquid Handler (Echo 550, Labcyte). Incubation was followed by 20 minutes fixation with 20 µl 10% formaldehyde at room temperature. Medium/formaldehyde solution was removed, plates were washed 3 times with 30 µl D-PBS (w/o $Ca^{2+}$ and $Ma^{2+}$) and permeabilization was done by adding 20 µl ice cold methanol for 20 minutes. Cells were washed again 3 times with 30 µl D-PBS and 20 µl blocking buffer (25 ml fetal bovine serum in 500 ml D-PBS) was added for 1 hour.

After removing blocking buffer 20 µl 1/1000 primary antibody rabbit. Phospho-Rpb1 CTD (Ser5) antibody was added which binds to the phosphorylated Serine5 of the heptapeptide sequences in the CTD of Rpb1. Primary antibody was removed, and plates were washed 3 times with 30 µl D-PBS followed by addition of 20 µl 1/2000 Alexa Fluor 488 goat anti rabbit IgG secondary antibody for final detection of Phospho-Rpb1 CTD (Ser5) together with 1/5000 HCS CellMask™ Deep Red stain for membrane staining and 1/5000 Hoechst 33258 for nucleus staining. Last, plates were washed 2 times with 30 µl D-PBS and wells were filled with 40 µL D-PBS, plates were sealed (Thermowell sealing tape) and stored at 4° C. until reading. Plates were read with Opera Phenix (Perkin Elmer) with 10× air objective. Data were calculated and analyzed in Phaedra.

$IC_{50}$ values were calculated using the following formula:

$$LC = \text{Average of the low control values} = \text{Cells treated with } 10\ \mu\text{M of } LDC4297$$

$$HC = \text{Average of the high control values} = \text{Cells treated with } 0.2\%\ DMSO$$

Average value of all HC's and all LC's are used for normalizations.

$$\%\ \text{Effect}=100-(\text{sample}-\text{LC})/(\text{HC}-\text{LC})\times 100\%$$

$$\text{Control}=(\text{sample}/\text{HC})\times 100$$

A best-fit curve is fitted by a minimum sum of squares method to the plot of % Control vs. compound concentration. From this an IC50 value can be obtained. An estimate of the slope of the plot in terms of the Hill coefficient is also obtained.

| Co. No. | CDK7 (20 nM) $pIC_{50}$ | CDK7 (5 nM) $pIC_{50}$ | pRNA polII Ser5 (A549) $pIC_{50}$ | Co. No. | CDK7 (20 nM) $pIC_{50}$ | CDK7 (5 nM) $pIC_{50}$ | pRNA polII Ser5 (A549) $pIC_{50}$ |
|---|---|---|---|---|---|---|---|
| 1 | 8.01 | 8.61 | ~7.34 | 34 | 7.94 | NT | 6.56 |
| 2 | 7.72 | 8.0 | 6.75 | 35 | 7.78 | NT | 6.7 |
| 3 | >8.01 | 8.3 | 7.22 | 36 | 7.19 | NT | 5.62 |
| 4 | 7.45 | | ~5.09 | 37 | 8.01 | 8.6 | ~7.47 |
| 5 | >8.01 | 8.67 | | 38 | 7.46 | NT | 5.86 |
| 6 | >8.01 | 8.42 | 6.08 | 39 | >7.7 | 8.3 | 6.4 |
| 7 | >8.01 | 8.35 | 6.03 | 40 | 7.96 | 8.14 | ~7.28 |
| 8 | >8.01 | 8.57 | 7.16 | 41 | 6.18 | NT | <5 |
| 9 | >8.01 | 8.21 | 6.51 | 42 | 7.39 | NT | 5.86 |
| 10 | >8.01 | 8.11 | 6.8 | 43 | 8.01 | 8.11 | 6.97 |
| 11 | 7.86 | | 5.87 | 44 | >7.7 | 8.04 | 5.51 |
| 12 | >8.01 | 8.49 | 7.03 | 45 | 7.62 | 7.65 | 6.36 |
| 13 | 8.01 | 8.85 | ~7.47 | 46 | 6.18 | NT | <5 |
| 14 | 7.89 | NT | 6.32 | 47 | >7.7 | 8.3 | ~7.15 |

-continued

| Co. No. | CDK7 (20 nM) $pIC_{50}$ | CDK7 (5 nM) $pIC_{50}$ | pRNA polII Ser5 (A549) $pIC_{50}$ | Co. No. | CDK7 (20 nM) $pIC_{50}$ | CDK7 (5 nM) $pIC_{50}$ | pRNA polII Ser5 (A549) $pIC_{50}$ |
|---|---|---|---|---|---|---|---|
| 15 | NT | NT | 7.01 | 48 | 7.59 | 7.92 | 6.88 |
| 16 | NT | NT | 7.39 | 49 | 6.62 | 7.2 | <5 |
| 17 | NT | NT | 6.44 | 50 | 7.6 | 8.05 | 7.14 |
| 18 | NT | NT | 6.31 | 51 | 7.29 | 8.08 | 5.88 |
| 19 | NT | NT | 7.38 | 52 | 7.97 | 7.9 | 5.61 |
| 20 | 8.01 | 8.19 | ~7.85 | 53 | 7.39 | 7.99 | 6.24 |
| 21 | 7.97 | NT | 6.52 | 54 | 7.91 | 8.29 | 6.91 |
| 22 | 8.01 | 8.19 | ~7.85 | 55 | 6.85 | 7.41 | 5.35 |
| 23 | 7.97 | NT | 6.52 | 56 | 6.85 | 7.44 | 5.29 |
| 24 | 7.96 | NT | 6.9 | 57 | 6.66 | 7.53 | 5.53 |
| 25 | 7.46 | NT | 6.11 | 58 | >8.01 | 8.63 | 7.64 |
| 26 | 7.85 | NT | 6.52 | 59 | >8.01 | 8.28 | 6.85 |
| 27 | 7.50 | NT | 5.68 | 60 | >8.01 | 8.45 | 6.67 |
| 28 | 6.59 | NT | <5 | 61 | >8.01 | 7.97 | 6.04 |
| 29 | 8.01 | 8.55 | 7.9 | 62 | >8.01 | 8.33 | 6.21 |
| 30 | 7.03 | NT | 5.41 | 63 | 7.38 | NT | <5 |
| 31 | 7.81 | NT | ~7.16 | 64 | >8.01 | NT | 6.85 |
| 32 | 7.9 | NT | 6.43 | 65 | 7.58 | 7.33 | 5.18 |
| 33 | 7.88 | NT | 6.79 | 66 | >8.01 | 8.56 | ~7.55 |
| 67 | >8.01 | 7.78 | 5.88 | 108 | 6.98 | 7.71 | 5.77 |
| 68 | 7.84 | NT | 5.62 | 109 | <5 | NT | <5 |
| 69 | >8.01 | 8.57 | 7.23 | 110 | >8.01 | 7.89 | 6.36 |
| 70 | >8.01 | 8.75 | 6.83 | 111 | 6.67 | NT | 5.08 |
| 71 | >8.01 | 8.54 | 6.92 | 112 | <5 | NT | <5 |
| 72 | 8.01 | 8.22 | 6.7 | 113 | 7.10 | NT | 5.76 |
| 73 | 7.44 | 8.24 | 7.2 | 114 | 7.96 | NT | 7.25 |
| 74 | 7.72 | 8.0 | 6.75 | 115 | 6.92 | NT | 5.2 |
| 75 | 7.46 | 8.04 | 7.24 | 116 | 7.43 | NT | 5.85 |
| 76 | NT | NT | ~7.48 | 117 | 7.79 | NT | <5 |
| 77 | 7.53 | 7.88 | 6.5 | 118 | 7.93 | NT | 6.57 |
| 78 | 7.93 | 8.37 | ~7.24 | 119 | 7.14 | NT | ~7.4 |
| 79 | 7.37 | 7.78 | 5.64 | 120 | 7.92 | NT | ~7.17 |
| 80 | NT | NT | 7.73 | 121 | NT | NT | >8.61 |
| 81 | NT | NT | 5.87 | 122a | <5 | NT | <5 |
| 82 | >8.01 | 8.67 | ~7.33 | 122b | 7.15 | 8.5 | ~7.2 |
| 83 | 6.1 | <6.7 | 7.15 | 123 | NT | NT | 5.62 |
| 84 | NT | NT | 5.95 | 124 | NT | NT | ~7.35 |
| 85 | NT | NT | ~7.51 | 125 | 6.47 | NT | 6.1 |
| 86 | NT | NT | 6.35 | 126 | 7.81 | 8.43 | ~8.41 |
| 87 | NT | NT | 6.18 | 127 | 6.63 | 7.12 | 5.82 |
| 88 | NT | NT | 7.54 | 128 | 7.73 | 8.17 | 6.99 |
| 89 | 6.1 | <6.7 | 7.15 | 129 | 7.93 | 8.31 | ~7.38 |
| 90 | 7.43 | 7.57 | 5.3 | 130 | 7.42 | 8.1 | NT |
| 91 | >8.01 | 8.67 | ~7.33 | 131 | 7.21 | 8.04 | NT |
| 92a | 5.11 | NT | <5 | 132 | 8.01 | 8.44 | ~7.09 |
| 92b | 7.92 | NT | ~7.17 | 133 | 7.91 | 8.09 | 7.01 |
| 93 | >8.01 | 8.52 | ~7.17 | 134 | >8.01 | 8.5 | ~7.17 |
| 97 | NT | NT | 6.23 | 135 | NT | NT | ~7.69 |
| 98 | NT | NT | ~7.6 | 136 | 7.94 | 7.8 | ~7.56 |
| 99 | NT | NT | 6.22 | 137 | 6.34 | NT | 6.02 |
| 100 | NT | NT | ~7.58 | 138a | NT | NT | <5 |
| 101 | 7.67 | NT | 5.35 | 138b | NT | NT | 6.74 |
| 102 | 6.98 | 7.71 | 5.77 | 139 | 7.04 | 7.31 | 5.9 |
| 103 | <5 | NT | <5 | 140a | 5.89 | NT | <5 |
| 104 | 7.89 | NT | 5.91 | 141 | 7.4 | 8.07 | <5 |
| 105 | >8.01 | 8.0 | 6.39 | 142 | 5.53 | NT | 5.38 |
| 106 | 5.22 | NT | <5 | 143 | >8.01 | 8.05 | 5.59 |
| 107 | <5 | NT | <5 | 144 | >8.01 | 8 | 6.12 |
| 145 | 7.17 | 7 | 5.53 | 180a | >8.01 | 8.68 | ~7.49 |
| 146 | 7.94 | 7.76 | 6.16 | 180b | 5.65 | NT | 5.41 |
| 147 | NT | NT | 6.09 | 181 | 6.9 | 6.98 | 5.6 |
| 148 | >8.01 | >8.6 | ~7.57 | 182 | 6.14 | NT | 5.37 |
| 149 | 5.3 | NT | 5.12 | 183 | <5 | NT | <5 |
| 150 | >8.01 | 8.5 | ~7.02 | 184 | 7.59 | NT | 6.27 |
| 151 | >8.01 | 8.2 | 6.25 | 185 | 7.37 | NT | 6.14 |
| 152 | >8.01 | 8.36 | 6.26 | 186 | <5 | NT | <5 |
| 153 | >8.01 | 8.16 | 5.94 | 187 | <5 | NT | <5 |
| 154 | >8.01 | 8.6 | 6.89 | 188 | >8.01 | 8.55 | 6.98 |
| 155 | >8.01 | 8.2 | 6.27 | 189 | 7.75 | 7.65 | 5.99 |
| 156 | NT | 8.49 | 6.9 | 190 | NT | NT | 6.62 |
| 157 | NT | NT | 6.75 | 191 | 6.53 | 7.41 | ~5.37 |
| 158 | NT | NT | 7.11 | 192 | 6.80 | 6.84 | 5.54 |
| 159 | 6.24 | NT | <5 | 193 | 6.75 | 7.05 | 5.44 |
| 160 | 6.96 | 8.58 | 6.87 | 194 | 7.75 | 8.21 | 6.96 |
| 161 | 6.74 | NT | <5 | 195a | 5.33 | NT | <5 |

-continued

| Co. No. | CDK7 (20 nM) $pIC_{50}$ | CDK7 (5 nM) $pIC_{50}$ | pRNA polII Ser5 (A549) $pIC_{50}$ | Co. No. | CDK7 (20 nM) $pIC_{50}$ | CDK7 (5 nM) $pIC_{50}$ | pRNA polII Ser5 (A549) $pIC_{50}$ |
|---|---|---|---|---|---|---|---|
| 162 | 6.95 | NT | NT | 195b | >8.01 | 8.31 | 7.14 |
| 163 | 6.83 | NT | 6.79 | 196 | NT | NT | 6.11 |
| 164 | 6.06 | NT | 5.39 | 197 | 6.11 | NT | 5.55 |
| 165 | 6.10 | NT | 5.49 | 198 | NT | NT | 6.63 |
| 166 | 7.74 | 7.85 | ~7.29 | 199 | >8.01 | 8.27 | ~7.23 |
| 167 | 6.25 | 6.95 | 5.24 | 200 | 7.46 | 7.77 | 6.49 |
| 168 | 5.87 | NT | <5 | 201 | 7.48 | 8.16 | ~7.71 |
| 169a | 6.33 | NT | <5 | 202 | 5.63 | NT | 5.16 |
| 170a | 6.1 | NT | <5 | 203 | 7.77 | 8.27 | 6.83 |
| 171a | 8.01 | 8.24 | 6.54 | 204a | 7.81 | 8.17 | 6.57 |
| 172 | >8;0 | 8.13 | 6.73 | 205 | 7.89 | NT | 6.29 |
| 173 | >8.0 | 8.78 | ~6.99 | 206 | 7.79 | 8.19 | 6.63 |
| 174 | 7.95 | 8.58 | 7.45 | 207 | NT | NT | NT |
| 175 | 7.52 | 8.13 | 6.78 | 208 | 7.66 | NT | 5.91 |
| 176 | 7.64 | 8.04 | 6.42 | 209 | 7.77 | 8.48 | 6.68 |
| 177a | 7.54 | 7.91 | 6.98 | 210 | >7.7 | 8.48 | 6.96 |
| 177b | <5 | NT | ~5.23 | 211 | >7.7 | 7.88 | 6.14 |
| 177c | 6.41 | 7.65 | ~7.01 | 212 | 7.88 | 8.32 | 6.74 |
| 178 | NT | NT | 5.43 | 213 | 6.8 | 6.9 | 5.86 |
| 179 | NT | NT | ~7.08 | 214 | 7.55 | 7.8 | 5.45 |

Example D: Prophetic Formulations

"Active ingredient" (a.i.) as used throughout these examples relates to a compound of Formula (I), including any tautomer or stereoisomeric form thereof, or a pharmaceutically acceptable addition salt or a solvate thereof; in particular to any one of the exemplified compounds.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient may be replaced with the same amount of any of the compounds according to the present invention, in particular by the same amount of any of the exemplified compounds.

The invention claimed is:

1. A compound of formula (Va) or (Vb), a tautomeric form, a stereochemically isomeric form, an isotopically labeled form, or a pharmaceutically acceptable salt or solvate thereof:

(Va)

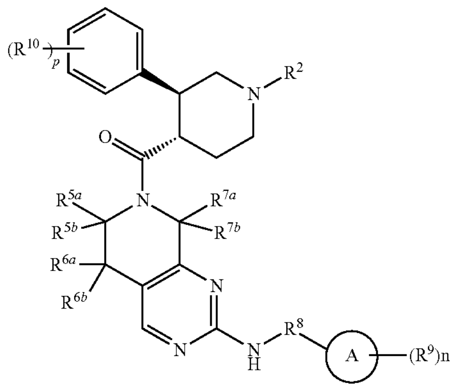

(Vb)

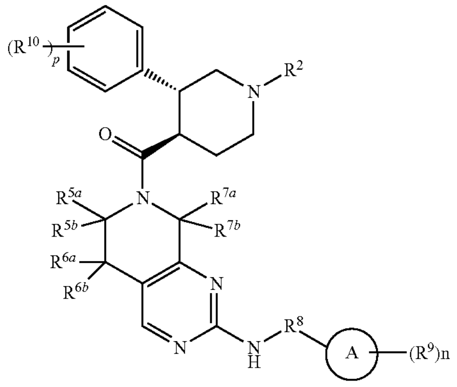

wherein, $R^2$ is hydrogen; halo$C_{1-6}$alkyl; $C_{1-6}$alkoxy; $C_{1-6}$alkyloxycarbonyl; $C_{2-6}$alkenyl; $C_{2-6}$alkynyl; $-C(=O)-NH_2$; $-C(=O)-NH(C_{1-4}alkyl)$; $-C(=O)-N(C_{1-4}alkyl)_2$; $C_{3-6}$cycloalkyl; phenyl; a 4 to 7 membered monocyclic heterocyclyl containing at least one heteroatom that is N, O or S; or $C_{1-6}$alkyl optionally substituted with deuterium, hydroxyl, $C_{1-6}$alkoxy, cyano, $C_{3-6}$cycloalkyl, phenyl, or with a 4 to 7 membered monocyclic heterocyclyl containing at least one heteroatom that is N, O or S;

each $R^{5a}$, $R^{5b}$, $R^{6a}$, $R^{6b}$, $R^{7a}$, and $R^{7b}$, independently, is hydrogen; $C_{1-6}$alkyl; halo$C_{1-6}$alkyl; or $R^{5a}$ and $R^{5b}$ form a $C_{3-6}$cycloalkyl together with the carbon atom to which they are bound; or $R^{6a}$ and $R^{6b}$ form a $C_{3-6}$cycloalkyl together with the carbon atom to which they are bound; or $R^{5b}$ and $R^{6a}$ form a cyclopropyl together with the carbon atoms to which they are bound;

$R^8$ is a direct bond, $C_{1-4}$alkanediyl optionally substituted with hydroxy, halo, deuterium, or $C_{1-4}$alkoxy; —$CH_2$—C(═O)—; a spiro-$C_{3-6}$cycloalkyl; or a 4 to 7 membered spiro-monocyclic heterocyclyl containing at least one heteroatom that I s N, O or S;

A is a $C_{3-6}$cycloalkyl; aryl; a 5 to 12 membered heteroaryl containing at least one heteroatom that is N, O or S; or a 3 to 12 membered heterocyclyl containing at least one heteroatom that is N, O or S;

$R^9$ is $C_{1-6}$alkyl optionally substituted with $C_{3-6}$cycloalkyl; cyano, halo; halo$C_{1-6}$alkyl; $C_{1-6}$alkoxy optionally substituted with $C_{3-6}$cycloalkyl; halo$C_{1-6}$alkoxy; hydroxyl; hydroxy$C_{1-6}$alkyl; oxo; —$SO_2$—$C_{1-4}$alkyl; —$SO_2$—$C_{3-6}$cycloalkyl; —$SO_2$—$NH_2$, —$SO_2$—NH($C_{1-4}$alkyl); —$SO_2$—N($C_{1-4}$alkyl)$_2$; —NH—C(═O)—$C_{2-6}$ alkenyl; —C(═O)—$C_{1-6}$alkyl; —C(═O)—$C_{1-6}$alkyl-$C_{3-6}$cycloalkyl; —C(═O)—$C_{3-6}$cycloalkyl; —C(═O)—$C_{2-6}$alkenyl; $C_{3-6}$cycloalkyl; spiro-$C_{3-6}$cycloalkyl; phenyl; a 4 to 7 membered monocyclic heterocyclyl containing at least one heteroatom that is N, O or S; or a 4 to 7 membered Spiro monocyclic heterocyclyl containing at least one heteroatom that is N, O or S;

n is 0, 1, 2, 3, 4, or 5;

$R^{10}$ is hydrogen, halo, hydroxy, mercapto, carboxyl, halo$C_{1-6}$alkyl, mono- or di($C_{1-6}$alkyl)amino, mono- or di($C_{1-6}$alkyl)aminocarbonyl, $C_{1-6}$alkylcarbonyl, $C_{1-6}$alkylcarbonylamino, $C_{1-6}$alkoxy, $C_{1-6}$alkoxycarbonyl, $C_{1-6}$alkylthio, cyano, nitro, halo$C_{1-6}$alkoxy, aminocarbonyl, $C_{3-6}$cycloalkyl, or $C_{1-6}$alkyl optionally substituted with deuterium, amino, hydroxy, mono- or di($C_{1-6}$alkyl)amino, $C_{1-6}$alkylcarbonylamino, [(mono- or di$C_{1-6}$alkyl)amino-$C_{1-6}$alkyl]carbonylamino, or with $C_{1-6}$alkylsulfonylamino; and p is 0, 1, 2, 3, 4, or 5.

2. The compound according to claim 1, the tautomeric form, the stereochemically isomeric form, the isotopically labeled form, or the pharmaceutically acceptable salt or solvate thereof, wherein;

$R^2$ is hydrogen; or $C_{1-6}$alkyl optionally substituted with deuterium, hydroxyl, $C_{1-6}$alkoxy, or with a 4 to 7 membered monocyclic heterocyclyl containing at least one heteroatom that is N, O or S;

each $R^{5a}$, $R^{5b}$, $R^{6a}$, $R^{6b}$, $R^{7a}$, and $R^{7b}$, independently, is hydrogen; $C_{1-6}$alkyl; halo$C_{1-6}$alkyl; or $R^{5a}$ and $R^{5b}$ form a $C_{3-6}$cycloalkyl together with the carbon atom to which they are bound; or $R^{6a}$ and $R^{6b}$ form a $C_{3-6}$cycloalkyl together with the carbon atom to which they are bound; or $R^{5b}$ and $R^{6a}$ form a cyclopropyl together with the carbon atoms to which they are bound;

$R^8$ is a direct bond, $C_{1-4}$alkanediyl optionally substituted with hydroxy, deuterium, or $C_{1-4}$alkoxy; —$CH_2$—C(═O)—; a spiro-$C_{3-6}$cycloalkyl; or a 4 to 7 membered spiro-monocyclic heterocyclyl containing at least one heteroatom that is N, O or S;

A is a $C_{3-6}$cycloalkyl; aryl; a 5 to 12 membered heteroaryl containing at least one heteroatom that is N, O or S;

$R^9$ is $C_{1-6}$alkyl optionally substituted with $C_{3-6}$cycloalkyl; halo; halo$C_{1-6}$alkyl; $C_{1-6}$alkoxy optionally substituted with $C_{3-6}$cycloalkyl; halo$C_{1-6}$alkoxy; hydroxyl; hydroxy$C_{1-6}$alkyl; oxo; —$SO_2$—$C_{3-6}$cycloalkyl; —C(═O)—$C_{1-6}$alkyl-$C_{3-6}$cycloalkyl; —C(═O)—$C_{3-6}$ cycloalkyl; $C_{3-6}$cycloalkyl; spiro-$C_{3-6}$cycloalkyl; a 4 to 7 membered monocyclic heterocyclyl containing at least one heteroatom that is N, O or S;

n is 0, 1, 2, 3, or 4;

$R^{10}$ is hydrogen, halo, hydroxy, mercapto, carboxyl, halo$C_{1-6}$alkyl, mono- or di($C_{1-6}$alkyl)amino, mono- or di($C_{1-6}$alkyl)aminocarbonyl, $C_{1-6}$alkylcarbonyl, $C_{1-6}$alkylcarbonylamino, $C_{1-6}$alkoxy, $C_{1-6}$alkoxycarbonyl, $C_{1-6}$alkylthio, cyano, nitro, halo$C_{1-6}$alkoxy, aminocarbonyl, $C_{3-6}$cycloalkyl, or $C_{1-6}$alkyl optionally substituted with deuterium, amino, hydroxy, mono- or di($C_{1-6}$alkyl)amino, $C_{1-6}$alkylcarbonylamino, [(mono- or di$C_{1-6}$alkyl)amino-$C_{1-6}$alkyl]carbonylamino, or with $C_{1-6}$alkylsulfonylamino; and p is 0, 1, 2, or 3.

3. The compound according to claim 1, the tautomeric form, the stereochemically isomeric form, the isotopically labeled form, or the pharmaceutically acceptable salt or solvate thereof, wherein $R^{5a}$ is $C_{1-6}$alkyl; or $R^{5a}$ and $R^{5b}$ form a cyclopropyl together with the carbon atom to which they are bound; or $R^{6a}$ and $R^{6b}$ form a cyclopropyl together with the carbon atom to which they are bound; or $R^{5b}$ and $R^{6a}$ form a cyclopropyl together with the carbon atoms to which they are bound.

4. The compound according to claim 1, the tautomeric form, the stereochemically isomeric form, the isotopically labeled form, or the pharmaceutically acceptable salt or solvate thereof, wherein:

$R^8$ is $C_{1-4}$alkanediyl optionally substituted with hydroxy or deuterium;

A is a 5 to 12 membered heteroaryl containing at least one heteroatom that is N, O or S;

$R^9$ is $C_{1-6}$alkyl; and n is 1.

5. The compound according to claim 1, the tautomeric form, the stereochemically isomeric form, the isotopically labeled form, or the pharmaceutically acceptable salt or solvate thereof, wherein the compound is:

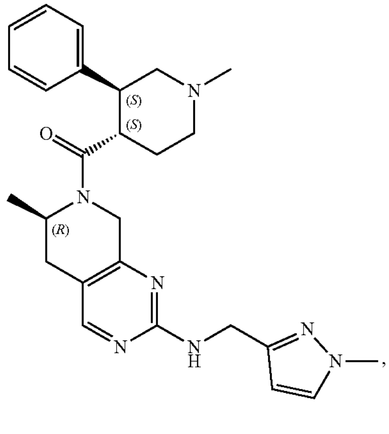

,

-continued
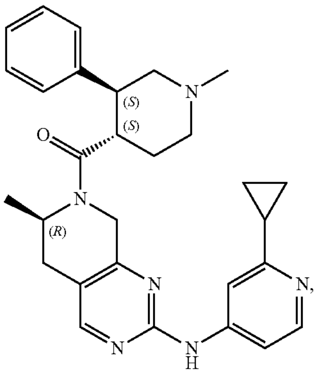
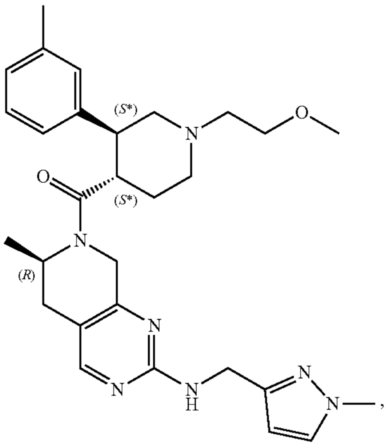
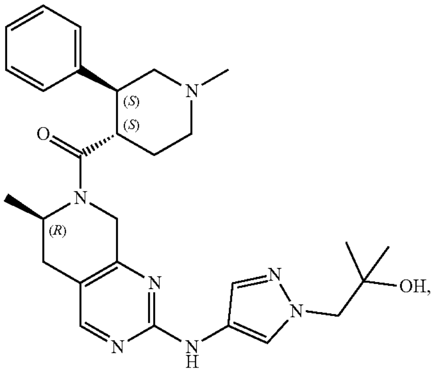
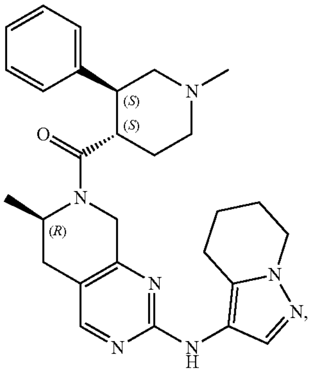
-continued
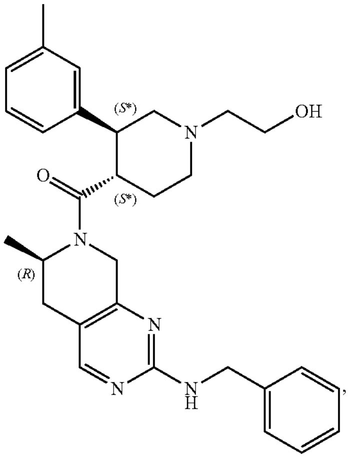
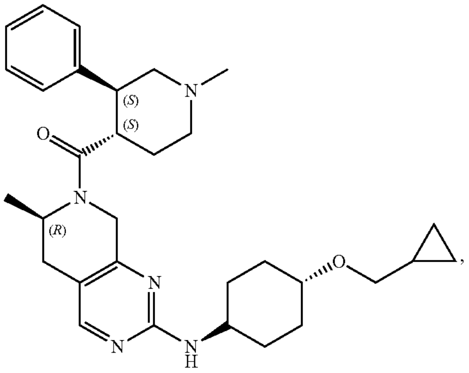
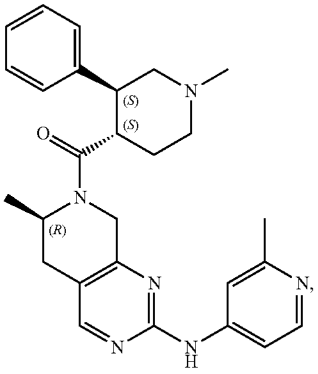
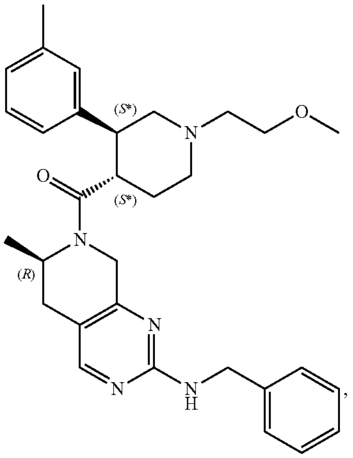

-continued
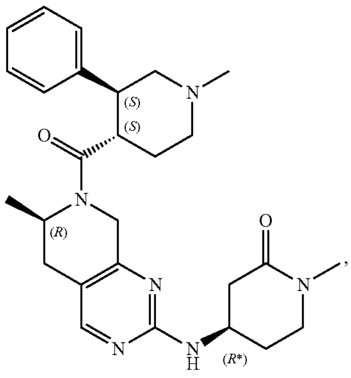
,
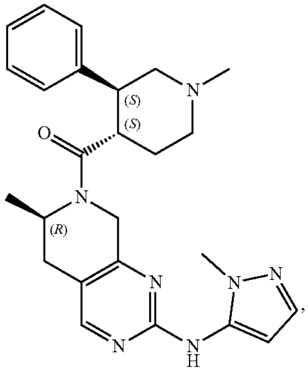
,
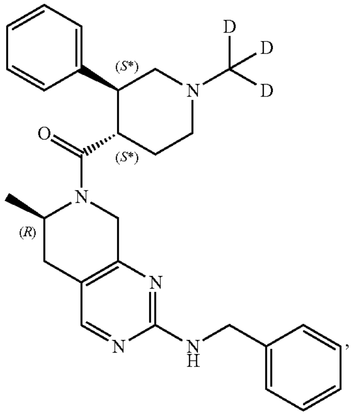
,
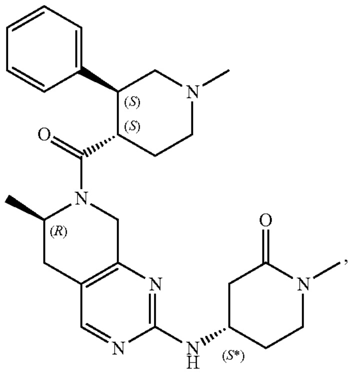
,
-continued
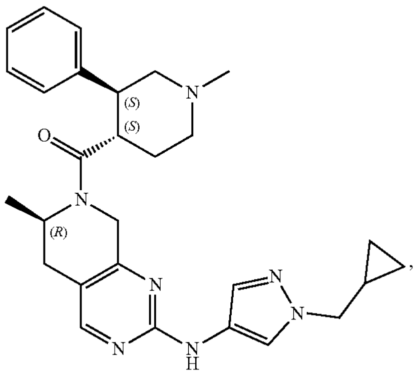
,
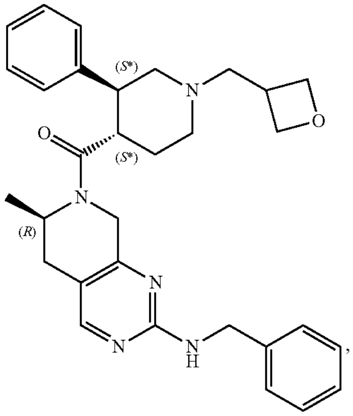
,
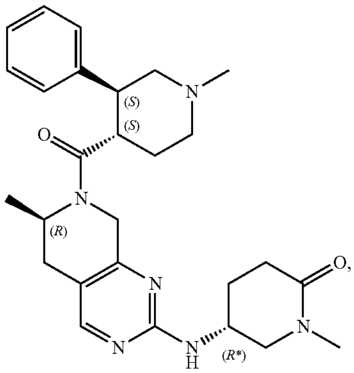
,
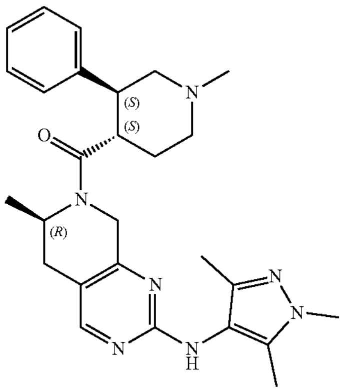
, -continued
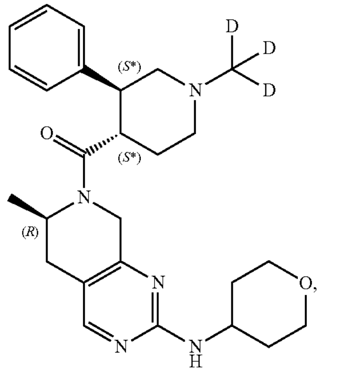
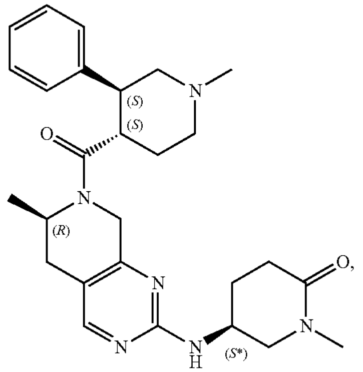
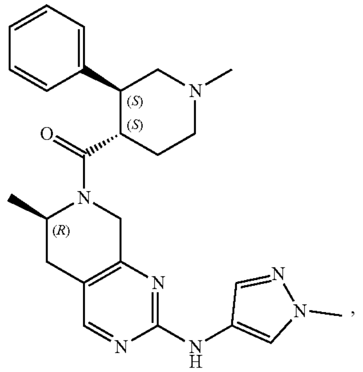
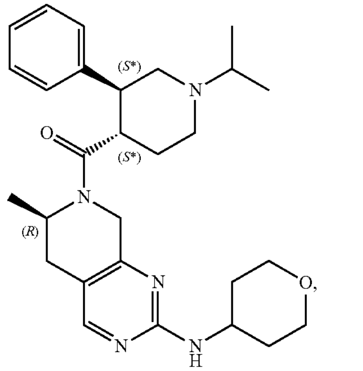
-continued
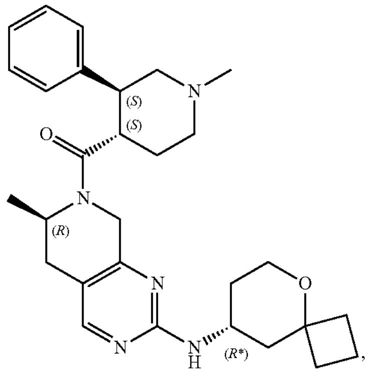
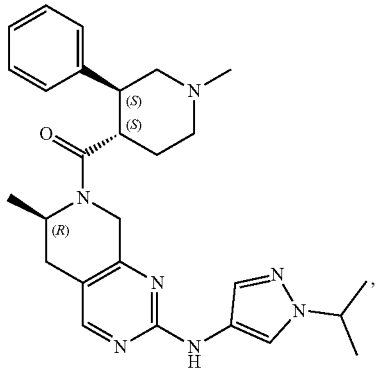
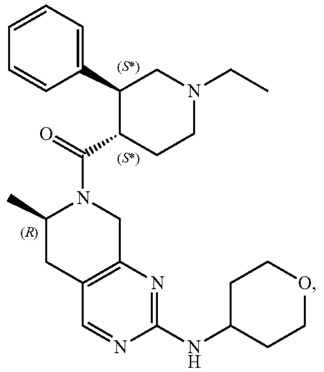
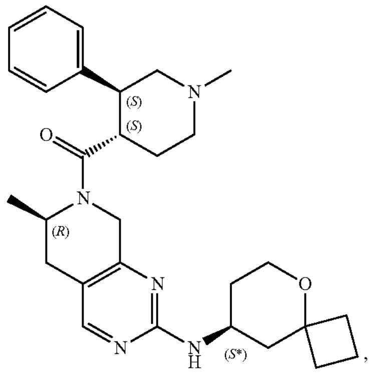

-continued
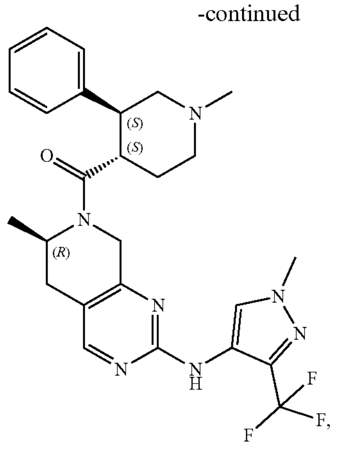
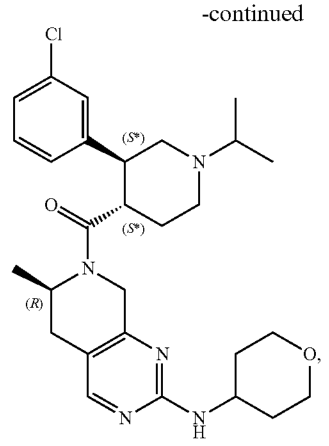
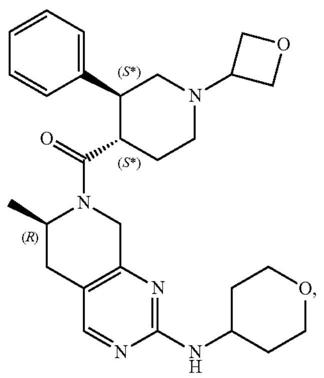
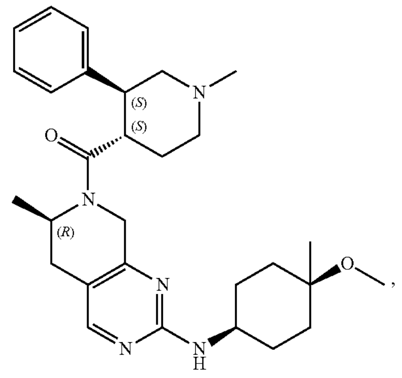
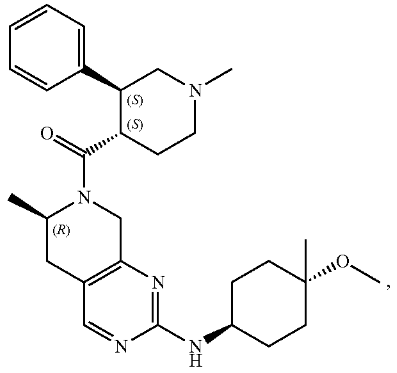
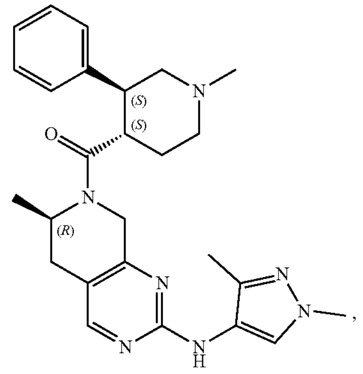
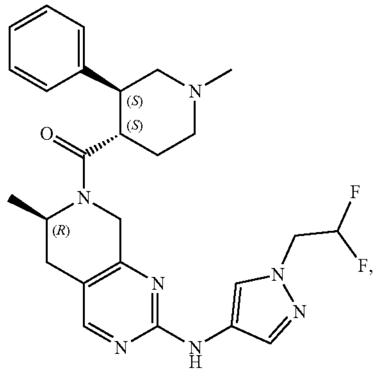
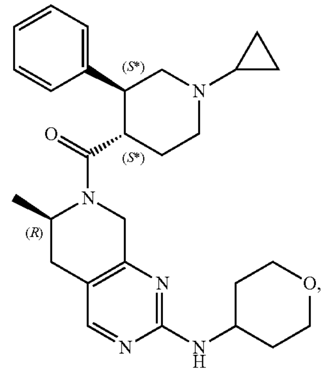
-continued -continued
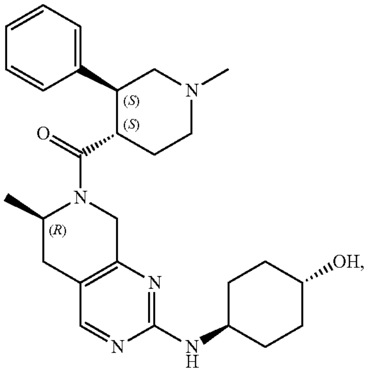
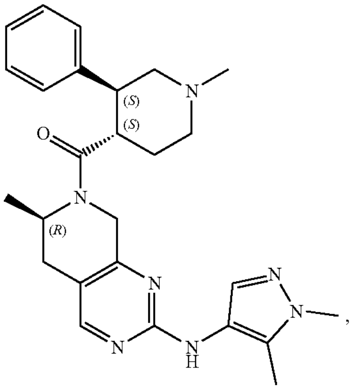
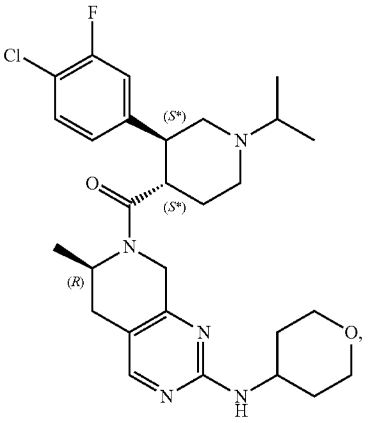
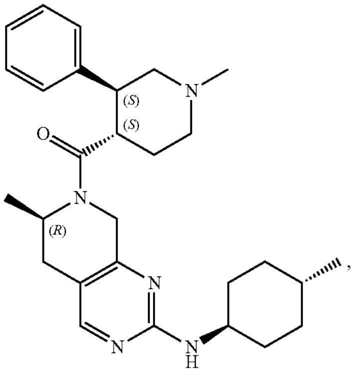
-continued
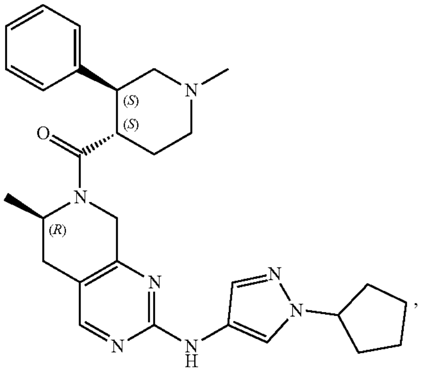
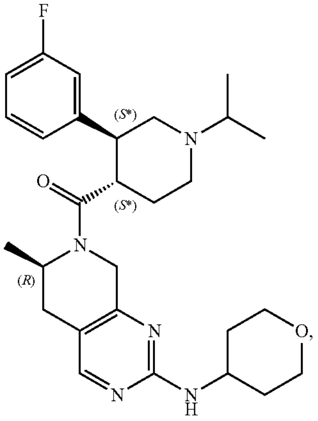
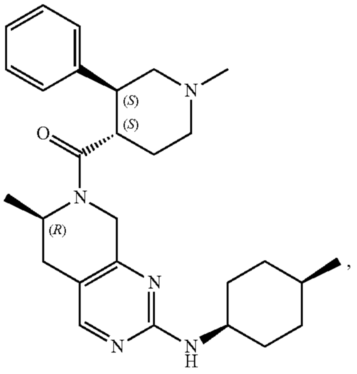
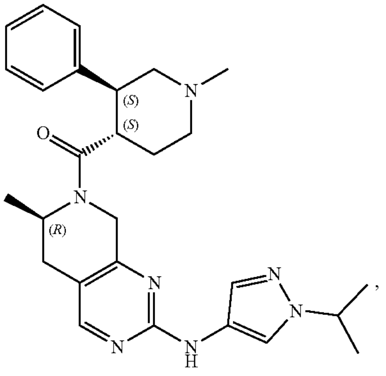

-continued
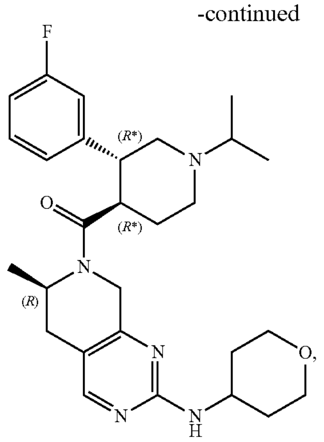
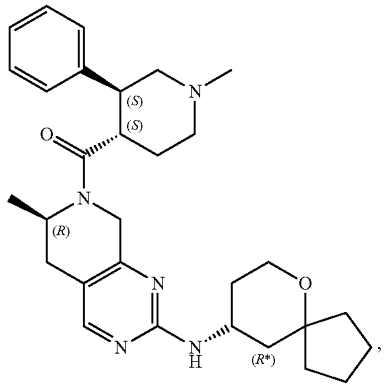
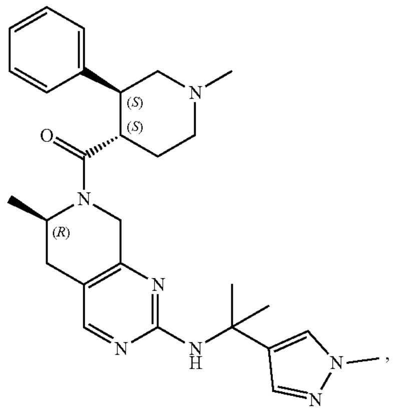
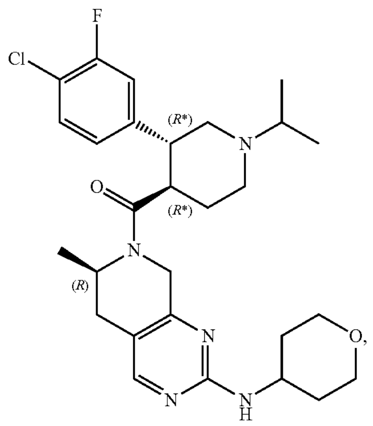
-continued
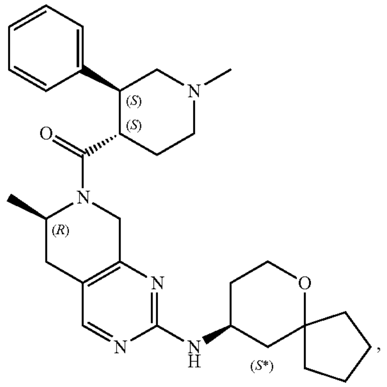
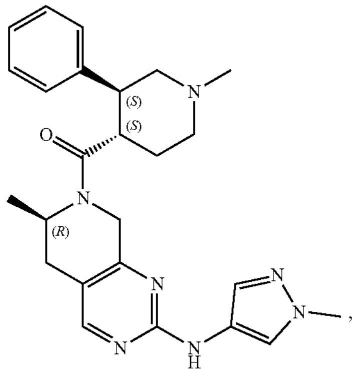
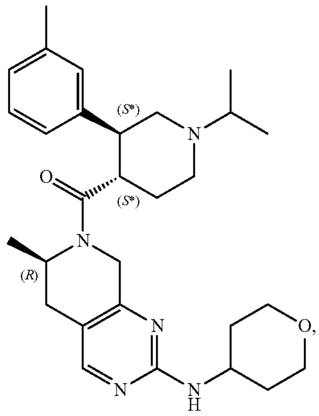
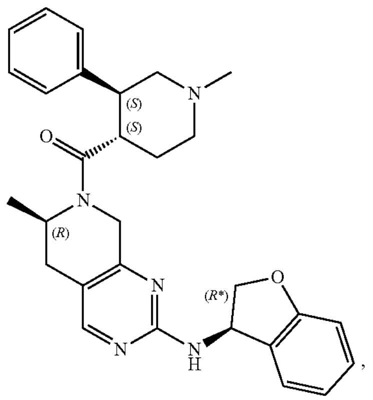

-continued
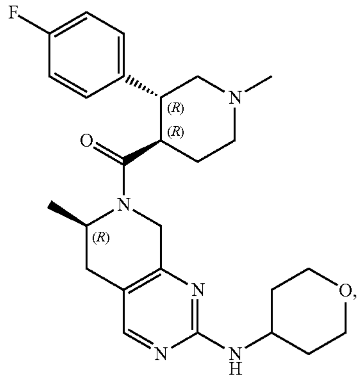
,
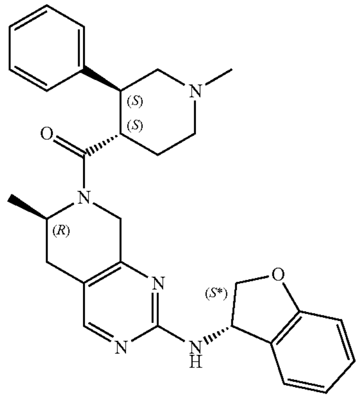
,
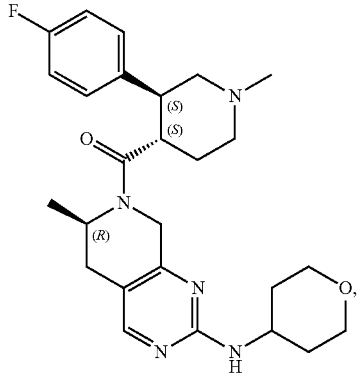
,
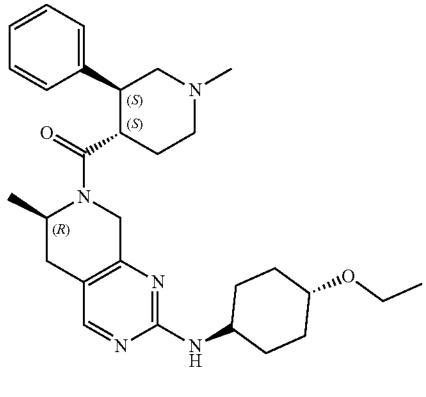
,
-continued
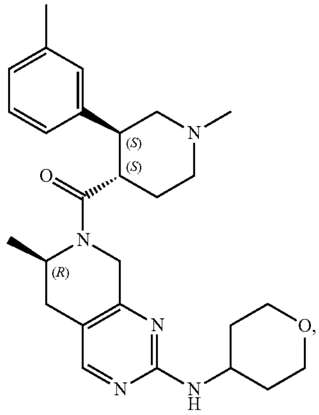
,
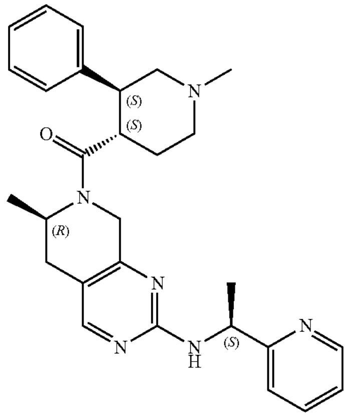
,
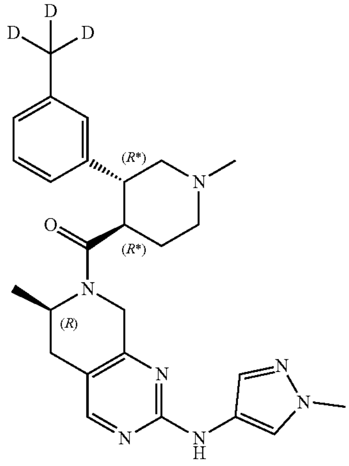
,
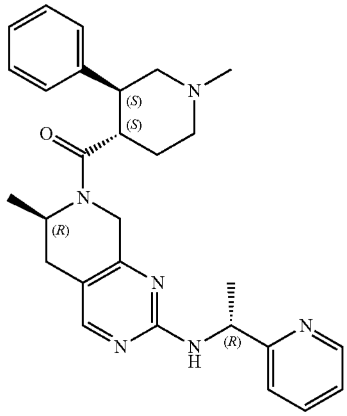
,

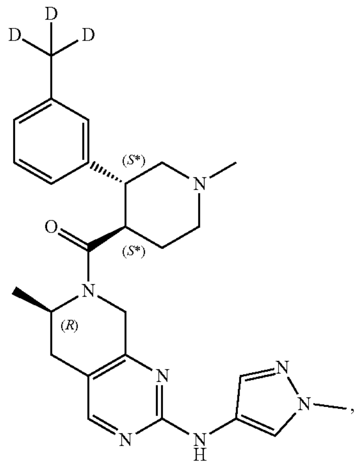
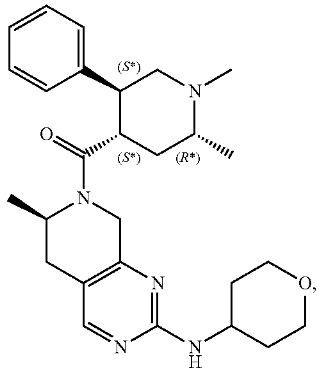
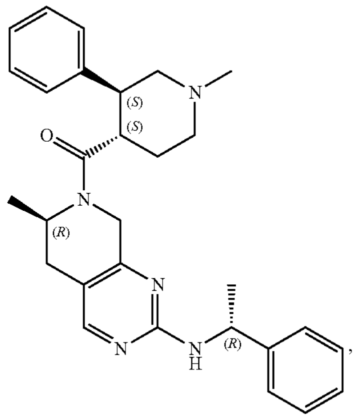
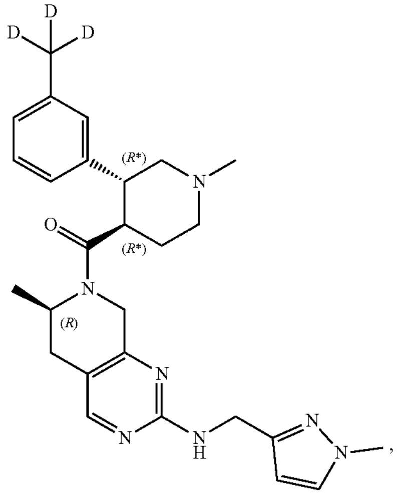
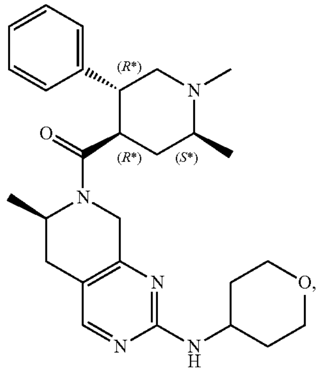
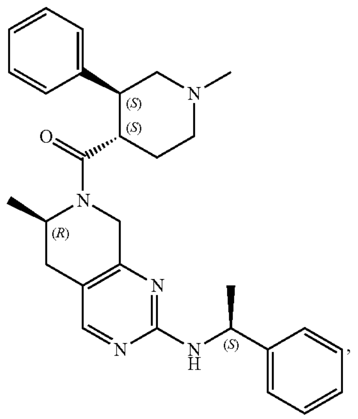

-continued
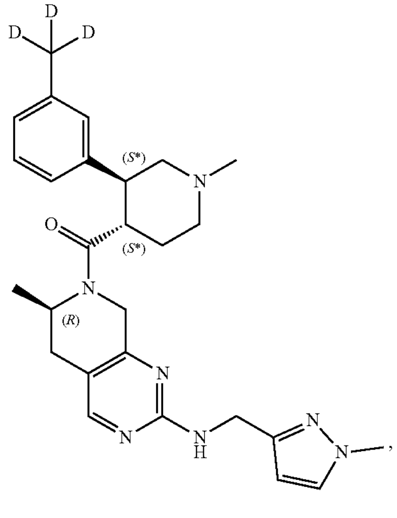
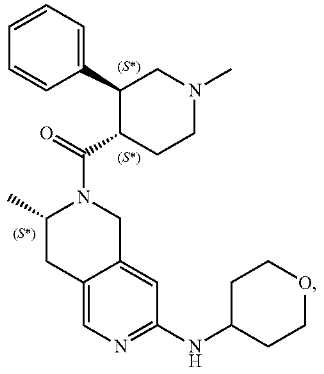
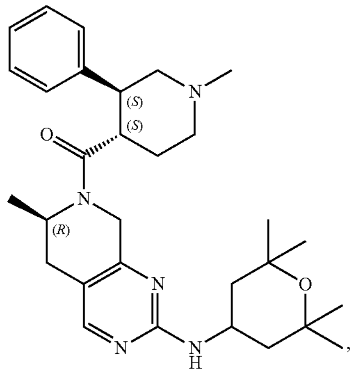
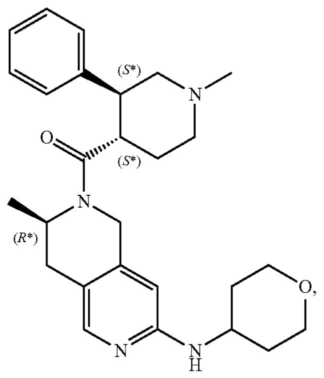
-continued
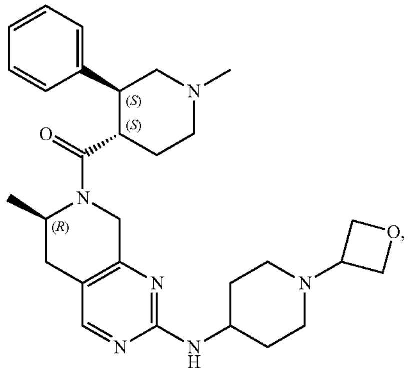
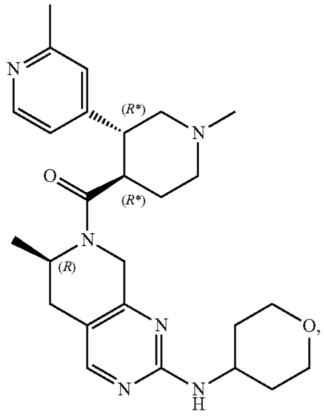
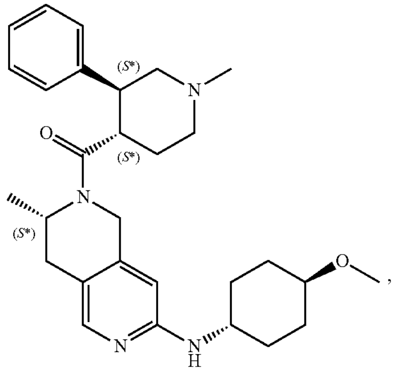
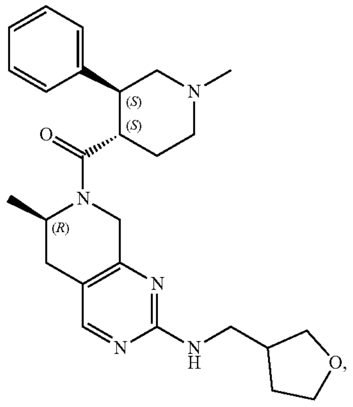

-continued
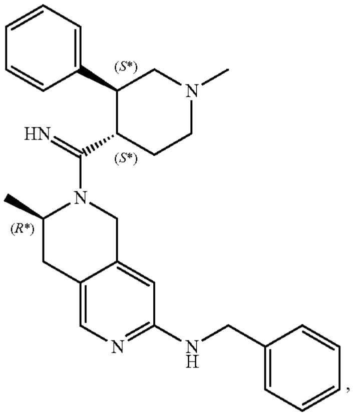
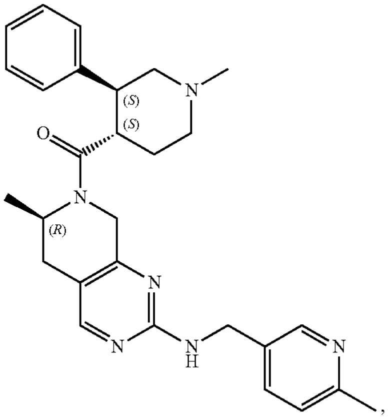
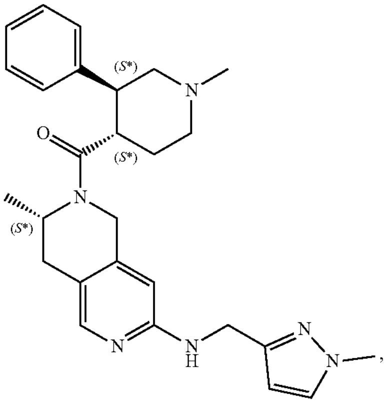
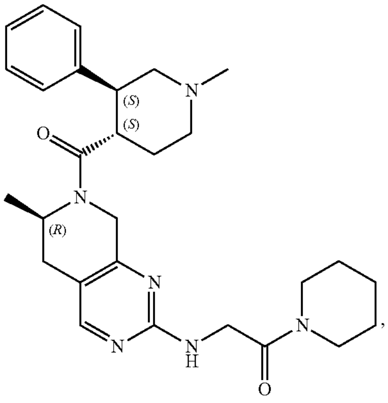
-continued
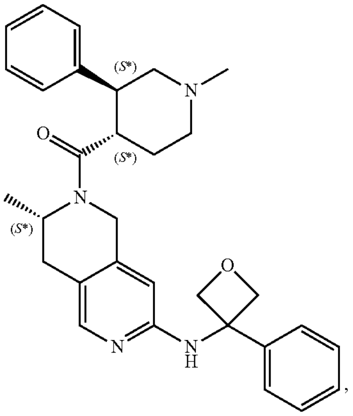
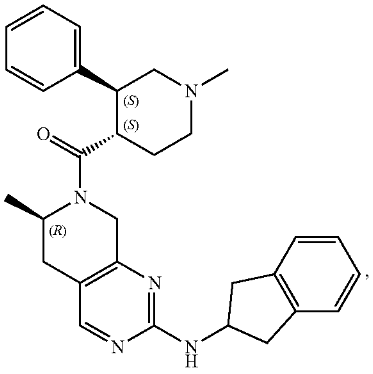
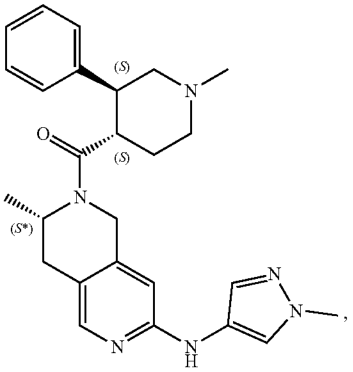
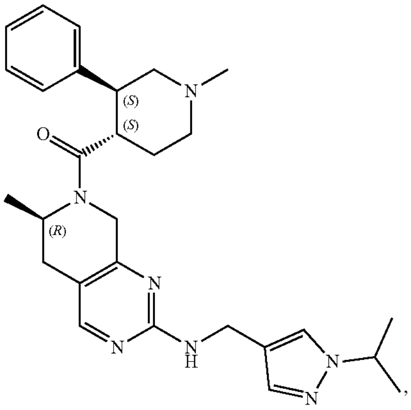

-continued
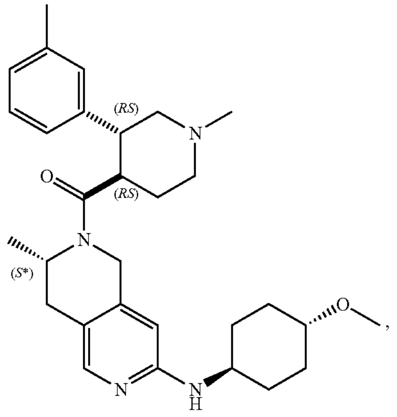
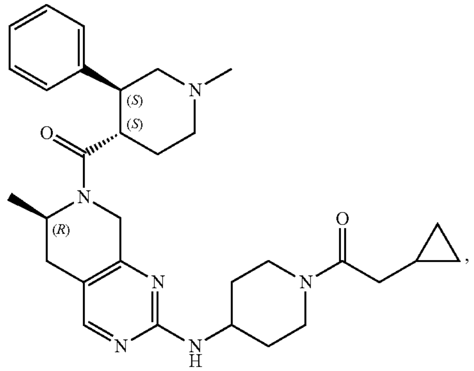
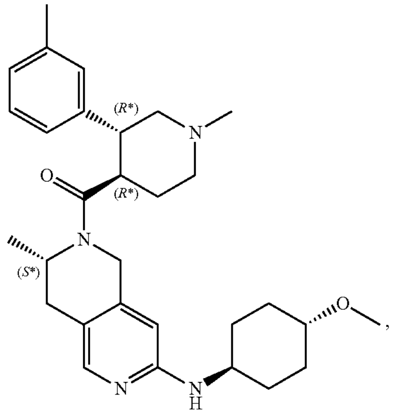
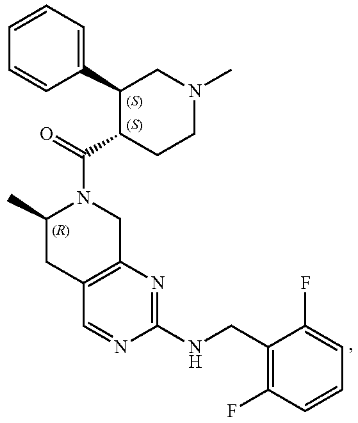
-continued
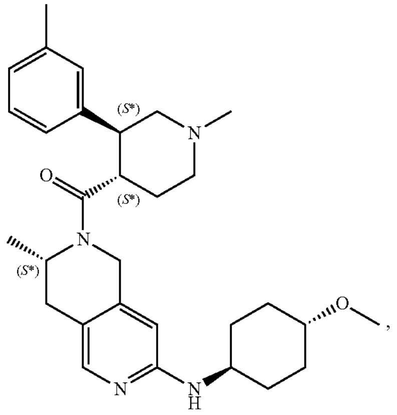
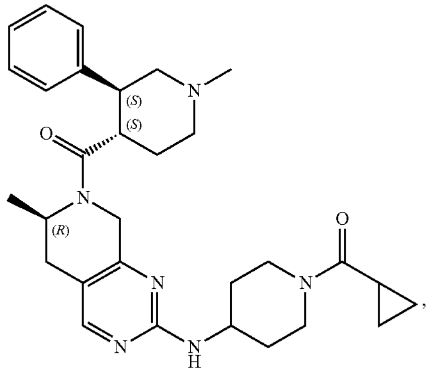
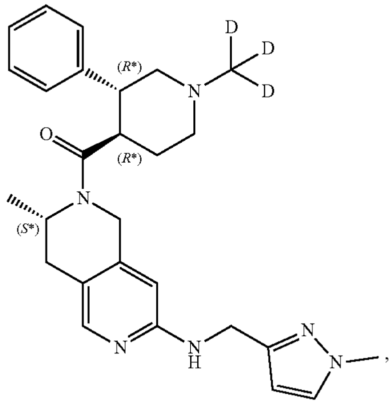
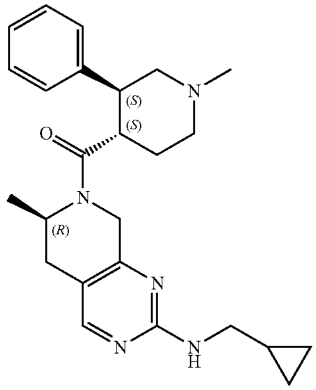

-continued
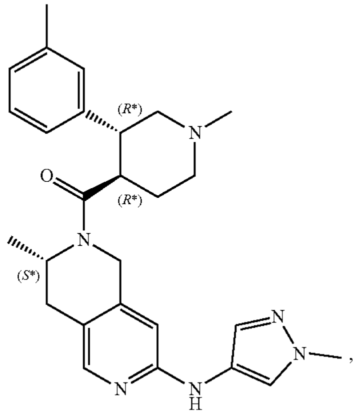
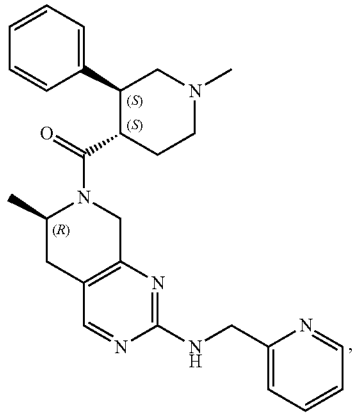
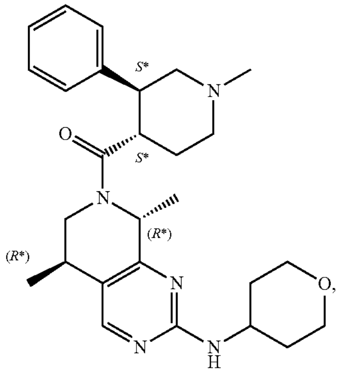
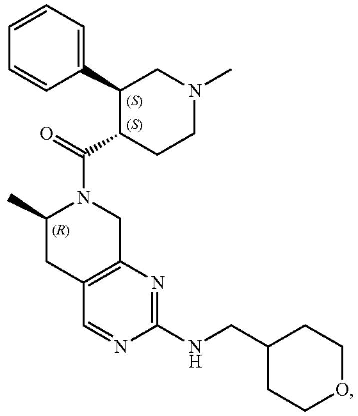
-continued
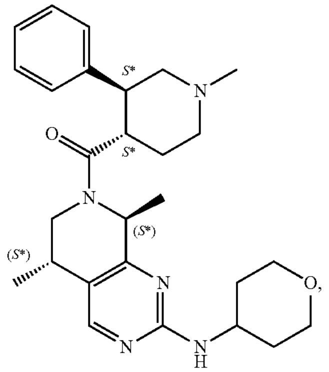
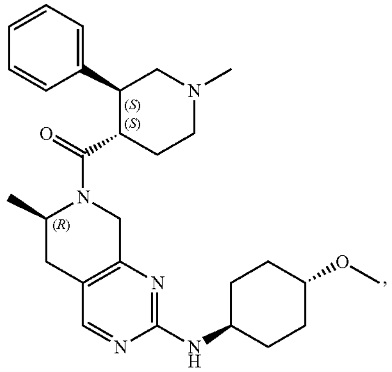
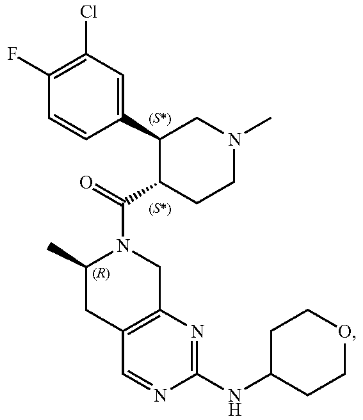
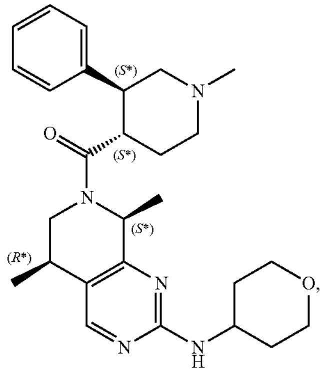

-continued
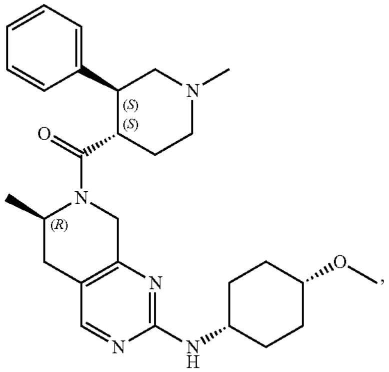
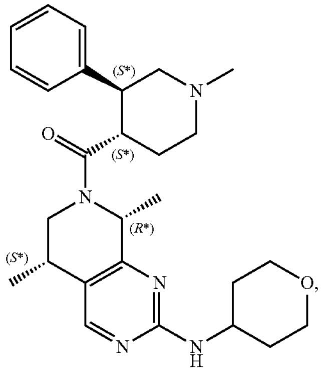
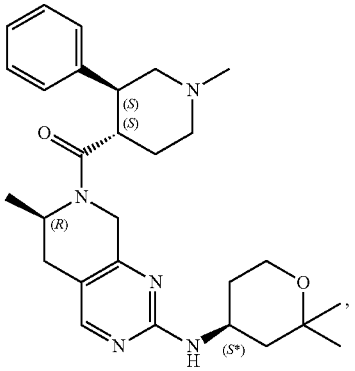
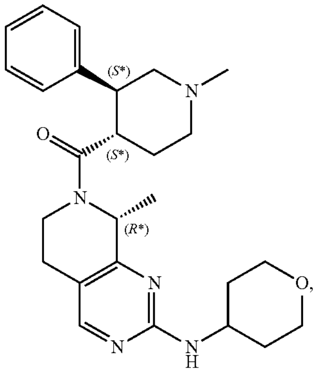
-continued
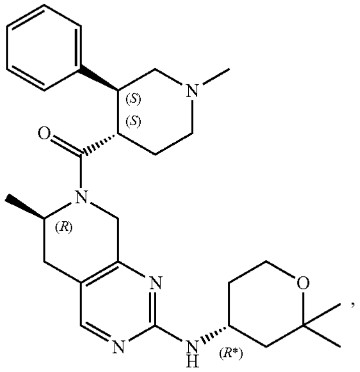
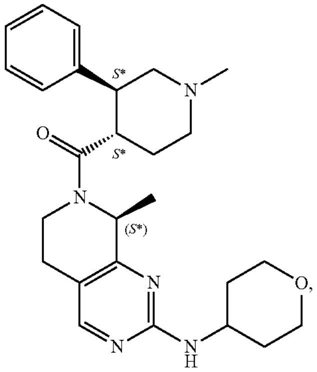
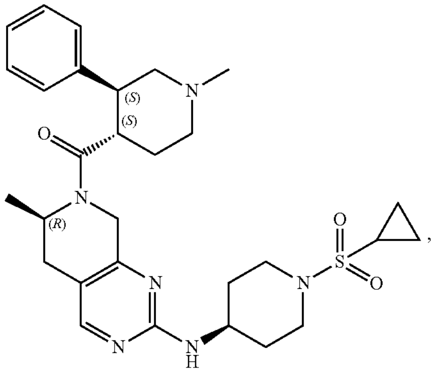
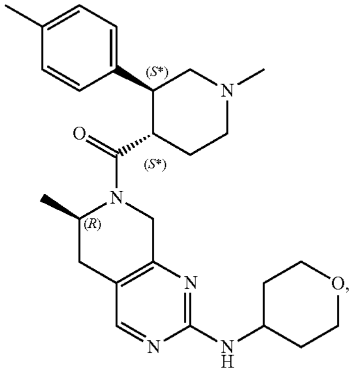

-continued
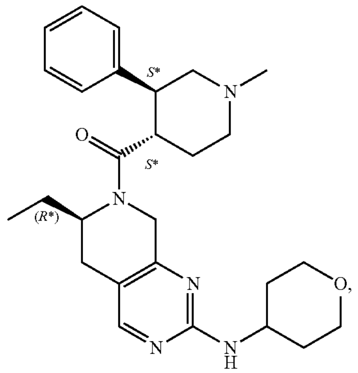
,
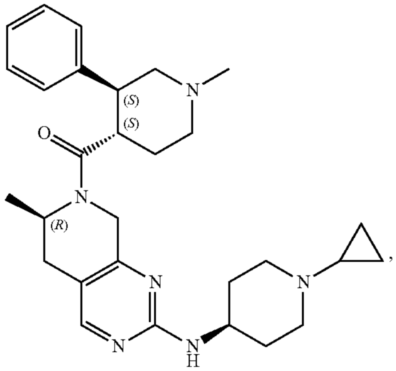
,
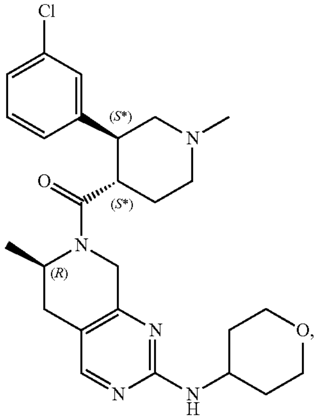
,
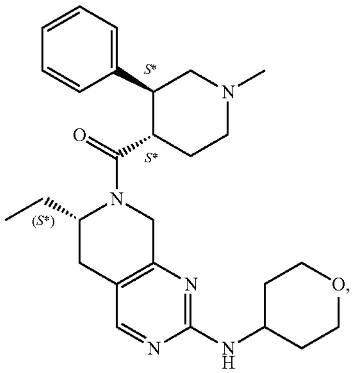
,
-continued
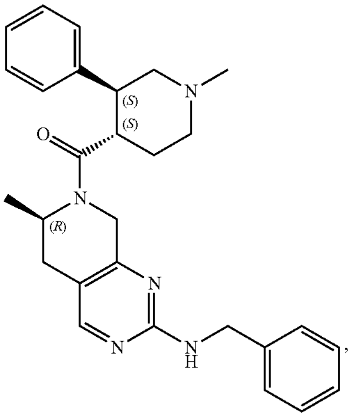
,
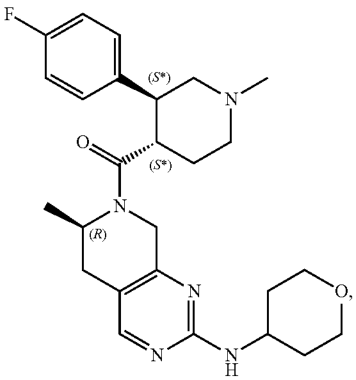
,
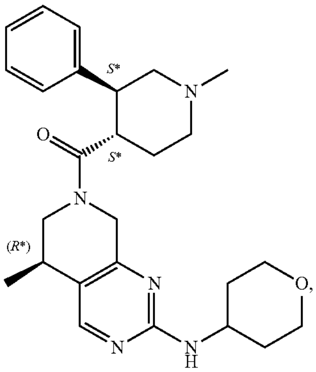
,
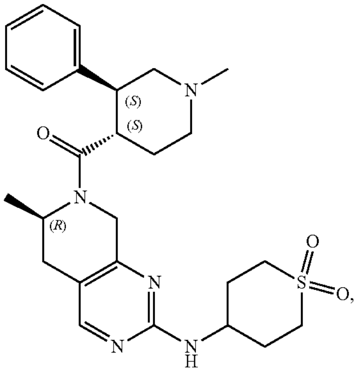
, -continued
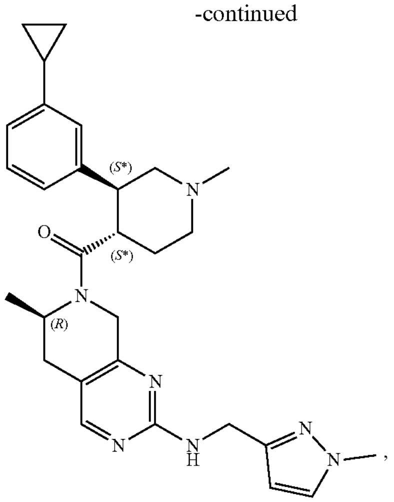
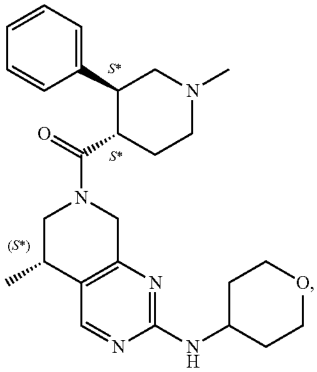
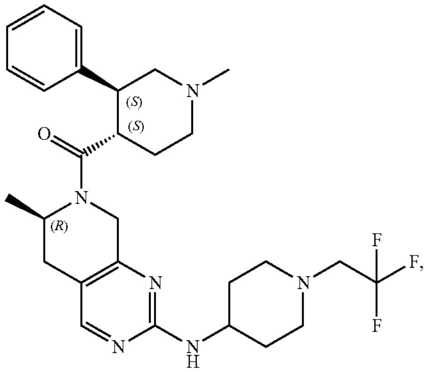
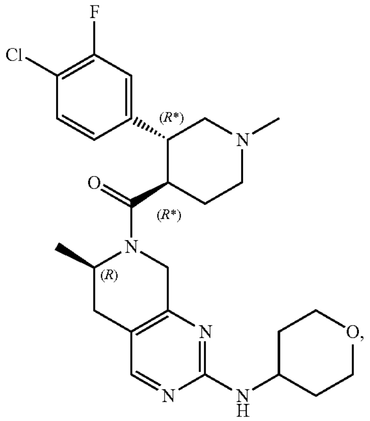
-continued
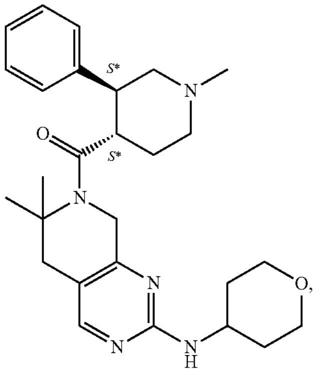
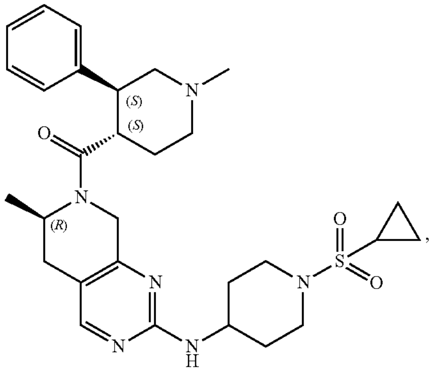
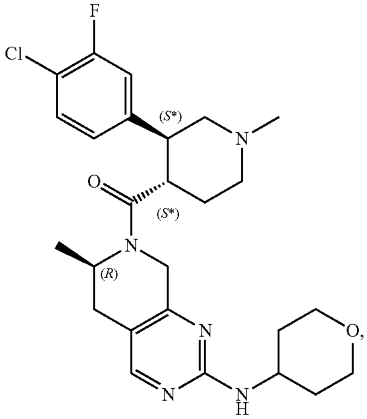
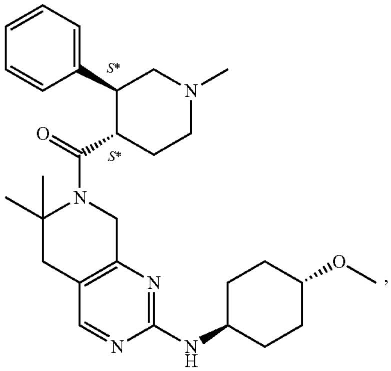

-continued
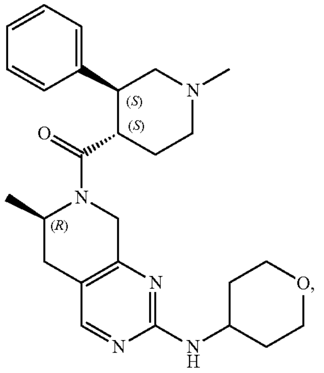
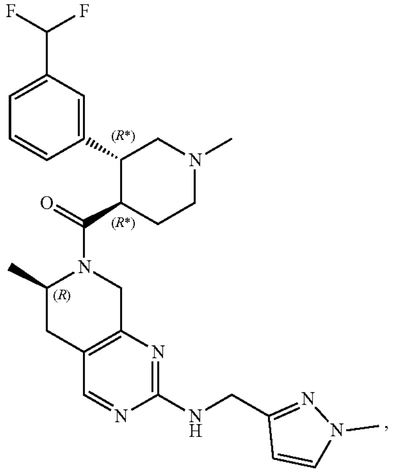
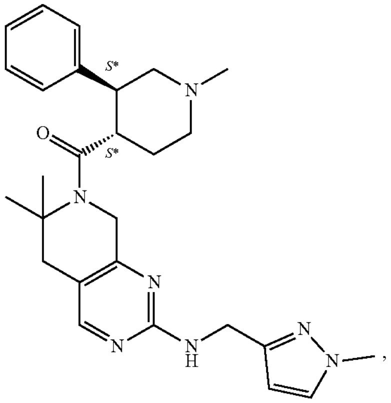
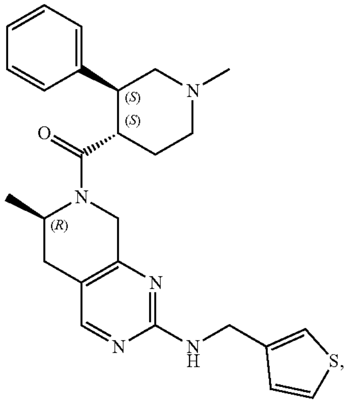
-continued
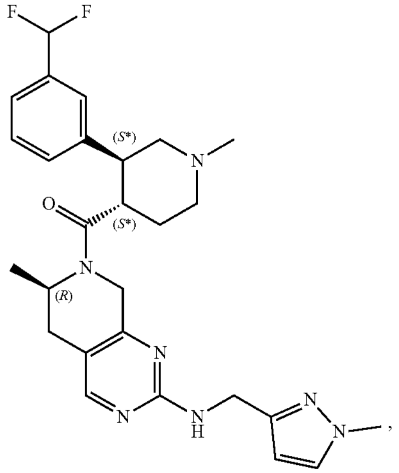
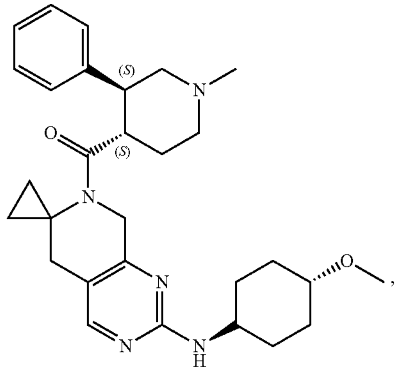
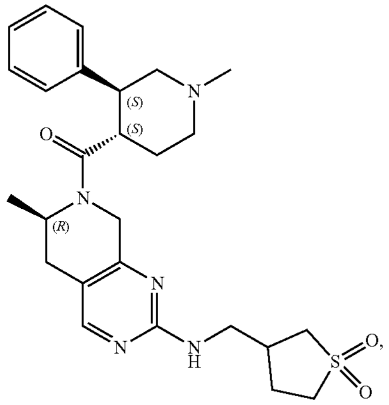
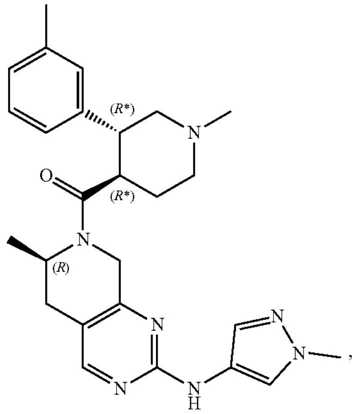

-continued
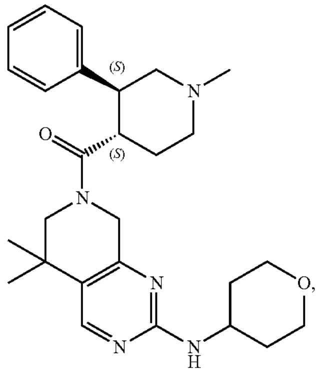
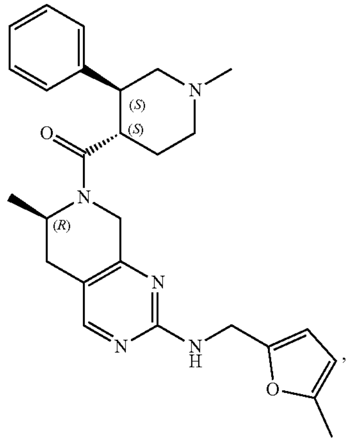
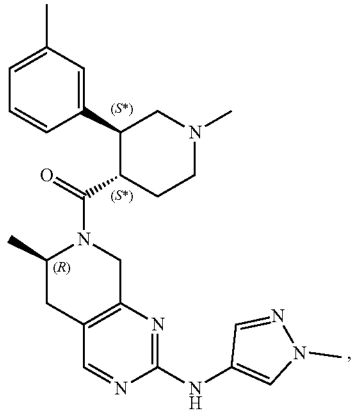
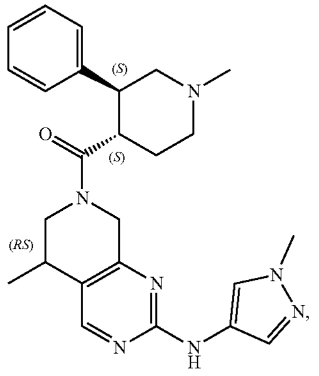
-continued
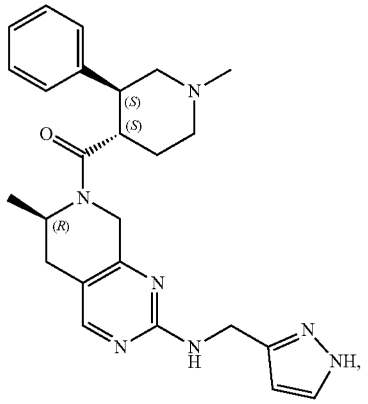
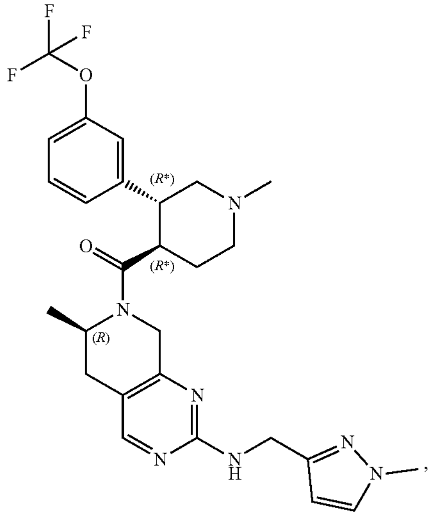
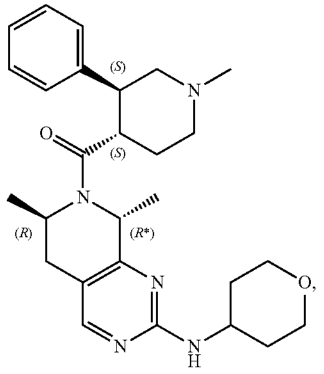
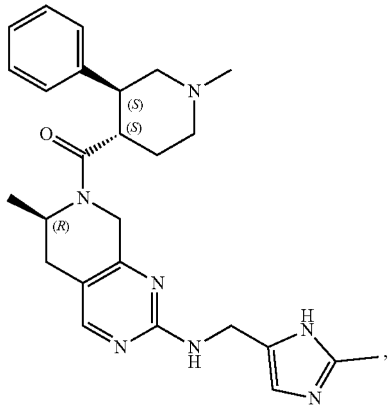

-continued
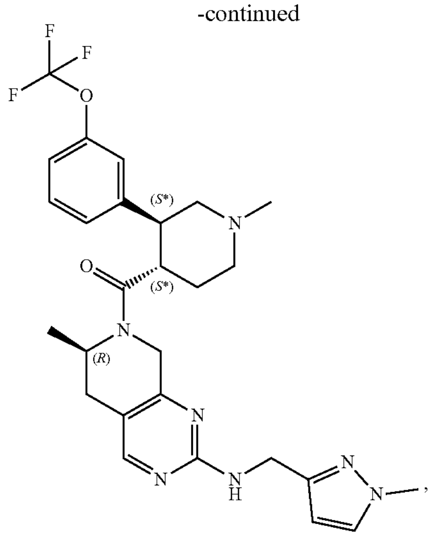
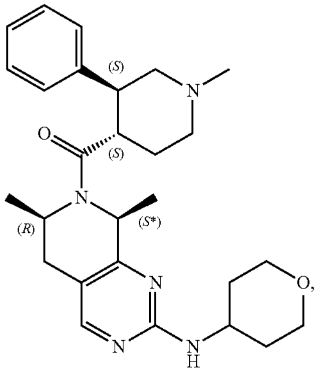
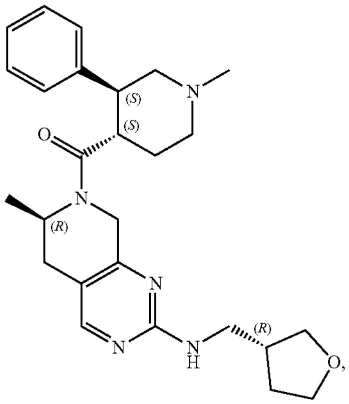
-continued
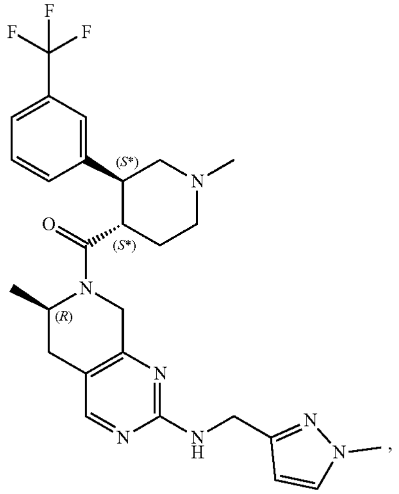
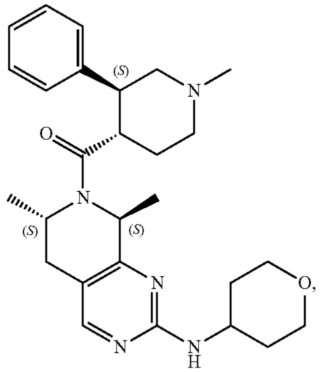
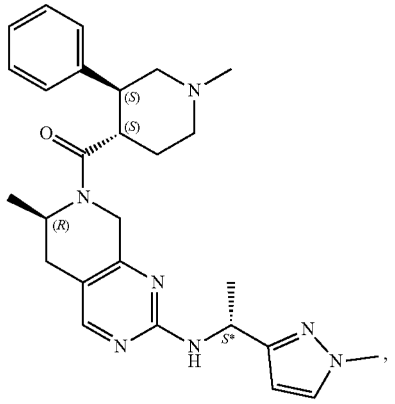
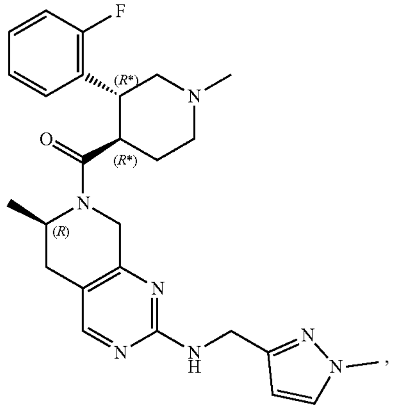

-continued
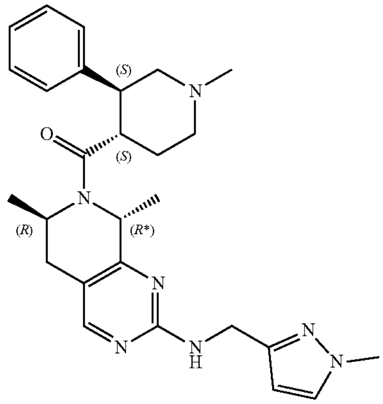
,
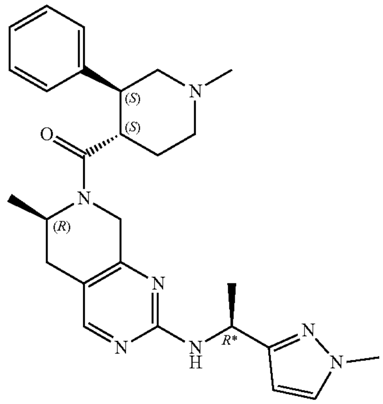
,
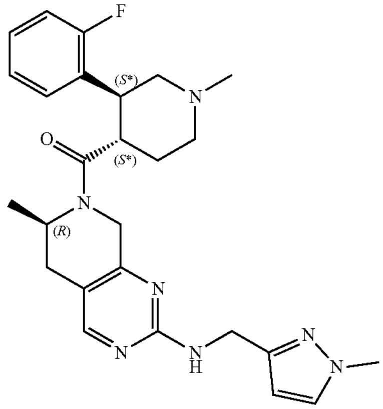
,
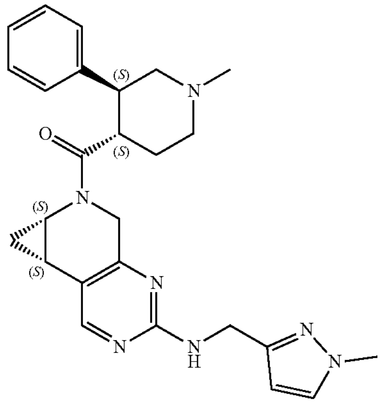
,
-continued
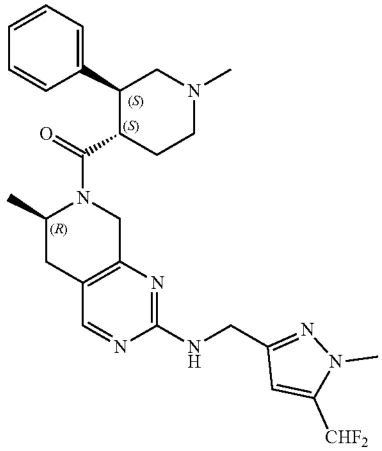
,
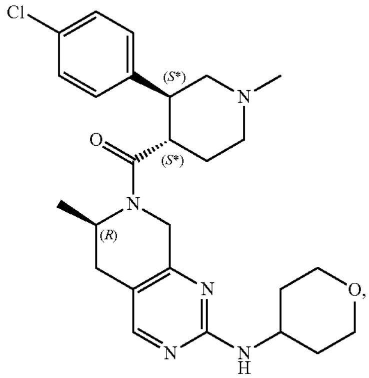
,
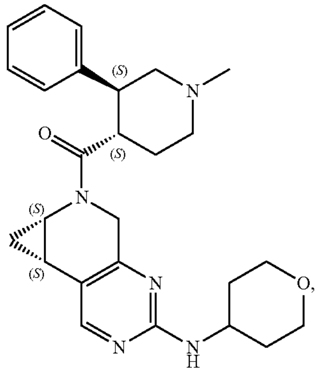
,
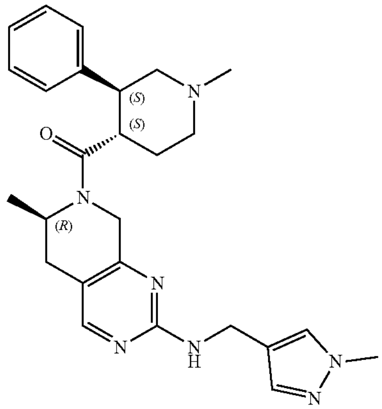
, -continued
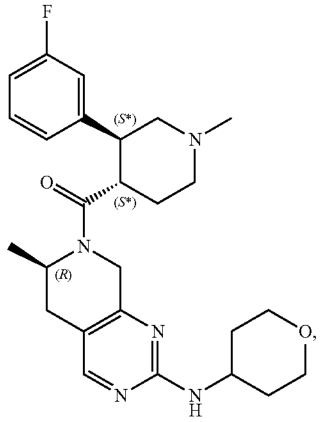
,
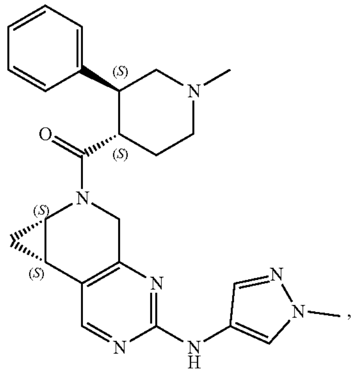
,
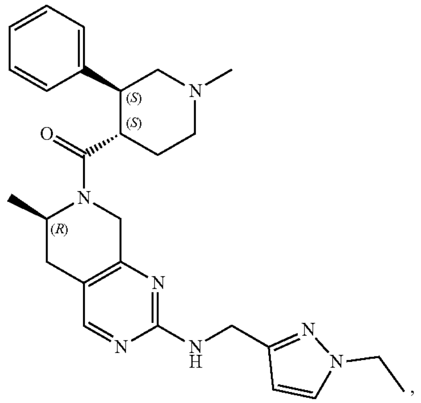
,
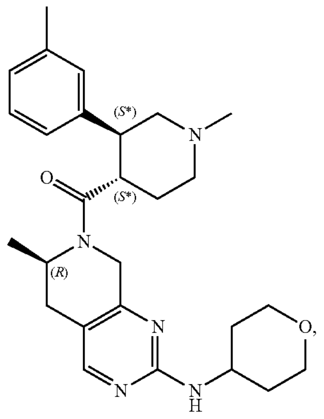
,
-continued
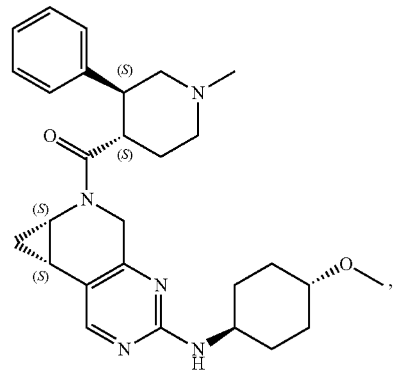
,
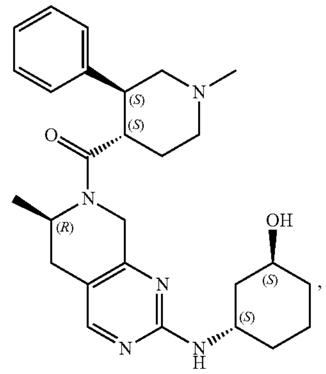
,
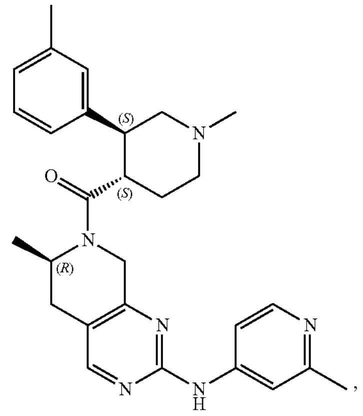
,
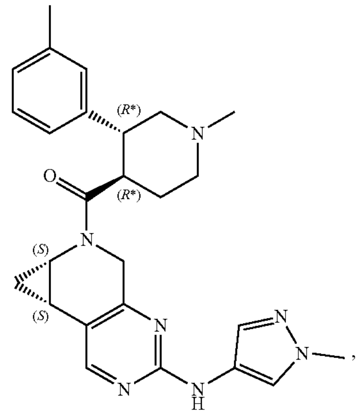
, -continued
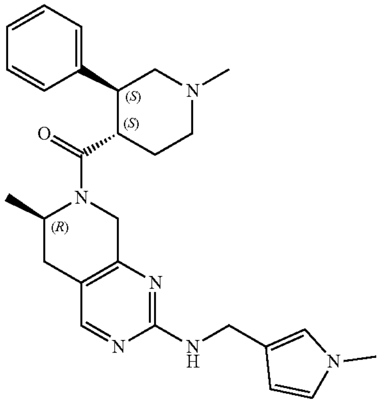
,
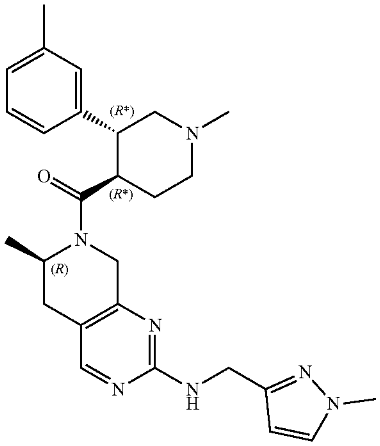
,
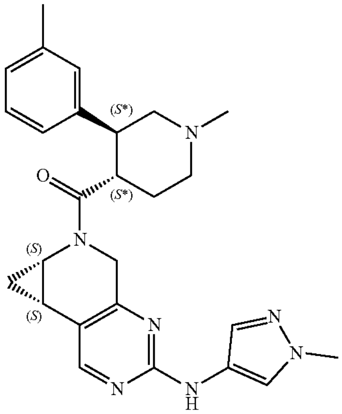
,
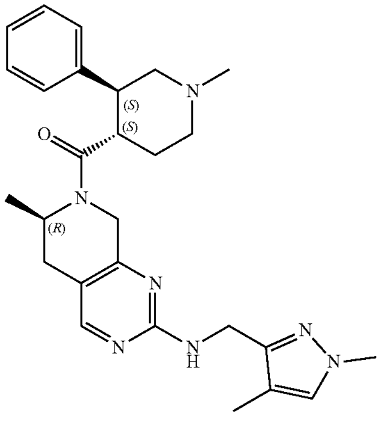
,
-continued
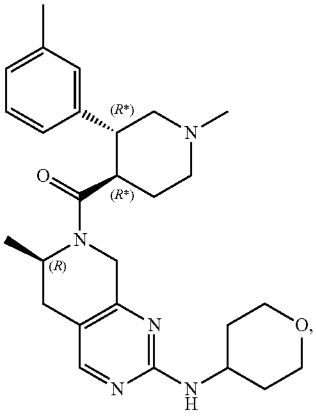
,
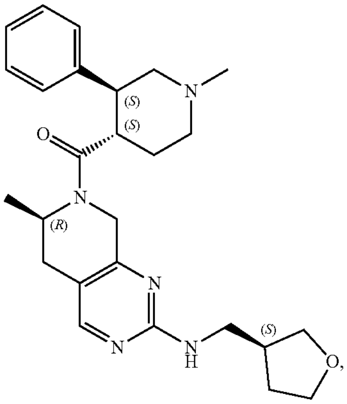
,
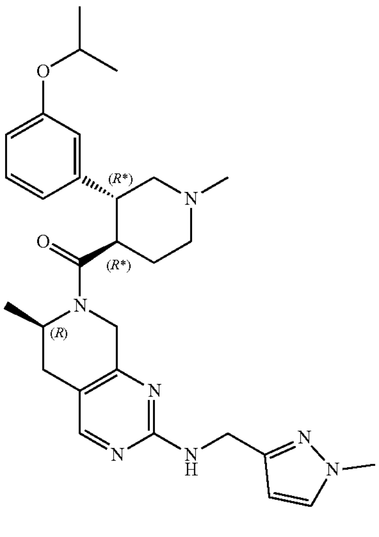
, -continued
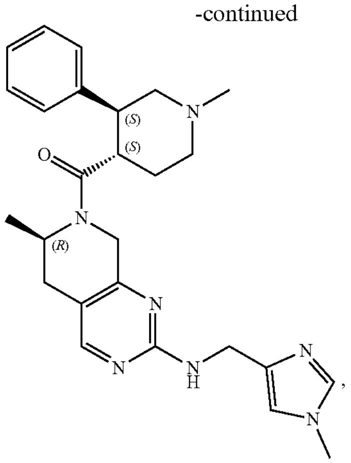
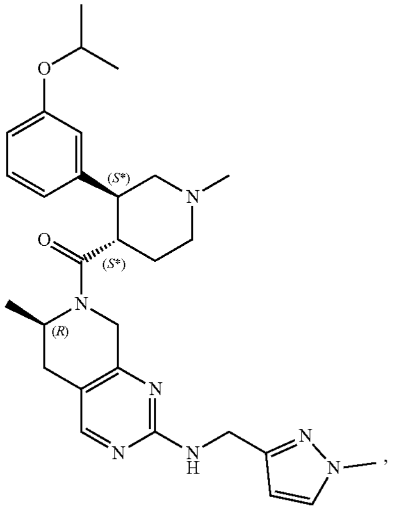
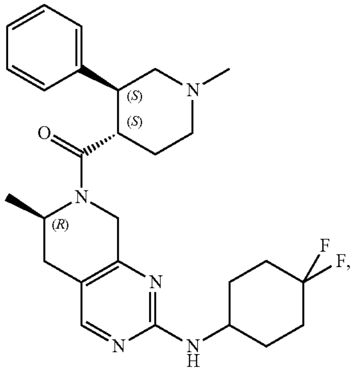
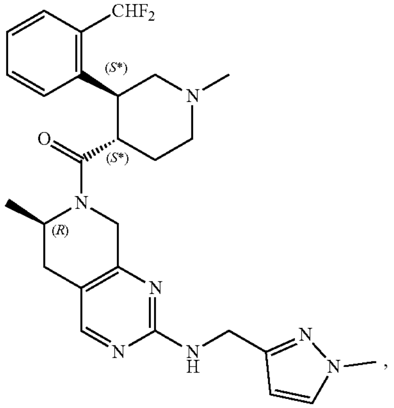
-continued
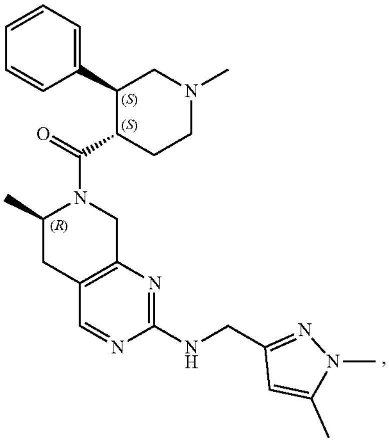
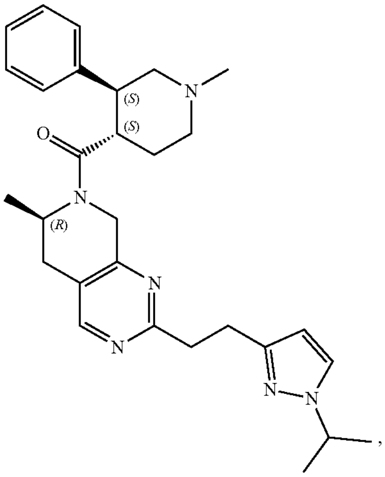
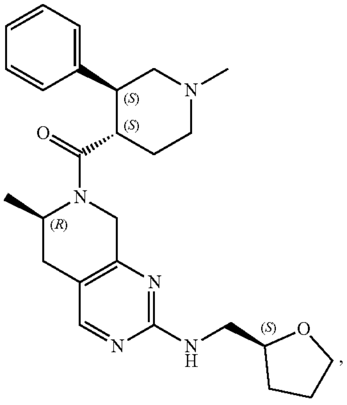
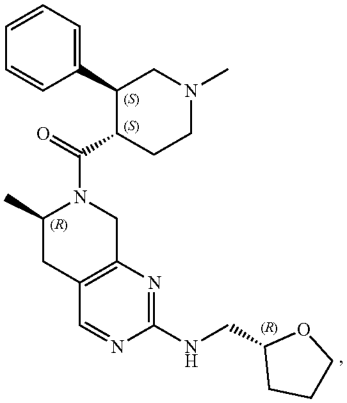

-continued
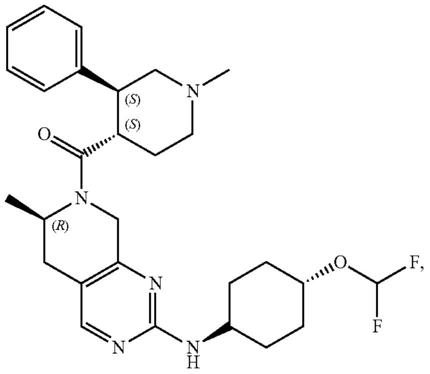
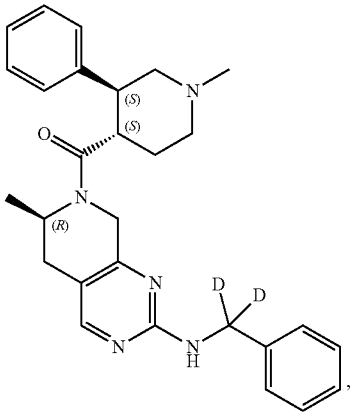
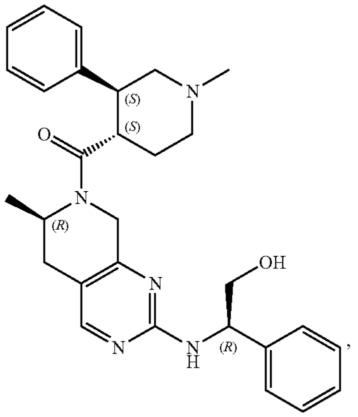
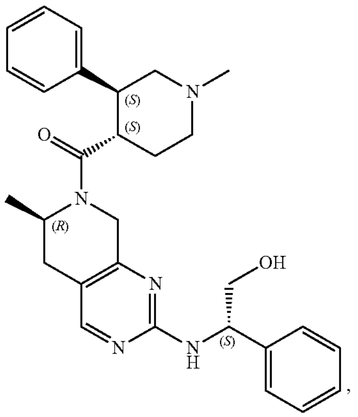
-continued
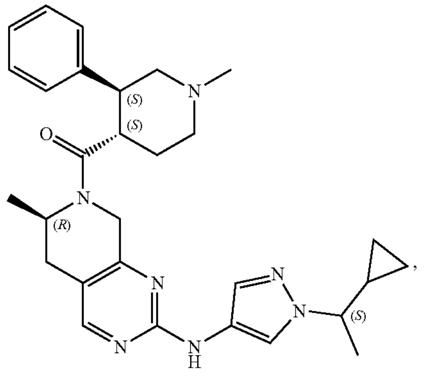
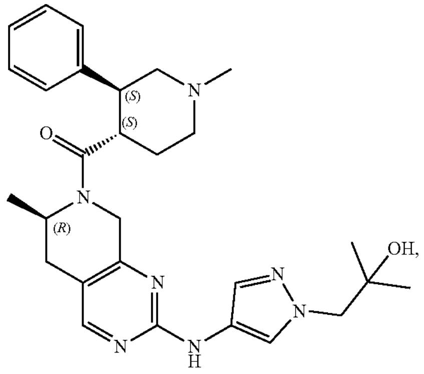
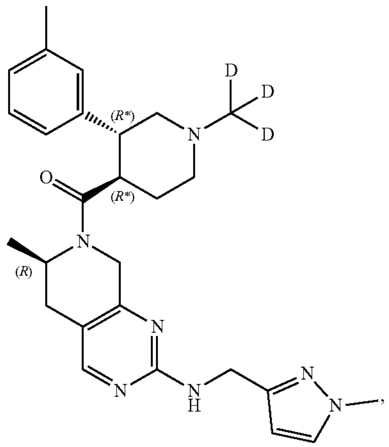
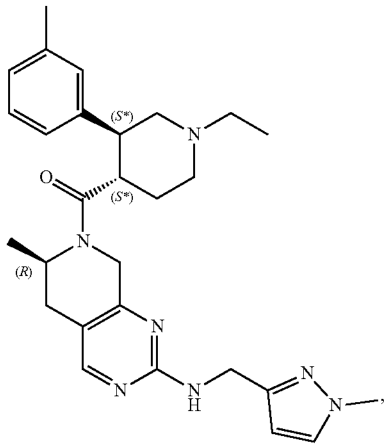

-continued

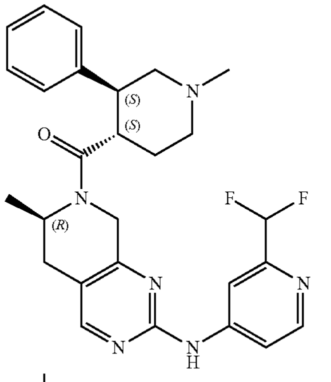

or

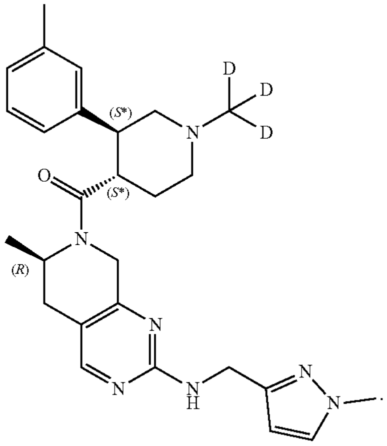

6. A pharmaceutical composition comprising the compound according to claim 1 and a pharmaceutically acceptable carrier.

7. A method for the treatment of a cancer having elevated or abnormal cyclin-dependent kinase 7 (CDK7) activity, wherein the method comprises administering to a subject in need thereof the compound of claim 1.

8. The method of claim 7, wherein the cancer is leukemia, lymphoma, melanoma, multiple myeloma, bone cancer, Ewing's sarcoma, triple-negative breast cancer (TNBC), brain cancer, neuroblastoma, or lung cancer.

9. The method of claim 7, wherein the subject is a mammal.

10. An in vitro method of modulating CDK7 activity comprising contacting the CDK7 protein, or portion thereof, with the compound, or the pharmaceutically acceptable salt or solvate thereof, according to claim 1.

11. A method for inhibiting the activity of cyclin-dependent kinase 7 (CDK7) in a subject in need thereof, wherein the method comprises administering the compound of claim 1 to the subject.

12. The method of claim 8, wherein the leukemia is chronic lymphocytic leukemia (CLL), acute lymphoblastic leukemia (ALL), T-cell acute lymphoblastic leukemia (T-ALL), chronic myelogenous leukemia (CML), or acute myeloid leukemia (AML).

13. The method of claim 8, wherein the lymphoma is Hodgkin's lymphoma or non-Hodgkin's lymphoma.

14. The method of claim 8, wherein the lung cancer is small cell lung cancer (SCLC) or large cell lung cancer.

15. The method of claim 8, wherein the bone cancer is osteosarcoma.

* * * * *